(12) United States Patent
Guirakhoo et al.

(10) Patent No.: US 8,691,550 B2
(45) Date of Patent: *Apr. 8, 2014

(54) VACCINES AGAINST JAPANESE ENCEPHALITIS VIRUS AND WEST NILE VIRUS

(75) Inventors: Farshad Guirakhoo, Melrose, MA (US); J. Jian Liu, Milpitas, CA (US); John A. Catalan, Newton, MA (US); Thomas P. Monath, Harvard, MA (US); Konstantin V. Pugachev, Natick, MA (US)

(73) Assignee: Sanofi Pasteur Biologics, LLC, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/251,424

(22) Filed: Oct. 3, 2011

(65) Prior Publication Data

US 2012/0201852 A1     Aug. 9, 2012

Related U.S. Application Data

(63) Continuation of application No. 11/577,569, filed as application No. PCT/US2005/037369 on Oct. 19, 2005, now Pat. No. 8,029,802.

(60) Provisional application No. 60/620,466, filed on Oct. 20, 2004, provisional application No. 60/620,948, filed on Oct. 21, 2004, provisional application No. 60/674,415, filed on Apr. 24, 2005, provisional application No. 60/674,546, filed on Apr. 25, 2005, provisional application No. 60/718,923, filed on Sep. 19, 2005.

(51) Int. Cl.
*C12N 7/00*     (2006.01)
*A61K 39/12*     (2006.01)

(52) U.S. Cl.
USPC .................................... 435/235.1; 424/218.1

(58) Field of Classification Search
None
See application file for complete search history.

(56) References Cited

U.S. PATENT DOCUMENTS

| | | | |
|---|---|---|---|
| 6,184,024 B1 | 2/2001 | Lai et al. | |
| 6,497,884 B1 | 12/2002 | Pletnev et al. | |
| 6,660,273 B2 | 12/2003 | Pletnev et al. | |
| 6,676,936 B1 | 1/2004 | Lai et al. | |
| 6,696,281 B1 | 2/2004 | Chambers et al. | |
| 6,962,708 B1 | 11/2005 | Chambers et al. | |
| 7,189,403 B2 | 3/2007 | Despres et al. | |
| 2008/0175862 A1 | 7/2008 | Pugachev et al. | |

FOREIGN PATENT DOCUMENTS

| | | |
|---|---|---|
| EP | 1809325 A2 | 4/2006 |
| RU | 20000107129 A | 10/1998 |
| RU | 2005118419 A | 11/2003 |
| WO | WO 98/37911 | 9/1998 |
| WO | WO 01/38499 | 5/2001 |
| WO | WO 01/39802 | 6/2001 |
| WO | WO 02/081753 | 10/2002 |
| WO | WO 03/103571 | 12/2003 |
| WO | WO-2004045529 A2 | 6/2004 |
| WO | WO 2005/082020 | 9/2005 |
| WO | WO-2006044857 A2 | 4/2006 |
| WO | WO 2006/116182 | 11/2006 |

OTHER PUBLICATIONS

Abe et al., "Establishment of an Analyzing Method for a Japanese Encephalitis Virus Neutralization Test in Vero Cells," Vaccine 21:1989-1994, 2003.
Arroyo et al., "ChimeriVax-West Nile Virus Live-Attenuated Vaccine: Preclinical Evaluation of Safety, Immunogenicity, and Efficacy," J. Virol. 78:12497-12507, 2004.
Arroyo et al., "Yellow Fever Vector Live-Virus Vaccines: West Nile Virus Vaccine Development," Trends Mol. Med. 7:350-354, 2001.
Arroyo et al., "Molecular Basis for Attenuation of Neurovirulence of a Yellow Fever Virus/Japanese Encephalitis Virus Chimera Vaccine (ChimeriVax-JE)," J. Virol. 75:934-942, 2001.
Chambers et al., "Neuroadapted Yellow Fever Virus 17D: Genetic and Biological Characterization of a Highly Mouse-Neurovirulent Virus and Its Infectious Molecular Clone," J. Virology 75:10912-10922, 2001.
Chambers et al., "Yellow Fever/Japanese Encephalitis Chimeric Viruses: Construction and Biological Properties," J. Virol. 73:3095-3101, 1999.
Definition of "attenuate" from http://dictionary.com dated Dec. 8, 2008.
Definition of "attenuate" from http://www.thefreedictionary.com dated Dec. 8, 2008.
dos Santos et al., "Complete Nucleotide Sequence of Yellow Fever Virus Vaccine Strains 17DD and 17D-213," Virus Res. 35(1):35-41, 1995.
Galler et al., "Genetic Variability Among Yellow Fever Virus 17D Substrains," Vaccine 16(9/10)1024-1028, 1998.
Guirakhoo et al., "A Single Amino Acid Substitution in the Envelope Protein of Chimeric Yellow Fever-Dengue 1 Vaccine Virus Reduces Neurovirulence for Suckling Mice and Viremia/Viscerotropism for Monkeys," J. Virol. 78:9998-10008, 2004.
Guirakhoo et al., "Construction, Safety, and Immunogenicity in Nonhuman Primates of a Chimeric Yellow Fever-Dengue Virus Tetravalent Vaccine," J. Virol. 75(16):7290-7304, 2001.
Guirakhoo et al., "Fusion Activity of Flaviviruses: Comparison of Mature and Immature (prM-containing) Tick-Borne Encephalitis Virions," J. Gen. Virol. 72:1323-1329, 1991.
Guirakhoo et al., "Immunogenicity, Genetic Stability, and Protective Efficacy of a Recombinant, Chimeric Yellow Fever—Japanese Encephalitis Virus (ChimeriVax-JE) as a Live, Attenuated Vaccine Candidate Against Japanese Encephalitis," Virology 257:363-372, 1999.
Guirakhoo et al., "The Murray Valley Encephalitis Virus prM Protein Confers Acid Resistance to Virus Particles and Alters the Expression of Epitopes within the R2 Domain of E Glycoprotein," Virology 191:921-931, 1992.

(Continued)

Primary Examiner — Stacy B. Chen
(74) Attorney, Agent, or Firm — Clark & Elbing LLP

(57) ABSTRACT

The invention provides attenuated Flavivirus vaccines, such as vaccines against Japanese encephalitis virus and West Nile virus, as well as methods of making and using these vaccines.

6 Claims, 19 Drawing Sheets

(56) References Cited

OTHER PUBLICATIONS

Guirakhoo et al., "Safety and Efficacy of Chimeric Yellow Fever-Dengue Virus Tetravalent Vaccine Formulations in Nonhuman Primates," J. Virol. 78:4761-4775, 2004.

Guirakhoo et al., "Viremia and Immunogenicity in Nonhuman Primates of a Tetravalent Yellow Fever-Dengue Chimeric Vaccine: Genetic Reconstructions, Dose Adjustment, and Antibody Responses Against Wild-Type Dengue Virus Isolates," *Virology* 298(1):146-159, 2002.

"Guidelines for the Production and Control of Japanese Encephalitis Vaccine (Live) for Human Use," W.H.O. Technical Report Series, No. 910, pp. 66-98, 2002.

Holbrook et al., "Amino Acid Substitution(s) in the Stem-Anchor Region of Langat Virus Envelope Protein Attenuates Mouse Neurovirulence," Virology 286:54-61, 2001.

Hombach et al., "Report on a WHO Consultation on Immunological Endpoints for Evaluation of New Japanese Encephalitis Vaccines, WHO, Geneva, Sep. 2-3, 2004," Vaccine 23:5205-5211, 2005.

Hurrelbrink et al., "Molecular Determinants of Virulence: The Structural and Functional Basis for Flavivirus Attenuation," Adv. Virus Res. 60:1-42, 2003.

Kofler et al., "Capsid Protein C of Tick-borne Encephalitis Virus Tolerates Large Internal Deletions and is a Favorable Target for Attenuation of Virulence," J. Virol. 76:3534-3543, 2002.

Kolykhalov et al., "Identification of a Highly Conserved Sequence Element at the 3' Terminus of Hepatitis C Virus Genome RNA," *J. Virol*. 70(6):3363-3371, 1996.
Kuhn et al., "Structure of Dengue Virus: Implications for Flavivirus Organization, Maturation, and Fusion," *Cell* 108(5):717-725, 2002.
Lai et al., "Chimeric Flaviviruses: Novel Vaccines Against Dengue Fever, Tick-borne Encephalitis, and Japanese Encephalitis," Adv. Virus Res. 61:469-509, 2003.
Lee et al., "Changes in the Dengue Virus Major Envelope Protein on Passaging and Their Localization on the Three-Dimensional Structure of the Protein," *Virology* 232(2):281-290, 1997.
Li et al., "The Flavivirus Precursor Membrane-Envelope Protein Complex: Structure and Maturation," Science 3919:1830-1834, 2008.
Lindenbach et al., "Flavivirdae: The Viruses and Their Replication," In *Fields Virology*, 4th Ed., Knipe and Howley (Eds.), Lippincott Williams and Wilkins, Philadelphia, PA, pp. 991-1041, 2001.
Lorenz et al., "Folding and Dimerization of Tick-Borne Encephalitis Virus Envelope Proteins prM and E in the Endoplasmic Reticulum," J. Virol. 76:5480-5491, 2002.
Maier et al., "A Single M Protein Mutation Affects the Acid Inactivation Threshold and Growth Kinetics of a Chimeric Flavivirus," Virology 362:468-474, 2007.
Meeting Report: WHO Informal Consultation on the Scientific Basis of Specifications for Production and Control of Inactivated Japanese Encephalitis Vaccines for Human Use, Geneva, Switzerland, pp. 1-19, Jun. 1-2, 2006.
Men et al., "Dengue Type 4 Virus Mutants Containing Deletions in the 3' Noncoding Region of the RNA Genome: Analysis of Growth Restriction in Cell Culture and Altered Viremia Pattern and Immunogenicity in Rhesus Monkeys," J. Virol. 70:3930-3937, 1996.
Monath et al., "Chimeric Live, Attenuated Vaccine Against Japanese Encephalitis (ChimeriVax-JE): Phase 2 Clinical Trials for Safety and Immunogenicity, Effect of Vaccine Dose and Schedule, and Memory Response to Challenge with Inactivated Japanese Encephalitis Antigen," J. Infect. Dis. 188:1213-1230, 2003.
Monath et al., "Clinical Proof of Principle for ChimeriVax™: Recombinant Live, Attenuated Vaccines Against Flavivirus Infections," Vaccine 20:1004-1018, 2002.
Monath et al., "Recombinant, Chimaeric Live, Attenuated Vaccine (ChimeriVax™) Incorporating the Envelope Genes of Japanese Encephalitis (SA14-14-2) Virus and the Capsid and Nonstructural Genes of Yellow Fever (17D) Virus Is Safe, Immunogenic and Protective in Non-Human Primates," Vaccine 17:1869-1882, 1999.
Monath et al., "Safety Testing for Neurovirulence of Novel Live, Attenuated Flavivirus Vaccines: Infant Mice Provide an Accurage Surrogate for the Test in Monkeys," *Biologicals* 33(3):131-144, 2005.
Monath et al., "Single Mutation in the Flavivirus Envelope Protein Hinge Region Increases Neurovirulence for Mice and Monkeys but Decreases Viscerotropism for Monkeys: Relevance to Development and Safety Testing of Live, Attenuated Vaccines," J. Virol. 76:1932-1943, 2002.
Monath et al., "West Nile Virus Vaccine," *Curr. Drug Targets Infect. Disord*. 1(1):37-50, 2001.
Mustafa et al., "Dengue Vaccine: The Current Status," MJAFI 64:161-164, 2008.
Mutebi et al., "Genetic Relationships and Evolution of Genotypes of Yellow Fever Virus and Other Members of the Yellow Fever Virus Group within the *Flavivirus* Genus Based on the 3' Noncoding Region," *J. Virol*. 78(18):9652-9665, 2004.
Pletnev et al., "Nucleotide Sequence of the Genome and Complete Amino Acid Sequence of the Polyprotein of Tick-Borne Encephalitis Virus," Virology 174(1):250-263, 1990.
Polyprotein [Japanese encephalitis virus]; SA14-14-2; GenBank: AAK11279.1; Feb. 20, 2001.
Polyprotein [Japanese encephalitis virus]; Nakayama; GenBank: ABQ52691.1; May 27, 2007.
Proutski et al., "Biological Consequences of Deletions within the 3'-Untranslated Region of Flaviviruses may be Due to Rearrangements of RNA Secondary Structure," *Virus Res*. 64(2):107-123, 1999.
Pugachev et al., "Heterogeneous Nature of the Genome of the ARILVAX Yellow Fever 17D Vaccine Revealed by Consensus Sequencing," Vaccine 20:996-999, 2002.
Pugachev et al., "Traditional and Novel Approaches to Flavivirus Vaccines," *Int. J. Parasitol*. 33(5-6):567-582, 2003.
Rice et al., "Nucleotide Sequence of Yellow Fever Virus: Implications for Flavivirus Gene Expression and Evolution," *Science* 229(4715):726-733, 1985.
Rice et al., "Transcription of Infectious Yellow Fever RNA from Full-Length cDNA Templates Produced by In Vitro Ligation," *New Biol*. 1(3):285-296, 1989.
Rey et al., "The Envelope Glycoprotein from Tick-Borne Encephalitis at 2 Å Resolution," Nature 375:291-298, 1995.
Sumiyoshi et al., "Complete Nucleotide Sequence of the Japanese Encephalitis Virus Genome RNA," Virology 161:497-510, 1987.
Tesh et al., "Efficacy of Killed Virus Vaccine, Live Attenuated Chimeric Virus Vaccine, and Passive Immunization for Prevention of West Nile Virus Encephalitis in Hamster Model," Emerg. Infect. Dis. 8:1392-1397, 2002.
Yoshii et al., "Single Point Mutation in Tick-borne Encephalitis Virus prM Protein Induces a Reduction of Virus Particle Secretion," J. Gen. Virol. 85:3049-3058, 2004.
Yu et al., "Structure of the Immature Dengue Virus at Low pH Primes Proteolytic Maturation," Science 319:1834-1837, 2008.
Communication from European Patent Application No. 05811861.3-2406, mailed Sep. 11, 2009.
English Translation of Office Action from Israeli Patent Application No. 182453 (translation mailed Oct. 25, 2009).
English Translation of Notice of Result of Examination as to Substance from Vietnam Patent Application No. 1-2007-00967, mailed Jun. 30, 2009.
Examination Report from New Zealand Patent Application No. 554542, mailed Aug. 1, 2008.
Examination Report from Singapore Patent Application No. 200702692-5, mailed Feb. 3, 2009.
Extended European Search Report for EP 05811861.3-2406, mailed Jun. 23, 2009 (search completed Jun. 8, 2009).
International Search Report from International Application No. PCT/US2005/037369, dated Jun. 20, 2006.
International Preliminary Report on Patentability from International Application No. PCT/US2005/037369, mailed Mar. 5, 2007.
Official Action from Eurasian Patent Application No. 200700904, mailed Jul. 24, 2008.

(56) References Cited

OTHER PUBLICATIONS

Official Action from Eurasian Patent Application No. 200700904, mailed Apr. 9, 2009.
Official Action from Chinese Patent Application No. 200580043790.0, dated Aug. 21, 2009.
Substantive Examination Adverse Report from Malaysian Patent Application No. PI 20054938, mailed Aug. 11, 2008.
Written Opinion from Singapore Patent Application No. 200702692-5, mailed May 27, 2008.
Written Opinion of International Searching Authority from International Application No. PCT/US2005/037369, completed May 30, 2006.
Definition of "attenuate" from Merriam-Webster's Medical Desk Dictionary, Merriam Webster, Inc., Springfield, MA, p. 63 (2006).
Monath, "Yellow Fever," Vaccines 3rd ed. Plotkin SA and Orenstein WA (eds), p. 815-823 (1999).

Note: Dotted line in 2B designates XbaI restriction site at nucleotide 10,708

FIG. 2B

```
                                                        C1 C2      C3                                    C4           C5
....,....1....,....2....,....3....,....4....,....5....,....6....,....7....,....8....,....9....,....10
MSGRKAQGKTLGVNMVRRGVRSLSNKIKQKTKQIGN RPGPSR GVQGFI FFF LFNILTGKKITAHLKRLWKMLDPRQGLAVL RKVK RVVASLMRGLSS RKR
```

α-helices        EE                    EEEE      HHHHHHHHHHHHHHHE        HHHHHHHHH    HHHHHHHHHHHHHHHHHHHHHHHHHH
                                                 α-Helix I               α-Helix II    α-Helix III Hydrophobic stretches

```
....,....13...,....14...,....15
RSHDVLTVQFLILGMLLMTGG
```
HHHHHHHHHHHHH

α-Helix IV

Fig. 3. Replication in HepG2 cells.
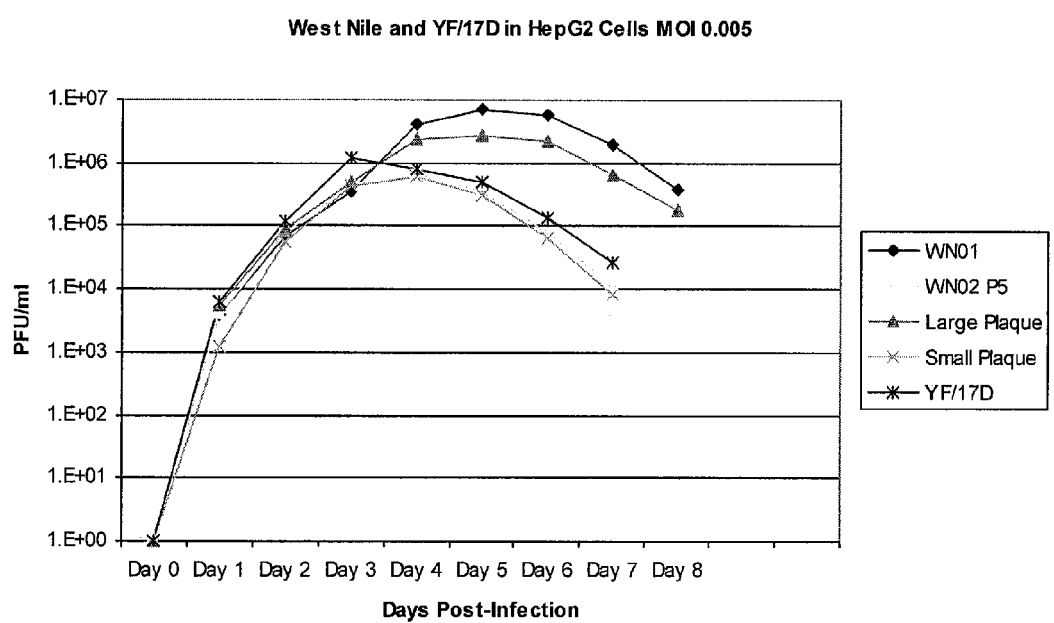

Fig. 4. Replication in THLE-3 cells.
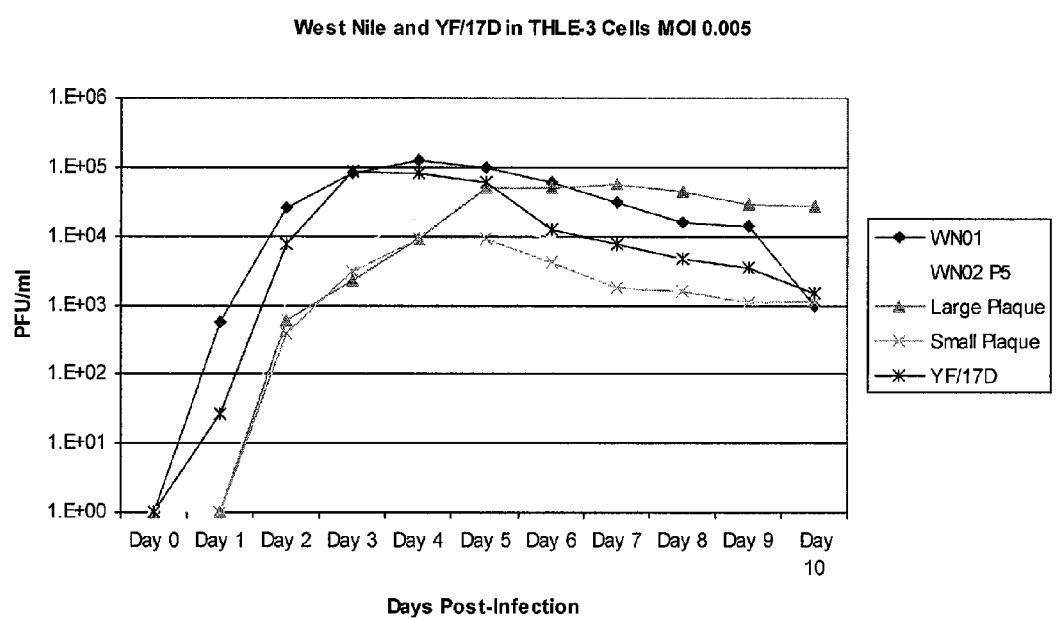

Fig. 5. Viremia in hamsters inoculated with ChimeriVax™-WN02 P5 (mixed plaque), S plaque (PMS, P10), or L plaque (PMS, P10) viruses.

ChimeriVax-WN02 Viremia in Hamsters
(JH 09-08-04)

| Days Post Infection | 0 | 1 | 2 | 3 | 4 | 5 |
|---|---|---|---|---|---|---|
| Small Plaque | 0 | 3.3 | 3.3 | 3.3 | 0.0 | 6.7 |
| Large Plaque | 0 | 190.0 | 630.0 | 642.9 | 442.9 | 38.5 |
| Mixed Plaque | 0 | 3.3 | 26.7 | 195.5 | 325.0 | 277.8 |

FIG. 6

```
In vitro RNA Transcripts
          │
          ▼
Uncloned P1 virus obtained after
electroporation of SF Vero cells
          │
          ▼                            Manufacturing passages
   Uncloned P2 PMS  ─────────────────► from uncloned P2 PMS
    │        │                                   │
    ▼        ▼                                   ▼
  P3 g.s.                              Uncloned P3 MS
                                       (E-107 mutation detected)
  P4 g.s.
  (M-60 mutation                       Uncloned P4 PS
  first detected)                      (E-107 mutation detected)

P5 g.s.                              Uncloned P5 VB
  (M-60 mutation                       (E-107 mutation detected)
  established)
              ╲
               ╲                       Cloned P7 PMS
                ╲                      (Clone A, non-mutant)
  P10 g.s.       ╲
  (M-60; no other                      Genetic stability
  mutations detected)                  Passages (g.s.) of
                                       cloned PMS viruses
                                         S P8 g.s.
                                           SS P9 g.s.
                                             SSS P10 g.s.
                                            SSF P10 g.s.

Cloned P10 PMS        S P11 g.s.
                  (Clone C; M-60 mutant)  SS P12 g.s.
                                            SSS P13 g.s.
                                           SSF P13 g.s.

F P11 g.s.
                                           FF P12 g.s.
                                             FFF P13 g.s.
```

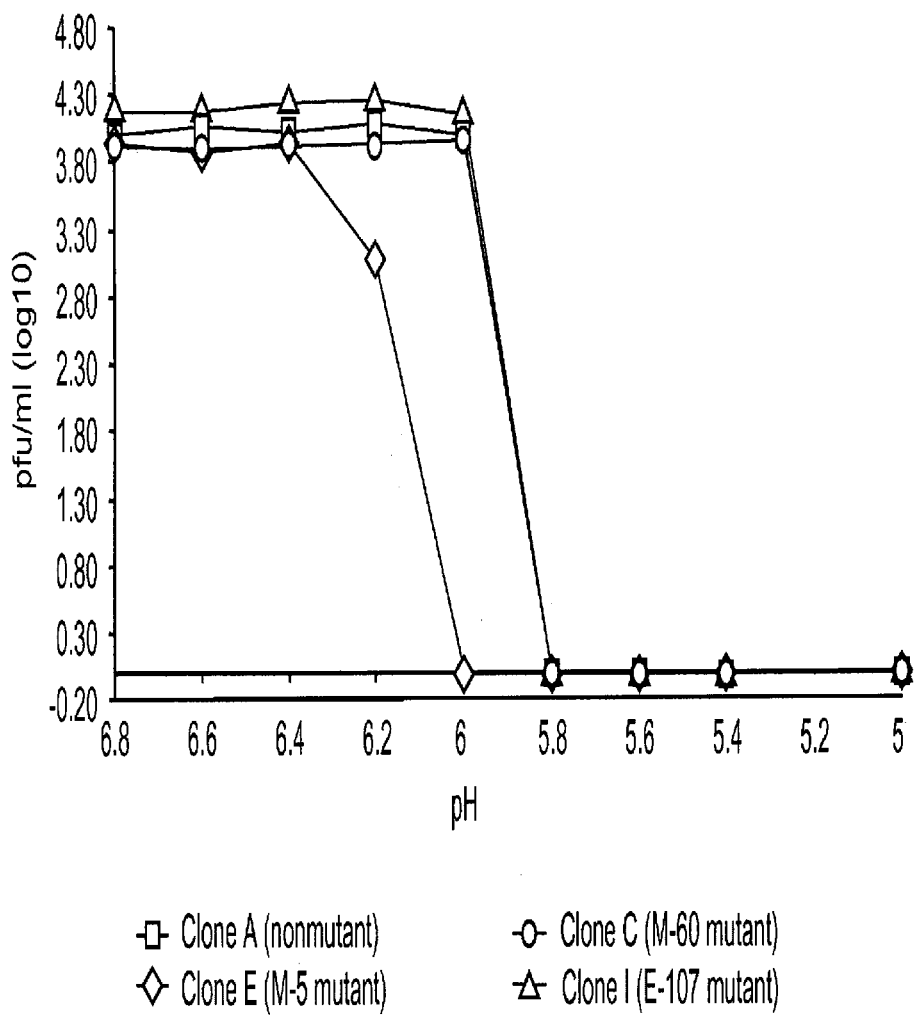

VACCINES AGAINST JAPANESE ENCEPHALITIS VIRUS AND WEST NILE VIRUS

CROSS-REFERENCE TO RELATED APPLICATIONS

This application is a continuation of, and claims priority from, U.S. patent application Ser. No. 11/577,569, filed Apr. 19, 2007, which is the U.S. national stage filing under 35 U.S.C. §371 of international patent application PCT/US2005/037369, filed Oct. 19, 2005, which claims the benefit of the filing dates of U.S. provisional patent applications 60/620,466, filed Oct. 20, 2004, 60/620,948, filed Oct. 21, 2004, 60/674,415, filed Apr. 24, 2005, 60/674,546, filed Apr. 25, 2005, and 60/718,923, filed Sep. 19, 2005.

FIELD OF THE INVENTION

This invention relates to vaccines against Japanese encephalitis virus and West Nile virus.

BACKGROUND OF THE INVENTION

The Flavivirus genus of the Flaviviridae family includes approximately 70 viruses, mostly arboviruses, many of which, such as yellow fever (YF), dengue (DEN), Japanese encephalitis (JE), and tick-borne encephalitis (TBE) viruses, are major human pathogens (rev. in Burke and Monath, Fields Virology, $4^{th}$ Ed.: 1043-1126, 2001). For example, Japanese encephalitis is the leading cause of viral encephalitis in Asia, where 30,000 to 50,000 new cases are reported each year. As another example, since the first cases were diagnosed in the New York area in 1999, West Nile virus has continued to spread rapidly across North America. The risks of this virus migrating into South America, as well as an epidemic in underdeveloped countries, are extremely high. Effective methods for preventing infection by these viruses are needed, with vaccination being the most cost effective measure.

The Flavivirus particle contains a nucleocapsid composed of viral RNA and capsid protein C. The nucleocapsid is surrounded by an envelope containing the envelope glycoprotein E (50-60 kDa) and a small membrane protein M (7-8 kDa). Translation of the genomic RNA results in a polyprotein precursor that is cleaved by cellular and viral proteases into viral proteins, in the order: C, prM/M, E, NS1, NS2A, NS2B, NS3, NS4A, 2K, NS4B, and NS5, where C through E are the structural components of the virion and NS1 through NS5 are nonstructural proteins required for replication (Lindenbach and Rice, Fields Virology, $4^{th}$ Ed.: 991-1041, 2001). The prM protein (~25 kDa) is the intracellular precursor for M. Immature virions containing prM are produced by budding into the lumen of the endoplasmic reticulum (ER) and are transported to the cell surface through the exocytosis pathway. Cleavage of prM occurs shortly prior to particle release in post-Golgi vesicles. Mature extracellular virus contains predominantly M protein, although a small fraction of uncleaved prM can also be present.

The E protein is the main functional and antigenic surface component of the virion. The molecular structure of the ectodomain of E, which forms a homodimer on the surface of mature viral particles at neutral pH, has been resolved by cryoelectron microscopy (Rey et al., Nature 375:291-298, 1995) and fitted into the electron density map of viral particles (Kuhn et al., Cell 108:717-725, 2002). During infection, the E protein functions as a class II fusion protein (Modis et al., Nature 427:313-319, 2004). Following virus binding to a cellular receptor and internalization, the acidic pH in the resulting endosomes triggers dissociation of the dimers such that the previously hidden hydrophobic fusion loop of each monomer is exposed outwardly. Concurrently, the loops insert into the cell (endosome) membrane and monomers rearrange into elongated trimers. Further refolding of the trimers brings the cell and viral membranes into close proximity and forces them to fuse, releasing the contents of the viral particle into the cytoplasm. Previous studies showed that some substitutions in the E protein of DEN and JE, which are selected during serial passages in mouse brain and in cultured monkey kidney and mosquito cells, have been localized in particular regions of the 3D structure of the protein, and were reported to be associated with changes in the fusion function of the viruses. The studies showed that the fusion pH threshold for some attenuated vaccines decreased by 0.6 to 1 pH unit by comparison with the corresponding parental virus isolate. Some changes in six residues in the DEN3 protein E (residues 54, 191, 202, 266, 268, and 277) map to the region in domain II. This region is proposed as a focus for the low-pH mediated conformational change required for the surface exposure of the conserved hydrophobic cd fusion loop (Lee et al., Virology 232:281-290, 1997).

There is no evidence that the small (mature) M protein plays a role in the events leading to virus internalization from the endosome or has any other appreciable function, while its intracellular precursor, prM, is known to be important for morphogenesis and transport of progeny viral particles. The prM protein also facilitates proper folding of E (Lorenz et al., J. Virol. 76:5480-5491, 2002) and functions to protect the E protein dimer from premature conformational rearrangement during passage of new particles towards the cell surface through acidic secretory compartments (Guirakhoo et al., J. Gen. Virol. 72:1323-1329, 1991; Guirakhoo et al., Virology 191:921-931, 1992).

ChimeriVax™ technology has been used to create live, attenuated vaccine candidates against medically important Flaviviruses. It employs the YF 17D vaccine virus as a vector in which the prM-E genes are replaced with the prM-E genes from a heterologous Flavivirus, such as JE, dengue, West Nile, or St. Louis encephalitis viruses (Monath et al., Vaccine 17:1869-1882, 1999; Monath et al., Curr. Drug Targets—Inf. Disorders 1:37-50, 2001; Monath et al., Vaccine 20:1004-1018, 2002; Guirakhoo et al., Virology 257:363-372, 1999; Guirakhoo et al., J. Virol. 75:7290-7304, 2001; Guirakhoo et al., Virology 298:146-159, 2002; Pugachev et al., Int. J. Parasitol. 33:567-582, 2003; Guirakhoo et al., J. Virol. 78:4761-4775, 2004). Previously, the ChimeriVax™-JE vaccine virus, containing the prM-E genes from the SA14-14-2 virus (live attenuated JE vaccine used in China), was propagated to high titers in Vero cells cultured in media supplemented with fetal bovine serum (FBS) (Monath et al., Biologicals 33:131-144, 2005). It was successfully tested in preclinical and Phase I and II clinical trials (Monath et al., Vaccine 20:1004-1018, 2002; Monath et al., J. Infect. Dis. 188:1213-1230, 2003). Similarly, successful Phase I clinical trials have been conducted with a ChimeriVax™-WN vaccine candidate, which contains the prM-E sequence from a West Nile virus (NY99 strain), with three specific amino acid changes incorporated into the E protein to increase attenuation (Arroyo et al., J. Virol. 78:12497-12507, 2004).

SUMMARY OF THE INVENTION

The invention provides recombinant Flaviviruses that include one or more membrane (M) protein mutations (e.g., substitutions, deletions, or insertions), such as mutations that attenuate the Flavivirus (e.g., mutations that decrease the viscerotropism/viremia of the Flavivirus), increase genetic stability of the Flavivirus during propagation in cell culture (e.g., manufacturing in serum free cultures), and/or increase vaccine virus yields. The Flaviviruses of the invention can be chimeric Flaviviruses, such as Flaviviruses that include capsid and non-structural proteins of a first Flavivirus (e.g., a yellow fever virus, such as YF 17D) and membrane and/or envelope proteins of a second Flavivirus (e.g., Japanese encephalitis virus, West Nile virus, a dengue virus (dengue-1, dengue-2, dengue-3, or dengue-4 virus), St. Louis encephalitis virus, Murray Valley encephalitis virus, tick-borne encephalitis virus, as well as any other Flavivirus that is a human/animal pathogen from the YF, JE, DEN, and TBE serocomplexes).

In the Flaviviruses of the invention, the mutation (e.g., substitution) can be in the transmembrane or ectodomain of membrane protein M. For example, the mutation can be in the region of amino acids 40-75 of the predicted membrane helix of the membrane protein M of the Flavivirus. As an example, the mutation can be a substitution of amino acid 60 of the membrane protein of a Flavivirus such as Japanese encephalitis virus (e.g., arginine to cysteine in the Japanese encephalitis virus M protein), or in a corresponding amino acid of another Flavivirus. Determination of which amino acid in a given Flavivirus "corresponds" to that of another Flavivirus can be carried out by standard amino acid sequence alignment, as is well known to those of skill in this art. As another example, the mutation can be a substitution of amino acid 66 of the membrane protein of a Flavivirus such as West Nile virus (e.g., a substitution of leucine with proline in the M protein of West Nile virus), or in a corresponding amino acid of another Flavivirus. In other examples, the mutation is at another membrane anchor amino acid, e.g., one or more amino acids selected from the group flanking the M66 residue, including positions 60, 61, 62, 63, 64, 65, and 66 of Japanese encephalitis virus or West Nile virus (or corresponding amino acids in other Flaviviruses) or other amino acid residues of the transmembrane domain.

We also provide for the first time evidence that the ectodomain of the M protein is of important functional significance, because a glutamine to proline change at the M5 residue increased the pH threshold of infection. Therefore, it can now be expected that Flavivirus attenuation can be achieved through amino acid changes or introduction of various deletions or insertions in the amino-terminal ectodomain, or surface part of the M protein, not only its C-terminal hydrophobic anchor. Thus, in other examples, the viruses of the invention include one or more mutations in the M protein ectodomain (residues 1-40) as described herein. This result is quite unexpected, given the lack of any known function of the mature M protein of Flaviviruses.

In addition to the membrane protein mutations noted above, in the case of chimeric Flaviviruses that include membrane and envelope proteins of a West Nile virus, the viruses of the invention can include one or more envelope protein mutations in amino acids selected from the group consisting of amino acids 107, 138, 176, 177, 224, 264, 280, 316, and 440. In other Flaviviruses, the mutations can be present in amino acids that correspond to these amino acids. As a specific example, the Flavivirus can include a mutation corresponding to mutation(s) in West Nile M protein amino acid 66 and E protein mutations at amino acids corresponding to West Nile virus amino acids 107, 316, and 440. In addition to the mutations described above, the Flaviviruses of the invention can also include one or more mutations in the hydrophobic pocket of the hinge region of the envelope protein, as described elsewhere herein. Further mutations that can be included in the viruses of the invention are mutations in the 3'UTR, the capsid protein, or other envelope protein regions, as described further below.

The invention also provides vaccine compositions that include the Flaviviruses described above and elsewhere herein and pharmaceutically acceptable carriers or diluents, as well as methods of inducing immune responses to Flaviviruses in patients by administration of such vaccine compositions. The patients treated according to such methods include those that do not have, but are at risk of developing, infection by the Flavivirus, as well as patients that are infected by the Flavivirus. Further, the invention includes the use of the Flaviviruses described herein in the prophylactic and therapeutic methods described herein, as well as in the manufacture of medicaments for these purposes.

The invention further provides methods of producing vaccines that include a Flavivirus as described herein, which involve introducing into the membrane protein of the Flavivirus a mutation that results in decreased viscerotropism/viremia, and/or increased genetic stability/yields. Further, the invention provides nucleic acid molecules (RNA or DNA) corresponding to the genomes of the Flaviviruses described herein (or the complements thereof), and methods of using such nucleic acid molecules to make the viruses of the invention.

The Flaviviruses of the invention are advantageous because, in having decreased virulence (shown, e.g., by decreased viscerotropism/viremia), they provide an additional level of safety, as compared to their non-mutated counterparts, when administered to patients. An additional advantage is that some mutations, such as the M-60 mutation in ChimeriVax™-JE, preclude accumulation of undesirable mutations during vaccine manufacture that otherwise could compromise safety, and increase manufacturing yields. Additional advantages of these viruses are provided by the fact that they can include sequences of yellow fever virus strain YF17D (e.g., sequences encoding capsid and non-structural proteins), which (i) has had its safety established for >60 years, during which over 350 million doses have been administered to humans, (ii) induces a long duration of immunity after a single dose, and (iii) induces immunity rapidly, within a few days of inoculation. In addition, the vaccine viruses of the invention cause an active infection in the treated patients. As the cytokine milieu and innate immune response of immunized individuals are similar to those in natural infection, the antigenic mass expands in the host, properly folded conformational epitopes are processed efficiently, the adaptive immune response is robust, and memory is established.

The beneficial aspects of mutations in the M protein on vaccine safety and manufacture in cell culture are novel and unexpected, given the lack of any known function of the mature M protein of Flaviviruses.

Other features and advantages of the invention will be apparent from the following detailed description, the drawings, and the claims.

BRIEF DESCRIPTION OF THE DRAWINGS

FIG. 2B is a schematic representation of the sequence of the capsid protein of YF 17D virus. Regions predicted by computer analysis to have α-helical secondary structure (α-helices I-IV), as well as hydrophobic regions (solid bars) and deletions introduced in this protein in certain ChimeriVax™-WN viruses (e.g., deletions C1 and C2; boxed) are indicated (SEQ ID NO:35).

FIG. 3 is a graph showing growth of the indicated viruses (WN01, WN02 P5, Large Plaque, Small Plaque, and YF/17D) in HepG2 cells.

FIG. 4 is a graph showing growth of the indicated viruses (WN01, WN02 P5, Large Plaque, Small Plaque, and YF/17D) in THLE-3 cells.

FIG. 5 is a graph showing the viremia in hamsters induced by the indicated viruses (WN02 P5; mixed plaque), Small Plaque (PMS, P10), and Large Plaque (PMS, P10)).

FIG. 6 is a schematic representation of the passage of SF ChimeriVax™-JE virus samples (g.s., experimental passages to study genetic stability).

FIG. 8A is a graph showing infectivities of the M-5 ChimeriVax™-JE mutant (Clone E) compared to P5 uncloned vaccine bulk and Clone I (E-107 mutant), non-mutant (Clone A), and M-60 mutant (Clone C) after treatment with a range of acidic pH. Of significance is the appearance of the slopes and at which pH the viruses lost infectivity, but not initial titers in diluted samples (e.g., at pH 6.8).

DETAILED DESCRIPTION

Figure 1A:
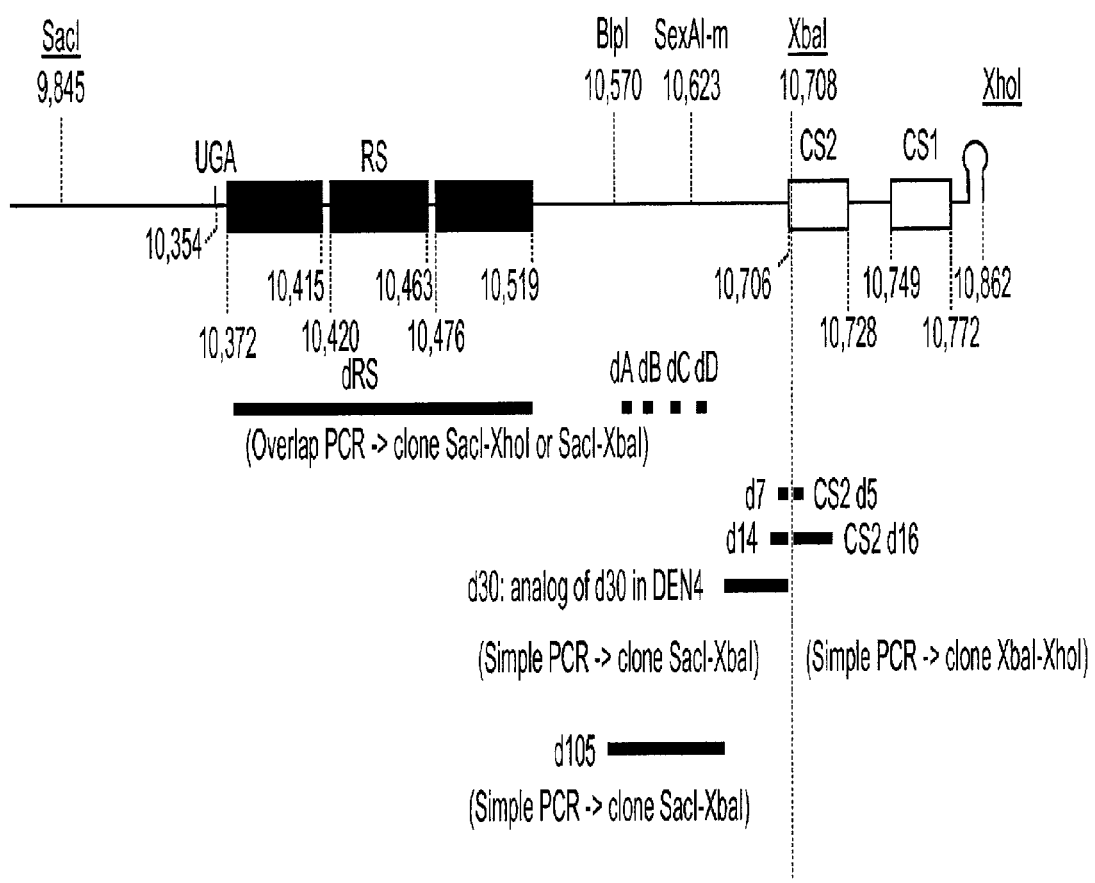
FIG. 1A is a schematic representation of the 3' untranslated region of yellow fever virus, which shows domains within this region (repeat sequences (RS), conserved sequences CS2, CS1, and the 3'-extreme stem-loop structure), as well as examples of mutations that can be included in the viruses of the invention (e.g., deletions dA, dB, dC, dD, d7, d14, CS2 d5, and CS2 d16).

The invention provides vaccines and methods for use in preventing and treating Flavivirus (e.g., Japanese encephalitis (JE) or West Nile (WN) virus) infection. The methods of the invention generally involve vaccination of subjects with a live, attenuated chimeric Flavivirus that consists of a first Flavivirus (e.g., yellow fever virus) in which one or more structural proteins (e.g., membrane and/or envelope proteins) have been replaced with those of a second Flavivirus (e.g., Japanese encephalitis (JE) and/or West Nile (WN) virus; also see below). The membrane proteins of the chimeras of the invention include one or more mutations, as is described further below. Also as is described below, structural proteins such as membrane and/or envelope proteins of other Flaviviruses can be used in place of those of Japanese encephalitis virus or West Nile virus in the chimeric viruses of the present invention. Further, the membrane protein mutations of the invention can also be used in intact, non-chimeric Flaviviruses (e.g., any of those listed herein), not including any replacements of structural proteins, and optionally with one or more additional mutations, such as those described herein.

A specific example of a chimeric virus that can be included in the vaccines of the invention is the human yellow fever vaccine strain, YF 17D (e.g., YF17D-204 (YF-VAX®, Sanofi-Pasteur, Swiftwater, Pa., USA; Stamaril®, Sanofi-Pasteur, Marcy-L'Etoile, France; ARILVAX™, Chiron, Speke, Liverpool, UK; FLAVIMUN®, Berna Biotech, Bern, Switzerland); YF17D-204 France (X15067, X15062); YF17D-204, 234 US (Rice et al., Science 229:726-733, 1985)), in which the membrane and envelope proteins have been replaced with the membrane and envelope proteins (including an M protein mutation, such as a substitution in M60, as described herein) of Japanese encephalitis virus. In another example, the YF 17D membrane and envelope proteins are replaced with those of a West Nile virus (including an M protein mutation, such as a substitution in M66, as described herein).

In other examples, another Flavivirus, such as a dengue virus (serotype 1, 2, 3, or 4), St. Louis encephalitis virus, Murray Valley encephalitis virus, yellow fever virus, including YF 17D strains, or any other Flavivirus, can provide the membrane and/or envelope proteins in such a chimeric virus. Additional Flaviviruses that can be attenuated according to the invention, whether as intact, non-chimeric viruses or as the source of membrane and/or envelope proteins in chimeras, include other mosquito-borne Flaviviruses, such as Kunjin, Rocio encephalitis, and Ilheus viruses; tick-borne Flaviviruses, such as Central European encephalitis, Siberian encephalitis, Russian Spring-Summer encephalitis, Kyasanur Forest Disease, Omsk Hemorrhagic fever, Louping ill, Powassan, Negishi, Absettarov, Hansalova, Apoi, and Hypr viruses; as well as viruses from the Hepacivirus genus (e.g., Hepatitis C virus). Other yellow fever virus strains, e.g., YF17DD (GenBank Accession No. U 17066), YF17D-213 (GenBank Accession No. U17067; dos Santos et al., Virus Res. 35:35-41, 1995), and yellow fever virus 17DD strains described by Galler et al., Vaccines 16(9/10):1024-1028, 1998, can also be used as the backbone viruses into which heterologous structural proteins can be inserted according to the invention.

The viruses listed above each have some propensity to infect visceral organs. The viscerotropism of these viruses may cause dysfunction of vital visceral organs, such as observed in YF vaccine-associated adverse disease events, albeit very infrequently. The replication of virus in these organs can also cause viremia and thus contribute to invasion of the central nervous system. Decreasing the viscerotropism of these viruses by mutagenesis according to the present invention can thus reduce the abilities of the viruses to cause adverse viscerotropic disease and/or to invade the brain and cause encephalitis.

The mutations of the invention result in beneficial effects to the viruses, which can include, for example, increased attenuation, stability, and/or replication. The mutations are present in the membrane protein, e.g., in the transmembrane region or in the ectodomain of the membrane protein. For example, the mutations can be in amino acid 60 or 66 of the membrane protein and/or in other amino acids within the predicted transmembrane domain (e.g., in any one or more of amino acids 40-75), or in the N-terminal ectodomain of the M protein (e.g., M-5). As a specific example, membrane protein amino acid 60 (arginine in wild type Japanese Encephalitis virus) can be replaced with another amino acid, such as cysteine. A substitution from arginine to cysteine at position M-60 in the ChimeriVax™-JE virus significantly reduced the viremia (viscerotropism) of the virus for humans in clinical trials in which variants of the vaccine with and without the M-60 mutation were tested (Tables 11A and 11B). In addition to cysteine, other amino acids, such as serine, threonine, glycine, methionine, etc., can substitute the wild type amino acid at position 60 of the membrane protein. In another example, membrane protein amino acid 66 (leucine in wild type West Nile virus) can be replaced with another amino acid, such as proline. In addition to proline, other hydrophobic amino acids, such as isoleucine, methionine, or valine, or small amino acids, such as alanine or glycine, can substitute the wild type amino acid at position 66 of the membrane protein. These mutations can also be present in corresponding amino acids of other Flaviviruses, as described herein.

As other examples of substitutions that can be made in membrane protein sequences, amino acids at positions 61, 62, 63, and/or 64 can be substituted, alone or in combination with each other, a mutation at position 60, a mutation at position 66, and/or another mutation(s). Examples of substitutions at these positions in the West Nile virus membrane protein sequence include: valine to alanine at position 61, valine to glutamic acid or methionine at position 62, phenylalanine to serine at position 63, and valine to isoleucine at position 64. These mutations can also be present in corresponding amino acids of other Flaviviruses, as described herein.

Examples of substitutions at these or surrounding positions in the JE virus membrane protein sequence include any of the remaining 20 amino acids with the expectation that a desired effect on viscerotropism and/or vaccine virus replication/stability in cell culture during manufacturing will be achieved. Other examples in chimeric or non-chimeric Flaviviruses include any amino acid substitutions, alone or in combinations, in the N-terminal ectodomain of the M protein composed of residues 1-~40 of the protein, as well as deletion(s) of various sizes (e.g., 1, 2, 3, 4, 5, etc., amino acids long) introduced into the ectodomain and/or the transmembrane domain of the M protein.

In addition to one or more of the membrane protein mutations noted above, the viruses of the invention can also include one or more additional mutations. For example, in the case of West Nile virus, such an additional mutation(s) can be in the region of position 107 (e.g., L to F), 316 (e.g., A to V), or 440 (e.g., K to R) (or a combination thereof) of the West Nile virus envelope protein. The mutations can thus be, for example, in one or more of amino acids 102-112, 138 (e.g., E to K), 176 (e.g., Y to V), 177 (e.g., T to A), 244 (e.g., E to G), 264 (e.g., Q to H), 280 (e.g., K to M), 311-321, and/or 435-445 of the West Nile envelope protein. As a specific example, using the sequence of West Nile virus strain NY99-flamingo 382-99 (GenBank Accession Number AF196835) as a reference, the lysine at position 107 can be replaced with phenylalanine, the alanine at position 316 can be replaced with valine, and/or the lysine at position 440 can be replaced with arginine. Examples of additional combinations of amino acids that can be mutated include are as follows: 176, 177, and 280; 176, 177, 244, 264, and 280; and 138, 176, 177, and 280. Further, these mutations can also be present in corresponding amino acids of other Flaviviruses, as described herein.

The ChimeriVax™-JE vaccine already includes all of the above-noted SA14-14-2 specific mutations as it contains the SA14-14-2-specific JE envelope. Additional amino acid changes in the E protein can also be selected and introduced based on the knowledge of the structure/function of the E protein for additional attenuation (e.g., as described below). These mutations can also be present in corresponding amino acids of other Flaviviruses, as described herein.

In addition to the amino acids noted above, the substitutions can be made with other amino acids, such as amino acids that would result in conservative changes from those noted above. Conservative substitutions typically include substitutions within the following groups: glycine, alanine, valine, isoleucine, and leucine; aspartic acid, glutamic acid, asparagine, and glutamine; serine and threonine; lysine and arginine; and phenylalanine and tyrosine.

The viruses of the invention (e.g., Japanese encephalitis and West Nile viruses, and chimeric Flaviviruses including membrane and envelope proteins from these or other flaviviruses) can also include in addition to the mutation(s) (e.g., membrane protein mutations) discussed above, one or more mutations in the hinge region or the hydrophobic pocket of the envelope protein, as such mutations have been shown to result in decreased viscerotropism (Monath et al., J. Virol. 76:1932-1943, 2002; WO 03/103571 A2; WO 05/082020; Guirakhoo et al., J. Virol. 78(18):9998-10008, 2004). The polypeptide chain of the envelope protein folds into three distinct domains: a central domain (domain I), a dimerization domain (domain II), and an immunoglobulin-like module domain (domain III). The hinge region is present between domains I and II and, upon exposure to acidic pH, undergoes a conformational change (hence the designation "hinge") that results in the formation of envelope protein trimers that are involved in the fusion of viral and endosomal membranes, after virus uptake by receptor-mediated endocytosis. Prior to the conformational change, the proteins are present in the form of dimers.

Numerous envelope amino acids are present in the hinge region including, for example, amino acids 48-61, 127-131, and 196-283 of yellow fever virus (Rey et al., Nature 375: 291-298, 1995). Any of these amino acids, or closely surrounding amino acids (and corresponding amino acids in other Flavivirus envelope proteins), can be mutated according to the invention, and tested for attenuation. Of particular interest are amino acids within the hydrophobic pocket of the hinge region. As a specific example, it has been shown that substituting envelope protein amino acid 204 (K to R), which is in the hydrophobic pocket of the hinge region, in a chimeric Flavivirus including dengue 1 envelope protein sequences inserted into a yellow fever virus vector results in attenuation (Guirakhoo et al., J. Viral. 78:9998-10008, 2004). This substitution leads to an alteration in the structure of the envelope protein, such that intermolecular hydrogen bonding between one envelope monomer and another in the wild type protein is disrupted and replaced with new intramolecular interactions within monomers. This observation led to a proposal that the attenuation resulting from this substitution is due to these new interactions, which change the structure of the protein in the pre-fusion conformation, most likely by altering the pH threshold that is required for fusion of viral membrane with the host cell, and provides a basis for the design of further attenuated mutants in which additional substitutions are used to increase intramolecular interactions in the hydrophobic pocket, leading to attenuation. Examples of such mutations/substitutions that can be made in the hydrophobic pocket, and included in the viruses of the invention, include substitutions in E202K, E204K, E252V, E253L, E257E, E258G, and E261H (and corresponding substitutions in other Flaviviruses). Any amino acid changes in the corresponding region of the E protein of JE and WN viruses can be designed and incorporated based on the knowledge of homologous protein structure.

The E gene contains functional domains within which amino acid changes may affect function and thereby reduce virulence, as described by Hurrelbrink and McMinn (Adv. Virus Dis. 60:1-42, 2003). The functional regions of the E protein in which mutations may be inserted that, together with the membrane deletions/mutations described in the present application, may result in an appropriately attenuated vaccine include: a) the putative receptor binding region on the external surface of domain III, b) the molecular hinge region between domains I and II, which determines the acid-dependent conformational changes of the E protein in the endosome and reduce the efficiency of virus internalization; c) the interface of prM and E proteins, a region of the E protein that interfaces with prM following the rearrangement from dimer to trimer after exposure to low pH in the endosome; d) the tip of the fusion domain of domain II, which is involved in fusion to the membrane of the endosome during internalization events; and e) the stem-anchor region, which is also functionally is involved in conformational changes of the E protein during acid-induced fusion events.

Figure 1B:
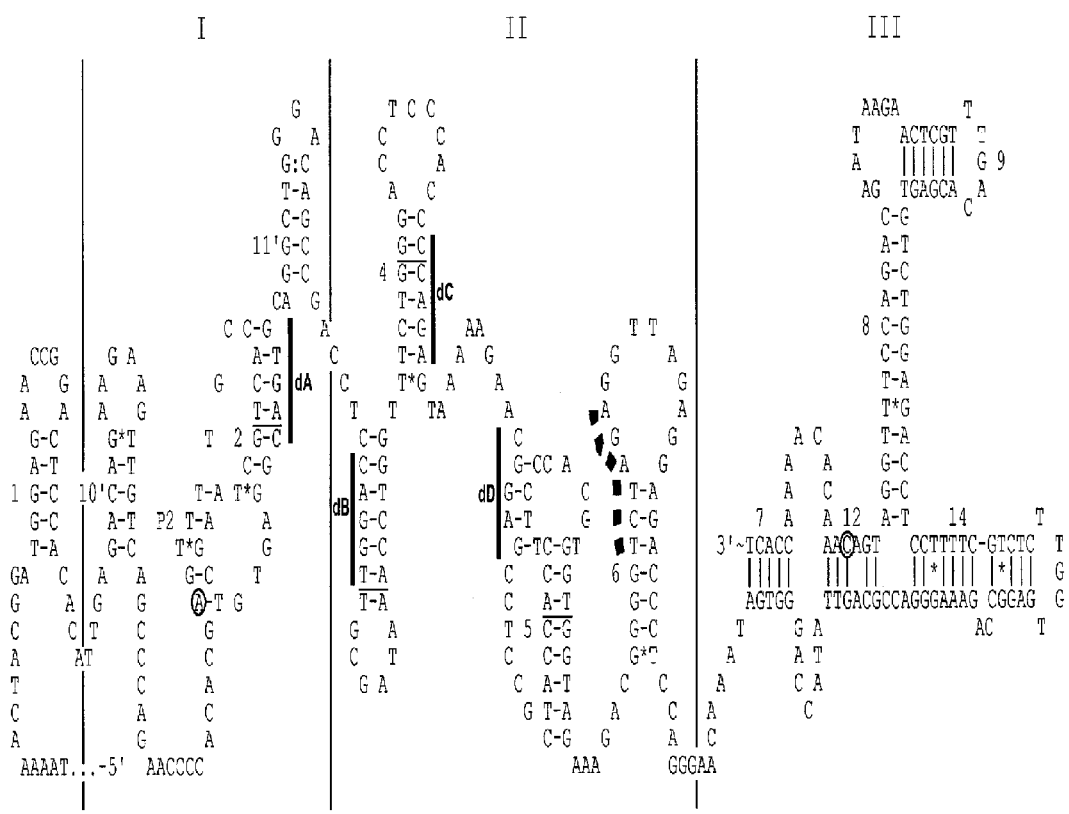
FIG. 1B is a schematic representation of the sequence and published secondary structure prediction of the 3' untranslated region of yellow fever 17D virus, from the middle of the $3^{rd}$ RS element to the end of the UTR (Proutski et al., J. Gen. Virol. 78:1543-1549, 1999) (SEQ ID NO:31).

Additional attenuating mutations that can be included with one or more membrane protein mutations in the viruses of the invention include mutations in the 3' untranslated region of the yellow fever virus backbone. The organization of the 3'UTR of a yellow fever virus vaccine strain, YF 17D, which is shared by all ChimeriVax™ viruses, is shown in FIG. 1A. It includes in order from the 3' end (i) a 3'-extreme stem-and-loop structure that has been hypothesized to function as a promoter for minus-strand RNA synthesis and is conserved for all Flaviviruses, (ii) two conserved sequence elements, CS1 and CS2, which share a high degree of nucleotide sequence homology with all mosquito-borne Flaviviruses, and (iii) unique for West African yellow fever virus strains, including the YF17D vaccine virus, three copies of a repeat sequence element (RS) located in the upstream portion of the 3'UTR (Chambers et al., Annu. Rev. Microbiol. 44:649-688, 1990). The 3'UTR also includes numerous stem-loop structures, such as those in the non-conserved region downstream from the RS elements, as depicted in FIG. 1B.

3'UTR mutations that can be included in the viruses of the invention generally are short, attenuating deletions of, for example, less than 30 nucleotides (e.g., 1, 2, 3, etc., and up to 29 (e.g., 2-25, 3-20, 4-15, 5-10, or 6-8 nucleotides in length); U.S. Patent Application Nos. 60/674,546 and 60/674,415). In some examples, the short 3'UTR deletions are designed to destabilize the secondary structure of one or more of the stem structures in the 3'UTR. In addition to deletions, mutations in such structures can also include substitutions that similarly result in stem structure destabilization. In certain examples, the stem-loop structures that are subject to the mutations are present in non-conserved regions of the 3'UTR or in conserved regions that can tolerate such mutations (e.g., in CS2). For example, the stem destabilizing mutations can be present in any one or more of the predicted stem structures shown in FIG. 1B, which shows four examples of such deletions (dA, dB, dC, and dD). Thus, in addition to these specific examples, other examples of 3'UTR mutations in yellow fever virus include mutations that comprise, e.g., 1-2, 3-8, 4-7, or 5-6 nucleotides of the following stem sequences, which are shown in FIG. 1B as read from 5' to 3': TGGAG, CTCCA, GACAG, TTGTC, AGTTT, GGCTG, CAGCC, AACCTGG, TTCTGGG, CTACCACC, GGTGGTAG, GGGGTCT, AGACCCT, AGTGG, and TTGACG. These mutations can also be present in corresponding amino acids of other Flaviviruses, as described herein.

In addition to stem destabilizing mutations, other short deletions in the 3'UTR can also be included with one or more membrane (and possibly other) mutations in the viruses of the invention. For example, the previously described Δ30 mutation (Men et al., J. Virol. 70:3930-3937, 1996; U.S. Pat. No. 6,184,024 B1) or mutations that fall within this sequence can be used. Thus, for example, the invention includes any viable deletions that are 1, 2, 3, etc., and up to 29 (e.g., 1-25, 2-20, 3-15, 4-14, 5-13, 6-12, 7-11, 8-10, or 9) nucleotides in length within this region. As a specific example, viruses of the invention can include deletion d7, in which the following nucleotides from this region in YF17D are deleted: nucleotides 345-351 (AAGACGG; numbering from the $1^{st}$ nucleotide of the 3'UTR, after the UGA termination codon of the viral ORF; FIG. 1A). Mutations that include deletion of, for example, 1, 2, 3, 4, or 5 additional nucleotides from the 3' or 5' end of this sequence are also included in the invention. In other examples, short deletions in conserved sequences CS1 and CS2 are included in the invention. These mutations can include deletion of, e.g., 1-29, 2-25, 3-20, 4-15, 5-10, or 6-8 nucleotides of these sequences. As two specific examples, nucleotides 360-364 (GGTTA; CS2d5; FIG. 1A) and/or nucleotides 360-375 (GGTTAGAGGAGACCCT; CS2d16; FIG. 1A) are deleted from CS2 of the YF17D-specific 3'UTR. Mutations that include deletion of, for example, 1, 2, 3, 4, or 5 additional nucleotides from the 3' or 5' end of this sequence can also be used. For other flavivirus 3'UTRs, similar mutations can be made, based on the secondary structures of the 3'UTR's. Predictions of secondary structures of 3'UTR of other flaviviruses have been published, e.g., for dengue, Kunjin, and TBE (see, e.g., Proutski et al., Virus Res. 64:107-123, 1999) and HCV (see, e.g., Kolykhalov et al., J. Virol. 70:3363-3371, 1996). Further, numerous 3'UTR nucleotide sequences for many strains of flaviviruses representing all four major serocomplexes (YF, JE, dengue, and TBE) are available from GenBank. Sequences of additional strains can be determined by virus sequencing. The secondary structures of these sequences can be easily predicted using standard software (e.g., mfold or RNAfold programs) to reveal potential stem-loop structures that can be subject to mutagenesis.

Figure 1C:
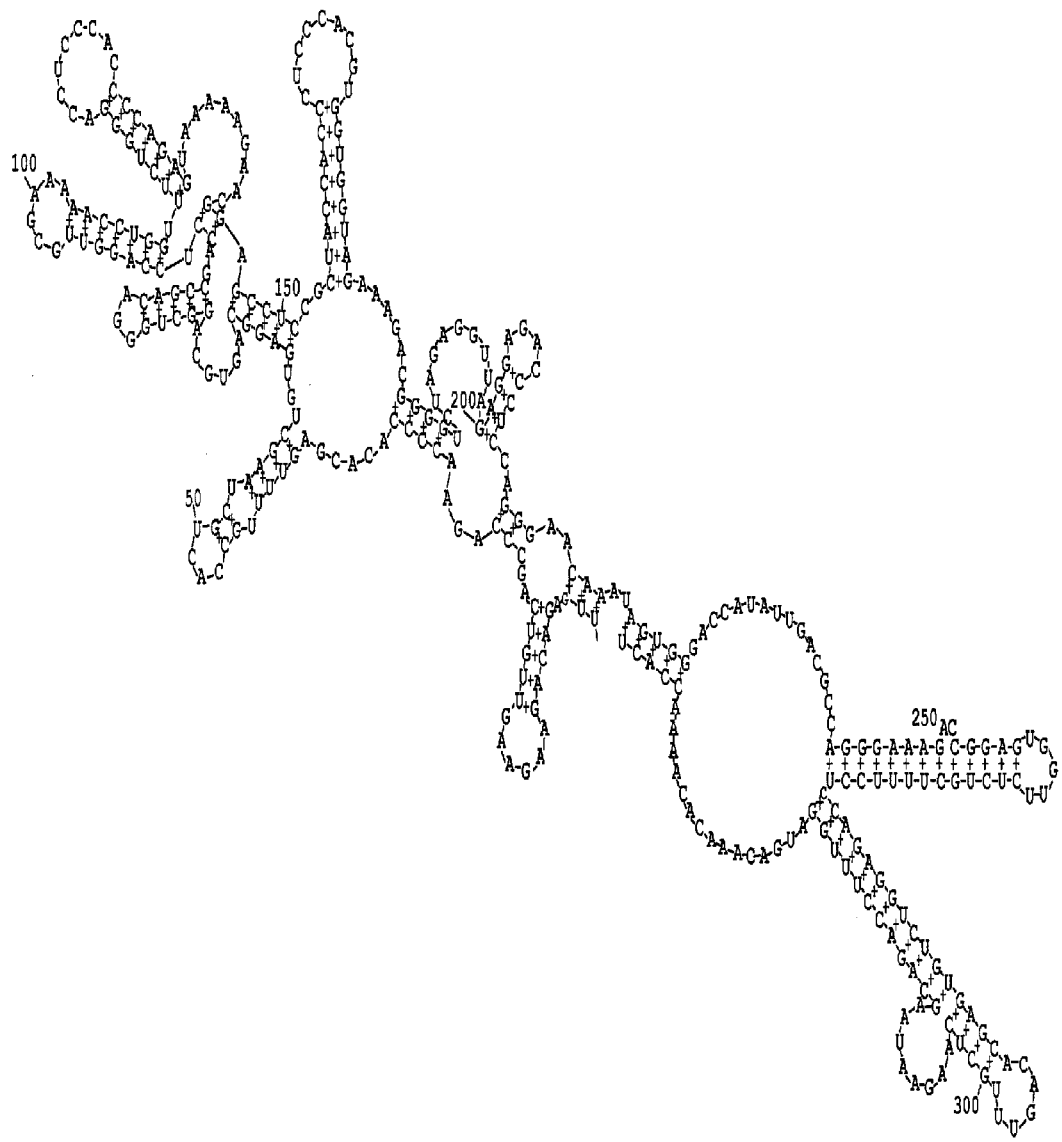
FIG. 1C is an illustration of the optimal YF 17D 3'UTR secondary structure prediction produced using the Zuker RNA folding algorithm (SEQ ID NO:32).
Figure 1D:
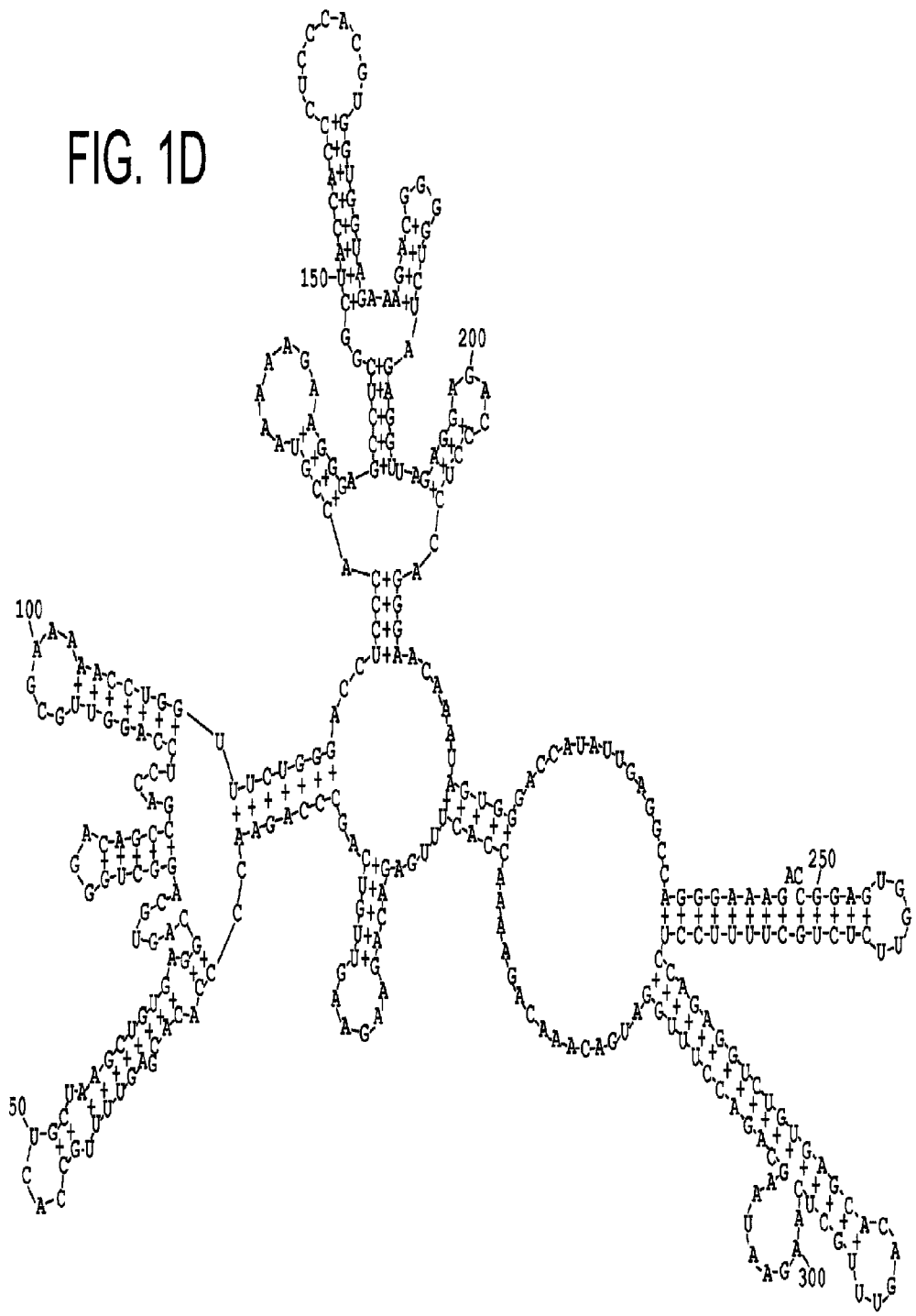
FIG. 1D is an illustration of the effects of 3'UTR deletions (shown for the dC deletion; Zuker method) on the optimal YF 17D structure (compare with FIG. 1C) (SEQ ID NO:33).

It should be noted that the true secondary structures of the 3'UTRs of Flaviviruses, including YF 17D virus, are unknown because there are no available methods to experimentally prove their existence in the context of whole viruses, and therefore published predictions, e.g., the one predicted for YF 17D by Proutski and co-workers (FIG. 1B), may be incorrect. Many alternative structures can be predicted to form in a relatively long RNA molecule (Zuker et al., N.A.R. 19:2707-2714, 2001), and it is possible that different structures (in plus or minus strands) form and function at different steps of the viral life cycle. True structures can be influenced by the formation of various pseudoknots (Olsthoorn et al., RNA 7:1370-1377, 2001) and long range RNA interactions (e.g., RNA cyclization and other interactions (Alvarez et al., J. Virol. 79:6631-6643, 2005)), as well as possible RNA interactions with host and viral proteins. To further complicate interpretation of published results of theoretical computer predictions, manual operations are often used, such as initial folding of partial sequences with subsequent forcing of initially predicted structures into structures of longer RNA sequences, the artificial use of N's during initial folding steps, and subjective selection of preferred structure elements (e.g., Mutebi et al., J. Virol. 78:9652-9665, 2004). To this end, we folded the 3'UTR RNA sequence of YF 17D using the commonly used Zuker's prediction algorithm. The predicted optimal structure is shown in FIG. 1C, which differs from the Proutsky prediction shown in FIG. 1B. It is important that the small deletions dA, dB, dC, dD, d7, and d14 in FIGS. 1A and 1B generally destabilized the predicted native YF 17D optimal (FIG. 1C) and suboptimal structures. An example of one such altered optimal structure (for the dC mutant) is shown in FIG. 1D. In contrast, the CS2d5 and CS2d16 deletions (FIGS. 1A and 1B) did not noticeably change the optimal native structure, indicating that these deletions may attenuate the virus (attenuation was demonstrated in the hamster model for ChimeriVax™-WN) by virtue of altering the sequence of CS2 per se rather than the 3'UTR structure, or alternatively by altering some suboptimal structures. Thus, even though some of the deletions were designed based on the Proutski structure prediction (FIG. 1B), their true effect may be due to destabilizing different structure elements than the predicted stem-loops in FIG. 1B.

Figure 2A:
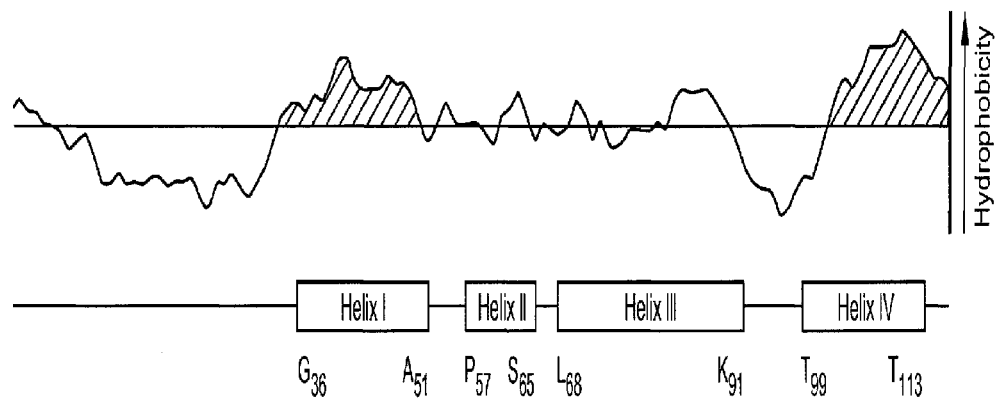
FIG. 2A is a schematic representation of the sequence of the capsid protein of tick-borne encephalitis virus, as well as deletions in this protein reported by Kofler et al., J. Virol. 76:3534-3543, 2002 (SEQ ID NO:34).

Additional mutations that can be included with membrane protein (and possibly other) mutations in the viruses of the invention are short deletion (e.g., deletions of 1, 2, 3, or 4 amino acids) mutations within the capsid protein. Examples of such mutations, provided in reference to the YF 17D virus capsid protein, include viable deletions affecting Helix I of the protein (see FIG. 2A). A specific example of such a mutation is mutation C2, which includes a deletion of amino acids PSR from Helix I (FIG. 2A). Other short mutations in this region (as well as corresponding mutations in other Flavivirus sequences) can be tested for viability and attenuation, and can also be used in the invention. Capsid protein sequences of other flaviviruses have been published, e.g., for TBE, WN, Kunjin, JE, and dengue viruses (e.g., Pletnev et al., Virology 174:250-263, 1990).

The following are specific examples of chimeric Flaviviruses, which were deposited with the American Type Culture Collection (ATCC) in Manassas, Va., U.S.A. under the terms of the Budapest Treaty and granted a deposit date of Jan. 6, 1998, that can be used to make viruses of the invention: Chimeric Yellow Fever 17D/Dengue Type 2 Virus (YF/DEN-2; ATCC accession number ATCC VR-2593) and Chimeric Yellow Fever 17D/Japanese Encephalitis SA14-14-2 Virus (YF/JE A1.3; ATCC accession number ATCC VR-2594). Details of making chimeric viruses that can be used in the invention are provided, for example, in U.S. Pat. No. 6,696,281 B1; international applications PCT/US98/03894 (WO 98/37911) and PCT/US00/32821 (WO 01/39802); and Chambers et al., J. Virol. 73:3095-3101, 1999, and are also provided below. These methods can be modified for use in the present invention by including a step of introducing one or more mutations as described herein into inserted sequences (e.g., Japanese encephalitis virus or West Nile virus membrane protein or other sequences). Methods that can be used for producing viruses in the invention are also described in PCT/US03/01319 (WO 03/060088 A2; also see below).

Mutations can be made in the viruses of the invention using standard methods, such as site-directed mutagenesis. One example of the type of mutation present in the viruses of the invention is substitutions, but other types of mutations, such as deletions and insertions, can be used as well. In addition, as is noted above, the mutations can be present singly or in the context of one or more additional mutations, whether within the membrane protein itself or in any combination of, e.g., 3'UTR, capsid, or envelope sequences.

The viruses (including chimeras) of the present invention can be made using standard methods in the art. For example, an RNA molecule corresponding to the genome of a virus can be introduced into primary cells, chick embryos, or diploid cell lines, from which (or the supernatants of which) progeny virus can then be purified. Another method that can be used to produce the viruses employs heteroploid cells, such as Vero cells (Yasumura et al., Nihon Rinsho 21:1201-1215, 1963). In this method, a nucleic acid molecule (e.g., an RNA molecule) corresponding to the genome of a virus is introduced into the heteroploid cells, virus is harvested from the medium in which the cells have been cultured, and harvested virus is treated with a nuclease (e.g., an endonuclease that degrades both DNA and RNA, such as Benzonase™; U.S. Pat. No. 5,173,418). In the case of Benzonase™, 15 units/mL can be used, and the conditioned medium refrigerated at 2-8° C. for about 16 or more hours to allow for digestion of nucleic acids. The nuclease-treated virus is then concentrated (e.g., by use of ultrafiltration using a filter having a molecular weight cut-off of, e.g., 500 kDa (e.g., a Pellicon-2 Mini unitrafilter cassette)), diafiltered against MEME without phenol red or FBS, formulated by the addition of lactose, and filtered into a sterile container. Details of this method are provided in WO 03/060088 A2. Further, cells used for propagation of viruses of the invention can be grown in serum free medium, as described below.

The viruses of the invention can be administered as primary prophylactic agents in those at risk of infection, or can be used as secondary agents for treating infected patients. Because the viruses are attenuated, they are particularly well-suited for administration to "at risk individuals" such as the elderly, children, or HIV infected persons. The vaccines can also be used in veterinary contexts, e.g., in the vaccination of horses against West Nile virus infection, or in the vaccination of domestic pets (e.g., cats, dogs, and birds), livestock (e.g., sheep, cattle, pigs, birds, and goats), and valuable animals such as rare birds. Further, the vaccines of the invention can include a virus, such as a chimeric virus, including a particular mutation (e.g., the M5, M60, and/or M66 mutation), in a mixture with viruses lacking such mutations.

Formulation of the viruses of the invention can be carried out using methods that are standard in the art. Numerous pharmaceutically acceptable solutions for use in vaccine preparation are well known and can readily be adapted for use in the present invention by those of skill in this art (see, e.g., *Remington's Pharmaceutical Sciences* (18$^{th}$ edition), ed. A. Gennaro, 1990, Mack Publishing Co., Easton, Pa.). In two specific examples, the viruses are formulated in Minimum Essential Medium Earle's Salt (MEME) containing 7.5% lactose and 2.5% human serum albumin or MEME containing 10% sorbitol. However, the viruses can simply be diluted in a physiologically acceptable solution, such as sterile saline or sterile buffered saline. In another example, the viruses can be administered and formulated, for example, in the same manner as the yellow fever 17D vaccine, e.g., as a clarified suspension of infected chicken embryo tissue, or a fluid harvested from cell cultures infected with the chimeric yellow fever virus.

The vaccines of the invention can be administered using methods that are well known in the art, and appropriate amounts of the vaccines to be administered can readily be determined by those of skill in the art. What is determined to be an appropriate amount of virus to administer can be determined by consideration of factors such as, e.g., the size and general health of the subject to whom the virus is to be administered. For example, the viruses of the invention can be formulated as sterile aqueous solutions containing between $10^2$ and $10^8$, e.g., $10^3$ to $10^7$ or $10^4$ to $10^6$, infectious units (e.g., plaque-forming units or tissue culture infectious doses) in a dose volume of 0.1 to 1.0 ml, to be administered by, for example, intramuscular, subcutaneous, or intradermal routes.

In addition, because Flaviviruses may be capable of infecting the human host via mucosal routes, such as the oral route (Gresikova et al., "Tick-borne Encephalitis," In *The Arboviruses, Ecology and Epidemiology*, Monath (ed.), CRC Press, Boca Raton, Fla., 1988, Volume IV, 177-203), the viruses can be administered by mucosal (e.g., oral) routes as well. Further, the vaccines of the invention can be administered in a single dose or, optionally, administration can involve the use of a priming dose followed by one or more booster doses that are administered, e.g., 2-6 months later, as determined to be appropriate by those of skill in the art.

Optionally, adjuvants that are known to those skilled in the art can be used in the administration of the viruses of the invention. Adjuvants that can be used to enhance the immunogenicity of the viruses include, for example, liposomal formulations, synthetic adjuvants, such as (e.g., QS21), muramyl dipeptide, monophosphoryl lipid A, or polyphosphazine. Although these adjuvants are typically used to enhance immune responses to inactivated vaccines, they can also be used with live vaccines. In the case of a virus delivered via a mucosal route, for example, orally, mucosal adjuvants such as the heat-labile toxin of *E. coli* (LT) or mutant derivations of LT can be used as adjuvants. In addition, genes encoding cytokines that have adjuvant activities can be inserted into the viruses. Thus, genes encoding cytokines, such as GM-CSF, IL-2, IL-12, IL-13, or IL-5, can be inserted together with foreign antigen genes to produce a vaccine that results in enhanced immune responses, or to modulate immunity directed more specifically towards cellular, humoral, or mucosal responses. Additional adjuvants that can optionally be used in the invention include toll-like receptor (TLR) modulators.

In the case of dengue viruses and/or chimeric Flaviviruses including membrane and envelope proteins of a dengue virus, against which optimal vaccination can involve the induction of immunity against all four of the dengue serotypes, the viruses of the invention can be used in the formulation of tetravalent vaccines. Any or all of the viruses used in such tetravalent formulations can include one or more mutations that decrease viscerotropism, as is described herein. The viruses can be mixed to form tetravalent preparations at any point during formulation, or can be administered in series. In the case of a tetravalent vaccine, equivalent amounts of each virus may be used. Alternatively, the amounts of each of the different viruses present in the administered vaccines can vary (WO 03/101397 A2).

The invention also includes nucleic acid molecules (e.g., RNA or DNA (e.g., cDNA) molecules) that correspond to the genomes of the viruses of the invention as described herein, or the complements thereof. These nucleic acid molecules can be used, for example, in methods of manufacturing the viruses of the invention. In such methods, a nucleic acid molecule corresponding to the genome of a virus is introduced into cells in which the virus can be produced and replicate (e.g., primary cells, chick embryos, diploid cell lines, or heteroploid cell lines (e.g., Vero cells)), and from which (or the supernatants of which) progeny virus can then be purified. These methods can further include virus purification steps, as is known in the art.

As is noted above, details of making chimeric viruses that can be used in the invention are provided, for example, in U.S. Pat. No. 6,696,281 B1; international applications PCT/US98/03894 (WO 98/37911) and PCT/US00/32821 (WO 01/39802); and Chambers et al., J. Virol. 73:3095-3101, 1999. Details of the construction of a chimeric Flavivirus including pre-membrane and envelope proteins of Japanese encephalitis virus (or West Nile virus), and capsid and nonstructural proteins of yellow fever virus, are provided as follows. These methods can readily be adapted by those of skill in the art for use in constructing chimeras including the mutations described herein, as well as chimeras including other pre-membrane and envelope sequences.

Briefly, derivation of a YF/JE chimera can involve the following. YF genomic sequences are propagated in two plasmids (YF5'3'IV and YFM5.2), which encode the YF sequences from nucleotides 1-2,276 and 8,279-10,861 (YF5'3'IV) and from 1,373-8,704 (YFM5.2) (Rice et al., The New Biologist 1:285-296, 1989). Full-length cDNA templates are generated by ligation of appropriate restriction fragments derived from these plasmids. YF sequences within the YF5'3'IV and YFM5.2 plasmids are then replaced by the corresponding JE sequences from the start of the prM protein (nucleotide 478, amino acid 128) through the E/NS1 cleavage site (nucleotide 2,452, amino acid 817).

Clones of authentic JE structural protein genes were generated from the JE SA14-14-2 strain (JE live, attenuated vaccine strain; JE SA14-14-2 virus is available from the Centers for Disease Control, Fort Collins, Colo. and the Yale Arbovirus Research Unit, Yale University, New Haven, Conn., which are World Health Organization-designated Reference Centers for Arboviruses in the United States). JE SA14-14-2 virus at passage level PDK-5 was obtained and passaged in LLC-MK$_2$ cells to obtain sufficient amounts of virus for cDNA cloning. The strategy used involved cloning the structural region in two pieces that overlap at an NheI site (JE nucleotide 1,125), which can then be used for in vitro ligation.

RNA was extracted from monolayers of infected LLC-MK$_2$ cells and first strand synthesis of negative sense cDNA was carried out using reverse transcriptase with a negative sense primer (JE nucleotide sequence 2, 456-71) containing nested XbaI and NarI restriction sites for cloning initially into pBluescript II KS(+), and subsequently into YFM5.2(NarI), respectively. First strand cDNA synthesis was followed by PCR amplification of the JE sequence from nucleotides 1,108-2,471 using the same negative sense primer and a positive sense primer (JE nucleotides sequence 1,108-1,130) containing nested XbaI and NsiI restriction sites for cloning into pBluescript and YFM5.2(NarI), respectively. JE sequences were verified by restriction enzyme digestion and nucleotide sequencing. The JE nucleotide sequence from nucleotides 1 to 1,130 was derived by PCR amplification of negative strand JE cDNA using a negative sense primer corresponding to JE nucleotides 1,116 to 1,130 and a positive sense primer corresponding to JE nucleotides 1 to 18, both containing an EcoRI restriction site. PCR fragments were cloned into pBluescript and JE sequences were verified by nucleotide sequencing. Together, this represents cloning of the JE sequence from nucleotides 1-2,471 (amino acids 1-792).

To insert the C terminus of the JE envelope protein at the YF E/NS1 cleavage site, a unique NarI restriction site was introduced into the YFM5.2 plasmid by oligonucleotide-directed mutagenesis of the signalase sequence at the E/NS1 cleavage site (YF nucleotides 2,447-2,452, amino acids 816-817) to create YFM5.2(NarI). Transcripts derived from templates incorporating this change were checked for infectivity and yielded a specific infectivity similar to the parental templates (approximately 100 plaque-forming units/250 nanograms of transcript). The JE sequence from nucleotides 1,108 to 2,471 was subcloned from several independent PCR-derived clones of pBluescript/JE into YFM5.2(NarI) using the unique NsiI and NarI restriction sites. YF5'3'IV/JE clones containing the YF 5' untranslated region (nucleotides 1-118) adjacent to the JE prM-E region were derived by PCR amplification.

To derive sequences containing the junction of the YF capsid and JE prM, a negative sense chimeric primer spanning this region was used with a positive sense primer corresponding to YF5'3'IV nucleotides 6,625-6,639 to generate PCR fragments that were then used as negative sense PCR primers in conjunction with a positive sense primer complementary to the pBluescript vector sequence upstream of the EcoRI site, to amplify the JE sequence (encoded in reverse orientation in the pBluescript vector) from nucleotide 477 (N-terminus of the prM protein) through the NheI site at nucleotide 1,125. The resulting PCR fragments were inserted into the YF5'3'IV plasmid using the NotI and EcoRI restriction sites. This construct contains the SP6 promoter preceding the YF 5'-untranslated region, followed by the sequence: YF (C) JE (prM-E), and contains the NheI site (JE nucleotide 1,125) required for in vitro ligation.

To use the NheI site within the JE envelope sequence as a 5' in vitro ligation site, a redundant NheI site in the YFM5.2 plasmid (nucleotide 5,459) was eliminated. This was accomplished by silent mutation of the YF sequence at nucleotide 5,461 (T C; alanine, amino acid 1820). This site was incorporated into YFM5.2 by ligation of appropriate restriction fragments and introduced into YFM5.2(NarI)/JE by exchange of an NsiI/NarI fragment encoding the chimeric YF/JE sequence.

To create a unique 3' restriction site for in vitro ligation, a BspEI site was engineered downstream of the AatII site normally used to generate full-length templates from YF5'3'IV and YFM5.2. (Multiple AatII sites are present in the JE structural sequence, precluding use of this site for in vitro ligation.) The BspEI site was created by silent mutation of YF nucleotide 8,581 (A C; serine, amino acid 2,860), and was introduced into YFM5.2 by exchange of appropriate restriction fragments. The unique site was incorporated into YFM5.2/JE by exchange of the XbaI/SphI fragment, and into the YF5'3'IV/JE(prM-E) plasmids by three-piece ligation of appropriate restriction fragments from these parent plasmids and from a derivative of YFM5.2 (BspEI) deleting the YF sequence between the EcoRI sites at nucleotides 1 and 6,912.

cDNA from a clone of the JE Nakayama strain, which has been extensively characterized in expression experiments and for its capacity to induce protective immunity (see, e.g., McIda et al., Virology 158:348-360, 1987; the JE Nakayama strain is available from the Centers for Disease Control, Fort Collins, Colo., and the Yale Arbovirus Research Unit, Yale University, New Haven, Conn.), was also used in the construction of chimeric flaviviruses. The Nakayama cDNA was inserted into the YF/JE chimeric plasmids using available restriction sites (HindIII to PvuII and BpmI to MunI) to replace the entire prM-E region in the two plasmid system except for a single amino acid, serine, at position 49, which was left intact in order to utilize the NheI site for in vitro ligation.

Procedures for generating full-length cDNA templates are essentially as described in Rice et al. (The New Biologist 1:285-96, 1989). In the case of chimeric templates, the plasmids YF5'31V/JE (prM-E) and YFM5.2/JE are digested with NheI/BspEI and in vitro ligation is performed using 300 nanograms of purified fragments in the presence of T4 DNA ligase. The ligation products are linearized with XhoI to allow run-off transcription. SP6 transcripts are synthesized using 50 nanograms of purified template, quantitated by incorporation of $^3$H-UTP, and integrity of the RNA is verified by non-denaturing agarose gel electrophoresis. Yields range from 5 to 10 micrograms of RNA per reaction using this procedure, most of which is present as full-length transcripts. Transfection of RNA transcripts in the presence of cationic liposomes is carried out as described by Rice et al. (supra) for YF 17D, to generate the chimeric viruses.

In the case of chimeric flaviviruses including West Nile virus and yellow fever virus sequences, the two-plasmid system described above can also be used. In one example, the West Nile (WN) virus prM and E genes used were cloned from WNV flamingo isolate 383-99, sequence GenBank accession number AF196835. Virus prME cDNA was obtained by RT-PCR (XL-PCR Kit, Perkin Elmer). The 5' end of WN prM gene was cloned precisely at the 3' end of the YF 17D capsid gene by overlap-extension PCR using Pwo polymerase (Roche). The 3' end of the E gene was also cloned precisely at the 5' end of the YF NS1 coding sequence by overlap-extension PCR. Silent mutations were introduced into the sequence of prM and E to create unique restriction sites Bsp EI and Eag I. Digestion of the two plasmids with these enzymes generated DNA fragments that were gel purified and ligated in vitro to produce a full-length chimeric cDNA. The cDNA was linearized with Xho I to facilitate in vitro transcription by SP6 polymerase (Epicentre). The RNA product was introduced into eukaryotic cell lines permissive for viral RNA translation and replication of the virus. As with the YF/JE chimera, described above, mutations of the invention can be introduced into YF/WN chimeras as described herein, using standard methods.

Other Flavivirus chimeras can be engineered with a similar strategy, using natural or engineered restriction sites and, for example, oligonucleotide primers as shown in Table 14.

The invention is based, in part, on the experimental results described in the following Examples.

EXAMPLES

Example 1

ChimeriVax™-WN

Experimental Results
Background and Summary

A chimeric yellow fever-West Nile (YF-WN) virus, ChimeriVax™-WN, was produced by insertion of pre-membrane (prM) and envelope (E) genes of a WN virus (NY99) into the YF17D backbone. The virus was produced in Vero cells under serum free conditions (at Passage 5, P5), evaluated for safety, immunogenicity, and efficacy in preclinical models, and has been tested in a phase I study in humans. Additional attenuation of the vaccine virus (P5) is determined by three SA14-14-2-specific mutations in the E protein (residues 107, 316, and 440). The vaccine virus was less neurovirulent than YF-VAX® when tested in mouse and monkeys inoculated by the IC route and protected mice, hamsters, and monkeys upon a single inoculation (Arroyo et al., J. Virol. 78:12497-12507, 2004; Tesh et al., Emer. Infect. Dis. 8:1392-1397, 2002). The vaccine virus contained a mixed population of viruses (exhibiting small, S, and large, L, plaque phenotypes), which differed by a single amino acid residue in the M protein at position 66 (M66). This mutation did not affect neurovirulence of the virus for 8 day old suckling mice (Arroyo et al., J. Virol. 78:12497-12507, 2004). In the current invention, we describe the discovery that the M66 mutation reduces viremia in the host and thus can be used to improve the safety of the current vaccine (ChimeriVax™-WN02, P5, mixed population of parent and mutant viruses) or the large plaque variant (non mutant) virus.

A nucleotide heterogeneity (~50%) of T and C (CTA/CCA) was observed in the consensus sequence of ChimeriVax™-West Nile vaccine virus at P5 produced in Vero cells under serum free conditions. This mutation would result in presence of viruses containing either amino acid Proline (mutant) or Leucine (parent wild type) in the membrane (M) protein at residue 66 (herein designated as M66 mutation). The sequences of ChimeriVax™WN02 and the ChimeriVax™WN02 M66 variant are provided in the enclosed sequence appendix, which also includes an alignment of the amino acid sequences of these proteins.

The M protein of West Nile virus contains 75 amino acids. The structure of the protein was predicted and compared to the structures of M proteins of JE SA14 (AAA67174), Kunjin (AAP78942), MVE (CAA27184), SLE MSI (AAP44973, and SLE CORAN (AAP44972) by submission of the protein sequence to the http://www.predictprotein.org website. In all predicted structures, the first 40 amino acids of the M protein (SLTVQTHGESTLANKKGAWMDSTKA-TRYLVKTESWILRN) are predicted to be a non-membrane region, whereas the remaining 35 amino acids (40-75) (PGY-ALVAAVIGWMLGSNTMQRVVFVVLLLLVAPAYS) are predicted to be within the viral membrane region. In addition, there are 9-10 charged amino acids (3-4 acidic, E or D) and 6 basic (R or K) within the first 40 amino acid residues, whereas there is only one charged amino acid (basic) at residue 60 of all 5 Flaviviruses (WNV, SLE, MVE, JE, and Kunjin) described here. Thus, it may be that the M60 residue plays a vital role in biology of the virus by interaction within its neighboring amino acids.

The plaque morphology of the vaccine virus at P5 revealed a mixed population of L and S plaque size phenotypes. The sequencing of the P2, P3, P4, and P5 viruses revealed that the mutation first appeared at P4 (10% of the total population) and reached ~50% in P5. The sequencing of the S and L plaque isolates of the vaccine virus showed that the mutation is responsible for a change in plaque size from L to S. Both S and L virus variants (prepared as research virus) did not significantly differ in their neurovirulence for 8 day old suckling mice (p=<0.0001).

Pre-Master Seed (PMS, P10) stocks of both L and S viruses were produced in Vero cells from ChimeriVax™-WN02 (p5) under "clean laboratory condition" by 3 rounds of direct plaque to plaque purifications and 2 rounds of virus amplification. The sequencing of P10 S and L viruses revealed a single amino acid difference in the M66 residue (S virus contained Proline at M66 residue, whereas L virus contained Leucine at this site). The M66 mutation seemed to be stable under large scale manufacturing conditions. When the S plaque virus (P10, PMS) was inoculated into hamsters by subcutaneous inoculation, it induced a very low level of viremia compared to the vaccine virus (P5) or the L plaque virus variant (P10, PMS). In sera of monkeys and humans inoculated with ChimeriVax™-WN P5 virus (contained ~50:50 S and L plaque variants), the majority of viruses were of L plaque size phenotype. In addition, it was shown that the S plaques grow to a lower titer than the L plaques in human hepatoma cell lines. These data indicated that the S plaque virus (ChimeriVax™-WN02 with M66 mutation) may induce a lower level of viremia in humans than ChimeriVax™-WN02 (without M66 mutation), and therefore could constitute a suitable (safe) WN vaccine candidate for "at risks individuals," such as the elderly, children, or HIV infected persons. Additional mutations in the M region were found by sequencing individual plaques isolated from large scale manufacturing passages (e.g., M62, M63, and M64) of PMS S plaque from P10 to P12 or monkeys inoculated with ChimeriVax™-WN02 vaccine (e.g., M60, M61, and M63). These mutations can also be used in the construction of viruses of the invention.

Production of PMS of S and L Plaque Viruses in Vero Cells

ChimeriVax™-WN02 vaccine material (P5) was grown in Serum Free Vero cells; 10 plaques identified as "small" (S) and 10 plaques identified as "large" (L) were picked. Each isolate was then passaged on Serum Free Vero cells, and one plaque was picked from each isolate. The procedure was repeated one final time, for a total of three rounds of plaque purification. The plaque purified isolates (P8) were amplified in T25 cm$^2$ flasks containing Serum Free Vero cells (and grown in serum free (SF) media), then harvested and stored at −80° C. Isolates were sequenced to find a PMS candidate free of spurious mutations. Two isolates were identified to be free of expressed (non-silent) mutations: one isolate was confirmed to be small plaque (M66 Proline) (Table 1), and the other contained a wt sequence (M66 Leucine) (Table 2). These two isolates were then grown in large flasks, aliquoted, and submitted to QC inventory as LP and SP PMS (P10) viruses.

Genetic Stability of SP viruses Produced at Large Scale

In order to determine if the S plaque phenotype is stable during a large scale manufacturing process, the small plaque PMS virus was passaged twice in a bioreactor by infecting Vero cells and growing under serum free conditions to produce the P12 virus. The P12 virus was harvested and plaqued in 6-well plates. The majority of the plaques were of small size. Twenty of the largest plaques available were picked, amplified on O-Vero (one passage), and the prME region was transcribed/amplified via Titan One-Tube RT-PCR kit (Roche). The cDNA fragments containing the M region were sequenced, and the morphology of the isolates was confirmed via immuno-staining using WN specific monoclonal antibodies. Thirteen of 20 plaques contained only M66 (the genetic marker responsible for SP morphology), and 5 isolates contained other mutations in addition to M66. Isolate #4 contained M63 (LP phenotype), and isolate #16 contained a mixed population of wt and M66. These data demonstrated that, despite the fact that some plaques appeared to be of large size, they contained the M66 mutation and upon amplification proved to be of S size. Only one plaque (#4) out of 20 appeared to be of L size, apparently due to a mutation at M63 from L to P. Plaque #16 appeared to produce a mixed population of large and small plaque size viruses containing both wt L and mutant P amino acids at position M66 (Table 3).

Growth of ChimeriVax™-WN Virus Variants in Hepatic Cells

Human hepatoma cell lines HepG2 and THLE-3 cells were infected with ChimeriVax™-WN01 (wild type prME), ChimeriVax™-WN02 P5 (containing mutations at E107, E313, E316, E440, M66 mixed L/P amino acids, mixed S and L plaques), ChimeriVax™-WN LP (E107, E313, E316, and E440, WNL), and ChimeriVax™-WN SP (E107, E313, E316, E440, and M66P, WNS) at an MOI of 0.005. Supernatants were collected daily and titrated on O-Vero cells using the standard neutral red double agarose overlay procedure.

In HepG2 cells (FIG. 3) the highest virus growth ($7 \times 10^6$ PFU/ml) was observed on Day 5 with WN01 (wild type prME), followed by that of LP ($2.7 \times 10^6$ PFU/ml) on Day 5. The virus peak with YF-VAX® was reached on Day 3 ($1.17 \times 10^6$ PFU/ml), followed by WN02 mixed vaccine virus ($6.4 \times 10^5$ PFU/ml) on Day 4. The lowest growth was found with the SP virus (peak titer on Day 4 was $6.1 \times 10^5$ PFU/ml), which contained a single amino acid substitution (L to P) at M66. In THLE-3 cells (FIG. 4), the same pattern as in HepG2 cells was observed with the exception that the titer of YF-VAX® was slightly higher than that of the LP virus. The highest titer was seen again with the WN01 ($1.3 \times 10^5$ PFU/ml, Day 4), followed by those of LP ($5.7 \times 10^4$ PFU/ml, Day 7), YF-VAX® ($8.8 \times 10^4$ PFU/ml, Day 4), and the mixed P5 virus ($1.8 \times 10^4$ PFU/ml, Day 4). The lowest titer was observed again with the SP virus ($9.2 \times 10^3$ PFU/ml, Day 4).

The induction of cytopathic effects (CPE) was recorded daily for each virus (Table 4). The CPE for WN 01 and the LP virus was first observed on Day 5 and was completed (100%) 2 days later, whereas SP or mixed plaque population induced CPE at an earlier time point (Day 3) and completely destroyed the cell monolayer one day earlier (Day 6) than WN01 or the LP. The induction of CPE with YF-VAX® was first observed on Day 3 and the monolayer was fully destroyed by Day 6 post inoculation. The induction of CPE in HepG2 cells may be due to apoptotic activity of the M protein, as has been shown with wild type dengue viruses (Catteau et al., J. Gen. Virol. 84:2781-2793, 2003). These data showed that the SP virus variant grows to a lower titer than those of mixed or LP viruses, indicating that the M66 mutation may have rendered the virus less hepatotropic for humans.

Lack of Detection of ChimeriVax™-WN, SP Viruses after Inoculation of Monkeys with Mixed (SP and LP Viruses) P5 Vaccine Virus A total of 8 naïve cynomolgus monkeys that lacked detectable antibodies to Flaviviruses, such as WN, JE, and YF viruses (as determined by plaque reduction neutralization test (PRNT)), were inoculated by the subcutaneous route with either ChimeriVax™-WN02 (P5) (n=4) or YF-VAX® (n=4). The purpose of this study was to evaluate viremia, biodistribution, and possible toxicity of the ChimeriVax™-WN02 vaccine during a 3 day observation period. The inoculated dose was ~$1.25 \times 10^5$ PFU/0.5 mL and $5.5 \times 10^4$ PFU/mL for ChimeriVax™-WN02 and YF-VAX®, respectively. Animals were bled daily and sacrificed on Day 4 post inoculation. Blood was used to determine the viremia level using a standard plaque assay on Vero cells, whereas collected tissues were either flash frozen for viral analysis or preserved for histopathological evaluations.

Viremia was assessed on monkey sera collected from Day 1 (before inoculation) through Day 4 (prior to euthanization). The assay was performed either by using agarose double overlay and neutral red staining (to isolate and sequence individual plaques) or by methyl cellulose overlay and crystal violet staining (to measure the level of viremia) as described (Monath et al., J. Virol. 74(4):1742-1751, 2000). The magnitude and duration of viremia in ChimeriVax™-WN02 inoculated monkeys were higher than those of YF-VAX® (Table 5). The highest titer of viremia for YF-VAX® was 200 PFU/mL (animal MF21157, Day 4). The highest titer of viremia for ChimeriVax™-WN P5 virus was 1000 PFU/mL (animal MF21191F, Day 4). All animals (4/4) inoculated with ChimeriVax™-WN02 virus were viremic for 3 days post inoculation, whereas only 2/4 animals inoculated with YF-VAX® became viremic (for only 2 days) (Table 5).

Because animals inoculated with ChimeriVax™-WN02 virus had received a mixture of SP and LP viruses, it was necessary to isolate various SP and LP viruses from sera to identify the virus variant (S or L) responsible for the high level of viremia. Sera of all 4 monkeys obtained from Day 2 to Day 4 post inoculation were diluted 1:2 and 1:10 and used to inoculate duplicate wells of 6-well plates seeded with Vero cells. After addition of the second agarose overlay with neutral red, individual plaques (4 S and 3 L plaques) were picked and directly sequenced to identify the presence of the M66 mutant virus (Table 6). None of the isolated plaques contained the M66 mutation (L to P substitution), indicating that the M66 mutant virus is not responsible for the high level of viremia that was detected in these animals. Interestingly, 3 other mutations were observed in the M region (M60, M61, and M63). It is possible that either these virus variants had existed in low quantity in the ChimeriVax™-WN02 vaccine virus (which could not be detected by consensus sequencing), or that they have been generated in vivo (monkeys) by mutations in the genome of the LP virus variants.

Viremia and Neutralizing Antibody Responses in Hamsters Inoculated with ChimeriVax™-WN SP (PMS, P10), LP (PMS, P10), or Mixed (P5, SP, and LP) Viruses The animals used in this study were maintained in microseparators under BL2 and handled according to an animal protocol approved by the IACUC throughout the study. Three ChimeriVax™-WN02 viruses (SP, PMS, P10; LP, PMS, P10, and the mix SP and LP vaccine virus, P5) were used to infect 7 week-old female Golden Syrian hamsters (*Mesocricetus auratus*) from Harlan Sprague-Dawley. Each virus was injected into a group of 15 hamsters via the subcutaneous route in the inguinal area. The infection dose was $10^5$ pfu, and the inoculum volume was 100 μl. An additional group of 5 animals was similarly injected with 100 μl of virus diluent as sham control. On the day of virus infection (Day 0) and each following day until 5 days post infection, blood samples were collected by retro orbital bleeding from all animals except the sham control group. The animals were anaesthetized by inhalation of isofluorane to effect prior to bleeding and inoculation. Virus concentration in the test samples were determined by direct plaquing of a 0.1 mL of 1:10 diluted serum sample in duplicate wells of Vero cell culture grown in 12-well-plates (FIG. 5).

As is shown in FIG. 5, a higher level (3 logs of pfu on average) of peak viremia was observed in serum samples collected from LP virus infected hamsters, while a very low level (<10 pfu) of viremia was seen in blood samples of SP virus inoculated hamsters. When the proportion of SP virus was increased (to 50% as for the mixed plaque virus) in the inoculum, the peak viremia titer was lowered to approximately half of the LP virus induced viremia level. Additionally, the viremia peak time was delayed for at least 1 day to 4 days post infection.

These data demonstrated that the LP and SP variants isolated from the same parent virus, ChimeriVax™-WN02, have different biological properties. The LP virus replicated to a higher level at a faster rate, in comparison with the SP virus in hamsters. In addition, mixing SP virus with LP (P5 virus) apparently counteracts some properties of the LP virus. This is shown in the hamster infection experiments, in which the presence of virus in blood was reduced to lower levels and the virus replication kinetics were slowed in mixed virus infected hamsters. In sum, the mutation at M66 (L to P) present in SP variant virus significantly reduced its viremia in hamsters.

Example 2

ChimeriVax™-JE and ChimeriVax™-DEN1-4

Background and Summary

In the study described below, we prepared and characterized a new ChimeriVax™-JE seed virus using Vero cells grown in serum-free (SF) media in order to eliminate any concerns about possible contamination of the vaccine with the prion agent of bovine transmissible encephalopathy. During propagation in SF culture, uncloned virus accumulated mutations not seen previously in serum-containing culture, which appeared to be adaptations to SF growth conditions increasing the rate of virus replication. These mutations occurred in the E or M proteins (E-107 F to L or M-60 R to C mutations) and suggested a functional significance of the M protein in the process of virus replication, which became noticeable during virus growth in SF conditions (see amino acid R at position 60 of the M-protein shown in Example 1 (ChimeriVax™-WN). The effects of mutations within the M (M60, M5 in ChimeriVax™-JE) or the E proteins (E-107 in ChimeriVax™-JE, E202/204 in ChimeriVax™-DEN1 and -DEN3 and E251 in ChimeriVax™-DEN2) on biological properties of the vaccine were defined. All of these chimeric viruses have already been tested in clinical trials.

Materials and Methods

Cells and Media

Vero cells were originally received from the American Type Culture Collection (ATCC; Manassas, Va.; CCL 81; African green monkey kidney cells). These cells were adapted to grow in SF media and were obtained from Baxter (Orth, Austria) at passage 133, and then were used directly by seeding into flasks or seeded starting from a cell bank at passage 136. In all experiments, the passage level of the Vero cells did not exceed passage 149. Cells and viruses were grown at 36° C. under 7.5% $CO_2$. Cells were propagated under SF conditions.

ChimeriVax™-JE Variants

The virus was initiated (passage P1) by electroporation of SF Vero cells with the same in vitro RNA transcripts (stored at −80° C.) that were used previously for production of a non-SF ChimeriVax™-JE vaccine candidate tested in preclinical and clinical trials (Monath et al., Vaccine 20:1004-1018, 2002) and prepared as described previously (Chambers et al., J. Virol. 73:3095-3101, 1999). Amplification passages were generally done at an MOI of 0.001 pfu/cell and viral harvests were collected on days 3-4 postinfection (when CPE was ~10%), clarified by slow speed centrifugation, supplemented with 10% sorbitol, and stored at −80° C. Cloned variants were produced in Baxter Vero cells by three consecutive plaque purifications using a standard agar-neutral red overlay method in the presence of gamma-irradiated FBS (HyClone; FBS was used because the cells failed to form plaques under agar prepared with SF media) followed by amplification in SF conditions. Plaque assays to determine virus titers in indicated samples were performed using a single methyl cellulose overlay method with visualization of plaques by crystal violet on day 5 post-infection.

ChimeriVax™-DEN Viruses

ChimeriVax™-DEN1-4 vaccine viruses were prepared by electroporation of Vero cells with RNA transcripts prepared from viral cDNA. Progeny viruses were subjected to three rounds of plaque purification to produce the Pre-Master Seed (PMS) viruses at passage 7 (P7). Three further passages were carried out using U.S. current Good Manufacturing Practices (cGMP) to produce the Vaccine lot (P10 viruses). Some mutations appeared in the E genes of the chimeras after multiple passages in Vero cells (Guirakhoo et al., J. Virol. 78:4761-4775, 2004). One of these mutations (E 204 in ChimeriVax™-DEN1) significantly reduced viscerotropism of the virus in non-human primates (Guirakhoo et al., J. Virol. 78:9998-10008, 2004).

Consensus Sequencing

Consensus sequencing of indicated virus samples was performed as previously described (Pugachev et al., Vaccine 20:996-999, 2003). Briefly, virion RNA extracted with the TRIZOL LS reagent (Life Technologies-Gibco BRL) was amplified in five overlapping cDNA amplicons of 2-3 kb in length with Titan One-Tube RT-PCR kit (Roche). Amplicons were sequenced using a collection of JE- and YF-specific oligonucleotide primers of both positive and negative orientation and CEQ Dye Terminator Cycle Sequencing kit (Beckman). Sequencing reaction products were resolved with a CEQ2000XL automated sequencer (Beckman Coulter). The data were aligned and analyzed with Sequencher 4.1.4 (GeneCodes) software. Nucleotide heterogeneities were registered when a heterogeneous signal was observed in all chromatograms representing both plus- and minus-strand sequencing reactions. For some viruses, only the first of the five cDNA amplicons (Fragment I) was sequenced that includes the structural genes.

Neurovirulence in Suckling Mice

The maintenance and care of mice was in compliance with the National Institutes of Health guidelines for the humane use of laboratory animals. Pregnant outbred ICR female mice were purchased from Taconic Farms (Germantown, N.Y.). Newborn mice were fostered and mixed into new groups 6 days prior to inoculation. Groups of 8 day-old suckling mice were inoculated with 0.02 ml of the indicated virus samples by the intracerebral (IC) route. Serial 1:10 dilutions of viruses used for inoculations were done in MEM-10% FBS. Undiluted inocula were back-titrated and the exact doses of each dilution were calculated. Mortalities were recorded over a period of 21 days. The YF 17D control virus was YF-VAX® (Aventis Pasteur, Swiftwater, Pa.) reconstituted from a commercial vaccine vial.

Monkey Safety and Efficacy Tests

Experiment 1. The neurovirulence/toxicity profile of new clone C (M-60) ChimeriVax™-JE Vaccine Master Viral Bank (MVB; P11) and Production Viral Bank (PVB; P12) stocks, as compared to YF-VAX® control (YF 17D vaccine virus), was studied according to GLP standards in cynomolgus monkeys. Thirty-three (33) experimentally-naïve, Flavivirus-seronegative cynomolgus monkeys (as determined by HAI test) were assigned to treatment groups as shown in Table 9. All monkeys were dosed via a single IC injection on Day 1, observed for 30 days, and then euthanized and necropsied. The monkeys were evaluated for clinical signs (twice daily), and changes in food consumption (daily), body weight (weekly), and clinical pathology indices. Clinical scores were assigned according to a clinical scoring system, based on the World Health Organization (WHO) requirements for yellow fever vaccine (WHO, Technical Report Series, No. 872, 1998). Blood samples were collected pre-inoculation on Day 1 and on Days 3, 5, 7, 15, and 31 for clinical pathology analysis (serum chemistry and hematology parameters). Additional blood samples were collected on Day 1 (pre-dose) and Days 2-11 for quantitative viremia determinations, and on Day 1 (pre-dose) and Day 31 for neutralizing antibody titer analyses. A complete necropsy was performed on Day 31 and tissues collected for preservation. Tissue was prepared for histopathology of the liver, spleen, heart, kidney, and adrenal glands. Histopathology of the brain and spinal cord was performed according to the methods described by Levenbook et al. (J. Biol. Stand. 15:305, 1987) and incorporated into the WHO requirements for the yellow fever vaccine (WHO, 1998).

Experiment 2. This experiment was conducted to compare the viremia, immune response, and safety of ChimeriVax™-JE Vaccine [original uncloned vaccine P5 produced previously in LS5 Vero cells in the presence of FBS (BB-IND #9167, Serial #000) containing no mutations except for an E491 L to F change in the hydrophobic tail of E protein] and new Clone C (M-60 mutant) ChimeriVax™-JE purified vaccine bulk preparation (P13) over a 30-day period following a single subcutaneous (SC) administration in cynomolgus monkeys according to GLP standards. Eighteen (18) experimentally-naïve, Flavivirus-seronegative (by HAI test) cynomolgus monkeys were assigned to treatment groups as shown in Table 10. All monkeys were dosed once on Day 1 via SC injection at a single site in one arm. The monkeys were evaluated for clinical signs of toxicity (twice daily), changes in body weight (weekly), and serum chemistry, hematology, and coagulation parameters. Blood samples were collected on Day 1 (pre-inoculation) and Days 4, 7, 15, and 31 for serum chemistry, hematology, and coagulation parameter analysis. Additional blood samples were collected on Day 1 (pre-inoculation) and Days 2-11 for quantitative viremia analysis, and on Day 1 (pre-inoculation) and Day 31 for Japanese encephalitis virus-specific serum antibody titer analysis.

pH Threshold of Virus Inactivation (Indirect Fusion Assay)

One of the consequences of exposure of Flaviviruses to low pH (in the absence of cell membranes) is induction of irreversible conformational changes in the E protein and virus inactivation (loss of potency). In the presence of cell membranes, these conformational changes are necessary for fusion of viral membrane with those of cellular membranes, resulting in release of viral genome into the host cells. The pH threshold for fusion of mosquito-borne viruses such as WN, DEN, YF, and JE can be measured by fusion from within (FFWI) using the mosquito cell line C6/36 (Guirakhoo et al., Virology 169(1):90-99, 1989). We were not, however, able to demonstrate any FFWI with all of our ChimeriVax™ viruses, probably due to lack of sufficient growth of these viruses in mosquitoes and mosquito cell lines (Johnson et al., Am. J. Trop. Med. Hyg. 70(1):89-97, 2004). We therefore attempted to measure the loss of virus potency after exposure to different pH levels, in an assay designated here as an "Indirect Fusion Assay." This assay determines indirectly the pH threshold at which the fusion of viral membranes with those of cellular membranes occurs.

Fusion was performed at pH 7.0, 6.8, 6.6, 6.4, 6.2, 6.0, 5.8, 5.6, 5.4, and 5.0, using 1×MEM supplemented with 2 mM L-Glutamine, 2.7% sodium bicarbonate, 10% HI FBS, and 1% antibiotic/antimycotic solution [(100 U/ml of penicillin, 0.1 mg/ml of streptomycin, 0.25 µg/ml Amphotericin (Sigma)] adjusted to the proper pH with MES (Sigma). An aliquot of each virus at $1 \times 10^4$ plaque forming unit (PFU)/ml was diluted ($10^{-1}$ dilution) in each pH medium. After 10 minutes of exposure at each pH value, 50% heat inactivated (HI) FBS was added to each vial and the pH of each solution was neutralized with sodium bicarbonate. A volume of 100 µl of each virus at each pH value was used to infect Vero-cell monolayers (seeded at a density of $9 \times 10^5$ cells/well, in 6-well plates) to determine its titer. Infection was performed in duplicate, so as to cause 50 PFU/well; two non-infected wells of cells were kept per plate and served as negative controls. The pH 7.0 and 6.8 samples were taken as references. Titers were analyzed using the standard plaque assay. In this assay, Vero cells were infected with serial dilutions of viruses ($10^{-1}$ to $10^{-6}$) into duplicate wells. After infection, the Vero monolayers were overlaid with 1×MEM (Sigma) supplemented with 2 mM L-Glutamine, 2.7% sodium bicarbonate, 5% HI FBS, 1% antibiotic/antimycotic solution [100 U/ml of penicillin, 0.1 mg/ml of streptomycin, 0.25 µg/ml Amphotericin (Sigma)], and 44% of 0.6% agarose (Sigma). Cells were incubated for 4 days at 37° C., 5% $CO_2$, and were then overlaid with a second overlay containing 1×MEM supplemented with 2 mM L-Glutamine, 2.6% sodium bicarbonate, 2% HI FBS, 1% antibiotic/antimycotic solution, 44% of 0.6% agarose, and 3% of Neutral red solution (Sigma). The plaques were counted 24 hours after the addition of the second overlay to determine the titer of the virus defined in plaque forming unit (PFU) per milliliter.

Virus Penetration Assay According to Vlaycheva et al. (*J. Virol.* 76:6172-6184, 2002)

To demonstrate that the M-60 mutation (and E-107 mutation) facilitates penetration in SF Vero cells, SF Vero cells were infected with Clone A, C, and I viruses, appropriately diluted in SF medium, for 5, 10, 20, or 60 minutes, and then treated for 3 minutes with 0.1 M glycine, 0.1 M NaCl, pH 3.0, to inactivate extracellular virus. Wells were washed twice with PBS, and then monolayers were overlaid with methylcellulose, followed by staining plaques on day 5 with crystal violet. Efficiency of penetration was calculated as the percentage of observed plaque numbers after glycine treatment, as compared to control infected wells that were treated with PBS instead of glycine.

Clinical Trials of ChimeriVax™-JE

A clinical study (protocol H-040-003) was performed. The vaccine administered to healthy adult male and female subjects had the native sequence at M60 (arginine). Healthy adult subjects/group received a subcutaneous dose of graded doses of ChimeriVax™-JE vaccine, and various control groups were included. Eleven to 33 subjects were tested per dose group. Viremia was measured daily by plaque assay in Vero cell monolayers. The same assay and laboratory determined viremia levels in both trials.

Safety assessments included the recording of adverse events, body temperature, physical examination, and laboratory tests (including measurement of viremia levels). Viremia was seen in the majority of subjects receiving ChimeriVax™-JE.

A second study (protocol H-040-007) was performed in healthy adult male and female subjects in which 31 or 32 subjects per group received graded subcutaneous doses (3, 4, or 5 $\log_{10}$ PFU) of ChimeriVax™-JE containing the M60 cysteine mutation. The dose range was similar to that in the previous study in subjects who had received 2.8, 3.8, and 4.8 $\log_{10}$ PFU.

Results

Adaptive Mutations in Uncloned SF ChimeriVax™-JE Virus, and Preparation of Cloned Variants A diagram of virus samples produced in this study is shown in FIG. 6. The initial uncloned passage 2 (P2) sample (Pre-Master Seed candidate; PMS) was obtained in SF culture by transfecting cells with in vitro RNA transcripts that had been used to produce the vaccine in FBS-containing media for previous studies (Monath et al., Vaccine 20:1004-1018, 2002) followed by an additional amplification passage. The full genome of this virus was sequenced and shown not to contain any detectable mutations (Table 7) (note that the consensus sequencing approach does not detect minor subpopulations; detection limit of mutations is ~10%). Small-scale passages starting from this P2 virus to P10 level were performed in T25 flasks to analyze its genetic stability (g.s.) during prolonged propagation in SF culture (FIG. 6; g.s. passages). The full genome sequences of the g.s. P5 and g.s. P10 passages had one nucleotide change from C to T at nucleotide 935 resulting in an R to C amino acid substitution at residue M-60 (Table 7). This mutation was first detectable as heterogeneity at the g.s. P4 passage, but not g.s. P3.

Despite the results of small-scale genetic stability analysis, when three large scale manufacturing SF passages were performed from the uncloned P2 PMS in roller bottles to produce candidate uncloned Master Seed (P3) and the Production Seed (P4), and then in 100 L bioreactors to produce vaccine bulk (P5), a different mutation accumulated, an F to L amino acid change at residue E-107 due to a T to C change at nucleotide 1301 observed as a 50:50% heterogeneity (Table 7). This was an unacceptable mutation because it is a reversion from the SA14-14-2 sequence to wild type JE sequence at a critical attenuating residue (Arroyo et al., J. Virol. 75:934-942, 2001) and thus could potentially compromise safety of the vaccine.

Based on considerations mentioned below, cloned PMS candidates were then generated by plaque purification, to stabilize the SF vaccine and prevent accumulation of undesirable mutations, such as E-107. Plaque purification removes random mutations in uncloned virus introduced by in vitro transcription characterized by low fidelity of RNA synthesis compared to viral RNA synthesis by YF 17D-specific RNA polymerase (Pugachev et al., J. Virol. 78:1032-1038, 2004). Starting from the uncloned P2 PMS virus, a biological clone at P7, Clone A virus, which did not have any amino acid substitutions was obtained by three sequential plaque purifications followed by two amplification passages in SF medium, and was designated non-mutant P7 Clone A PMS. Its genome contained two silent nucleotide changes, at nucleotides 6952 and 7147 (Table 7). These changes were acceptable because they did not change the amino acid sequence of viral proteins and were located outside cis-acting RNA elements essential for efficient virus replication. A Clone C P10 virus containing the M-60 mutation (designated M-60 P10 Clone C PMS variant) was produced similarly starting from the P5 g.s. virus (FIG. 6). In addition to the desired M-60 mutation, it only contained a silent nucleotide change at nucleotide 3616 (Table 7). Additionally, research-grade Clone I and Clone E viruses were later also isolated from the uncloned P5 vaccine bulk virus by a single plaque purification (selecting large plaque) and one amplification passage in Vero cells. The Clone I contained a single amino acid change at the E-107 residue, which was a reversion to wild type from amino acid F to amino acid L. Thus, Clone I represents a pure population of the E-107 revertant. Clone E contained a single amino acid mutation at the N-terminus of the M protein, a Q to P amino acid change at residue M-5.

To ascertain genetic stability of the cloned PMS variants, relatively large scale g.s. passages mimicking manufacturing events were performed in SF culture (FIG. 6) (sequential passages designated S were done in T-225 flasks, and passages designates F were done in a 5 or 15 L bioreactor in which Vero cells were grown on Cytodex I microcarrier beads). Sequencing of the prM-E region only (cDNA Fragment I) was performed for the SSS and SSF samples (obtained by three Static passages, or two Static plus one Fermenter passages, respectively) of both candidates, and the FFF sample of the M-60 variant. None of these g.s. samples had any detectable mutations in the prM or E proteins of the viruses other than the M-60 mutation in Clone C. There was no trace of the E-107 mutation (Table 7). This indicated that an acceptable level of genetic stability was achieved due to plaque-purification. The high genetic stability of the M-60 variant was subsequently confirmed during manufacturing of new Master (P11) and Production Virus (P12) Seeds produced in cell factories and final vaccine bulk (P13) produced in a 50 L bioreactor, all of which retained the M-60 mutation, but had no other detectable changes in their full genomes by consensus sequencing.

Effects of the M-60 and E-107 Mutations on Virus Growth in SF Vero Cells

Figure 7:
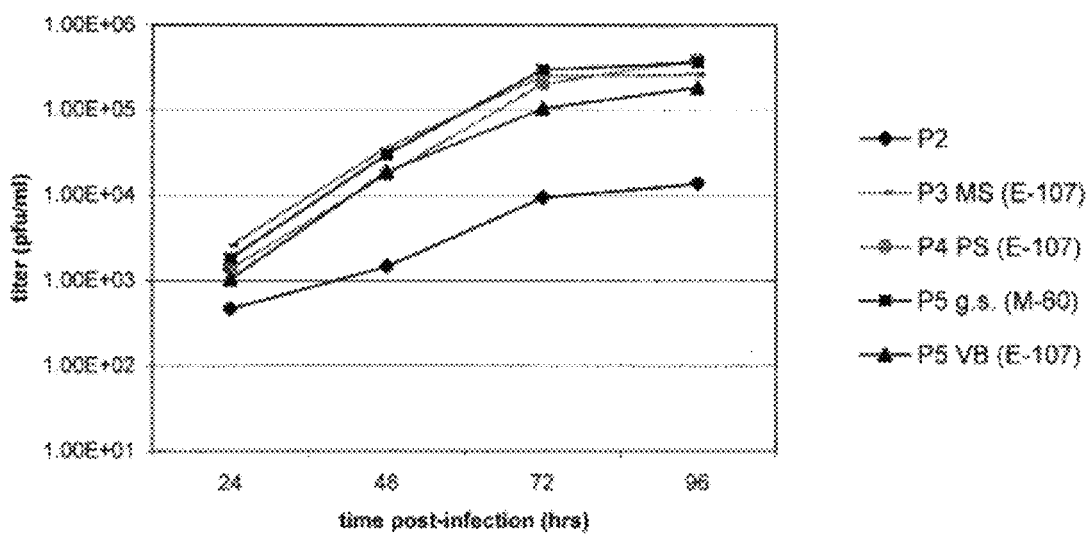
FIG. 7 is a graph showing growth curves of SF ChimeriVax™-JE viruses of the invention (uncloned P2, P3 MS (E-107), P4 PS (E-107), P5 g.s. (M-60), and P5 VB (E-107)) at the indicated times post-infection, which shows higher growth rates in SF culture of virus samples containing the M-60 [arginine (R)→cysteine (C) and E-107 phenylalanine (F)→leucine (L)] mutants as compared to nonmutant virus (P2).

To compare growth kinetics of the non-mutant, M-60 mutant, and E-107 mutant viruses in SF culture, cells were infected at an MOI of 0.001 pfu/ml (confirmed by back-titration) with the uncloned P2 PMS, the uncloned P5 g.s. sample (M-60 mutant), or the uncloned P5 vaccine bulk variant (containing the E-107 mutation), as well as the uncloned P3 Master Seed and P4 Production Seed viruses also containing a proportion of the E-107 mutation. Daily aliquots of virus-containing media were harvested and titrated by plaque assay. As shown in FIG. 7, the M-60 virus grew faster than the non-mutant P2 virus and produced significantly (more than 10 times) higher titers on days 3 and 4 post-infection. The E-107 mutation also enhanced virus replication similarly to the M-60 mutation. Thus, both the M-60 and E-107 mutations clearly conferred a growth advantage in SF culture. In support of this conclusion, daily samples from the S, SSS, and SSF g.s. passages of both the non-mutant lone A and M-60 mutant clone C viruses (see FIG. 6) were collected and titered to analyze growth kinetics with the result that the M-60 mutant invariably produced up to 10 times higher peak titers (close to 8 $\log_{in}$ pfu/ml) compared to non-mutant. Additionally, this conclusion was confirmed by comparing growth curves of Clones A, C, and I viruses in small scale SF culture, as Clones C (M-60) and I (E-107) invariably grew to higher titers than Clone A (non-mutant).

Effects of the M-60 and E-107 Mutations on Neurovirulence of ChimeriVax™-JE in Suckling Mice Mouse neurovirulence tests have been used to ensure that neurovirulence of ChimeriVax™ vaccine candidates does not exceed that of the YF 17D vector. The YF 17D vaccine is lethal for mice of all ages after IC inoculation. In contrast, ChimeriVax™ vaccines are significantly more attenuated. Since adult mice generally are not sensitive to detect subtle differences in neurovirulence, e.g., those due to a single amino acid change, a more sensitive suckling mouse model using survival analysis can be used for that purpose (Guirakhoo et al., Virology 257:363-372, 1999; Guirakhoo et al., Virology 298:146-159, 2002; Monath et al., J. Virol. 76:1932-1943, 2002).

Eight day-old suckling mice were inoculated IC with serial dilutions of the clone A P7 virus, clone C P10 virus (M-60 mutation), uncloned P5 vaccine bulk (E-107 mutation), as well as a previously produced FBS-containing control ChimeriVax™-JE virus (P5 Quality Control Reference Standard virus; no mutations), YF 17D positive control (YF-VAX®), or mock inoculated with diluent. Mortalities over a period of 21 days, median IC 50% lethal dose values ($LD_{50}$), and average survival times (AST) of mice that died are shown in Table 8. As expected, YF-VAX® was highly neurovirulent. Inoculation of 2.4 $\log_{10}$ PFU of this virus caused 100% mortality with a short AST of 8.8 days. Both the P7 non-mutant and P10 M-60 mutant clones were as highly attenuated as the original FBS-containing version of the chimera, with $LD_{50}$ values >5 $\log_{10}$ PFU and longer AST. Thus, the M-60 mutation does not change the highly attenuated phenotype of the vaccine in this animal model. The uncloned P5 vaccine bulk virus was significantly more virulent compared to the clones, with an IC $LD_{50}$ of 3.1 $\log_{10}$, PFU, but was less virulent compared to YF-VAX®. Subsequently, manufacturing passages (Master Seed, Production Seed, and Vaccine bulk) of the cloned M-60 vaccine were examined in this test under GLP conditions, with similar results. This confirmed the high genetic/phenotypic stability that was achieved by plaque purification and the use of M-60 mutation.

Analysis of Safety and Efficacy in Nonhuman Primates
Experiment 1

In this experiment, neurovirulence of Clone C (M-60 mutant) ChimeriVax™-JE Vaccine Master Viral Bank (MVB) and Production Viral Bank (PVB) were compared after IC administration to cynomolgus monkeys, using YF-VAX® virus as a control (Table 9).

No vaccine-related clinical signs or changes in food consumption, body weight, or serum chemistry, and hematology parameters were observed. Lymphoid hyperplasia, consisting of increased size and number of lymphoid nodules in the spleen, was noted for 9 of 11, 4 of 11, and 8 of 11 monkeys from Groups 1-3, respectively. Although this finding is a common background finding in cynomolgus monkeys, the group incidences were greater than normal in these monkeys and were considered secondary to the expected immune response induced by the vaccines. It is noteworthy that similar changes occurred in both the ChimeriVax™-JE treatment groups and the YF-VAX® reference control group. [Some of the monkeys in all three groups developed low level postinoculation viremia of short duration, which was within acceptable limits, and all animals seroconverted to viruses used for inoculation. On Day 31, yellow fever virus-specific neutralizing antibody titers for the YF-VAX®-treated monkeys ranged from 2.07 to >6.13 in the LNI assay, and no YF-VAX®-treated monkeys had cross-reactive antibodies to JE virus in the $PRNT_{50}$ assay. All ChimeriVax™-JE MVB vaccine-treated monkeys had JE neutralizing antibody titers ≥320 (range 320 to >20480) and had no cross-reacting antibody to YF virus in the LNI assay. All ChimeriVax™-JE PVB vaccine-treated monkeys had JE neutralizing antibody titers ≥160 (range 160 to >20480) and had no cross-reacting antibody to YF virus. There was no discernible relation between magnitude or duration of detectable viremia and the magnitude of JE-neutralizing antibody titer induction].

The ChimeriVax™-JE MVB and PVB preparations exhibited minimal neurovirulence in this test. The most comprehensive measure of neurovirulence in the monkey neurovirulence test for Flavivirus vaccines is the combined group mean lesion score, representing the average of the mean target area and mean discriminator area scores. The target areas in cynomolgus monkeys are the substantia nigra and the cervical and lumbar enlargements of the spinal cord and represent regions of the central nervous system (CNS) that are injured by all Flaviviruses. The discriminator areas are the globus pallidus, putamen, anterior and medial thalamic nuclei, and lateral thalamic nucleus, and represent regions of the CNS that are injured selectively by strains of YF 17D (and presumably other Flaviviruses) having different virulence properties, and that discriminate between a reference strain and a strain having increased neurovirulence. The combined mean lesion scores for monkeys treated with the ChimeriVax™-JE MVB and PVB preparations were significantly lower than for the YF-VAX® reference control group (p<0.05). The mean discriminator center scores for the two groups of monkeys treated with the ChimeriVax™-JE MVB and PVB were also significantly lower than for the YF-VAX® reference control group (p<0.05) (Table 9). There was no statistically significant difference between mean scores for the 2 groups of monkeys that received the ChimeriVax™-JE vaccine preparations, and both preparations demonstrated similarly low neurovirulence in the monkey neurovirulence test.

Thus, the results of the monkey neurovirulence test show that the new (M60, Clone C) plaque-purified MVB and PVB have a satisfactory safety profile. The test articles displayed no clinical toxicity, and had significantly lower discriminator and combined lesion scores on neuropathological examination than the reference control (YF-VAX®). The test articles did not differ from the reference control (YF-VAX®) in viscerotropism, as measured by quantitative viremia.

Experiment 2

This experiment was done to compare viremia, immune response, and safety of the original uncloned PS ChimeriVax™-JE Vaccine [produced previously in Vero cells in the presence of FBS, had no mutation except for E491 L to F change located in the hydrophobic tail of the E protein, which appears to be a benign mutation in terms of biological phenotype, and it has already been tested in clinical trials (Monath et al., J. Infect. Dis. 188:1213-1230, 2003; Monath et al., Vaccine 20:1004-1018, 2002)] and the new Clone C (M-60 mutant) ChimeriVax™-JE purified vaccine bulk (P13) following a single subcutaneous (SC) administration in cynomolgus monkeys. ChimeriVax™-JE virus was detected in the sera of 5 (100%) of 5 seronegative monkeys inoculated with original uncloned P5 ChimeriVax™-JE vaccine. The duration of viremia was 2-5 days with titers ranging from 20 to 790 PFU/mL. The mean peak viremia (±SD) was 244 (±310) PFU/mL, and the mean number of viremic days was 3.4 (±1.34) (Table 10).

ChimeriVax™-JE virus was detected in the sera of 4 (100%) of 4 seronegative monkeys inoculated with the new P13 JE vaccine purified bulk. The duration of viremia was 2-5 days with titers ranging from 50 to 290 PFU/mL. The mean peak viremia (±SD) was 160 (±123) PFU/mL, and the mean number of viremic days was 3.75 (±1.26) (Table 10). Neither mean peak viremia nor number of viremic days differed significantly between the two treatment groups (p-values 0.6290 and 0.7016, respectively; ANOVA).

All seronegative monkeys seroconverted following treatment with the original uncloned P5 ChimeriVax™-JE Vaccine or P13 JE Vaccine Purified Bulk (Table 10). On Day 31, sera from 5 (100%) of 5 monkeys inoculated with uncloned P5 Vaccine had JE virus neutralizing antibody titers ranging from 640 to 5120 (geometric mean titer=1689). Sera from 4 (100%) of 4 monkeys inoculated with P13 ChimeriVax™-JE Vaccine Purified Bulk had JE virus neutralizing antibody titers ranging from 320 to 2560 (geometric mean titer=761). Antibody titers did not differ significantly between treatment groups (p=0.2986, ANOVA).

Thus, the new M-60 vaccine was compared to the original uncloned ChimeriVax™-JE vaccine (no mutations except for E491) with respect to safety (viremia) and immunogenicity. The new vaccine was slightly less viscerotropic (a desirable feature) but still highly immunogenic. The differences in the magnitude of viremia and immunogenicity were not statistically significant.

Effects of M-5, M-60, and E-107 Mutations on the pH Threshold of Virus Infectivity ChimeriVax™-JE vaccine was produced by insertion of prM and E genes from SA14-14-2 strain of JE virus into backbone of YF 17D virus. The envelope of SA14-14-2 virus (present in ChimeriVax™-JE) differed from its parent SA14 virus by 10 amino acids: E107 L to F, E138 E to K, E176 I to V, E177 T to A, E227 P to S, E244 E to G, E264 Q to H, E279 K to M, E315 A to V, and E439 K to R (Guirakhoo et al., Virology 257:363-372, 1999). By site-directed mutagenesis it was shown that some of these residues were involved in attenuation of ChimeriVax™-JE virus. Mutants or revertants of ChimeriVax™-JE were selected to identify whether mutations have altered the pH threshold of these viruses. To determine whether the M-60, E-107, or M-5 mutations affect virus infectivity in a pH-dependent fashion, a standard assay for pH threshold of infectivity was performed as described in Materials and Methods. The following viruses were tested: (1) ChimeriVax™-JE non-mutant (clone A, P7 containing all 10 SA14-14-2 mutations in the E protein); (2) ChimeriVax™-JE E107 F to L revertant (clone I P6, containing 9 E protein mutations); (3) ChimeriVax™-JE M60 R to C mutant (clone C, P10 containing all 10 E protein mutations), and (4) M-5 Q to P mutant (clone E, P6 containing all 10 E protein mutations) (Table 12).

Non-mutant clone A P7 virus, M-60 mutant clone C P10 virus, M-5 mutant clone E, and uncloned P5 virus containing the E-107 mutation were treated with a range of decreasing pHs followed by titration of residual viral infectivity. Infectivity of three viruses (clone A control virus, Clone C M60 mutant, and Clone I E-107 mutant) started to drop uniformly after pH 6.0 and was lost at pH 5.8 (pH threshold 5.9), except for M5 mutant Clone E virus. The M-5 mutant had a significantly higher pH threshold (pH 6.3) compared to all other viruses (pH 5.9) (FIG. 5A). This is the first direct evidence that the ectodomain of M protein plays an essential role in the process of infection of cells by a Flavivirus. Thus, the N-terminus of M protein may function in the process of fusion triggered by a low pH in endosomes following virus adsorption and internalization, which is a function attributed previously solely to the envelope E protein.

The pH threshold of 5.9 for fusion of ChimeriVax™-JE viruses is lower than those described for other wild-type (wt) Flaviviruses (Guirakhoo et al., J. Gen. Virol. 72:1323-1329, 1991) and may be involved in attenuation of the virus.

Figure 8B:
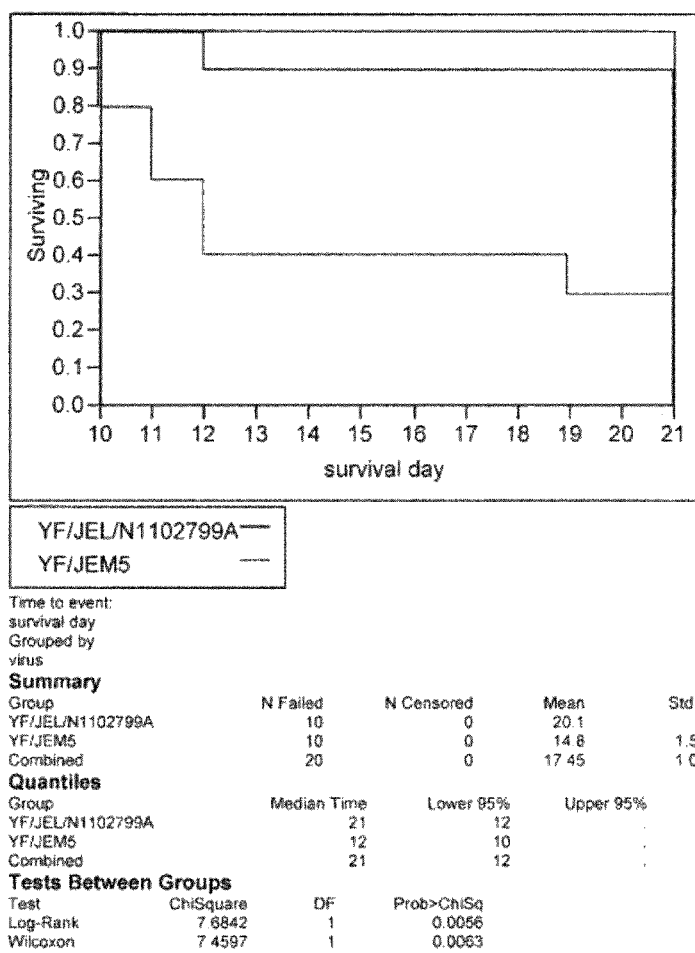
FIG. 8B is a Survival Plot of ChimeriVax™-JE vaccine (1.9 $\log_{10}$ PFU/dose, as determined by back titration of inocula) in comparison to ChimeriVax™-JE M5 mutant (1.4 $\log_{10}$ PFU/dose, as determined by back titration of inocula) in 3-4 day old suckling mice inoculated by the intracerebral route.
Figure 8C:
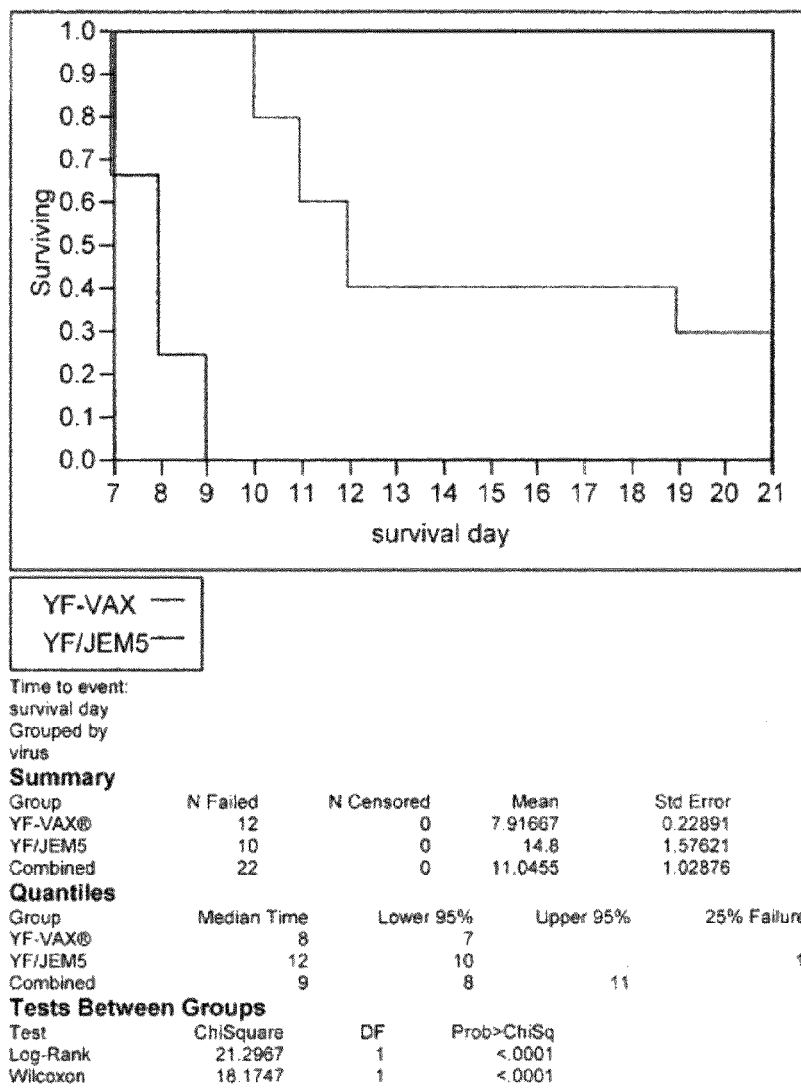
FIG. 8C is a Survival Plot of ChimeriVax™-JE M5 mutant virus (1.4 $\log_{10}$ PFU/dose as determined by back titration of inocula) in comparison to YF-VAX® (0.9 $\log_{10}$ PFU/dose as determined by back titration of inocula) in 3-4 day old suckling mice inoculated by the intracerebral route.
Figure 8D:
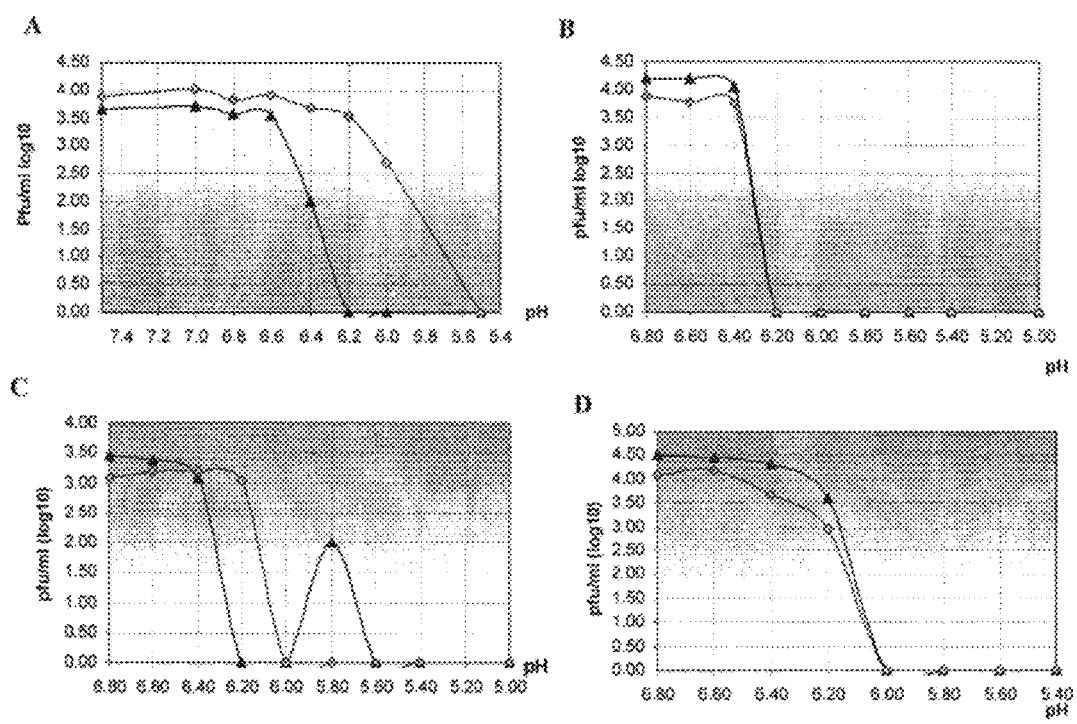
FIG. 8D shows the results of an Indirect Fusion assay, which provides a comparison of P7 and P10 of ChimeriVax™-DEN1-4 viruses. The virus output for each experiment was determined by standard plaque assay. A, ChimeriVax™-DEN1 PMS P7 (triangles) and P10 (diamonds); B, ChimeriVax™-DEN2 PMS P7 (triangles) and P10 (diamonds); C, ChimeriVax™-DEN3 PMS P7 (triangles) and P10 (diamonds); D, ChimeriVax™-DEN4 PMS P7 (triangles) and P10 (diamonds).

These data demonstrated that the E-107 mutation in the E region of ChimeriVax™-JE did not change the pH threshold for fusion. Generally, a low pH threshold means that more protonization of specific amino acids is required for conformational changes in the E-protein to occur that are necessary for transition from dimer to trimer. It is likely that one or more SA14-14-2 specific mutations (other than the E107 mutation, which is located within the conserved fusion peptide) are responsible for retaining the low pH threshold (pH 5.9) for fusion and consequently attenuated phenotype of the virus for the host. Apparently, the M-5 mutation is capable of increasing this threshold from 5.9 to 6.3, which is closer to those of wt Flaviviruses (Guirakhoo et al., Virology:169(1):90-99, 1989; Guirakhoo et al., J. Gen. Virol. 72:1323-1329, 1991). An increase in pH threshold for fusion should theoretically decrease the attenuated phenotype of the virus, because the viruses can fuse at higher pHs with less protonization required for transition to a fusion active state. This appeared to be true, since M5 virus inoculated at 1.4 $\log_{10}$ PFU into 3-4 day old suckling mice by the intracerebral route was significantly more virulent than the control virus (ChimeriVax™-JE vaccine virus without the M5 mutation) inoculated at 1.7 $\log_{10}$ PFU (p=0056) (FIG. 8B). Nevertheless, the M5 mutant virus (at a dose of 1.4 $\log_{10}$ PFU) remained significantly less neurovirulent than YF-VAX® (at a dose of 0.9 $\log_{10}$ PFU) in 3-4 day old suckling mice (FIG. 8C), indicating than the SA14-14-2 mutations within the envelope protein of the vaccine virus are still providing a sufficient level of attenuation for this virus.

Mutations in Other Chimeras that Affect pH Threshold for Fusion

The Indirect Fusion Assay was performed using two groups of each ChimeriVax™-DEN vaccines viruses: ChimeriVax™-DEN1-4 P7 containing no E protein mutations and ChimeriVax™-DEN1-4 P10 which contained single mutations in the E protein, except for ChimeriVax™-DEN4 P10. Viruses were incubated with media of different pH for 10 minutes at room temperature. The titers were determined, after returning the pH to the neutral pH, using a standard plaque assay. As shown in Table 13, the threshold for virus inactivation (fusion) was similar between P7 and P10 of ChimeriVax™-DEN2 and DEN4 viruses (pH 6.4). In contrast, the pH threshold for ChimeriVax™-DEN1 P10 was 0.4 units lower than that of ChimeriVax™-DEN1 P7 virus (pH 6.0 vs. pH 6.4). The difference in pH threshold was less dramatic for ChimeriVax™-DEN3 P10 virus (pH 6.4 vs. pH 6.2).

The maximum virus inactivation occurred at pH 6.2 for all P7 of ChimeriVax™-DEN viruses except for that of ChimeriVax™-DEN4, which was slightly lower (pH 6.0). It appeared that ChimeriVax™-DEN1 P10 required a significantly lower pH for complete inactivation (pH 5.6). Both ChimeriVax™-DEN1 and -DEN3 viruses contain an amino acid substitution at E-204 from K to R (the E-protein of DEN3 is 2 amino acids shorter than other 3 serotypes, therefore, the E-202 residue in this virus is homologous to E-204 in DEN1). The less dramatic difference in fusion threshold for the DEN3 chimera might be due to presence of WT (K) and mutant R amino acids (E204K/R) in P10 virus stock as was shown by consensus sequencing (K:R=50:50) (Pugachev et al., J. Virol. 78:1032-1038, 2004). Since no change in threshold for virus inactivation was observed with DEN2 P10 chimera, despite the E251 mutation, it can be concluded that the mutation at this residue is not involved in viral fusion process (FIG. 5D).

Figure 8E:
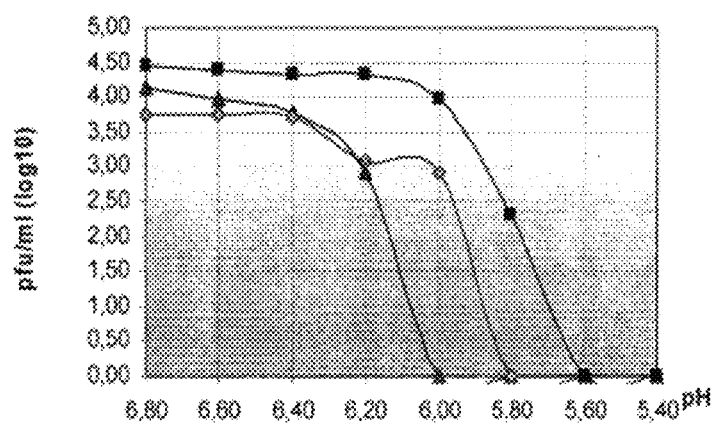
FIG. 8E shows the results of an Indirect Fusion assay with the ChimeriVax™-DEN3, comparing the PMS (P7) vaccine with the Vaccine lot (P10) and the P15 virus. The virus output for each experiment was determined by standard plaque assay. ChimeriVax™-DEN3 PMS P7 (triangles), P10 (diamonds), and P15 (squares).

In order to determine if the presence of K/R heterogeneity in P10 of ChimeriVax™-DEN3 was responsible for its non-dramatic change in pH threshold for fusion, the indirect fusion assay was performed using P7 (no mutation, E202K), P10 (50% mutation, E202K/R), and P15 (complete mutation, E202R) viruses. As shown in FIG. 8E, the pH threshold for inactivation (fusion) of ChimeriVax™-DEN3 P10 was at pH 6.2, which was between those for ChimeriVax™-DEN3 P7 (pH 6.4) and ChimeriVax™-DEN3 P15 (pH 6.0) viruses. Since the E202 K to R mutation was the only amino acid substitution detected in E-protein of these chimeras, it is most likely that this mutation is responsible for a 0.4 pH shift in pH threshold for fusion of the P15 virus.

Figure 8F:
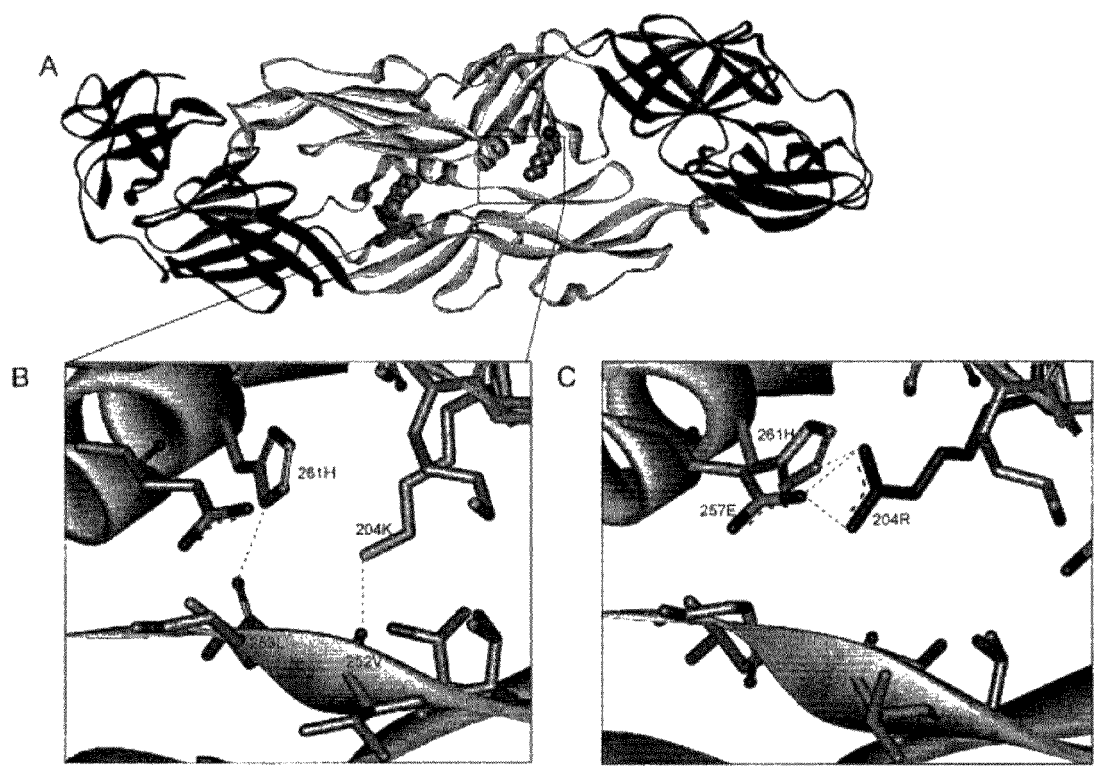
FIG. 8F shows the structure of a DEN1 E-protein dimer (amino acids 1 to 394) of ChimeriVax™-DEN1 virus (Guirakhoo et al., J. Virol. 78:9998-10008, 2004). (A) The position of the positively charged lysine (K) at residue 204 of the P7 (PMS, 204K) virus is shown by CPK (displays spheres sized to van der Waal radii) representation. Three structural domains are shown in black (domain I), light grey (domain II), and dark grey (domain III). (B) Close up of marked area in panel A. (C) The same area as in panel B from the E protein model of the mutant DEN1 virus (P10, 204R shown in black). Selected amino acids in panel B and C are shown in stick representation. Medium grey, carbon; dark grey, nitrogen; black, oxygen; light grey, sulfur.

As mentioned above, the E204 K to R mutation, which occurred during cell culture manufacture of the vaccine, lowered the pH threshold for fusion by 0.4 units of pH. The E204 K to R mutation appears to generate new intramolecular H bonds and a new salt bridge, which might have a significant impact on the dissociation of the E dimers. The structure of the ChimeriVax™-DEN1 (PMS, P7) E protein was modelled based on the atomic coordinates of 394 residues of the DEN2 E-protein ectodomain (S1 strain) determined in the presence of the detergent n-octyl-β-D-glucoside (Modis et al., Proc. Natl. Acad. Sci. U.S.A. 100:6986-6991, 2003). The K residue at position 204 was changed to R to mimic the mutant virus, and the modelling was repeated to represent the E-protein structure of the ChimeriVax™-DEN1 (VL, P10) virus (Guirakhoo et al., J. Virol. 78:9998-10008, 2004). The K residue at position 204 (204K) is located within a short loop, in a hydrophobic pocket lined by residues, which have been shown to influence neurovirulence or the pH threshold for fusion (Lee et al., Virology 232:281-290, 1997; Lindenbach et al., 2001 Flaviviridae: the viruses and their replication. *Fields Virology*, eds. Knipe D. M., and Howley P. M. [Lippincott Williams and Wilkins, Philadelphia], 1, 991-1004; Monath et al., J. Virol. 76:1932-1943, 2002). In FIG. 8F, the homology model of the E-homodimer structure of the vaccine virus (204R) is compared to that of the PMS (204K) virus. The side chains of 204K and 261H of one of E monomer appeared to make H bonds with the backbone atoms of 252V and 253L residues, respectively, on the opposite monomer. At position 204, the R in the E protein of the vaccine virus (VL P10) is predicted to reorient itself so that these hydrogen (H) bonds are lost. Instead the side chain of the mutant R is in proximity with 261H and 257E, resulting in the generation of new intramolecular H bonds between 204R and 261H, and probably of a new salt bridge between 204R and 257E. Since the pk of Histidine could be approximately 6.0, which is slightly below the fusion threshold (pH ~6.4), the initial hypothesis by Guirakhoo et al., (J. Virol. 78:9998-10008, 2004) was that the predicted new H bonds between 204R and 261H and the salt bridge between 204R and 257E, might affect the pH threshold of fusion. This theory turned out to be true, since the experiments described here revealed that the threshold for fusion of ChimeriVax™-DEN1 is around 6.0, which is 0.4 pH units lower than its P7 virus (pH 6.4). Apparently, the new intermolecular bonds introduced by R at residue 204 strengthen the association of the E-dimer so that the transition to low pH requires more protonization of appropriate residues (e.g., H 261). The lower threshold for fusion affects viscerotropism of the virus in monkeys and reduces neurovirulence for suckling mice inoculated by the i.c. route (Guirakhoo et al., J. Virol. 78:9998-10008, 2004).

The E202 K to R substitution in the E-protein of the ChimeriVax™-DEN3 P10 vaccine is homologous to the E204 mutation in the ChimeriVax™-DEN1 P10 vaccine. As with ChimeriVax™-DEN1 P10, ChimeriVax™-DEN3 P10 (heterogenous at residue 202 containing both K and R residue) showed a lower pH threshold (~0.2 pH unit) for fusion when compared to P7. The pH threshold for fusion was further lowered (0.4 pH unit, similar to ChimeriVax™-DEN1 P10) when the mutation was fixed at P15 of ChimeriVax™-DEN3. This data showed that the residue 202/204 may be a universal determinant of attenuation in all dengue viruses. Currently, ChimeriVax™-DEN3 and -DEN4 P10 vaccine viruses do not contain this mutation and both viruses induce a higher viremia levels in monkeys (Guirakhoo et al., J. Virol. 78:4761-4775, 2004) inoculated with a tetravalent vaccine formulation. It remains to be seen if K to R mutation in ChimeriVax™-DEN3 or ChimeriVax™-DEN4 would lower their viscerotropism in their hosts.

It was previously reported that WT-JE had a pH threshold for fusion of 6.4 (Guirakhoo et al., J. Gen. Virol. 72:1323-1329, 1991). In this study, all variants of ChimeriVax™-JE had a pH threshold of 5.9. The low pH threshold observed in these experiments is likely due to the presence of one or more of the 10 attenuating mutations in the envelope protein of ChimeriVax™-JE. This mutation might strengthen the association of the E-protein dimer so that a lower pH is required for dissociation and transition to trimer structure and subsequent fusion. The data presented here showed that neither the E107 F to L mutation (located in the cd-loop of the domain II of the E-protein) nor the E279 M to K mutation (located within the hydrophobic pocket of the domain II) was responsible for lowering the pH threshold. It is possible that other mutations in the JE E protein may affect the pH threshold for fusion. Analysis of the crystal structure of TBE virus E protein, which closely resembles the JE E protein, can help to predict the residues that, if altered, could change the pH threshold for fusion. Based on this model, it is likely that the mutations in residues E244 G and/or E264 H are responsible for a lower pH threshold, than the WT JE, for fusion of ChimeriVax™-JE virus.

Effect of the M-60 and E-107 Mutations on Efficiency of Virus Penetration

Figure 9A:
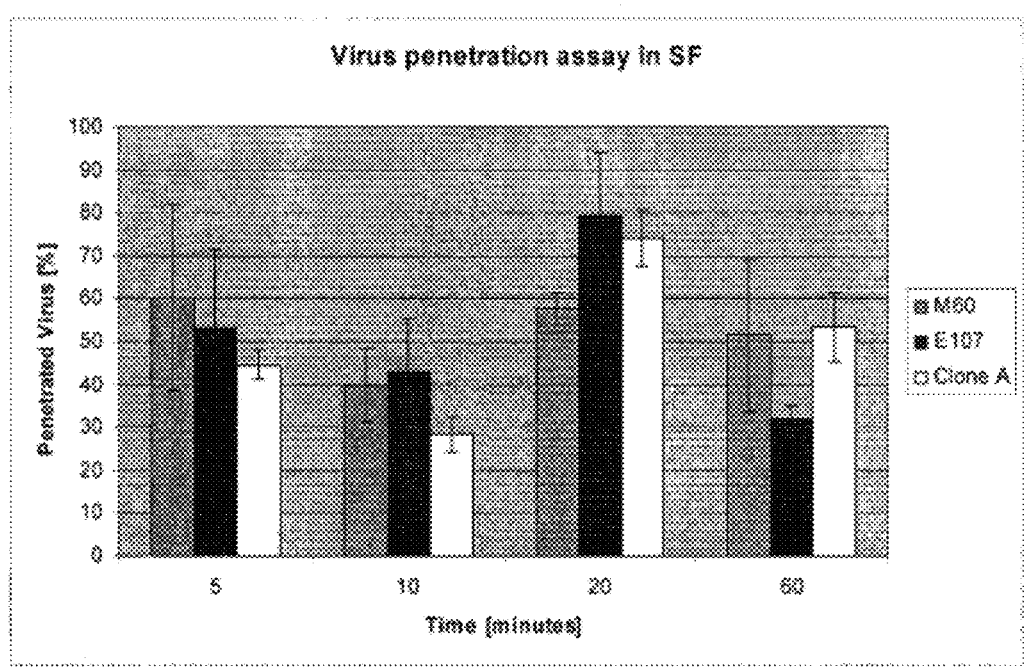
FIG. 9A is a graph showing the penetration efficiency of ChimeriVax™-JE viruses M60 mutant (Clone C), E107 mutant (Clone I), and non-mutant (Clone A) at the indicated times. These results indicate that the M60 mutation facilitates penetration in SF Vero cells apparent at the 5 and 10 minute time points. SF Vero cells were infected with appropriately diluted viruses (Clones A, C, and I in serum free medium) for 5, 10, 20, or 60 minutes, and then were treated for 3 minutes with a solution of 0.1 M glycine, 0.1 M NaCl, pH 3.0, to inactivate extracellular virus. Wells were washed twice with PBS, and then monolayers were overlaid with methyl-cellulose followed by staining plaques on day 5 with crystal violet. Efficiency of penetration is shown as percentages of observed plaque numbers after glycine treatment as compared to control infected wells that were treated with PBS instead of glycine.
Figure 9B:
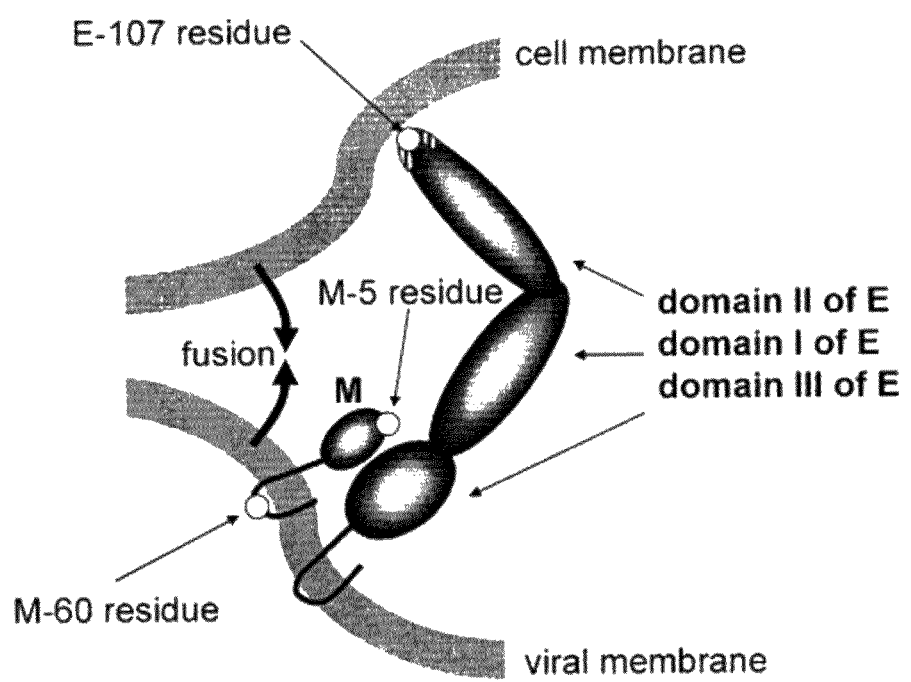
FIG. 9B is a schematic representation of the locations of the E-107, M-5, and M-60 amino acid residues in the envelope proteins E and M, illustrating the hypothetical effect of the M-5 residue on fusion. The dashed stretch at the tip of domain II of the E protein containing the E-107 residue represents the fusion peptide (c-d loop), which inserts into cell membrane (Rey et al., Nature 375:291-298, 1995). The M-5 residue is in the N terminal part of the ectodomain of the M protein. The E protein monomers rearrange into trimeric complexes, which fold to force the cell and virus membranes to fuse (Modis et al., Nature 427(6972):313-319, 2004). The M protein may be a functional component of the complexes, e.g., facilitating fusion of the viral membrane with the cell membrane via its interaction with the E protein. The M-60 residue is between the two C-terminal transmembrane stretches of M and may participate in the interaction of the cell and viral membranes during fusion.

The effects of the M-60 (Clone C virus) and E-107 (Clone I virus) mutations on virus penetration into SF Vero cells were examined using the method of Chambers (Vlaycheva et al., J. Virol. 76:6172-6184, 2002). In this experiment, SF Vero cells were infected with appropriately diluted viruses (to yield ~50 plaques/well at each time point) for 5, 10, 20, or 60 minutes. Un-internalized virus is inactivated by addition of acidic glycine solution, while control parallel wells are treated with PBS (neutral pH). Cells are washed with PBS and overlaid with methyl-cellulose overlay, followed by visualization and counting of plaques on day 5. The efficiency of penetration is presented as a percentage of the average number of plaques in glycine-treated wells relative to the number of plaques in control, PBS treated wells. A preliminary penetration test result is shown in FIG. 9A. It is important that the percentages of penetrated Clone C and Clone I viruses were higher than the non-mutant Clone A virus at 5 and 10 minute time points, at which effects of mutations on penetration are more likely to be detected. The result is not statistically significant as evidenced by standard deviation bars and needs to be confirmed in additional repeat tests. Nevertheless, this experiment suggested that both the M-60 and E-107 mutations could improve the efficiency of membrane fusion of ChimeriVax™-JE virus to cells grown in SF conditions. A possible mechanism of the effect of the M-60 and E-107 residues on process of membrane fusion is illustrated in FIG. 9B. The M-60 residue is located in the viral membrane, while the E-107 residue inserts into the cell membrane, and the two membranes are forced to fuse following low pH-dependent rearrangement of the E protein (which based on our data could be facilitated by the M protein ectodomain). A more appropriate amino acid at either of these two residues may facilitate fusion of the membranes.

Because our data establish for the first time that both the ectodomain of the M protein and its transmembrane domain are of functional significance, the entire M protein can now be considered an attractive target for mutagenesis to attenuate Flaviviruses for the purpose of developing new live attenuated vaccines. For example, random or specific (following further analysis of protein structure) amino acid changes, or deletions of increasing length, e.g., of 1, 2, 3, 4, 5, etc., amino acids, can be incorporated throughout the protein with the expectation that biological phenotype of the virus will be altered, resulting in significant attenuation.

Results from Clinical Trial

The viremia profiles of ChimeriVax™-JE with the arginine and cysteine M60 residues as obtained from the clinical trials noted above are compared in Tables 11 A and B. In subjects receiving ChimeriVax™-JE M60 arginine, 67-100% of the subjects were viremic on one or more days, compared to 29-50% for subjects receiving ChimeriVax™-JE M60 cysteine. The mean maximum viremia levels in subjects receiving ChimeriVax™-JE M60 arginine ranged from 13 to 40 PFU/ml, compared to mean maximum viremia levels of 3.5-6.3 PFU/ml in the case of ChimeriVax™-JE M60 cysteine. The duration of viremia was also notably longer in the case of ChimeriVax™-JE M60 arginine.

These data demonstrated that the level of viremia is notably lower in the case of the vaccine containing the M60 mutation. Viremia is a measure of viscerotropism (virulence) of the vaccine virus. A vaccine with reduced viremia is considered safer, since cell damage and dysfunction of organs sustaining virus replication and contributing to viremia is reduced, as is the likelihood that the virus will cross the blood brain barrier and invade the central nervous system. In other experiments, it was shown that the M60 mutant was as highly immunogenic in humans as the non-mutant.

TABLE 1

Consensus sequence of small plaque (P10 PMS) (P/N IT-0116; L/N I020504A) (plaque purified from p5 Run 1 Vaccine Lot).

| Position | Amino Acid change | NT position | NT change |
|---|---|---|---|
| M(66) | Leucine → Proline | 954 | CTA → CCA |
| E(313) | Glycine → aRginine | 1919 | GGG → AGG |
| | Asparagine (silent) | 2926 | AAC → AAT |
| | Glycine (silent) | 7126 | GGA → GGG |

TABLE 2

Consensus sequence of large plaque PMS (P10, PMS) (P/N IT-0117; L/N I030804A) (derived from p5 Run 1 Vaccine Lot).

| Position | Amino Acid change | NT position | NT change |
|---|---|---|---|
| E(313) | Glycine → aRginine | 1919 | GGG → AGG |
| | Glycine (Silent) | 7126 | GGA → GGG |

TABLE 3

Sequence of large plaques isolated after 2 additional passages of the S plaque PMS (p10) in Vero cells under serum free conditions.

| LP Isolate | Position | Amino Acid Change | NT # | NT change | Immuno-Stain |
|---|---|---|---|---|---|
| #3, #7, #8, #9, #10, #11, #12, #13, #14, #18, #19, #20 | M66 | Leucine → Proline | 954 | CTA → CCA | SP |
| #1 | M62 | Valine → Methionine | 941 | TGT → TAT | SP |
| | M66 | Leucine → Proline | 954 | CTA → CCA | |
| #2 | M62 | Valine → Glycine | 942 | GTG → GGG | SP |
| | | Valine → Glutamic Acid | 942 | GTG → GAG | |
| | M66 | Leucine → Proline | 954 | CTA → CCA | |
| #4 | M63 | Phenylalanine → Serine | 945 | TTT → TCT | LP |
| #5 | M62 | Valine → Alanine | 942 | GTG → GCG | SP |
| | M66 | Leucine → Proline | | | |
| #6 | M66 | Leucine → Proline | 954 | CTA → CCA | SP |
| | M64 | Valine (Silent) | 949 | GTC → GTT | |
| #15 | M62 | Valine → Alanine | 942 | GTG → GCG | SP |
| | M66 | Leucine → Proline | 954 | CTA → CCA | |
| #16 | wt | Leucine | N/A | CTA | LP/SP |
| | M66 | Leucine → Proline | 954 | CTA → CCA | |
| #17 | M64 | Valine → Isoleucine | 947 | GTC → ATC | SP |
| | M66 | Leucine → Proline | 954 | CTA → CCA | |

TABLE 4

Observed CPE for HepG2.

| | \multicolumn{9}{c}{Days Post Infection} |
|---|---|---|---|---|---|---|---|---|---|
| | 0 | 1 | 2 | 3 | 4 | 5 | 6 | 7 | 8 |
| WN01 | 0% | 0% | 0% | 0% | 0% | 30% | 90% | ~100% | 100% |
| WN02 P5 | 0% | 0% | 0% | 5% | 30% | 50% | ~100% | 100% | |
| WNL | 0% | 0% | 0% | 0% | 0% | 30% | 90% | ~100% | 100% |
| WNS | 0% | 0% | 0% | 5% | 30% | 50% | ~100% | 100% | |
| YF/17D | 0% | 0% | 0% | 20% | 50% | 70% | ~100% | 100% | |

| | 0 | 1 | 2 | 3 | 4 | 5 | 6 | 7 | 8 |
|---|---|---|---|---|---|---|---|---|---|
| WN01 | 0% | 0% | 0% | 0% | 0% | 30% | 90% | ~100% | 100% |
| WN02 P5 | 0% | 0% | 0% | 5% | 30% | 50% | ~100% | 100% | |
| WNL | 0% | 0% | 0% | 0% | 0% | 30% | 90% | ~100% | 100% |
| WNS | 0% | 0% | 0% | 5% | 30% | 50% | ~100% | 100% | |
| YF/17D | 0% | 0% | 0% | 20% | 50% | 70% | ~100% | 100% | |

TABLE 5

Viremia in monkeys inoculated with ChimeriVax ™-WN02 vaccine or YF-VAX ®.

| Treatment Group | Monkey Number | Day 1** | Day 2 | Day 3 | Day 4 |
|---|---|---|---|---|---|
| YF-Vax ® | MF21157M | 0 | 0 | 20 | 200 |
| YF-Vax ® | MF21214F | 0 | 0 | 0 | 0 |
| YF-Vax ® | MF21151M | 0 | 0 | 10 | 60 |
| YF-Vax ® | MF21252F | 0 | 0 | 0 | 0 |
| ChimeriVax ™-WN Vaccine (P5) | MF2808M | 0 | 30 | 790 | 820 |
| ChimeriVax ™-WN Vaccine (P5) | MF21205F | 0 | 50 | 160 | 100 |
| ChimeriVax ™-WN Vaccine (P5) | MF21139M | 0 | 10 | 180 | 70 |
| ChimeriVax ™-WN Vaccine (P5) | MF21191F | 0 | 80 | 970 | 1000 |

*Viremia expressed as pfu/mL
**Day 1: Study Day 1, monkeys inoculated on Study Day 1
Zero PFU/mL means below the limit of detection, theoretical assay cutoff = 10 PFU/mL

TABLE 6

Sequence of the M region of YF-WN chimera obtained directly from a plaque isolate from viremic monkeys inoculated with WN02 vaccine virus.

| Monkey # | Day of viremia | Plaque Isolate # | Visible Plaque Morphology (at time of picking) | M66 Present? | Additional M Mutations |
|---|---|---|---|---|---|
| 21205 | 4 | #4 | SP | NO | NO |
| 2808 | 3 | #8 | SP | NO | NO |
| 2808 | 3 | #9 | LP | NO | M60 (R to G) |
| 21191 | 2 | #10 | LP | NO | NO |
| 21191 | 1 | #14 | SP | NO | M61 (V to A) |
| 21191 | 1 | #15 | SP | NO | NO |
| 21191 | 1 | #16 | LP | NO | M63 (F to S) |

TABLE 7

Nucleotide and amino acid sequences of the uncloned and cloned SF ChimeriVax ™-JE samples (see FIG. 6).

| Candidate | Passage | Part of genome sequenced | Protein - a.a. No.[b] | Nt No.[a] | Nucleotide change/ heterogeneity | Amino acid change/ heterogen. | Comments |
|---|---|---|---|---|---|---|---|
| Uncloned | P2 (PMS) | Full genome | — | — | — | — | No mutations |
| | P3 g.s. from PMS | a.a. M-60 only | — | — | — | — | No M-60 mutation |
| | P4 g.s. from PMS | a.a. M-60 only | M-60 | 935 | c/T | R/C | M-60 mutation first detectable and dominant |
| | P5 g.s. from PMS | Full genome | M-60 | 935 | C to T | R to C | M-60 mutation located in the cytoplasmic hydrophilic stretch of the M protein |
| | P10 g.s. from PMS | 95% full genome | M-60 | 935 | C to T | R to C | M-60 is the only detected mutation |
| | cGMP P3 (MS) Baxter | prM-E | E-107 | 1301 | T/c | F/L | Reversion to WT first detectable |
| | cGMP P4 (PS) Baxter | prM-E | E-107 | 1301 | T/c | F/L | Reversion to WT |
| | cGMP P5 (VB) Baxter | Full genome | E-107 | 1301 | T/C | F/L | Reversion to WT (~50%). |
| M-60 mutant clone C | P10 PMS | Full genome | M-60 | 935 | C to T | R to C | Desired/expected |
| | | | NS2A-26 | 3616 | A to G | — | Silent |
| | SSS P13 g.s. | prM-E | M-60 | 935 | C to T | R to C | No subpopulations detected |
| | SSF P13 g.s. | prM-E | M-60 | 935 | C to T | R to C | No subpopulations detected |
| | FFF P13 g.s. | prM-E | M-60 | 935 | C to T | R to C | No subpopulations detected |
| Non-mutant clone A | P7 PMS | Full genome | NS4B-12 | 6952 | C to T | — | Silent |
| | | | NS4B-77 | 7147 | T to C | — | Silent |
| | SSS P10 g.s. | prM-E | — | — | — | — | No subpopulations detected |

TABLE 7-continued

Nucleotide and amino acid sequences of the uncloned and cloned SF ChimeriVax ™-JE samples (see FIG. 6).

| Candidate | Passage | Part of genome sequenced | Protein - a.a. No.[b] | Nt No.[a] | Nucleotide change/ heterogeneity | Amino acid change/ heterogen. | Comments |
|---|---|---|---|---|---|---|---|
| | SSF P10 g.s. | prM-E | — | — | — | — | No subpopulations detected |

[a]From the beginning of the genome
[b]From the N-terminus of indicated protein

TABLE 8

Neurovirulence of clone A P7, clone C P10, uncloned P5, FBS-containing standard, and YF-VAX ® viruses in 8 day-old suckling mice.

| Virus | a.a. change | Dilution | Inoculation Dose Log$_{10}$ PFU | Mortality No. dead/No. inoculated (% mortality) | LD$_{50}$ Log$_{10}$ PFU | AST days |
|---|---|---|---|---|---|---|
| Clone A P7 PMS | None | Neat | 5.1 | 1/11 (9%) | >5.1 | 11 |
| | | 10$^{-1}$ | 4.1 | 3/11 (27%) | | 14 |
| | | 10$^{-2}$ | 3.1 | 1/10 (10%) | | 14 |
| | | 10$^{-3}$ | 2.1 | 1/12 (8.3%) | | 11 |
| | | 10$^{-4}$ | 1.1 | 0/12 (0%) | | N/A |
| Clone C P10 PMS | M-60 | Neat | 5.5 | 2/11 (18%) | >5.5 | 11 |
| | | 10$^{-1}$ | 4.5 | 0/10 (0%) | | N/A |
| | | 10$^{-2}$ | 3.5 | 1/12 (8.3%) | | 13 |
| | | 10$^{-3}$ | 2.5 | 0/12 (0%) | | N/A |
| | | 10$^{-4}$ | 1.5 | 0/12 (0%) | | N/A |
| Uncloned P5 VB | E-107 | Neat | 5.3 | 9/10 (90%) | 3.1 | 9.4 |
| | | 10$^{-1}$ | 4.3 | 10/11 (91%) | | 10.7 |
| | | 10$^{-2}$ | 3.3 | 9/11 (82%) | | 11.8 |
| | | 10$^{-3}$ | 2.3 | 1/11 (9%) | | 14 |
| | | 10$^{-4}$ | 1.3 | 1/10 (10%) | | 9 |
| FBS-containing standard virus | none | Neat | 5.3 | 0/10 (0%) | >5.3 | N/A |
| | | 10$^{-1}$ | 4.3 | 0/10 (0%) | | N/A |
| | | 10$^{-2}$ | 3.3 | 2/9 (22%) | | 16.5 |
| | | 10$^{-3}$ | 2.3 | 0/11 (0%) | | N/A |
| YF-VAX ® | N/A | 10$^{-1}$ | 2.4 | 10/10 (100%) | <2.4 | 8.8 |
| Sham (MEM-10% FBS) | N/A | N/A | N/A | 0/10 (0%) | N/A | N/A |

TABLE 9

Neurovirulence for Cynomolgus Monkeys of M-60 (Clone C) Master and Production seeds vs. YF-VAX ® control.

| Group No. | Number Male/ Female | Treatment | Dose (PFU[1]/ 0.25 mL inoculum) | Lesion scores (group mean; SD (ran | | |
|---|---|---|---|---|---|---|
| | | | | Target areas | Discriminator Areas | Combined |
| 1 | 6/5 | YF-VAX ® (Commercial Yellow Fever Vaccine) | 5.5 × 10$^4$ | 0.436 SD 0.190 (0.25-0.81) | 0.610 SD 0.417 (0.25-1.38) | 0.526 SD 0.194 (0.29-0.87) |
| 2 | 5/6 | ChimeriVax ™-JE Vaccine Master Viral Bank P11 (M-60) | 1.0 × 10$^5$ | 0.196 SD 0.210 (0-0.56) | 0.183 SD 0.177 (0-0.44) | 0.191 SD 0.163 (0-0.47) |
| 3 | 6/5 | ChimeriVax ™-JE Vaccine Production Viral Bank P12 (M-60) | 1.0 × 10$^5$ | 0.223 SD 0.349 (0-0.56) | 0.106 SD 0.138 (0-0.31) | 0.167 SD 0.231 (0-0.63) |

[1]PFU = plaque-forming units

[2]4 of 11, 2 of 11, and 1 of 11 animals in groups 1, 2, and 3, respectively, were excluded from score calculations because they were found to be JE-seropositive on day 1 (pre-inoculation) in a retrospective PRNT50 test, which is more sensitive than HAI test used for prescreening.

TABLE 10

Comparison of magnitudes of viremia and immunogenicity in cynomolgus monkeys inoculated SC with the original uncloned P5 ChimeriVax ™-JE vaccine produced in FBS-containing medium (containing no mutations except for E491) and the new Clone C P13 purified vaccine bulk (M-60 mutant).

| Group No. | Number of Male/Female | Sample | Dose (PFU) | Viremia[1] Mean peak titer ± SD (PFU/ml) | Viremia[1] Mean duration ± SD (days) | Neutralizing antibody titer on day 31 (geometric mean PRNT$_{50}$ titer (min., max))[1] |
|---|---|---|---|---|---|---|
| 1 | 3/3 | Diluent | 0 | 0 | 0 | N/D |
| 2 | 3/3 | ChimeriVax ™-JE original uncloned P5 Vaccine | $1.0 \times 10^4$ | 244 ± 310 | 3.4 ± 1.34 | 1689 (640, 5120) |
| 3 | 3/3 | Clone C (M-60) ChimeriVax ™-JE vaccine, purified bulk, P13 | $1.0 \times 10^4$ | 160 ± 123 | 3.75 ± 1.26 | 761 (320, 2560) |

[1] 2 of 6, 1 of 6, and 2 of 6 animals in groups 1, 2, and 3, respectively, were excluded from calculations of the values because they were found to be JE-seropositive on day 1 (pre-inoculation) in a retrospective PRNT50 test, which is more sensitive than HAI test used for prescreening.

TABLE 11A

Viremia profiles in subjects enrolled in Study H-040-003 in which ChimeriVax ™-JE with the M60 arginine amino acid was administered. The dose range in bold is similar to that given in another study (H-040-007) in which the mutant M-60 cysteine vaccine was administered.

| | Dose Log$_{10}$ PFU ChimeriVax ™-JE M60 arginine | | | | |
|---|---|---|---|---|---|
| Viremia | 5.8 (n = 10) | 4.8 (n = 33) | 3.8 (n = 11) | 2.8 (n = 11) | 1.8 (n = 11) |
| Viremic on 1 or more days [No. viremic/total (%)] | 5/10 (50%) | 22/33 (67%) | 9/11 (82%) | 11/11 (100%) | 9/11 (82%) |
| Mean peak viremia (PFU/mL) | 7.0 | 13.0 | 16.4 | 40.9 | 18.2 |
| Range in peak viremia (PFU/mL) | 0-20 | 0-40 | 0-50 | 0-220 | 0-50 |
| Mean duration (days) | 0.9 | 1.6 | 1.4 | 2.7 | 2.2 |
| Range in duration (days) | 0-4 | 0-5 | 0-3 | 1-6 | 0-5 |

TABLE 11B

Viremia profiles in subjects enrolled in Study H-040-007 in which ChimeriVax ™-JE with the M60 cysteine amino acid was administered.

| | Dose Log$_{10}$ PFU ChimeriVax ™-JE M60 cysteine | | |
|---|---|---|---|
| Viremia | 5.0 N = 31 | 4.0 N = 32 | 3.0 N = 32 |
| Viremic on 1 or more days [No. viremic/total (%)] | 9/31 (29%) | 16/32 (50%) | 13/32 41%) |
| Mean peak viremia (PFU/mL) | 3.5 | 6.3 | 4.4 |
| Range in peak viremia (PFU/mL) | 0-20 | 0-30 | 0-10 |
| Mean duration (days) | 0.3 | 0.8 | 0.6 |
| Range in duration (days) | 0-2 | 0-4 | 0-3 |

TABLE 12

Values of pH threshold for fusion found with the fusion assay for each ChimeriVax ™-JE vaccine.

| Virus | pH threshold for fusion |
|---|---|
| ChimeriVax ™-JE parent, clone A P7 (contains all 10 E mutations) | 5.9 |
| ChimeriVax ™-JE clone C P10 (M60 R to C mutant, contains all 10 E mutations) | 5.9 |
| ChimeriVax ™-JE clone I P6 (E107 F to L revertant, contains 9 E mutations) | 5.9 |
| ChimeriVax ™-JE clone E P6 (M5 Q to P mutant, contains all 10 E mutations) | 6.3 |

TABLE 13

Values of pH threshold for fusion found with the indirect fusion assay for each couple of ChimeriVax ™-DEN P7 and P10.

| Virus | pH Threshold for fusion |
|---|---|
| ChimeriVax ™-DEN1 PMS P7 | 6.4 |
| ChimeriVax ™-DEN1 VL P10 | 6.0 |
| ChimeriVax ™-DEN2 PMS P7 | 6.4 |
| ChimeriVax ™-DEN2 VL P10 | 6.4 |
| ChimeriVax ™-DEN3 PMS P7 | 6.4 |
| ChimeriVax ™-DEN3 VL P10 | 6.2 |
| ChimeriVax ™-DEN4 PMS P7 | 6.4 |
| ChimeriVax ™-DEN4 VL P10 | 6.4 |

TABLE 14

Engineering of YF/Flavivirus chimeras

| Virus | Chimeric C/prM junction[1] | Chimeric E/NS1 junction[2] | 5' ligation[3] | 3' ligation[4] | Sites[5] eliminated or (created) |
|---|---|---|---|---|---|
| YF/WN | X-cactgggagagcttgaaggtc (SEQ ID NO: 1) | aaagccagttgcagccgcggtttaa (SEQ ID NO: 2) | AatII | NsiI | |
| YF/DEN-1 | X-aaggtagactggtgggctccc (SEQ ID NO: 3) | gatcctcagtaccaaccgcggtttaa (SEQ ID NO: 4) | AatII | SphI | SphI in DEN |
| YF/DEN-2 | X-aaggtagattggtgtgcattg (SEQ ID NO: 5) | aaccctcagtaccaccgcggtttaa (SEQ ID NO: 6) | AatII | SphI | |
| YF/DEN-3 | X-aaggtgaattgaagtgctcta (SEQ ID NO: 7) | accccagcaccacccgcggtttaa (SEQ ID NO: 8) | AatII | SphI | XhoI in DEN (SphI in DEN) |
| YF/DEN-4 | X-aaaaggaacagttgttctcta (SEQ ID NO: 9) | acccgaagtgtcaaccgcggtttaa (SEQ ID NO: 10) | AatII | NsiI | |
| YF/SLE | X-aacgtgaatagttggatagtc (SEQ ID NO: 11) | accgttggtcgcacccgcggtttaa (SEQ ID NO: 12) | AatII | SphI | AatII in SLE |
| YF/MVE | X-aatttcgaaaggtggaaggtc (SEQ ID NO: 13) | gaccggtgtttacagccgcggtttaa (SEQ ID NO: 14) | AatII | AgeI | (AgeI in YF) |
| YF/TBE | X-tactgcgaacgacgttgccac (SEQ ID NO: 15) | actgggaacctcacccgcggtttaa (SEQ ID NO: 16) | AatII | AgeI | (AgeI in YF) |

[1,2] The column illustrates the oligonucleotide used to generate chimeric YF/Flavivirus primers corresponding to the C/prM or E/NS1 junction. (See text). X = carboxyl terminal coding sequence of the YF capsid. The underlined region corresponds to the targeted heterologous sequence immediately upstream of the NarI site (antisense - ccgcgg). This site allows insertion of PCR products into the Yfm5.2 (NarI) plasmid required for generating full-length cDNA templates. Other nucleotides are specific to the heterologous virus. Oligonucleotide primers are listed 5' to 3'.
[3,4] The unique restriction sites used for creating restriction fragments that can be isolated and ligated in vitro to produce full-length chimeric cDNA templates are listed. Because some sequences do not contain convenient sites, engineering of appropriate sites is required in some cases (footnote 5).
[5] In parentheses are the restriction enzyme sites that must be created either in the YF backbone or the heterologous virus to allow efficient in vitro ligation. Sites not in parentheses must be eliminated. All such modifications are done by silent mutagenesis of the cDNA for the respective clone. Blank spaces indicate that no modification of the cDNA clones is required.

ChimerivaxWN02 Final Product Bottled (Run 1)
L/N# 02H01; P/N# FP-0008
[Strand]

```
  1 NGTAAATCCT GTGTGCTAAT TGAGGTGCAT TGGTCTGCAA

41 ATCGAGTTGC TAGGCAATAA ACACATTTGG ATTAATTTTA

81 ATCGTTCGTT GAGCGATTAG CAGAGAACTG ACCAGAACAT
                                              M
121 GTCTGGTCGT AAAGCTCAGG GAAAAACCCT GGGCGTCAAT
      S   G   R   K   A   Q   G   K   T   L   G   V   N

161 ATGGTACGAC GAGGAGTTCG CTCCTTGTCA AACAAAATAA
    M   V   R   R   G   V   R   S   L   S   N   K   I

201 AACAAAAAAC AAAACAAATT GGAAACAGAC CTGGACCTTC
    K   Q   K   T   K   Q   I   G   N   R   P   G   P   S

241 AAGAGGTGTT CAAGGATTTA TCTTTTTCTT TTTGTTCAAC
    R   G   V   Q   G   F   I   F   F   F   L   F   N

281 ATTTTGACTG GAAAAAAGAT CACAGCCCAC CTAAAGAGGT
      I   L   T   G   K   K   I   T   A   H   L   K   R

321 TGTGGAAAAT GCTGGACCCA AGACAAGGCT TGGCTGTTCT
      L   W   K   M   L   D   P   R   Q   G   L   A   V   L

361 AAGGAAAGTC AAGAGAGTGG TGGCCAGTTT GATGAGAGGA
      R   K   V   K   R   V   V   A   S   L   M   R   G

401 TTGTCCTCAA GGAAACGCCG TTCCCATGAT GTTCTGACTG
      L   S   S   R   K   R   R   S   H   D   V   L   T

441 TGCAATTCCT AATTTTGGGA ATGCTGTTGA TGACGGGTGG
      V   Q   F   L   I   L   G   M   L   L   M   T   G
```

```
 481 AGTTACCCTC TCTAACTTCC AAGGGAAGGT GATGATGACG
      V  T  L   S  N  F  Q   G  K  V   M  M  T

521 GTAAATGCTA CTGACGTCAC AGATGTCATC ACGATTCCAA
      V  N  A  T   D  V  T   D  V  I   T  I  P

561 CAGCTGCTGG AAAGAACCTA TGCATTGTCA GAGCAATGGA
      T  A  A  G   K  N  L   C  I  V  R   A  M  D

601 TGTGGGATAC ATGTGCGATG ATACTATCAC TTATGAATGC
      V  G  Y   M  C  D  D   T  I  T   Y  E  C

641 CCAGTGCTGT CGGCTGGTAA TGATCCAGAA GACATCGACT
      P  V  L  S   A  G  N   D  P  E   D  I  D

681 GTTGGTGCAC AAAGTCAGCA GTCTACGTCA GGTATGGAAG
      C  W  C  T   K  S  A   V  Y  V  R   Y  G  R

721 ATGCACCAAG ACACGCCACT CAAGACGCAG TCGGAGGTCA
      C  T  K   T  R  H  S   R  R  S   R  R  S

761 CTGACAGTGC AGACACACGG AGAAAGCACT CTAGCGAACA
      L  T  V  Q   T  H  G   E  S  T   L  A  N

801 AGAAGGGGGC TTGGATGGAC AGCACCAAGG CCACAAGGTA
      K  K  G  A   W  M  D   S  T  K  A   T  R  Y

841 TTTGGTAAAA ACAGAATCAT GGATCTTGAG GAACCCTGGA
      L  V  K   T  E  S  W   I  L  R   N  P  G

881 TATGCCCTGG TGGCAGCCGT CATTGGTTGG ATGCTTGGGA
      Y  A  L  V   A  A  V   I  G  W   M  L  G

921 GCAACACCAT GCAGAGAGTT GTGTTTGTCG TGCTATTGCT
      S  N  T  M   Q  R  V   V  F  V   V  L  L  L

961 TTTGGTGGCC CCAGCTTACA GCTTCAACTG CCTTGGAATG
      L  V  A   P  A  Y  S   F  N  C   L  G  M

1001 AGCAACAGAG ACTTCTTGGA AGGAGTGTCT GGAGCAACAT
      S  N  R  D   F  L  E   G  V  S   G  A  T

1041 GGGTGGATTT GGTTCTCGAA GGCGACAGCT GCGTGACTAT
      W  V  D  L   V  L  E   G  D  S   C  V  T  I

1081 CATGTCTAAG GACAAGCCTA CCATCGACGT CAAGATGATG
      M  S  K   D  K  P  T   I  D  V   K  M  M

1121 AATATGGAGG CGGCCAACCT GGCAGAGGTC CGCAGTTATT
      N  M  E  A   A  N  L   A  E  V   R  S  Y

1161 GCTATTTGGC TACCGTCAGC GATCTCTCCA CCAAAGCTGC
      C  Y  L  A   T  V  S   D  L  S  T   K  A  A

1201 ATGCCCGACC ATGGGAGAAG CTCACAATGA CAAACGTGCT
      C  P  T   M  G  E  A   H  N  D   K  R  A

1241 GACCCAGCTT TTGTGTGCAG ACAAGGAGTG GTGGACAGGG
      D  P  A  F   V  C  R   Q  G  V   D  R

1281 GCTGGGGCAA CGGCTGCGGA TTTTTTGGCA AAGGATCCAT
      G  W  G  N   G  C  G   F  F  G   K  G  S  I

1321 TGACACATGC GCCAAATTTG CCTGCTCTAC CAAGGCAATA
      D  T  C   A  K  F  A   C  S  T   K  A  I

1361 GGAAGAACCA TCTTGAAAGA GAATATCAAG TACGAAGTGG
      G  R  T  I   L  K  E   N  I  K   Y  E  V

1401 CCATTTTTGT CCATGGACCA ACTACTGTGG AGTCGCACGG
      A  I  F  V   H  G  P   T  T  V   E  S  H  G

1441 AAATTACTCC ACACAGGTTG GAGCCACTCA GGCCGGCCGA
      N  Y  S   T  Q  V  G   A  T  Q   A  G  R

1481 TTCAGCATCA CTCCTGCTGC GCCTTCATAC ACACTAAAGC
      F  S  I  T   P  A  A   P  S  Y   T  L  K

1521 TTGGAGAATA TGGAGAGGTG ACAGTGGACT GTGAACCACG
      L  G  E  Y   G  E  V   T  V  D   C  E  P  R
```

```
1561  GTCAGGGATT GACACCAATG CATACTACGT GATGACTGTT
       S  G  I  D  T  N  A  Y  Y  V  M  T  V

1601  GGAACAAAGA CGTTCTTGGT CCATCGTGAG TGGTTCATGG
       G  T  K  T  F  L  V  H  R  E  W  F  M

1641  ACCTCAACCT CCCTTGGAGC AGTGCTGGAA GTACTGTGTG
       D  L  N  L  P  W  S  S  A  G  S  T  V  W

1681  GAGGAACAGA GAGACGTTAA TGGAGTTTGA GGAACCACAC
       R  N  R  E  T  L  M  E  F  E  E  P  H

1721  GCCACGAAGC AGTCTGTGAT AGCATTGGGC TCACAAGAGG
       A  T  K  Q  S  V  I  A  L  G  S  Q  E

1761  GAGCTCTGCA TCAAGCTTTG GCTGGAGCCA TTCCTGTGGA
       G  A  L  H  Q  A  L  A  G  A  I  P  V  E

1801  ATTTTCAAGC AACACTGTCA AGTTGACGTC GGGTCATTTG
       F  S  S  N  T  V  K  L  T  S  G  H  L

1841  AAGTGTAGAG TGAAGATGGA AAAATTGCAG TTGAAGGGAA
       K  C  R  V  K  M  E  K  L  Q  L  K  G

1881  CAACCTATGG CGTCTGTTCA AAGGCTTTCA AGTTTCTTAG
       T  T  Y  G  V  C  S  K  A  F  K  F  L  R

1921  GACTCCCGTG GACACCGGTC ACGGCACTGT GGTGTTGGAA
       T  P  V  D  T  G  H  G  T  V  V  L  E

1961  TTGCAGTACA CTGGCACGGA TGGACCTTGC AAAGTTCCTA
       L  Q  Y  T  G  T  D  G  P  C  K  V  P

2001  TCTCGTCAGT GGCTTCATTG AACGACCTAA CGCCAGTGGG
       I  S  S  V  A  S  L  N  D  L  T  P  V  G

2041  CAGATTGGTC ACTGTCAACC CTTTTGTTTC AGTGGCCACG
       R  L  V  T  V  N  P  F  V  S  V  A  T

2081  GCCAACGCTA AGGTCCTGAT TGAATTGGAA CCACCCTTTG
       A  N  A  K  V  L  I  E  L  E  P  P  F

2121  GAGACTCATA CATAGTGGTG GGCAGAGGAG AACAACAGAT
       G  D  S  Y  I  V  V  G  R  G  E  Q  Q  I

2161  CAATCACCAT TGGCACAAGT CTGGAAGCAG CATTGGCAAA
       N  H  H  W  H  K  S  G  S  S  I  G  K

2201  GCCTTTACAA CCACCCTCAA AGGAGCGCAG AGACTAGCCG
       A  F  T  T  L  K  G  A  Q  R  L  A

2241  CTCTAGGAGA CACAGCTTGG GACTTTGGAT CAGTTGGAGG
       A  L  G  D  T  A  W  D  F  G  S  V  G  G

2281  GGTGTTCACT AGTGTTGGGC GGGCTGTCCA TCAAGTGTTC
       V  F  T  S  V  G  R  A  V  H  Q  V  F

2321  GGAGGAGCAT TCCGCTCACT GTTCGGAGGC ATGTCCTGGA
       G  G  A  F  R  S  L  F  G  G  M  S  W

2361  TAACGCAAGG ATTGCTGGGG GCTCTCCTGT TGTGGATGGG
       I  T  Q  G  L  L  G  A  L  L  W  M  G

2401  CATCAATGCT CGTGATAGGT CCATAGCTCT CACGTTTCTC
       I  N  A  R  D  R  S  I  A  L  T  F  L

2441  GCAGTTGGAG GAGTTCTGCT CTTCCTCTCC GTGAACGTGG
       A  V  G  G  V  L  L  F  L  S  V  N  V

2481  GCGCCGATCA AGGATGCGCC ATCAACTTTG GCAAGAGAGA
       G  A  D  Q  G  C  A  I  N  F  G  K  R  E

2521  GCTCAAGTGC GGAGATGGTA TCTTCATATT TAGAGACTCT
       L  K  C  G  D  G  I  F  I  F  R  D  S

2561  GATGACTGGC TGAACAAGTA CTCATACTAT CCAGAAGATC
       D  D  W  L  N  K  Y  S  Y  Y  P  E  D

2601  CTGTGAAGCT TGCATCAATA GTGAAAGCCT CTTTTGAAGA
       P  V  K  L  A  S  I  V  K  A  S  F  E  E
```

```
2641 AGGGAAGTGT GGCCTAAATT CAGTTGACTC CCTTGAGCAT
      G  K  C   G  L  N  S   V  D  S   L  E  H

2681 GAGATGTGGA GAAGCAGGGC AGATGAGATC AATGCCATTT
      E  M  W  R   S  R  A   D  E  I   N  A  I

2721 TTGAGGAAAA CGAGGTGGAC ATTTCTGTTG TCGTGCAGGA
      F  E  E  N   E  V  D   I  S  V  V   V  Q  D

2761 TCCAAAGAAT GTTTACCAGA GAGGAACTCA TCCATTTTCC
      P  K  N   V  Y  Q  R   G  T  H   P  F  S

2801 AGAATTCGGG ATGGTCTGCA GTATGGTTGG AAGACTTGGG
      R  I  R  D   G  L  Q   Y  G  W   K  T  W

2841 GTAAGAACCT TGTGTTCTCC CCAGGGAGGA AGAATGGAAG
      G  K  N  L   V  F  S   P  G  R  K   N  G  S

2881 CTTCATCATA GATGGAAAGT CCAGGAAAGA ATGCCCGTTT
      F  I  I   D  G  K  S   R  K  E   C  P  F

2921 TCAAACCGGG TCTGGAATTC TTTCCAGATA GAGGAGTTTG
      S  N  R  V   W  N  S   F  Q  I   E  E  F

2961 GGACGGGAGT GTTCACCACA CGCGTGTACA TGGACGCAGT
      G  T  G  V   F  T  T   R  V  Y  M   D  A  V

3001 CTTTGAATAC ACCATAGACT GCGATGGATC TATCTTGGGT
      F  E  Y   T  I  D  C   D  G  S   I  L  G

3041 GCAGCGGTGA ACGGAAAAAA GAGTGCCCAT GGCTCTCCAA
      A  A  V  N   G  K  K   S  A  H   G  S  P

3081 CATTTTGGAT GGGAAGTCAT GAAGTAAATG GGACATGGAT
      T  F  W  M   G  S  H   E  V  N  G   T  W  M

3121 GATCCACACC TTGGAGGCAT TAGATTACAA GGAGTGTGAG
      I  H  T   L  E  A  L   D  Y  K   E  C  E

3161 TGGCCACTGA CACATACGAT TGGAACATCA GTTGAAGAGA
      W  P  L  T   H  T  I   G  T  S   V  E  E

3201 GTGAAATGTT CATGCCGAGA TCAATCGGAG CCCAGTTAG
      S  E  M  F   M  P  R   S  I  G  G   P  V  S

3241 CTCTCACAAT CATATCCCTG GATACAAGGT TCAGACGAAC
      S  H  N   H  I  P  G   Y  K  V   Q  T  N

3281 GGACCTTGGA TGCAGGTACC ACTAGAAGTG AAGAGAGAAG
      G  P  W  M   Q  V  P   L  E  V   K  R  E

3321 CTTGCCCAGG GACTAGCGTG ATCATTGATG GCAACTGTGA
      A  C  P  G   T  S  V   I  I  D   G  N  C  D

3361 TGGACGGGGA AAATCAACCA GATCCACCAC GGATAGCGGG
      G  R  G   K  S  T  R   S  T  T   D  S  G

3401 AAAGTTATTC CTGAATGGTG TTGCCGCTCC TGCACAATGC
      K  V  I  P   E  W  C   C  R  S   C  T  M

3441 CGCCTGTGAG CTTCCATGGT AGTGATGGGT GTTGGTATCC
      P  P  V  S   F  H  G   S  D  G   C  W  P

3481 CATGGAAATT AGGCCAAGGA AAACGCATGA AAGCCATCTG
      M  E  I   R  P  R  K   T  H  E   S  H  L

3521 GTGCGCTCCT GGGTTACAGC TGGAGAAATA CATGCTGTCC
      V  R  S  W   V  T  A   G  E  I   H  A  V

3561 CTTTTGGTTT GGTGAGCATG ATGATAGCAA TGGAAGTGGT
      P  F  G  L   V  S  M   M  I  A  M   E  V  V

3601 CCTAAGGAAA AGACAGGGAC CAAAGCAAAT GTTGGTTGGA
      L  R  K   R  Q  G  P   K  Q  M   L  V  G

3641 GGAGTAGTGC TCTTGGGAGC AATGCTGGTC GGGCAAGTAA
      G  V  V  L   L  G  A   M  L  V   G  Q  V

3681 CTCTCCTTGA TTTGCTGAAA CTCACAGTGG CTGTGGGATT
      T  L  L  D   L  L  K   L  T  V   A  V  G  L
```

```
3721 GCATTTCCAT GAGATGAACA ATGGAGGAGA CGCCATGTAT
      H  F  H   E  M  N  N   G  G  D   A  M  Y

3761 ATGGCGTTGA TTGCTGCCTT TTCAATCAGA CCAGGGCTGC
      M  A  L  I  A  A  F   S  I  R   P  G  L

3801 TCATCGGCTT TGGGCTCAGG ACCCTATGGA GCCCTCGGGA
      L  I  G  F  G  L  R   T  L  W  S   P  R  E

3841 ACGCCTTGTG CTGACCCTAG GAGCAGCCAT GGTGGAGATT
      R  L  V   L  T  L  G   A  A  M  V  E  I

3881 GCCTTGGGTG GCGTGATGGG CGGCCTGTGG AAGTATCTAA
      A  L  G  G   V  M  G   G  L  W  K  Y  L

3921 ATGCAGTTTC TCTCTGCATC CTGACAATAA ATGCTGTTGC
      N  A  V  S   L  C  I   L  T  I  N   A  V  A

3961 TTCTAGGAAA GCATCAAATA CCATCTTGCC CCTCATGGCT
      S  R  K   A  S  N  T   I  L  P   L  M  A

4001 CTGTTGACAC CTGTCACTAT GGCTGAGGTG AGACTTGCCG
      L  L  T  P   V  T  M   A  E  V   R  L  A

4041 CAATGTTCTT TTGTGCCATG GTTATCATAG GGTCCTTCA
      A  M  F  F   C  A  M   V  I  I  G   V  L  H

4081 CCAGAATTTC AAGGACACCT CCATGCAGAA GACTATACCT
      Q  N  F   K  D  T  S   M  Q  K   T  I  P

4121 CTGGTGGCCC TCACACTCAC ATCTTACCTG GCTTGACAC
      L  V  A  L   T  L  T   S  Y  L   G  L  T

4161 AACCTTTTTT GGGCCTGTGT GCATTTCTGG CAACCCGCAT
      Q  P  F  L   G  L  C   A  F  L  A   T  R  I

4201 ATTTGGGCGA AGGAGTATCC CAGTGAATGA GGCACTCGCA
      F  G  R   R  S  I  P   V  N  E   A  L  A

4241 GCAGCTGGTC TAGTGGGAGT GCTGGCAGGA CTGGCTTTTC
      A  A  G  L   V  G  V   L  A  G   L  A  F

4281 AGGAGATGGA GAACTTCCTT GGTCCGATTG CAGTTGGAGG
      Q  E  M   E  N  F  L   G  P  I   A  V  G  G

4321 ACTCCTGATG ATGCTGGTTA GCGTGGCTGG GAGGGTGGAT
      L  L  M   M  L  V  S   V  A  G   R  V  D

4361 GGGCTAGAGC TCAAGAAGCT TGGTGAAGTT TCATGGGAAG
      G  L  E  L   K  K  L   G  E  V   S  W  E

4401 AGGAGGCGGA GATCAGCGGG AGTTCCGCCC GCTATGATGT
      E  E  A  E   I  S  G   S  S  A  R   Y  D  V

4441 GGCACTCAGT GAACAAGGGG AGTTCAAGCT GCTTTCTGAA
      A  L  S   E  Q  G  E   F  K  L   L  S  E

4481 GAGAAAGTGC CATGGGACCA GGTTGTGATG ACCTCGCTGG
      E  K  V  P   W  D  Q   V  V  M   T  S  L

4521 CCTTGGTTGG GGCTGCCCTC CATCCATTTG CTCTTCTGCT
      A  L  V  G   A  A  L   H  P  F  A   L  L  L

4561 GGTCCTTGCT GGGTGGCTGT TTCATGTCAG GGAGCTAGG
      V  L  A   G  W  L  F   H  V  R   G  A  R

4601 AGAAGTGGGG ATGTCTTGTG GGATATTCCC ACTCCTAAGA
      R  S  G  D   V  L  W   D  I  P   T  P  K

4641 TCATCGAGGA ATGTGAACAT CTGGAGGATG GGATTTATGG
      I  I  E  E   C  E  H   L  E  D  G   I  Y  G

4681 CATATTCCAG TCAACCTTCT TGGGGGCCTC CCAGCGAGGA
      I  F  Q   S  T  F  L   G  A  S   Q  R  G

4721 GTGGGAGTGG CACAGGGAGG GGTGTTCCAC ACAATGTGGC
      V  G  V  A   Q  G  G   V  F  H   T  M  W

4761 ATGTCACAAG AGGAGCTTTC CTTGTCAGGA ATGGCAAGAA
      H  V  T  R   G  A  F   L  V  R  N   G  K  K
```

-continued

```
4801 GTTGATTCCA TCTTGGGCTT CAGTAAAGGA AGACCTTGTC
      L  I  P  S  W  A  S  V  K  E  D  L  V

4841 GCCTATGGTG GCTCATGGAA GTTGGAAGGC AGATGGGATG
      A  Y  G  G  S  W  K  L  E  G  R  W  D

4881 GAGAGGAAGA GGTCCAGTTG ATCGCGGCTG TTCCAGGAAA
      G  E  E  E  V  Q  L  I  A  A  V  P  G  K

4921 GAACGTGGTC AACGTCCAGA CAAAACCGAG CTTGTTCAAA
      N  V  V  N  V  Q  T  K  P  S  L  F  K

4961 GTGAGGAATG GGGGAGAAAT CGGGGCTGTC GCTCTTGACT
      V  R  N  G  G  E  I  G  A  V  A  L  D

5001 ATCCGAGTGG CACTTCAGGA TCTCCTATTG TTAACAGGAA
      Y  P  S  G  T  S  G  S  P  I  V  N  R  N

5041 CGGAGAGGTG ATTGGGCTGT ACGGCAATGG CATCCTTGTC
      G  E  V  I  G  L  Y  G  N  G  I  L  V

5081 GGTGACAACT CCTTCGTGTC CGCCATATCC CAGACTGAGG
      G  D  N  S  F  V  S  A  I  S  Q  T  E

5121 TGAAGGAAGA AGGAAAGGAG GAGCTCCAAG AGATCCCGAC
      V  K  E  E  G  K  E  E  L  Q  E  I  P  T

5161 AATGCTAAAG AAAGGAATGA CAACTGTCCT TGATTTTCAT
      M  L  K  K  G  M  T  T  V  L  D  F  H

5201 CCTGGAGCTG GAAGACAAG ACGTTTCCTC CCACAGATCT
      P  G  A  G  K  T  R  R  F  L  P  Q  I

5241 TGGCCGAGTG CGCACGGAGA CGCTTGCGCA CTCTTGTGTT
      L  A  E  C  A  R  R  R  L  R  T  L  V  L

5281 GGCCCCCACC AGGGTTGTTC TTTCTGAAAT GAAGGAGGCT
      A  P  T  R  V  V  L  S  E  M  K  E  A

5321 TTTCACGGCC TGGACGTGAA ATTCCACACA CAGGCTTTTT
      F  H  G  L  D  V  K  F  H  T  Q  A  F

5361 CCGCTCACGG CAGCGGGAGA GAAGTCATTG ATGCCATGTG
      S  A  H  G  S  G  R  E  V  I  D  A  M  C

5401 CCATGCCACC CTAACTTACA GGATGTTGGA ACCAACTAGG
      H  A  T  L  T  Y  R  M  L  E  P  T  R

5441 GTTGTTAACT GGGAAGTGAT CATTATGGAT GAAGCCCATT
      V  V  N  W  E  V  I  I  M  D  E  A  H

5481 TTTTGGATCC AGCCAGCATA GCCGCTAGAG GTTGGGCAGC
      F  L  D  P  A  S  I  A  A  R  G  W  A  A

5521 GCACAGAGCT AGGGCAAATG AAAGTGCAAC AATCTTGATG
      H  R  A  R  A  N  E  S  A  T  I  L  M

5561 ACAGCCACAC CGCCTGGGAC TAGTGATGAA TTTCCACATT
      T  A  T  P  P  G  T  S  D  E  F  P  H

5601 CAAATGGTGA AATAGAAGAT GTTCAAACGG ACATACCCAG
      S  N  G  E  I  E  D  V  Q  T  D  I  P  S

5641 TGAGCCCTGG AACACAGGGC ATCACTGGAT CCTGGCTGAC
      E  P  W  N  T  G  H  D  W  I  L  A  D

5681 AAAAGGCCCA CGGCATGGTT CCTTCCATCC ATCAGAGCTG
      K  R  P  T  A  W  F  L  P  S  I  R  A

5721 CAAATGTCAT GGCTGCCTCT TTGCGTAAGG CTGGAAAGAG
      A  N  V  M  A  A  S  L  R  K  A  G  K  S

5761 TGTGGTGGTC CTGAACAGGA AAACCTTTGA GAGAGAATAC
      V  V  V  L  N  R  K  T  F  E  R  E  Y

5801 CCCACGATAA AGCAGAAGAA ACCTGACTTT ATATTGGCCA
      P  T  I  K  Q  K  K  P  D  F  I  L  A

5841 CTGACATAGC TGAAATGGGA GCCAACCTTT GCGTGGAGCG
      T  D  I  A  E  M  G  A  N  L  C  V  E  R
```

```
5881 AGTGCTGGAT TGCAGGACGG CTTTTAAGCC TGTGCTTGTG
      V  L  D   C  R  T  A   F  K  P   V  L  V

5921 GATGAAGGGA GGAAGGTGGC AATAAAAGGG CCACTTCGTA
      D  E  G  R   K  V  A   I  K  G   P  L  R

5961 TCTCCGCATC CTCTGCTGCT CAAAGGAGGG GGCGCATTGG
      I  S  A  S   S  A  A   Q  R  R  G   R  I  G

6001 GAGAAATCCC AACAGAGATG GAGACTCATA CTACTATTCT
      R  N  P   N  R  D  G   D  S  Y   Y  Y  S

6041 GAGCCTACAA GTGAAAATAA TGCCCACCAC GTCTGCTGGT
      E  P  T  S   E  N  N   A  H  H   V  C  W

6081 TGGAGGCCTC AATGCTCTTG ACAACATGG AGGTGAGGGG
      L  E  A  S   M  L  L   D  N  M  E   V  R  G

6121 TGGAATGGTC GCCCCACTCT ATGGCGTTGA AGGAACTAAA
      G  M  V   A  P  L  Y   G  V  E   G  T  K

6161 ACACCAGTTT CCCCTGGTGA AATGAGACTG AGGGATGACC
      T  P  V  S   P  G  E   M  R  L   R  D  D

6201 AGAGGAAAGT CTTCAGAGAA CTAGTGAGGA ATTGTGACCT
      Q  R  K  V   F  R  E   L  V  R  N   C  D  L

6241 GCCCGTTTGG CTTTCGTGGC AAGTGGCCAA GGCTGGTTTG
      P  V  W   L  S  W  Q   V  A  K   A  G  L

6281 AAGACGAATG ATCGTAAGTG GTGTTTTGAA GGCCCTGAGG
      K  T  N  D   R  K  W   C  F  E   G  P  E

6321 AACATGAGAT CTTGAATGAC AGCGGTGAAA CAGTGAAGTG
      E  H  E  I   L  N  D   S  G  E  T   V  K  C

6361 CAGGGCTCCT GGAGGAGCAA AGAAGCCTCT GCGCCCAAGG
      R  A  P   G  G  A  K   K  P  L   R  P  R

6401 TGGTGTGATG AAAGGGTGTC ATCTGACCAG AGTGCGCTGT
      W  C  D  E   R  V  S   S  D  Q   S  A  L

6441 CTGAATTTAT TAAGTTTGCT GAAGGTAGGA GGGGAGCTGC
      S  E  F  I   K  F  A   E  G  R  R   G  A  A

6481 TGAAGTGCTA GTTGTGCTGA GTGAACTCCC TGATTTCCTG
      E  V  L   V  V  L  S   E  L  P   D  F  L

6521 GCTAAAAAAG GTGGAGAGGC AATGGATACC ATCAGTGTGT
      A  K  K   G  E  A  M   D  T  I   S  V

6561 TCCTCCACTC TGAGGAAGGC TCTAGGGCTT ACCGCAATGC
      F  L  H  S   E  E  G   S  R  A  Y   R  N  A

6601 ACTATCAATG ATGCCTGAGG CAATGACAAT AGTCATGCTG
      L  S  M   M  P  E  A   M  T  I   V  M  L

6641 TTTATACTGG CTGGACTACT GACATCGGGA ATGGTCATCT
      F  I  L  A   G  L  L   T  S  G   M  V  I

6681 TTTTCATGTC TCCCAAAGGC ATCAGTAGAA TGTCTATGGC
      F  F  M  S   P  K  G   I  S  R   M  S  M  A

6721 GATGGGCACA ATGGCCGGCT GTGGATATCT CATGTTCCTT
      M  G  T   M  A  G  C   G  Y  L   M  F  L

6761 GGAGGCGTCA AACCCACTCA CATCTCCTAT GTCATGCTCA
      G  G  V  K   P  T  H   I  S  Y   V  M  L

6801 TATTCTTTGT CCTGATGGTG GTTGTGATCC CCGAGCCAGG
      I  F  F  V   L  M  V   V  V  I  P   E  P  G

6841 GCAACAAAGG TCCATCCAAG ACAACCAAGT GGCATACCTC
      Q  Q  R   S  I  Q  D   N  Q  V   A  Y  L

6881 ATTATTGGCA TCCTGACGCT GGTTTCAGCG GTGGCAGCCA
      I  I  G   I  L  T  L   V  S  A   V  A  A

6921 ACGAGCTAGG CATGCTGGAG AAAACCAAAG AGGACCTCTT
      N  E  L  G   M  L  E   K  T  K   E  D  L  F
```

```
6961 TGGGAAGAAG AACTTAATTC CATCTAGTGC TTCACCCTGG
      G  K  K   N  L  I  P   S  S  A   S  P  W

7001 AGTTGGCCGG ATCTTGACCT GAAGCCAGGA GCTGCCTGGA
      S  W  P  D   L  D  L   K  P  G   A  A  W

7041 CAGTGTACGT TGGCATTGTT ACAATGCTCT CTCCAATGTT
      T  V  Y  V   G  I  V   T  M  L   S  P  M  L

7081 GCACCACTGG ATCAAAGTCG AATATGGCAA CCTGTCTCTG
      H  H  W   I  K  V  E   Y  G  N   L  S  L

7121 TCTGGAATAG CCCAGTCAGC CTCAGTCCTT TCTTTCATGG
      S  G  I  A   Q  S  A   S  V  L   S  F  M

7161 ACAAGGGGAT ACCATTCATG AAGATGAATA TCTCGGTCAT
      D  K  G  I   P  F  M   K  M  N  I   S  V  I

7201 AATGCTGCTG GTCAGTGGCT GGAATTCAAT ACAGTGATG
      M  L  L   V  S  G  W   N  S  I   T  V  M

7241 CCTCTGCTCT GTGGCATAGG GTGCGCCATG CTCCACTGGT
      P  L  L  C   G  I  G   C  A  M   L  H  W

7281 CTCTCATTTT ACCTGGAATC AAAGCGCAGC AGTCAAAGCT
      S  L  I  L   P  G  I   K  A  Q  Q   S  K  L

7321 TGCACAGAGA AGGGTGTTCC ATGGCGTTGC CAAGAACCCT
      A  Q  R   R  V  F  H   G  V  A   K  N  P

7361 GTGGTTGATG GAATCCAAC AGTTGACATT GAGGAAGCTC
      V  V  D  G   N  P  T   V  D  I   E  E  A

7401 CTGAAATGCC TGCCCTTTAT GAGAAGAAAC TGGCTCTATA
      P  E  M  P   A  L  Y   E  K  K   L  A  L  Y

7441 TCTCCTTCTT GCTCTCAGCC TAGCTTCTGT TGCCATGTGC
      L  L  L   A  L  S  L   A  S  V   A  M  C

7481 AGAACGCCCT TTTCATTGGC TGAAGGCATT GTCCTAGCAT
      R  T  P  F   S  L  A   E  G  I   V  L  A

7521 CAGCTGCCTT AGGGCCGCTC ATAGAGGGAA ACACCAGCCT
      S  A  A  L   G  P  L   I  E  G   N  T  S  L

7561 TCTTTGGAAT GGACCCATGG CTGTCTCCAT GACAGGAGTC
      L  W  N  G   P  M  A   V  S  M   T  G  V

7601 ATGAGGGGGA ATCACTATGC TTTTGTGGGA GTCATGTACA
      M  R  G  N   H  Y  A   F  V  G   V  M  Y

7641 ATCTATGGAA GATGAAAACT GGACGCCGGG GGAGCGCGAA
      N  L  W  K   M  K  T   G  R  R   G  S  A  N

7681 TGGAAAAACT TTGGGTGAAG TCTGGAAGAG GGAACTGAAT
      G  K  T   L  G  E  V   W  K  R   E  L  N

7721 CTGTTGGACA AGCGACAGTT TGAGTTGTAT AAAAGGACCG
      L  L  D  K   R  Q  F   E  L  Y   K  R  T

7761 ACATTGTGGA GGTGGATCGT GATACGGCAC GCAGGCATTT
      D  I  V  E   V  D  R   D  T  A   R  R  H  L

7801 GGCCGAAGGG AAGGTGGACA CCGGGGTGGC GGTCTCCAGG
      A  E  G   K  V  D  T   G  V  A   V  S  R

7841 GGGACCGCAA AGTTAAGGTG GTTCCATGAG CGTGGCTATG
      G  T  A  K   L  R  W   F  H  E   R  G  Y

7881 TCAAGCTGGA AGGTAGGGTG ATTGACCTGG GGTGTGGCCG
      V  K  L  E   G  R  V   I  D  L   G  C  R

7921 CGGAGGCTGG TGTTACTACG CTGCTGCGCA AAAGGAAGTG
      G  G  W   C  Y  Y  A   A  A  Q   K  E  V

7961 AGTGGGGTCA AAGGATTTAC TCTTGGAAGA GACGGCCATG
      S  G  V  K   G  F  T   L  G  R   D  G  H

8001 AGAAACCCAT GAATGTGCAA AGTCTGGGAT GGAACATCAT
      E  K  P  M   N  V  Q   S  L  G   W  N  I  I
```

-continued

```
8041 CACCTTCAAG GACAAAACTG ATATCCACCG CCTAGAACCA
       T  F  K   D  K  T  D   I  H  R   L  E  P

8081 GTGAAATGTG ACACCCTTTT GTGTGACATT GGAGAGTCAT
       V  K  C   D  T  L  L   C  D  I   G  E  S

8121 CATCGTCATC GGTCACAGAG GGGGAAAGGA CCGTGAGAGT
       S  S  S   S  V  T  E   G  E  R   T  V  R  V

8161 TCTTGATACT GTAGAAAAAT GGCTGGCTTG TGGGGTTGAC
       L  D  T   V  E  K  W   L  A  C   G  V  D

8201 AACTTCTGTG TGAAGGTGTT AGCTCCATAC ATGCCAGATG
       N  F  C   V  K  V  L   A  P  Y   M  P  D

8241 TTCTTGAGAA ACTGGAATTG CTCCAAAGGA GGTTTGGCGG
       V  L  E   K  L  E  L   L  Q  R  R   F  G  G

8281 AACAGTGATC AGGAACCCTC TCTCCAGGAA TTCCACTCAT
       T  V  I   R  N  P  L   S  R  N   S  T  H

8321 GAAATGTACT ACGTGTCTGG AGCCCGCAGC AATGTCACAT
       E  M  Y  Y   V  S  G   A  R  S   N  V  T

8361 TTACTGTGAA CCAAACATCC CGCCTCCTGA TGAGGAGAAT
       F  T  V  N   Q  T  S   R  L  L  M   R  R  M

8401 GAGGCGTCCA ACTGGAAAAG TGACCCTGGA GGCTGACGTC
       R  R  P   T  G  K  V   T  L  E   A  D  V

8441 ATCCTCCCAA TTGGGACACG CAGTGTTGAG ACAGACAAGG
       I  L  P   I  G  T  R   S  V  E   T  D  K

8481 GACCCCTGGA CAAAGAGGCC ATAGAAGAAA GGGTTGAGAG
       G  P  L  D   K  E  A   I  E  E  R   V  E  R

8521 GATAAAATCT GAGTACATGA CCTCTTGGTT TTATGACAAT
       I  K  S   E  Y  M  T   S  W  F   Y  D  N

8561 GACAACCCCT ACAGGACCTG GCACTACTGT GGCTCCTATG
       D  N  P   Y  R  T  W   H  Y  C   G  S  Y

8601 TCACAAAAAC CTCCGGAAGT GCGGCGAGCA TGGTAAATGG
       V  T  K  T   S  G  S   A  A  S  M   V  N  G

8641 TGTTATTAAA ATTCTGACAT ATCCATGGGA CAGGATAGAG
       V  I  K   I  L  T  Y   P  W  D   R  I  E

8681 GAGGTCACAA GAATGGCAAT GACTGACACA ACCCCTTTTG
       E  V  T  R   M  A  M   T  D  T   T  P  F

8721 GACAGCAAAG AGTGTTTAAA GAAAAAGTTG ACACCAGAGC
       G  Q  Q  R   V  F  K   E  K  V   D  T  R  A

8761 AAAGGATCCA CCAGCGGGAA CTAGGAAGAT CATGAAAGTT
       K  D  P   P  A  G  T   R  K  I   M  K  V

8801 GTCAACAGGT GGCTGTTCCG CCACCTGGCC AGAGAAAAGA
       V  N  R  W   L  F  R   H  L  A   R  E  K

8841 ACCCCAGACT GTGCACAAAG GAAGAATTTA TTGCAAAAGT
       N  P  R  L   C  T  K   E  E  F  I   A  K  V

8881 CCGAAGTCAT GCAGCCATTG GAGCTTACCT GGAAGAACAA
       R  S  H   A  A  I  G   A  Y  L   E  E  Q

8921 GAACAGTGGA AGACTGCCAA TGAGGCTGTC CAAGACCCAA
       E  Q  W  K   T  A  N   E  A  V   Q  D  P

8961 AGTTCTGGGA ACTGGTGGAT GAAGAAAGGA AGCTGCACCA
       K  F  W  E   L  V  D   E  E  R  K   L  H  Q

9001 ACAAGGCAGG TGTCGGACTT GTGTGTACAA CATGATGGGG
       Q  G  R   C  R  T  C   V  Y  N   M  M  G

9041 AAAAGAGAGA AGAAGCTGTC AGAGTTTGGG AAAGCAAAGG
       K  R  E  K   K  L  S   E  F  G   K  A  K

9081 GAAGCCGTGC CATATGGTAT ATGTGGCTGG GAGCGCGGTA
       G  S  R  A   I  W  Y   M  W  L   G  A  R  Y
```

```
9121 TCTTGAGTTT GAGGCCCTGG GATTCCTGAA TGAGGACCAT
      L   E   F   E   A   L   G   F   L   N   E   D   H

9161 TGGGCTTCCA GGGAAAACTC AGGAGGAGGA GTGGAAGGCA
      W   A   S   R   E   N   S   G   G   G   V   E   G

9201 TTGGCTTACA ATACCTAGGA TATGTGATCA GAGACCTGGC
      I   G   L   Q   Y   L   G   Y   V   I   R   D   L   A

9241 TGCAATGGAT GGTGGTGGAT TCTACGCGGA TGACACCGCT
      A   M   D   G   G   G   F   Y   A   D   D   T   A

9281 GGATGGGACA CGCGCATCAC AGAGGCAGAC CTTGATGATG
      G   W   D   T   R   I   T   E   A   D   L   D   D

9321 AACAGGAGAT CTTGAACTAC ATGAGCCCAC ATCACAAAAA
      E   Q   E   I   L   N   Y   M   S   P   H   H   K   K

9361 ACTGGCACAA GCAGTGATGG AAATGACATA CAAGAACAAA
      L   A   Q   A   V   M   E   M   T   Y   K   N   K

9401 GTGGTGAAAG TGTTGAGACC AGCCCCAGGA GGGAAAGCCT
      V   V   K   V   L   R   P   A   P   G   G   K   A

9441 ACATGGATGT CATAAGTCGA CGAGACCAGA GAGGATCCGG
      Y   M   D   V   I   S   R   R   D   Q   R   G   S   G

9481 GCAGGTAGTG ACTTATGCTC TGAACACCAT CACCAACTTG
      Q   V   V   T   Y   A   L   N   T   I   T   N   L

9521 AAAGTCCAAT TGATCAGAAT GGCAGAAGCA GAGATGGTGA
      K   V   Q   L   I   R   M   A   E   A   E   M   V

9561 TACATCACCA ACATGTTCAA GATTGTGATG AATCAGTTCT
      I   H   H   Q   H   V   Q   D   C   D   E   S   V   L

9601 GACCAGGCTG GAGGCATGGC TCACTGAGCA CGGATGTGAC
      T   R   L   E   A   W   L   T   E   H   G   C   D

9641 AGACTGAAGA GGATGGCGGT GAGTGGAGAC GACTGTGTGG
      R   L   K   R   M   A   V   S   G   D   D   C   V

9681 TCCGGCCCAT CGATGACAGG TTCGGCCTGG CCCTGTCCCA
      V   R   P   I   D   D   R   F   G   L   A   L   S   H

9721 TCTCAACGCC ATGTCCAAGG TTAGAAAGGA CATATCTGAA
      L   N   A   M   S   K   V   R   K   D   I   S   E

9761 TGGCAGCCAT CAAAAGGGTG GAATGATTGG GAGAATGTGC
      W   Q   P   S   K   G   W   N   D   W   E   N   V

9801 CCTTCTGTTC CCACCACTTC CATGAACTAC AGCTGAAGGA
      P   F   C   S   H   H   F   H   E   L   Q   L   K   D

9841 TGGCAGGAGG ATTGTGGTGC CTTGCCGAGA ACAGGACGAG
      G   R   R   I   V   V   P   C   R   E   Q   D   E

9881 CTCATTGGGA GAGGAAGGGT GTCTCCAGGA AACGGCTGGA
      L   I   G   R   G   R   V   S   P   G   N   G   W

9921 TGATCAAGGA ACAGCTTGC CTCAGCAAAG CCTATGCCAA
      M   I   K   E   T   A   C   L   S   K   A   Y   A   N

9961 CATGTGGTCA CTGATGTATT TTCACAAAAG GGACATGAGG
      M   W   S   L   M   Y   F   H   K   R   D   M   R

10001 CTACTGTCAT TGGCTGTTTC CTCAGCTGTT CCCACCTCAT
       L   L   L   S   L   A   V   S   S   A   V   P   T   S

10041 GGGTTCCACA AGGACGCACA ACATGGTCGA TTCATGGGAA
       W   V   P   Q   G   R   T   T   W   S   I   H   G   K

10081 AGGGGAGTGG ATGACCACGG AAGACATGCT TGAGGTGTGG
       G   E   W   M   T   T   E   D   M   L   E   V   W

10121 AACAGAGTAT GGATAACCAA CAACCCACAC ATGCAGGACA
       N   R   V   W   I   T   N   N   P   H   M   Q   D

10161 AGACAATGGT GAAAAAATGG AGAGATGTCC CTTATCTAAC
       K   T   M   V   K   K   W   R   D   V   P   Y   L   T
```

```
10201 CAAGAGACAA GACAAGCTGT GCGGATCACT GATTGGAATG
        K  R  Q   D  K  L   C  G  S   L  I  G  M

10241 ACCAATAGGG CCACCTGGGC CTCCCACATC CATTTAGTCA
        T  N  R  A   T  W  A   S  H  I   H  L  V

10281 TCCATCGTAT CCGAACGCTG ATTGGACAGG AGAAATACAC
        I  H  R  I   R  T  L   I  G  Q   E  K  Y  T

10321 TGACTACCTA ACAGTCATGG ACAGGTATTC TGTGGATGCT
        D  Y  L   T  V  M  D   R  Y  S   V  D  A

10361 GACCTGCAAC TGGGTGAGCT TATCTGAAAC ACCATCTAAC
        D  L  Q  L   G  E  L   I

10401 AGGAATAACC GGGATACAAA CCACGGGTGG AGAACCGGAC

10441 TCCCCACAAC CTGAAACCGG GATATAAACC ACGGCTGGAG

10481 AACCGGACTC CGCACTTAAA ATGAAACAGA ACCGGGATA

10521 AAAACTACGG ATGGAGAACC GGACTCCACA CATTGAGACA

10561 GAAGAAGTTG TCAGCCCAGA ACCCCACACG AGTTTTGCCA

10601 CTGCTAAGCT GTGAGGCAGT GCAGGCTGGG ACAGCCGACC

10641 TCCAGGTTGC GAAAAACCTG GTTTCTGGGA CCTCCCACCC

10681 CAGAGTAAAA AGAACGGAGC CTCCGCTACC ACCCTCCCAC

10721 GTGGTGGTAG AAAGACGGGG TCTAGAGGTT AGAGGAGACC

10761 CTCCAGGGAA CAAATAGTGG GACCATATTG ACGCCAGGGA

10801 AAGACCGGAG TGGTTCTCTG CTTTTCCTCC AGAGGTCTGT

10841 GAGCACAGTT TGCTCAAGAA TAAGCAGACC TTTGGATGAC

10881 AAACACAAAA CCACAA

Chimerivax WN02 M66 variant
[Strand]
    1 NGTAAATCCT GTGTGCTAAT TGAGGTGCAT TGGTCTGCAA

41 ATCGAGTTGC TAGGCAATAA ACACATTTGG ATTAATTTTA

81 ATCGTTCGTT GAGCGATTAG CAGAGAACTG ACCAGAACAT
                                                 M

121 GTCTGGTCGT AAAGCTCAGG GAAAAACCCT GGGCGTCAAT
        S  G  R   K  A  Q  G   K  T  L   G  V  N

161 ATGGTACGAC GAGGAGTTCG CTCCTTGTCA AACAAAATAA
        M  V  R  R   G  V  R   S  L  S   N  K  I

201 AACAAAAAAC AAAACAAATT GGAAACAGAC CTGGACCTTC
        K  Q  K  T   K  Q  I   G  N  R   P  G  P  S

241 AAGAGGTGTT CAAGGATTTA TCTTTTTCTT TTTGTTCAAC
        R  G  V   Q  G  F   I  F  F   F  L  F  N

281 ATTTTGACTG GAAAAAAGAT CACAGCCCAC CTAAAGAGGT
        I  L  T  G   K  K  I   T  A  H   L  K  R

321 TGTGGAAAAT GCTGGACCCA AGACAAGGCT GGCTGTTCT
        L  W  K  M   L  D  P   R  Q  G   L  A  V  L

361 AAGGAAAGTC AAGAGAGTGG TGGCCAGTTT GATGAGAGGA
        R  K  V   K  R  V  V   A  S  L   M  R  G

401 TTGTCCTCAA GGAAACGCCG TTCCCATGAT GTTCTGACTG
        L  S  S  R   K  R  R   S  H  D   V  L  T

441 TGCAATTCCT AATTTTGGGA ATGCTGTTGA TGACGGGTGG
        V  Q  F  L   I  L  G   M  L  L   M  T  G  G

481 AGTTACCCTC TCTAACTTCC AAGGGAAGGT GATGATGACG
        V  T  L   S  N  F  Q   G  K  V   M  M  T
```

```
521 GTAAATGCTA CTGACGTCAC AGATGTCATC ACGATTCCAA
     V  N  A  T    D  V  T    D  V  I    T  I  P

561 CAGCTGCTGG AAAGAACCTA TGCATTGTCA GAGCAATGGA
     T  A  A  G    K  N  L    C  I  V  R    A  M  D

601 TGTGGGATAC ATGTGCGATG ATACTATCAC TTATGAATGC
     V  G  Y    M  C  D  D    T  I  T    Y  E  C

641 CCAGTGCTGT CGGCTGGTAA TGATCCAGAA GACATCGACT
     P  V  L  S    A  G  N    D  P  E    D  I  D

681 GTTGGTGCAC AAAGTCAGCA GTCTACGTCA GGTATGGAAG
     C  W  C  T    K  S  A    V  Y  V  R    Y  G  R

721 ATGCACCAAG ACACGCCACT CAAGACGCAG TCGGAGGTCA
      C  T  K    T  R  H  S    R  R  S    R  R  S

761 CTGACAGTGC AGACACACGG AGAAAGCACT CTAGCGAACA
      L  T  V  Q    T  H  G    E  S  T    L  A  N

801 AGAAGGGGGC TTGGATGGAC AGCACCAAGG CCACAAGGTA
      K  K  G  A    W  M  D    S  T  K  A    T  R  Y

841 TTTGGTAAAA ACAGAATCAT GGATCTTGAG GAACCCTGGA
       L  V  K    T  E  S  W    I  L  R    N  P  G

881 TATGCCCTGG TGGCAGCCGT CATTGGTTGG ATGCTTGGGA
       Y  A  L  V    A  A  V    I  G  W    M  L  G

921 GCAACACCAT GCAGAGAGTT GTGTTTGTCG TGCCATTGCT
      S  N  T  M    Q  R  V    V  F  V  V    P  L  L

961 TTTGGTGGCC CCAGCTTACA GCTTCAACTG CCTTGGAATG
       L  V  A    P  A  Y  S    F  N  C    L  G  M

1001 AGCAACAGAG ACTTCTTGGA AGGAGTGTCT GGAGCAACAT
       S  N  R  D    F  L  E    G  V  S    G  A  T

1041 GGGTGGATTT GGTTCTCGAA GGCGACAGCT GCGTGACTAT
       W  V  D  L    V  L  E    G  D  S    C  V  T  I

1081 CATGTCTAAG GACAAGCCTA CCATCGACGT CAAGATGATG
        M  S  K    D  K  P  T    I  D  V    K  M  M

1121 AATATGGAGG CGGCCAACCT GGCAGAGGTC CGCAGTTATT
       N  M  E  A    A  N  L    A  E  V    R  S  Y

1161 GCTATTTGGC TACCGTCAGC GATCTCTCCA CCAAAGCTGC
        C  Y  L  A    T  V  S    D  L  S  T    K  A  A

1201 ATGCCCGACC ATGGGAGAAG CTCACAATGA CAAACGTGCT
        C  P  T    M  G  E  A    H  N  D    K  R  A

1241 GACCCAGCTT TTGTGTGCAG ACAAGGAGTG GTGGACAGGG
        D  P  A  F    V  C  R    Q  G  V    V  D  R

1281 GCTGGGGCAA CGGCTGCGGA TTTTTTGGCA AAGGATCCAT
        G  W  G  N    G  C  G    F  F  G  K    G  S  I

1321 TGACACATGC GCCAAATTTG CCTGCTCTAC CAAGGCAATA
        D  T  C    A  K  F  A    C  S  T    K  A  I

1361 GGAAGAACCA TCTTGAAAGA GAATATCAAG TACGAAGTGG
       G  R  T  I    L  K  E    N  I  K    Y  E  V

1401 CCATTTTTGT CCATGGACCA ACTACTGTGG AGTCGCACGG
       A  I  F  V    H  G  P    T  T  V  E    S  H  G

1441 AAAATTACTCC ACACAGGTTG GAGCCACTCA GGCCGGCCGA
       N  Y  S    T  Q  V  G    A  T  Q    A  G  R

1481 TTCAGCATCA CTCCTGCTGC GCCTTCATAC ACACTAAAGC
        F  S  I  T    P  A  A    P  S  Y    T  L  K

1521 TTGGAGAATA TGGAGAGGTG ACAGTGGACT GTGAACCACG
        L  G  E  Y    G  E  V    T  V  D    C  E  P  R

1561 GTCAGGGATT GACACCAATG CATACTACGT GATGACTGTT
        S  G  I    D  T  N  A    Y  Y  V    M  T  V
```

```
1601 GGAACAAAGA CGTTCTTGGT CCATCGTGAG TGGTTCATGG
      G  T  K  T   F  L  V   H  R  E   W  F  M

1641 ACCTCAACCT CCCTTGGAGC AGTGCTGGAA GTACTGTGTG
      D  L  N  L   P  W  S   S  A  G  S   T  V  W

1681 GAGGAACAGA GAGACGTTAA TGGAGTTTGA GGAACCACAC
      R  N  R   E  T  L  M   E  F  E   E  P  H

1721 GCCACGAAGC AGTCTGTGAT AGCATTGGGC TCACAAGAGG
      A  T  K  Q   S  V  I   A  L  G   S  Q  E

1761 GAGCTCTGCA TCAAGCTTTG GCTGGAGCCA TTCCTGTGGA
      G  A  L  H   Q  A  L   A  G  A  I   P  V  E

1801 ATTTTCAAGC AACACTGTCA AGTTGACGTC GGGTCATTTG
      F  S  S   N  T  V  K   L  T  S   G  H  L

1841 AAGTGTAGAG TGAAGATGGA AAAATTGCAG TTGAAGGGAA
      K  C  R  V   K  M  E   K  L  Q   L  K  G

1881 CAACCTATGG CGTCTGTTCA AAGGCTTTCA GTTTCTTAG
      T  T  Y  G   V  C  S   K  A  F  K   F  L  R

1921 GACTCCCGTG ACACCGGTC ACGGCACTGT GGTGTTGGAA
      T  P  V   D  T  G  H   G  T  V   V  L  E

1961 TTGCAGTACA CTGGCACGGA TGGACCTTGC AAAGTTCCTA
      L  Q  Y  T   G  T  D   G  P  C   K  V  P

2001 TCTCGTCAGT GGCTTCATTG AACGACCTAA CGCCAGTGGG
      I  S  S  V   A  S  L   N  D  L   T  P  V  G

2041 CAGATTGGTC ACTGTCAACC CTTTTGTTTC AGTGGCCACG
      R  L  V   T  V  N  P   F  V  S   V  A  T

2081 GCCAACGCTA AGGTCCTGAT TGAATTGGAA CCACCCTTTG
      A  N  A  K   V  L  I   E  L  E   P  P  F

2121 GAGACTCATA CATAGTGGTG GGCAGAGGAG AACAACAGAT
      G  D  S  Y   I  V  V   G  R  E   Q  Q  I

2161 CAATCACCAT TGGCACAAGT CTGGAAGCAG CATTGGCAAA
      N  H  H   W  H  K  S   G  S  S   I  G  K

2201 GCCTTTACAA CCACCCTCAA AGGAGCGCAG AGACTAGCCG
      A  F  T  T   T  L  K   G  A  Q   R  L  A

2241 CTCTAGGAGA CACAGCTTGG GACTTTGGAT CAGTTGGAGG
      A  L  G  D   T  A  W   D  F  G   S  V  G  G

2281 GGTGTTCACT AGTGTTGGGC GGGCTGTCCA TCAAGTGTTC
      V  F  T   S  V  G  R   A  V  H   Q  V  F

2321 GGAGGAGCAT TCCGCTCACT GTTCGGAGGC ATGTCCTGGA
      G  G  A  F   R  S  L   F  G  G   M  S  W

2361 TAACGCAAGG ATTGCTGGGG CTCTCCTGT TGTGGATGGG
      I  T  Q  G   L  L  G   A  L  L   W  M  G

2401 CATCAATGCT CGTGATAGGT CGATAGCTCT CACGTTTCTC
      I  N  A  R   D  R  S   I  A  L   T  F  L

2441 GCAGTTGGAG GAGTTCTGCT CTTCCTCTCC GTGAACGTGG
      A  V  G  G   V  L  L   F  L  S   V  N  V

2481 GCGCCGATCA AGGATGCGCC ATCAACTTTG GCAAGAGAGA
      G  A  D  Q   G  C  A   I  N  F   G  K  R  E

2521 GCTCAAGTGC GGAGATGGTA TCTTCATATT TAGAGACTCT
      L  K  C   G  D  G  I   F  I  F   R  D  S

2561 GATGACTGGC TGAACAAGTA CTCATACTAT CCAGAAGATC
      D  D  W  L   N  K  Y   S  Y  Y   P  E  D

2601 CTGTGAAGCT TGCATCAATA GTGAAAGCCT CTTTTGAAGA
      P  V  K  L   A  S  I   V  K  A   S  F  E  E

2641 AGGGAAGTGT GGCCTAAATT CAGTTGACTC CCTTGAGCAT
      G  K  C   G  L  N  S   V  D  S   L  E  H
```

```
2681 GAGATGTGGA GAAGCAGGGC AGATGAGATC AATGCCATTT
      E  M  W  R  S  R  A  D  E  I  N  A  I

2721 TTGAGGAAAA CGAGGTGGAC ATTTCTGTTG TCGTGCAGGA
      F  E  E  N  E  V  D  I  S  V  V  V  Q  D

2761 TCCAAAGAAT GTTTACCAGA GAGGAACTCA TCCATTTTCC
      P  K  N  V  Y  Q  R  G  T  H  P  F  S

2801 AGAATTCGGG ATGGTCTGCA GTATGGTTGG AAGACTTGGG
      R  I  R  D  G  L  Q  Y  G  W  K  T  W

2841 GTAAGAACCT TGTGTTCTCC CCAGGGAGGA AGAATGGAAG
      G  K  N  L  V  F  S  P  G  R  K  N  G  S

2881 CTTCATCATA GATGGAAAGT CCAGGAAAGA ATGCCCGTTT
      F  I  I  D  G  K  S  R  K  E  C  P  F

2921 TCAAACCGGG TCTGGAATTC TTTCCAGATA GAGGAGTTTG
      S  N  R  V  W  N  S  F  Q  I  E  E  F

2961 GGACGGGAGT GTTCACCACA CGCGTGTACA TGGACGCAGT
      G  T  G  V  F  T  T  R  V  Y  M  D  A  V

3001 CTTTGAATAC ACCATAGACT GCGATGGATC TATCTTGGGT
      F  E  Y  T  I  D  C  D  G  S  I  L  G

3041 GCAGCGGTGA ACGGAAAAAA GAGTGCCCAT GGCTCTCCAA
      A  A  V  N  G  K  K  S  A  H  G  S  P

3081 CATTTTGGAT GGGAAGTCAT GAAGTAAATG GACATGGAT
      T  F  W  M  G  S  H  E  V  N  G  T  W  M

3121 GATCCACACC TTGGAGGCAT TAGATTACAA GGAGTGTGAG
      I  H  T  L  E  A  L  D  Y  K  E  C  E

3161 TGGCCACTGA CACATACGAT TGGAACATCA GTTGAAGAGA
      W  P  L  T  H  T  I  G  T  S  V  E  E

3201 GTGAAATGTT CATGCCGAGA TCAATCGGAG CCCAGTTAG
      S  E  M  F  M  P  R  S  I  G  G  P  V  S

3241 CTCTCACAAT CATATCCCTG GATACAAGGT TCAGACGAAC
      S  H  N  H  I  P  G  Y  K  V  Q  T  N

3281 GGACCTTGGA TGCAGGTACC ACTAGAAGTG AAGAGAGAAG
      G  P  W  M  Q  V  P  L  E  V  K  R  E

3321 CTTGCCCAGG GACTAGCGTG ATCATTGATG GCAACTGTGA
      A  C  P  G  T  S  V  I  I  D  G  N  C  D

3361 TGGACGGGGA AAATCAACCA GATCCACCAC GGATAGCGGG
      G  R  G  K  S  T  R  S  T  T  D  S  G

3401 AAAGTTATTC CTGAATGGTG TTGCCGCTCC TGCACAATGC
      K  V  I  P  E  W  C  C  R  S  C  T  M

3441 CGCCTGTGAG CTTCCATGGT AGTGATGGGT GTTGGTATCC
      P  P  V  S  F  H  G  S  D  G  C  W  Y  P

3481 CATGGAAATT AGGCCAAGGA AAACGCATGA AAGCCATCTG
      M  E  I  R  P  R  K  T  H  E  S  H  L

3521 GTGCGCTCCT GGGTTACAGC TGGAGAAATA CATGCTGTCC
      V  R  S  W  V  T  A  G  E  I  H  A  V

3561 CTTTTGGTTT GGTGAGCATG ATGATAGCAA TGGAAGTGGT
      P  F  G  L  V  S  M  M  I  A  M  E  V  V

3601 CCTAAGGAAA AGACAGGGAC CAAAGCAAAT GTTGGTTGGA
      L  R  K  R  Q  G  P  K  Q  M  L  V  G

3641 GGAGTAGTGC TCTTGGGAGC AATGCTGGTC GGGCAAGTAA
      G  V  V  L  G  A  M  L  V  G  Q  V

3681 CTCTCCTTGA TTTGCTGAAA CTCACAGTGG CTGTGGGATT
      T  L  L  D  L  L  K  L  T  V  A  V  G  L

3721 GCATTTCCAT GAGATGAACA ATGGAGGAGA CGCCATGTAT
      H  F  H  E  M  N  N  G  G  D  A  M  Y
```

-continued

```
3761 ATGGCGTTGA TTGCTGCCTT TTCAATCAGA CCAGGGCTGC
      M  A  L  I  A  A  F  S  I  R  P  G  L

3801 TCATCGGCTT TGGGCTCAGG ACCCTATGGA GCCCTCGGGA
      L  I  G  F  G  L  R  T  L  W  S  P  R  E

3841 ACGCCTTGTG CTGACCCTAG GAGCAGCCAT GGTGGAGATT
      R  L  V  L  T  L  G  A  A  M  V  E  I

3881 GCCTTGGGTG GCGTGATGGG CGGCCTGTGG AAGTATCTAA
      A  L  G  G  V  M  G  G  L  W  K  Y  L

3921 ATGCAGTTTC TCTCTGCATC CTGACAATAA ATGCTGTTGC
      N  A  V  S  L  C  I  L  T  I  N  A  V  A

3961 TTCTAGGAAA GCATCAAATA CCATCTTGCC CCTCATGGCT
      S  R  K  A  S  N  T  I  L  P  L  M  A

4001 CTGTTGACAC CTGTCACTAT GGCTGAGGTG AGACTTGCCG
      L  L  T  P  V  T  M  A  E  V  R  L  A

4041 CAATGTTCTT TTGTGCCATG GTTATCATAG GGTCCTTCA
      A  M  F  F  C  A  M  V  I  I  G  V  L  H

4081 CCAGAATTTC AAGGACACCT CCATGCAGAA GACTATACCT
      Q  N  F  K  D  T  S  M  Q  K  T  I  P

4121 CTGGTGGCCC TCACACTCAC ATCTTACCTG GGCTTGACAC
      L  V  A  L  T  L  T  S  Y  L  G  L  T

4161 AACCTTTTTT GGGCCTGTGT GCATTTCTGG CAACCCGCAT
      Q  P  F  L  G  L  C  A  F  L  A  T  R  I

4201 ATTTGGGCGA AGGAGTATCC CAGTGAATGA GGCACTCGCA
      F  G  R  R  S  I  P  V  N  E  A  L  A

4241 GCAGCTGGTC TAGTGGGAGT GCTGGCAGGA CTGGCTTTTC
      A  A  G  L  V  G  V  L  A  G  L  A  F

4281 AGGAGATGGA GAACTTCCTT GGTCCGATTG CAGTTGGAGG
      Q  E  M  E  N  F  L  G  P  I  A  V  G  G

4321 ACTCCTGATG ATGCTGGTTA GCGTGGCTGG GAGGGTGGAT
      L  L  M  M  L  V  S  V  A  G  R  V  D

4361 GGGCTAGAGC TCAAGAAGCT TGGTGAAGTT TCATGGGAAG
      G  L  E  L  K  K  L  G  E  V  S  W  E

4401 AGGAGGCGGA GATCAGCGGG AGTTCCGCCC GCTATGATGT
      E  E  A  E  I  S  G  S  S  A  R  Y  D  V

4441 GGCACTCAGT GAACAAGGGG AGTTCAAGCT GCTTTCTGAA
      A  L  S  E  Q  G  E  F  K  L  L  S  E

4481 GAGAAAGTGC CATGGGACCA GGTTGTGATG ACCTCGCTGG
      E  K  V  P  W  D  Q  V  V  M  T  S  L

4521 CCTTGGTTGG GGCTGCCCTC CATCCATTTG CTCTTCTGCT
      A  L  V  G  A  A  L  H  P  F  A  L  L  L

4561 GGTCCTTGCT GGGTGGCTGT TTCATGTCAG GGGAGCTAGG
      V  L  A  G  W  L  F  H  V  R  G  A  R

4601 AGAAGTGGGG ATGTCTTGTG GGATATTCCC ACTCCTAAGA
      R  S  G  D  V  L  W  D  I  P  T  P  K

4641 TCATCGAGGA ATGTGAACAT CTGGAGGATG GGATTTATGG
      I  I  E  E  C  E  H  L  E  D  G  I  Y  G

4681 CATATTCCAG TCAACCTTCT TGGGGGCCTC CCAGCGAGGA
      I  F  Q  S  T  F  L  G  A  S  Q  R  G

4721 GTGGGAGTGG CACAGGGAGG GGTGTTCCAC ACAATGTGGC
      V  G  V  A  Q  G  G  V  F  H  T  M  W

4761 ATGTCACAAG AGGAGCTTTC CTTGTCAGGA ATGGCAAGAA
      H  V  T  R  G  A  F  L  V  R  N  G  K  K

4801 GTTGATTCCA TCTTGGGCTT CAGTAAAGGA AGACCTTGTC
      L  I  P  S  W  A  S  V  K  E  D  L  V
```

```
4841 GCCTATGGTG GCTCATGGAA GTTGGAAGGC AGATGGGATG
      A  Y  G  G   S  W  K    L  E  G  R    W  D

4881 GAGAGGAAGA GGTCCAGTTG ATCGCGGCTG TTCCAGGAAA
      G  E  E  E   V  Q  L    I  A  A  V    P  G  K

4921 GAACGTGGTC AACGTCCAGA CAAAACCGAG CTTGTTCAAA
      N  V  V   N  V  Q  T    K  P  S    L  F  K

4961 GTGAGGAATG GGGGAGAAAT CGGGGCTGTC GCTCTTGACT
      V  R  N  G   G  E  I    G  A  V    A  L  D

5001 ATCCGAGTGG CACTTCAGGA TCTCCTATTG TTAACAGGAA
      Y  P  S  G   T  S  G    S  P  I  V    N  R  N

5041 CGGAGAGGTG ATTGGGCTGT ACGGCAATGG CATCCTTGTC
      G  E  V   I  G  L  Y    G  N  G    I  L  V

5081 GGTGACAACT CCTTCGTGTC CGCCATATCC AGACTGAGG
      G  D  N  S   F  V  S    A  I  S  Q    T  E

5121 TGAAGGAAGA AGGAAAGGAG GAGCTCCAAG AGATCCCGAC
      V  K  E  E   G  K  E    E  L  Q  E    I  P  T

5161 AATGCTAAAG AAAGGAATGA CAACTGTCCT TGATTTTCAT
      M  L  K   K  G  M  T    T  V  L    D  F  H

5201 CCTGGAGCTG GAAGACAAG ACGTTTCCTC CCACAGATCT
      P  G  A  G   K  T  R    R  F  L  P    Q  I

5241 TGGCCGAGTG CGCACGGAGA CGCTTGCGCA CTCTTGTGTT
      L  A  E  C   A  R  R    R  L  R  T    L  V  L

5281 GGCCCCCACC AGGGTTGTTC TTTCTGAAAT GAAGGAGGCT
      A  P  T   R  V  V  L    S  E  M    K  E  A

5321 TTTCACGGCC TGGACGTGAA ATTCCACACA CAGGCTTTTT
      F  H  G  L   D  V  K    F  H  T  Q    A  F

5361 CCGCTCACGG CAGCGGGAGA GAAGTCATTG ATGCCATGTG
      S  A  H  G   S  G  R    E  V  I  D    A  M  C

5401 CCATGCCACC CTAACTTACA GGATGTTGGA ACCAACTAGG
      H  A  T   L  T  Y  R    M  L  E    P  T  R

5441 GTTGTTAACT GGGAAGTGAT CATTATGGAT GAAGCCCATT
      V  V  N  W   E  V  I    I  M  D  E    A  H

5481 TTTTGGATCC AGCCAGCATA GCCGCTAGAG GTTGGGCAGC
      F  L  D  P   A  S  I    A  A  R  G    W  A  A

5521 GCACAGAGCT AGGGCAAATG AAAGTGCAAC AATCTTGATG
      H  R  A   R  A  N  E    S  A  T    I  L  M

5561 ACAGCCACAC CGCCTGGGAC TAGTGATGAA TTTCCACATT
      T  A  T  P   P  G  T    S  D  E  F    P  H

5601 CAAATGGTGA AATAGAAGAT GTTCAAACGG ACATACCCAG
      S  N  G  E   I  E  D    V  Q  T  D    I  P  S

5641 TGAGCCCTGG AACACAGGGC ATGACTGGAT CCTGGCTGAC
      E  P  W   N  T  G  H    D  W  I    L  A  D

5681 AAAAGGCCCA CGGCATGGTT CCTTCCATCC ATCAGAGCTG
      K  R  P  T   A  W  F    L  P  S  I    R  A

5721 CAAATGTCAT GGCTGCCTCT TTGCGTAAGG CTGGAAAGAG
      A  N  V  M   A  A  S    L  R  K  A    G  K  S

5761 TGTGGTGGTC CTGAACAGGA AAACCTTTGA GAGAGAATAC
      V  V  V   L  N  R  K    T  F  E    R  E  Y

5801 CCCACGATAA AGCAGAAGAA ACCTGACTTT ATATTGGCCA
      P  T  I  K   Q  K  K    P  D  F  I    L  A

5841 CTGACATAGC TGAAATGGGA GCCAACCTTT GCGTGGAGCG
      T  D  I  A   E  M  G    A  N  L  C    V  E  R

5881 AGTGCTGGAT TGCAGGACGG CTTTTAAGCC TGTGCTTGTG
      V  L  D  C   R  T  A    F  K  P  V    L  V
```

```
5921 GATGAAGGGA GGAAGGTGGC AATAAAAGGG CCACTTCGTA
      D   E   G   R   K   V   A   I   K   G   P   L   R

5961 TCTCCGCATC CTCTGCTGCT CAAAGGAGGG GGCGCATTGG
      I   S   A   S   S   A   A   Q   R   R   G   R   I   G

6001 GAGAAATCCC AACAGAGATG GAGACTCATA CTACTATTCT
      R   N   P   N   R   D   G   D   S   Y   Y   Y   S

6041 GAGCCTACAA GTGAAAATAA TGCCCACCAC GTCTGCTGGT
      E   P   T   S   E   N   N   A   H   H   V   C   W

6081 TGGAGGCCTC AATGCTCTTG GACAACATGG AGGTGAGGGG
      L   E   A   S   M   L   L   D   N   M   E   V   R   G

6121 TGGAATGGTC GCCCCACTCT ATGGCGTTGA AGGAACTAAA
      G   M   V   A   P   L   Y   G   V   E   G   T   K

6161 ACACCAGTTT CCCCTGGTGA AATGAGACTG AGGGATGACC
      T   P   V   S   P   G   E   M   R   L   R   D   D

6201 AGAGGAAAGT CTTCAGAGAA CTAGTGAGGA ATTGTGACCT
      Q   R   K   V   F   R   E   L   V   R   N   C   D   L

6241 GCCCGTTTGG CTTTCGTGGC AAGTGGCCAA GGCTGGTTTG
      P   V   W   L   S   W   Q   V   A   K   A   G   L

6281 AAGACGAATG ATCGTAAGTG GTGTTTTGAA GGCCCTGAGG
      K   T   N   D   R   K   W   C   F   E   G   P   E

6321 AACATGAGAT CTTGAATGAC AGCGGTGAAA CAGTGAAGTG
      E   H   E   I   L   N   D   S   G   E   T   V   K   C

6361 CAGGGCTCCT GGAGGAGCAA AGAAGCCTCT GCGCCCAAGG
      R   A   P   G   G   A   K   K   P   L   R   P   R

6401 TGGTGTGATG AAAGGGTGTC ATCTGACCAG AGTGCGCTGT
      W   C   D   E   R   V   S   S   D   Q   S   A   L

6441 CTGAATTTAT TAAGTTTGCT GAAGGTAGGA GGGGAGCTGC
      S   E   F   I   K   F   A   E   G   R   R   G   A   A

6481 TGAAGTGCTA GTTGTGCTGA GTGAACTCCC TGATTTCCTG
      E   V   L   V   V   L   S   E   L   P   D   F   L

6521 GCTAAAAAAG GTGGAGAGGC AATGGATACC ATCAGTGTGT
      A   K   K   G   E   A   M   D   T   I   S   V

6561 TCCTCCACTC TGAGGAAGGC TCTAGGGCTT ACCGCAATGC
      F   L   H   S   E   E   G   S   R   A   Y   R   N   A

6601 ACTATCAATG ATGCCTGAGG CAATGACAAT AGTCATGCTG
      L   S   M   M   P   E   A   M   T   I   V   M   L

6641 TTTATACTGG CTGGACTACT GACATCGGGA ATGGTCATCT
      F   I   L   A   G   L   L   T   S   G   M   V   I

6681 TTTTCATGTC TCCCAAAGGC ATCAGTAGAA TGTCTATGGC
      F   F   M   S   P   K   G   I   S   R   M   S   M   A

6721 GATGGGCACA ATGGCCGGCT GTGGATATCT CATGTTCCTT
      M   G   T   M   A   G   C   G   Y   L   M   F   L

6761 GGAGGCGTCA AACCCACTCA CATCTCCTAT GTCATGCTCA
      G   G   V   K   P   T   H   I   S   Y   V   M   L

6801 TATTCTTTGT CCTGATGGTG GTTGTGATCC CCGAGCCAGG
      I   F   F   V   L   M   V   V   V   I   P   E   P   G

6841 GCAACAAAGG TCCATCCAAG ACAACCAAGT GGCATACCTC
      Q   Q   R   S   I   Q   D   N   Q   V   A   Y   L

6881 ATTATTGGCA TCCTGACGCT GGTTTCAGCG GTGGCAGCCA
      I   I   G   I   L   T   L   V   S   A   V   A   A

6921 ACGAGCTAGG CATGCTGGAG AAAACCAAAG AGGACCTCTT
      N   E   L   G   M   L   E   K   T   K   E   D   L   F

6961 TGGGAAGAAG AACTTAATTC CATCTAGTGC TTCACCCTGG
      G   K   K   N   L   I   P   S   S   A   S   P   W
```

```
7001 AGTTGGCCGG ATCTTGACCT GAAGCCAGGA GCTGCCTGGA
      S  W  P  D  L  D  L  K  P  G  A  A  W

7041 CAGTGTACGT TGGCATTGTT ACAATGCTCT CTCCAATGTT
      T  V  Y  V  G  I  V  T  M  L  S  P  M  L

7081 GCACCACTGG ATCAAAGTCG AATATGGCAA CCTGTCTCTG
      H  H  W  I  K  V  E  Y  G  N  L  S  L

7121 TCTGGAATAG CCCAGTCAGC CTCAGTCCTT TCTTTCATGG
      S  G  I  A  Q  S  A  S  V  L  S  F  M

7161 ACAAGGGGAT ACCATTCATG AAGATGAATA TCTCGGTCAT
      D  K  G  I  P  F  M  K  M  N  I  S  V  I

7201 AATGCTGCTG GTCAGTGGCT GGAATTCAAT AACAGTGATG
      M  L  L  V  S  G  W  N  S  I  T  V  M

7241 CCTCTGCTCT GTGGCATAGG GTGCGCCATG CTCCACTGGT
      P  L  L  C  G  I  G  C  A  M  L  H  W

7281 CTCTCATTTT ACCTGGAATC AAAGCGCAGC AGTCAAAGCT
      S  L  I  L  P  G  I  K  A  Q  Q  S  K  L

7321 TGCACAGAGA AGGGTGTTCC ATGGCGTTGC CAAGAACCCT
      A  Q  R  R  V  F  H  G  V  A  K  N  P

7361 GTGGTTGATG GAATCCAAC AGTTGACATT GAGGAAGCTC
      V  V  D  G  N  P  T  V  D  I  E  E  A

7401 CTGAAATGCC TGCCCTTTAT GAGAAGAAAC TGGCTCTATA
      P  E  M  P  A  L  Y  E  K  K  L  A  L  Y

7441 TCTCCTTCTT GCTCTCAGCC TAGCTTCTGT TGCCATGTGC
      L  L  L  A  L  S  L  A  S  V  A  M  C

7481 AGAACGCCCT TTTCATTGGC TGAAGGCATT GTCCTAGCAT
      R  T  P  F  S  L  A  E  G  I  V  L  A

7521 CAGCTGCCTT AGGGCCGCTC ATAGAGGGAA ACACCAGCCT
      S  A  A  L  G  P  L  I  E  G  N  T  S  L

7561 TCTTTGGAAT GGACCCATGG CTGTCTCCAT GACAGGAGTC
      L  W  N  G  P  M  A  V  S  M  T  G  V

7601 ATGAGGGGGA ATCACTATGC TTTTGTGGGA GTCATGTACA
      M  R  G  N  H  Y  A  F  V  G  V  M  Y

7641 ATCTATGGAA GATGAAAACT GGACGCCGGG GGAGCGCGAA
      N  L  W  K  M  K  T  G  R  R  G  S  A  N

7681 TGGAAAAACT TTGGGTGAAG TCTGGAAGAG GGAACTGAAT
      G  K  T  L  G  E  V  W  K  R  E  L  N

7721 CTGTTGGACA AGCGACAGTT TGAGTTGTAT AAAAGGACCG
      L  L  D  K  R  Q  F  E  L  Y  K  R  T

7761 ACATTGTGGA GGTGGATCGT GATACGGCAC GCAGGCATTT
      D  I  V  E  V  D  R  D  T  A  R  R  H  L

7801 GGCCGAAGGG AAGGTGGACA CCGGGGTGGC GGTCTCCAGG
      A  E  G  K  V  D  T  G  V  A  V  S  R

7841 GGGACCGCAA AGTTAAGGTG GTTCCATGAG CGTGGCTATG
      G  T  A  K  L  R  W  F  H  E  R  G  Y

7881 TCAAGCTGGA AGGTAGGGTG ATTGACCTGG GGTGTGGCCG
      V  K  L  E  G  R  V  I  D  L  G  C  R

7921 CGGAGGCTGG TGTTACTACG CTGCTGCGCA AAAGGAAGTG
      G  G  W  C  Y  Y  A  A  A  Q  K  E  V

7961 AGTGGGGTCA AAGGATTTAC TCTTGGAAGA GACGGCCATG
      S  G  V  K  G  F  T  L  G  R  D  G  H

8001 AGAAACCCAT GAATGTGCAA AGTCTGGGAT GGAGAGTCAT
      E  K  P  M  N  V  Q  S  L  G  W  N  I  I

8041 CACCTTCAAG GACAAAACTG ATATCCACCG CCTAGAACCA
      T  F  K  D  K  T  D  I  H  R  L  E  P
```

```
8081 GTGAAATGTG ACACCCTTTT GTGTGACATT GGAGAGTCAT
      V  K  C  D  T  L  L  C  D  I  G  E  S

8121 CATCGTCATC GGTCACAGAG GGGGAAAGGA CCGTGAGAGT
      S  S  S  S  V  T  E  G  E  R  T  V  R  V

8161 TCTTGATACT GTAGAAAAAT GGCTGGCTTG TGGGGTTGAC
      L  D  T  V  E  K  W  L  A  C  G  V  D

8201 AACTTCTGTG TGAAGGTGTT AGCTCCATAC ATGCCAGATG
      N  F  C  V  K  V  L  A  P  Y  M  P  D

8241 TTCTTGAGAA ACTGGAATTG CTCCAAAGGA GGTTTGGCGG
      V  L  E  K  L  E  L  L  Q  R  R  F  G  G

8281 AACAGTGATC AGGAACCCTC TCTCCAGGAA TTCCACTCAT
      T  V  I  R  N  P  L  S  R  N  S  T  H

8321 GAAATGTACT ACGTGTCTGG AGCCCGCAGC AATGTCACAT
      E  M  Y  Y  V  S  G  A  R  S  N  V  T

8361 TTACTGTGAA CCAAACATCC CGCCTCCTGA TGAGGAGAAT
      F  T  V  N  Q  T  S  R  L  L  M  R  R  M

8401 GAGGCGTCCA ACTGGAAAAG TGACCCTGGA GGCTGACGTC
      R  R  P  T  G  K  V  T  L  E  A  D  V

8441 ATCCTCCCAA TTGGGACACG CAGTGTTGAG ACAGACAAGG
      I  L  P  I  G  T  R  S  V  E  T  D  K

8481 GACCCCTGGA CAAAGAGGCC ATAGAAGAAA GGGTTGAGAG
      G  P  L  D  K  E  A  I  E  E  R  V  E  R

8521 GATAAAATCT GAGTACATGA CCTCTTGGTT TTATGACAAT
      I  K  S  E  Y  M  T  S  W  F  Y  D  N

8561 GACAACCCCT ACAGGACCTG GCACTACTGT GGCTCCTATG
      D  N  P  Y  R  T  W  H  Y  C  G  S  Y

8601 TCACAAAAAC CTCCGGAAGT GCGGCGAGCA TGGTAAATGG
      V  T  K  T  S  G  S  A  A  S  M  V  N  G

8641 TGTTATTAAA ATTCTGACAT ATCCATGGGA CAGGATAGAG
      V  I  K  I  L  T  Y  P  W  D  R  I  E

8681 GAGGTCACAA GAATGGCAAT GACTGACACA ACCCCTTTTG
      E  V  T  R  M  A  M  T  D  T  T  P  F

8721 GACAGCAAAG AGTGTTTAAA GAAAAAGTTG ACACCAGAGC
      G  Q  Q  R  V  F  K  E  K  V  D  T  R  A

8761 AAAGGATCCA CCAGCGGGAA CTAGGAAGAT CATGAAAGTT
      K  D  P  P  A  G  T  R  K  I  M  K  V

8801 GTCAACAGGT GGCTGTTCCG CCACCTGGCC AGAGAAAAGA
      V  N  R  W  L  F  R  H  L  A  R  E  K

8841 ACCCCAGACT GTGCACAAAG GAAGAATTTA TTGCAAAAGT
      N  P  R  L  C  T  K  E  E  F  I  A  K  V

8881 CCGAAGTCAT GCAGCCATTG GAGCTTACCT GGAAGAACAA
      R  S  H  A  A  I  G  A  Y  L  E  E  Q

8921 GAACAGTGGA AGACTGCCAA TGAGGCTGTC CAAGACCCAA
      E  Q  W  K  T  A  N  E  A  V  Q  D  P

8961 AGTTCTGGGA ACTGGTGGAT GAAGAAAGGA AGCTGCACCA
      K  F  W  E  L  V  D  E  E  R  K  L  H  Q

9001 ACAAGGCAGG TGTCGGACTT GTGTGTACAA CATGATGGGG
      Q  G  R  C  R  T  C  V  Y  N  M  M  G

9041 AAAAGAGAGA AGAAGCTGTC AGAGTTTGGG AAAGCAAAGG
      K  R  E  K  K  L  S  E  F  G  K  A  K

9081 GAAGCCGTGC CATATGGTAT ATGTGGCTGG GAGCGCGGTA
      G  S  R  A  I  W  Y  M  W  L  G  A  R  Y

9121 TCTTGAGTTT GAGGCCCTGG GATTCCTGAA TGAGGACCAT
      L  E  F  E  A  L  G  F  L  N  E  D  H
```

```
9161 TGGGCTTCCA GGGAAAACTC AGGAGGAGGA GTGGAAGGCA
      W  A  S  R  E  N  S  G  G  G  V  E  G

9201 TTGGCTTACA ATACCTAGGA TATGTGATCA GAGACCTGGC
      I  G  L  Q  Y  L  G  Y  V  I  R  D  L  A

9241 TGCAATGGAT GGTGGTGGAT TCTACGCGGA TGACACCGCT
      A  M  D  G  G  G  F  Y  A  D  D  T  A

9281 GGATGGGACA CGCGCATCAC AGAGGCAGAC CTTGATGATG
      G  W  D  T  R  I  T  E  A  D  L  D  D

9321 AACAGGAGAT CTTGAACTAC ATGAGCCCAC ATCACAAAAA
      E  Q  E  I  L  N  Y  M  S  P  H  K  K

9361 ACTGGCACAA GCAGTGATGG AAATGACATA CAAGAACAAA
      L  A  Q  A  V  M  E  M  T  Y  K  N  K

9401 GTGGTGAAAG TGTTGAGACC AGCCCCAGGA GGGAAAGCCT
      V  V  K  V  L  R  P  A  P  G  G  K  A

9441 ACATGGATGT CATAAGTCGA CGAGACCAGA GAGGATCCGG
      Y  M  D  V  I  S  R  R  D  Q  R  G  S  G

9481 GCAGGTAGTG ACTTATGCTC TGAACACCAT CACCAACTTG
      Q  V  V  T  Y  A  L  N  T  I  T  N  L

9521 AAAGTCCAAT TGATCAGAAT GGCAGAAGCA GAGATGGTGA
      K  V  Q  L  I  R  M  A  E  A  E  M  V

9561 TACATCACCA ACATGTTCAA GATTGTGATG AATCAGTTCT
      I  H  H  Q  H  V  Q  D  C  D  E  S  V  L

9601 GACCAGGCTG GAGGCATGGC TCACTGAGCA CGGATGTGAC
      T  R  L  E  A  W  L  T  E  H  G  C  D

9641 AGACTGAAGA GGATGGCGGT GAGTGGAGAC GACTGTGTGG
      R  L  K  R  M  A  V  S  G  D  D  C  V

9681 TCCGGCCCAT CGATGACAGG TTCGGCCTGG CCCTGTCCCA
      V  R  P  I  D  D  R  F  G  L  A  L  S  H

9721 TCTCAACGCC ATGTCCAAGG TTAGAAAGGA CATATCTGAA
      L  N  A  M  S  K  V  R  K  D  I  S  E

9761 TGGCAGCCAT CAAAAGGGTG GAATGATTGG GAGAATGTGC
      W  Q  P  S  K  G  W  N  D  W  E  N  V

9801 CCTTCTGTTC CCACCACTTC CATGAACTAC AGCTGAAGGA
      P  F  C  S  H  H  F  H  E  L  Q  L  K  D

9841 TGGCAGGAGG ATTGTGGTGC CTTGCCGAGA ACAGGACGAG
      G  R  R  I  V  V  P  C  R  E  Q  D  E

9881 CTCATTGGGA GAGGAAGGGT GTCTCCAGGA AACGGCTGGA
      L  I  G  R  G  R  V  S  P  G  N  G  W

9921 TGATCAAGGA ACAGCTTGC CTCAGCAAAG CCTATGCCAA
      M  I  K  E  T  A  C  L  S  K  A  Y  A  N

9961 CATGTGGTCA CTGATGTATT TTCACAAAAG GGACATGAGG
      M  W  S  L  M  Y  F  H  K  R  D  M  R

10001 CTACTGTCAT TGGCTGTTTC CTCAGCTGTT CCCACCTCAT
       L  L  S  L  A  V  S  S  A  V  P  T  S

10041 GGGTTCCACA AGGACGCACA ACATGGTCGA TTCATGGGAA
       W  V  P  Q  G  R  T  T  W  S  I  H  G  K

10081 AGGGGAGTGG ATGACCACGG AAGACATGCT TGAGGTGTGG
       G  E  W  M  T  T  E  D  M  L  E  V  W

10121 AACAGAGTAT GGATAACCAA CAACCCACAC ATGCAGGACA
       N  R  V  W  I  T  N  N  P  H  M  Q  D

10161 AGACAATGGT GAAAAAATGG AGAGATGTCC CTTATCTAAC
       K  T  M  V  K  K  W  R  D  V  P  Y  L  T

10201 CAAGAGACAA GACAAGCTGT GCGGATCACT GATTGGAATG
       K  R  Q  D  K  L  C  G  S  L  I  G  M
```

```
10241  ACCAATAGGG CCACCTGGGC CTCCCACATC CATTTAGTCA
        T  N  R  A   T  W  A   S  H  I   H  L  V

10281  TCCATCGTAT CCGAACGCTG ATTGGACAGG AGAAATACAC
        I  H  R  I   R  T  L   I  G  Q   E  K  Y  T

10321  TGACTACCTA ACAGTCATGG ACAGGTATTC TGTGGATGCT
         D  Y  L   T  V  M  D   R  Y  S   V  D  A

10361  GACCTGCAAC TGGGTGAGCT TATCTGAAAC ACCATCTAAC
        D  L  Q  L   G  E  L   I

10401  AGGAATAACC GGGATACAAA CCACGGGTGG AGAACCGGAC

10441  TCCCCACAAC CTGAAACCGG GATATAAACC ACGGCTGGAG

10481  AACCGGACTC CGCACTTAAA ATGAAACAGA AACCGGGATA

10521  AAAACTACGG ATGGAGAACC GGACTCCACA CATTGAGACA

10561  GAAGAAGTTG TCAGCCCAGA ACCCCACACG AGTTTTGCCA

10601  CTGCTAAGCT GTGAGGCAGT GCAGGCTGGG ACAGCCGACC

10641  TCCAGGTTGC GAAAAACCTG GTTTCTGGGA CCTCCCACCC

10681  CAGAGTAAAA AGAACGGAGC CTCCGCTACC ACCCTCCCAC

10721  GTGGTGGTAG AAAGACGGGG TCTAGAGGTT AGAGGAGACC

10761  CTCCAGGGAA CAAATAGTGG GACCATATTG ACGCCAGGGA

10801  AAGACCGGAG TGGTTCTCTG CTTTTCCTCC AGAGGTCTGT

10841  GAGCACAGTT TGCTCAAGAA TAAGCAGACC TTTGGATGAC

10881  AAACACAAAA CCACAA
```

DNA Strider ™ 1317 ###

WN 02 × M66 Variant = → DNA Alignment

DNA sequence 10896 bp *GTAAATCCTGT . . . ACAAAACCACAA linear

DNA sequence 10896 bp *GTAAATCCTGT . . . ACAAAACCACAA linear

Layout:            Compacted

Method:            Blocks (Martinez)

Mimmatch penalty: Smaller (1)

Gap penalty:       Medium (2)

Translation:       Off

```
     1  *GTAAATCCTGTGTGCTAATTGAGGTGCATTGGTCTGCAAATCGAGTTGCTAGGCAATAAACACATTTGGATTAATTTTA    80
     1  ................................................................................    80

81  ATCGTTCGTTGAGCGATTAGCAGAGAACTGACCAGAACATGTCTGGTCGTAAAGCTCAGGGAAAAACCCTGGGCGTCAAT   160
    81  ................................................................................   160

161  ATGGTACGACGAGGAGTTCGCTCCTTGTCAAACAAAATAAAACAAAAAACAAAACAAATTGGAAACAGACCTGGACCTTC   240
   161  ................................................................................   240

241  AAGAGGTGTTCAAGGATTTATCTTTTTCTTTTTGTTCAACATTTTGACTGGAAAAAAGATCACAGCCCACCTAAAGAGGT   320
   241  ................................................................................   320

321  TGTGCAAAATGCTGGACCCAAGACAAGGCTTGGCTGTTCTAAGGAAAGTCAAGAGAGTGGTGGCCAGTTTGATGAGAGGA   400
   321  ................................................................................   400

401  TTGTCCTCAAGGAAACGCCGTTCCCATGATGTTCTGACTGTGCAATTCCTAATTTTGGGAATGCTGTTGATGACCAGTGG   480
   401  ................................................................................   480

481  AGTTACCCTCTCTAACTTCCAAGGGAAGGTGATGATGACGGTAAATGCTACTGACGTCACAGATGTCATCACGATTCCAA   560
   481  ................................................................................   560

561  CAGCTGCTGGAAAGAACCTATGCATTGTCAGAGCAATGGATGTGGGATACATGTGCGATGATACTATCACTTATGAATGC   640
   561  ................................................................................   640

641  CCAGTGCTGTCGGCTGGTAATGATCCAGAAGACATCGACTGTTGGTGCACAAAGTCAGCAGTCTACGTCAGGTATGGAAG   720
   641  ................................................................................   720
```

-continued

```
 721 ATGCACCAAGACACGCCACTCAAGACGCAGTCGGAGGTCACTGACAGTGCAGACACACGGAGAAAGCACTCTAGCGAACA  800
 721 ................................................................................  800

801 AGAAGGGGGCTTGGATGGACAGCACCAAGGCCACAAGGTATTTGGTAAAAACAGAATCATGGATCTTGAGGAACCCTGGA  880
 801 ................................................................................  880

881 TATGCCCTGGTGGCAGCCGTCATTGGTTGGATGCTTGGGAGCAACACCATGCAGAGAGTTGTGTTTGTCGTGCTATTGCT  960
 881 .........................................................................C......  960

961 TTTGGTGGCCCCAGCTTACAGCTTCAACTGCCTTGGAATGAGCAACAGAGACTTCTTGGAAGGAGTGTCTGGAGCAACAT 1040
 961 ................................................................................ 1040

1041 GGGTGGATTTGGTTCTCGAAGGCGACAGCTGCGTGACTATCATGTCTAAGGACAAGCCTACCATCGACGTCAAGATGATG 1120
1041 ................................................................................ 1120

1121 AATATGGAGGCGGCCAACCTGGCAGAGGTCCGCAGTTATTGCTATTTGGCTACCGTCAGCGATCTCTCCACCAAAGCTGC 1200
1121 ................................................................................ 1200

1201 ATGCCCGACCATGGGAGAAGCTCACAATGACAAACGTGCTGACCCAGCTTTTGTGTGCAGACAAGGAGTGGTGGACAGGG 1280
1201 ................................................................................ 1280

1281 GCTGGGGCAACGGCTGCGGATTTTTTGGCAAAGGATCCATTGACACATGCGCCAAATTTGCCTGCTCTACCAAGGCAATA 1360
1281 ................................................................................ 1360

1361 GGAAGAACCATCTTGAAAGAGAATATCAAGTACGAAGTGGCCATTTTTGTCCATGGACCAACTACTGTGGAGTCGCACGG 1440
1361 ................................................................................ 1440
```

WN 02 × M66 Variant = → DNA Alignment

```
1441 AAATTACTCCACACAGGTTGGAGCCACTCAGGCCGGCCGATTCAGCATCACTCCTGCTGCGCCTTCATACACACTAAAGC 1520
1441 ................................................................................ 1520

1521 TTGGAGAATATGGAGAGGTGACAGTGGACTGTGAACCACGGTCAGGGATTGACACCAATGCATACTACGTGATGACTGTT 1600
1521 ................................................................................ 1600

1601 GGAACAAAGACGTTCTTGGTCCATCGTGAGTGGTTCATGGACCTCAACCTCCCTTGGAGCAGTGCTGGAAGTACTGTGTG 1680
1601 ................................................................................ 1680

1681 GAGGAACAGAGAGACGTTAATGGAGTTTGAGGAACCACACGCCACGAAGCAGTCTGTGATAGCATTGGGCTCACAAGAGG 1760
1681 ................................................................................ 1760

1761 GAGCTCTCCATCAAGCTTTGGCTGGAGCCATTCCTGTGGAATTTTCAAGCAACACTGTCAAGTTGACGTCGGGTCATTTG 1840
1761 ................................................................................ 1840

1841 AAGTGTAGAGTGAAGATGGAAAAATTGCAGTTGAAGGGAACAACCTATGGCGTCTGTTCAAAGGCTTTCAAGTTTCTTAG 1920
1841 ................................................................................ 1920

1921 GACTCCCGTGGACACCGGTCACGGCACTGTGGTGTTGGAATTGCAGTACACTGGCACGGATGGACCTTGCAAAGTTCCTA 2000
1921 ................................................................................ 2000

2001 TCTCGTCAGTGGCTTCATTGAACGACCTAACGCCAGTGGGCAGATTGGTCACTGTCAACCCTTTTGTTTCAGTGGCCACG 2080
2001 ................................................................................ 2080

2081 GCCAACGCTAAGGTCCTGATTGAATTGGAACCACCCTTTGGAGACTCATACATAGTGGTGGGCAGAGGAGAACAACAGAT 2160
2081 ................................................................................ 2160

2161 CAATCACCATTGGCACAAGTCTGGAAGCAGCATTGCCAAAGCCTTTACAACCACCCTCAAAGGAGCGCAGAGACTAGCCG 2240
2161 ................................................................................ 2240

2241 CTCTAGGAGACACAGCTTGGGACTTTGGATCAGTTGGAGGGGTGTTCACTAGTGTTGGGCGGGCTGTCCATCAAGTGTTC 2320
2241 ................................................................................ 2320

2321 GGAGGAGCATTCCGCTCACTGTTCGGAGGCATGTCCTGGATAACGCAAGGATTGCTGGGGGCTCTCCTGTTGTGGATGGG 2400
2321 ................................................................................ 2400

2401 CATCAATGCTCGTGATAGGTCCATAGCTCTCACGTTTCTCGCAGTTGGAGGAGTTCTGCTCTTCCTCTCCGTGAACGTGG 2480
2401 ................................................................................ 2480

2481 GCGCCGATCAAGGATGCGCCATCAACTTTGGCAAGAGAGACCTCAAGTGCGGAGATGGTATCTTCATATTTAGAGACTCT 2560
2481 ................................................................................ 2560

2561 GATGACTGGCTGAACAAGTACTCATACTATCCAGAAGATCCTGTGAAGCTTGCATCAATAGTGAAAGCCTCTTTTGAAGA 2640
2561 ................................................................................ 2640

2641 AGGGAAGTGTGGCCTAAATTCAGTTGACTCCCTTGAGCATGAGATGTGGAGAAGCAGGGCACATGAGATCAATGCCATTT 2720
2641 ................................................................................ 2720

2721 TTGAGGAAAACGAGGTGGACATTTCTGTTGTCGTGCAGGATCCAAAGAATGTTTACCAGAGAGGAACTCATCCATTTTCC 2800
2721 ................................................................................ 2800

2801 AGAATTCGGGATGGTCTGCAGTATGGTTGGAAGACTTGGGGTAAGAACCTTGTGTTCTCCCCAGGGAGGAAGAATGGAAG 2880
```

```
2801                                                                            2880
     ............................................................................

2881 CTTCATCATAGATGGAAAGTCCAGGAAAGAATGCCCGTTTTCAAACCGGGTCTGGAATTCTTTCCAGATAGAGGAGTTTG 2960
2881 ............................................................................  2960

2961 GGACGGGAGTGTTCACCACACGCGTGTACATGGACGCAGTCTTTGAATACACCATAGACTCCGATGGATCTATCTTGGGT 3040
2961 ............................................................................  3040

3041 GCAGCGGTGAACGGAAAAAGAGTGCCCATGGCTCTCCAACATTTTGGATGGGAAGTCATGAAGTAAATGGGACATGGAT  3120
3041 ............................................................................  3120

3121 GATCCACACCTTGGAGGCATTAGATTACAAGGAGTGTGAGTGGCCACTGACACATACGATTGGAACATCAGTTGAAGAGA 3200
3121 ............................................................................  3200

3201 GTGAAATGTTCATGCCGAGATCAATCGGAGGCCCAGTTAGCTCTCACAATCATATCCCTGGATACAAGGTTCAGACGAAC 3280
3201 ............................................................................  3280

3281 GGACCTTGGATGCAGGTACCACTAGAAGTGAAGAGAGAAGCTTGCCCAGGGACTAGCGTGATCATTGATGGCAACTGTGA 3360
3281 ............................................................................  3360

3361 TGGACGGGGAAAATCAACCAGATCCACCACGGATAGCGGGAAAGTTATTCCTGAATGGTGTTGCCGCTCCTGCACAATGC 3440
3361 ............................................................................  3440

3441 CGCCTGTGAGCTTCCATGGTAGTGATGGGTGTTGGTATCCCATGGAAATTAGGCCAAGGAAAACGCATGAAAGCCATCTG 3520
3441 ............................................................................  3520

3521 GTGCGCTCCTGGGTTACAGCTGGAGAAATACATGCTGTCCCTTTTGGTTTGGTGAGCATGATGATAGCAATGGAAGTGGT 3600
3521 ............................................................................  3600

3601 CCTAAGGAAAAGACAGGGACCAAAGCAAATGTTGGTTGGAGGAGTAGTGCTCTTGGGAGCAATGCTGGTCGGGCAAGTAA 3680
3601 ............................................................................  3680

3681 CTCTCCTTGATTTGCTGAAACTCACAGTGGCTGTGGGATTGCATTTCCATGAGATGAACAATGGAGGAGACGCCATGTAT 3760
3681 ............................................................................  3760

3761 ATGGCGTTGATTGCTGCCTTTTCAATCAGACCAGGGCTGCTCATCGGCTTTGGGCTCAGGACCCTATGGAGCCCTCGGGA 3840
3761 ............................................................................  3840

3841 ACGCCTTGTGCTGACCCTAGGAGCAGCCATGGTGGAGATTGCCTTGGGTGGCGTGATGGGCGGCCTGTGGAAGTATCTAA 3920
3841 ............................................................................  3920

3921 ATGCAGTTTCTCTCTGCATCCTGACAATAAATGCTGTTGCTTCTAGGAAAGCATCAAATACCATCTTGCCCCTCATGGCT 4000
3921 ............................................................................  4000

4001 CTGTTGACACCTGTCACTATGGCTGAGGTGAGACTTGCCGCAATGTTCTTTTGTGCCATGGTTATCATAGGGGGCCTTCA 4080
4001 ............................................................................  4080

4081 CCAGAATTTCAAGGACACCTCCATGCAGAAGACTATACCTCTGGTGGCCCTCACACTCACATCTTACCTGGGCTTGACAC 4160
4081 ............................................................................  4160

4161 AACCTTTTTTGGGCCTGTGTGCATTTCTGGCAACCCGCATATTTGGGCGAAGGAGTATCCCAGTGAATGAGGCACTCGCA 4240
4161 ............................................................................  4240

4241 GCAGCTGGTCTAGTGGGAGTGCTGGCAGGACTGGCTTTTCAGGAGATGGAGAACTTCCTTGGTCCGATTGCAGTTGGAGG 4320
4241 ............................................................................  4320

4321 ACTCCTGATGATGCTGGTTAGCCTGGCTGGGAGGGTGGATGGGCTAGAGCTCAAGAAGCTTGGTGAAGTTTCATGGGAAG 4400
4321 ............................................................................  4400

4401 AGGAGGCGGAGATCAGCGGGAGTTCCGCCCGCTATGATGTGGCACTCAGTGAACAAGGGGAGTTCAAGCTGCTTTCTGAA 4480
4401 ............................................................................  4480

4481 GAGAAAGTGCCATGGGACCAGGTTGTGATGACCTCGCTGGCCTTGGTTGGGGCTGCCCTCCATCCATTTGCTCTTCTGCT 4560
4481 ............................................................................  4560

4561 GGTCCTTGCTGGGTGGCTGTTTCATGTCAGGGGAGCTAGGAGAAGTGGGGATGTCTTGTGGGATATTCCCACTCCTAAGA 4640
4561 ............................................................................  4640

4641 TCATCGAGGAATGTGAACATCTGGAGGATGGGATTTATGGCATATTCCAGTCAACCTTCTTGGGGGCCTCCCAGCGAGGA 4720
4641 ............................................................................  4720

4721 GTGGGAGTGGCACAGGGAGGGGTGTTCCACACAATGTGGCATGTCACAAGAGGAGCTTTCCTTGTCAGGAATGGCAAGAA 4800
4721 ............................................................................  4800

4801 GTTGATTCCATCTTGGGCTTCAGTAAAGGAAGACCTTGTCGCCTATGGTGGCTCATGGAAGTTGGAAGGCAGATGGGATG 4880
4801 ............................................................................  4880

4881 GAGAGGAAGAGGTCCAGTTGATCGCGGCTGTTCCAGGAAAGAACGTGGTCAACGTCCAGACAAAACCGAGCTTGTTCAAA 4960
4881 ............................................................................  4960

4961 GTGAGGAATGGGGGAGAAATCGGGGCTGTCGCTCTTGACTATCCGAGTGGCACTTCAGGATCTCCTATTGTTAACAGGAA 5040
```

```
4961                                                                            5040
     ............................................................................

5041 CGGAGAGGTGATTGGGCTGTACGGCAATGGCATCCTTGTCGGTGACAACTCCTTCGTGTCCGCCATATCCCAGACTGAGG 5120
5041 ............................................................................ 5120

5121 TGAAGGAAGAAGGAAAGGAGGAGCTCCAAGAGATCCCGACAATGCTAAAGAAACGAATGACAACTGTCCTTGATTTTCAT 5200
5121 ............................................................................ 5200

5201 CCTGGAGCTGGGAAGACAAGACGTTTCCTCCCACAGATCTTGGCCGAGTGCGCACGGAGACGCTTGCGCACTCTTGTGTT 5280
5201 ............................................................................ 5280

5281 GGCCCCCACCAGGGTTGTTCTTTCTGAAATGAAGGAGGCTTTTCACGGCCTGGACGTGAAATTCCACACACAGGCTTTTT 5360
5281 ............................................................................ 5360

5361 CCGCTCACGGCAGCGGGAGAGAAGTCATTGATGCCATGTGCCATGCCACCCTAACTTACAGGATGTTGGAACCAACTAGG 5440
5361 ............................................................................ 5440

5441 GTTGTTAACTGGGAAGTGATCATTATGGATGAAGCCCATTTTTTGGATCCAGCCAGCATACCCGCTAGAGGTTGGGCAGC 5520
5441 ............................................................................ 5520

5521 CCACAGAGCTAGGGCAAATGAAAGTGCAACAATCTTGATGAGAGCCACACCGCCTGGCACTAGTGATGAATTTCCACATT 5600
5521 ............................................................................ 5600

5601 CAAATCGTGAAATAGAAGATGTTCAAACGGACATACCCAGTGAGCCCTGGAACACAGGGCATGACTGGATCCTGGCTGAC 5680
5601 ............................................................................ 5680

5681 AAAAGGCCCACGGCATGGTTCCTTCCATCCATCAGAGCTGCAAATGTCATGGCTGCCTCTTTGCGTAAGGCTGGAAAGAG 5760
5681 ............................................................................ 5760

5761 TGTGGTGGTCCTGAACAGGAAAACCTTTGAGAGAGAATACCCCACGATAAAGCAGAAGAAACCTGACTTTATATTGGCCA 5840
5761 ............................................................................ 5840

5841 CTGACATAGCTGAAATGGGAGCCAACCTTTGCGTGGAGCGAGTGCTGGATTGCAGGACGGCTTTTAAGCCTGTGCTTGTG 5920
5841 ............................................................................ 5920

5921 GATGAAGGGAGGAAGGTGGCAATAAAAGGGCCACTTCGTATCTCCGCATCCTCTGCTGCTCAAAGGAGGGGGCGCATTGG 6000
5921 ............................................................................ 6000

6001 GAGAAATCCCAACAGAGATGGAGACTCATACTACTATTCTGAGCCTACAAGTGAAAATAATGCCCACCACGTCTGCTGGT 6080
6001 ............................................................................ 6080

6081 TGGAGGCCTCAATGCTCTTGGACAACATGGAGGTGAGGGGTGGAATGGTCGCCCCACTCTATGGCGTTGAAGGAACTAAA 6160
6081 ............................................................................ 6160

6161 ACACCAGTTTCCCCTGGTGAAATGAGACTGAGGGATGACCAGAGGAAAGTCTTCAGAGAACTAGTGAGGAATTGTGACCT 6240
6161 ............................................................................ 6240

6241 GCCCGTTTGGCTTTCGTGGCAAGTGGCCAAGGCTGGTTTGAAGACGAATGATCGTAAGTGGTGTTTTGAAGGCCCTGAGG 6320
6241 ............................................................................ 6320

6321 AACATGAGATCTTGAATGACAGCGGTGAAACAGTGAAGTGCAGGGCTCCTGGAGGAGCAAAGAAGCCTCTGCGCCCAAGG 6400
6321 ............................................................................ 6400

6401 TGGTGTGATGAAAGGGTGTCATCTGACCAGAGTGCGCTGTCTGAATTTATTAAGTTTGCTGAAGGTAGGAGGGGAGCTGC 6480
6401 ............................................................................ 6480

6481 TGAAGTGCTAGTTGTGCTGAGTGAACTCCCTGATTTCCTGGCTAAAAAGGTGGAGAGGCAATGGATACCATCAGTGTGT 6560
6481 ............................................................................ 6560

6561 TCCTCCACTCTGAGGAAGGCTCTAGGGCTTACCGCAATGCACTATCAATGATGCCTGAGGCAATGACAATAGTCATGCTG 6640
6561 ............................................................................ 6640

6641 TTTATACTGGCTGGACTACTGACATCGGGAATGGTCATCTTTTTCATGTCTCCCAAAGGCATCAGTAGAATGTCTATGGC 6720
6641 ............................................................................ 6720

6721 GATGGGCACAATGGCCGGCTGTGGATATCTCATGTTCCTTGGAGGCGTCAAACCCACTCACATCTCCTATGTCATGCTCA 6800
6721 ............................................................................ 6800

6801 TATTCTTTGTCCTGATGGTGGTTGTGATCCCCGAGCCAGGGCAACAAAGGTCCATCCAAGACAACCAAGTGGCATACCTC 6880
6801 ............................................................................ 6880

6881 ATTATTGGCATCCTGACGCTGGTTTCAGCGGTGGCAGCCAACGAGCTAGGCATGCTGGAGAAAACCAAAGAGGACCTCTT 6960
6881 ............................................................................ 6960

6961 TGGGAAGAAGAACTTAATTCCATCTAGTGCTTCACCCTGGAGTTGGCCGGATCTTGACCTGAAGCCAGGAGCTGCCTGGA 7040
6961 ............................................................................ 7040

7041 CAGTGTACGTTGGCATTGTTACAATGCTCTCTCCAATGTTGCACCACTGGATCAAAGTCGAATATGGCAACCTGTCTCTG 7120
7041 ............................................................................ 7120

7121 TCTGGAATAGCCCAGTCAGCCTCAGTCCTTTCTTTCATGGACAAGGGGATACCATTCATGAAGATGAATATCTCGGTCAT 7200
```

```
7121                                   ................................................................   7200

7201   AATGCTGCTGGTCAGTGGCTGGAATTCAATAACAGTGATGCCTCTGCTCTGTGGCATAGGGTGCGCCATGCTCCACTGGT   7280
7201                                   ................................................................   7280

7281   CTCTCATTTTACCTGGAATCAAAGCGCAGCAGTGAAAGCTTGCACAGAGAAGGGTGTTCCATGGCGTTGCCAAGAACCCT   7360
7281                                   ................................................................   7360

7361   GTGGTTGATGGGAATCCAACAGTTGACATTGAGGAAGCTCCTGAAATGCCTGCCCTTTATGAGAAGAAACTGGCTCTATA   7440
7361                                   ................................................................   7440

7441   TCTCCTTCTTGCTCTCAGCCTAGCTTCTGTTGCCATGTGCAGAACGCCCTTTTCATTGGCTGAAGGCATTGTCCTAGCAT   7520
7441                                   ................................................................   7520

7521   CAGCTGCCTTAGGGCCGCTCATAGAGGGAAACACCAGCCTTCTTTGGAATGGACCCATGGCTGTCTCCATGACAGGAGTC   7600
7521                                   ................................................................   7600

7601   ATGAGGGGGAATCACTATGCTTTTGTGGGAGTCATGTACAATCTATGGAAGATGAAAACTGGACGCCGGGGGAGCGCGAA   7680
7601                                   ................................................................   7680

7681   TGGAAAAACTTTGGCTGAAGTCTGGAAGAGGGAACTGAATCTGTTGGACAAGCGACAGTTTGAGTTGTATAAAAGGACCG   7760
7681                                   ................................................................   7760

7761   ACATTGTGGAGGTGGATCGTGATACGGCACGCAGGCATTTGGCCGAAGGGAAGGTGGACACCGGGGTGGCGGTCTCCAGG   7840
7761                                   ................................................................   7840

7841   GGGACCGCAAACTTAACGTGGTTCCATGACCGTGGCTATGTCAAGCTGGAAGGTAGGGTGATTGACCTGGGGTCAGGCCG   7920
7841                                   ................................................................   7920

7921   CGGAGGCTGGTGTTACTACGCTGCTGCGCAAAAGGAAGTGAGTGGGGTCAAAGGATTTACTCTTGGAAGAGACGGCCATG   8000
7921                                   ................................................................   8000

8001   AGAAACCCATGAATGTGCAAAGTCTGGGATGGAACATCATCACCTTCAAGGACAAAACTGATATCCACCGCCTAGAACCA   8080
8001                                   ................................................................   8080

8081   GTGAAATGTGACACCCTTTTGTGTGACATTGGAGAGTCATCATCGTCATCGGTCACAGAGGGGGAAAGGACCGTGAGAGT   8160
8081                                   ................................................................   8160

8161   TCTTGATACTGTAGAAAAATGGCTGGCTTGTGGGGTTGACAACTTCTGTGTGAAGGTGTTAGCTCCATACATGCCAGATG   8240
8161                                   ................................................................   8240

8241   TTCTTGAGAAACTGGAATTGCTCCAAAGGAGGTTTGGCGGAACAGTGATCAGGAACCCTCTCTCCAGGAATTCCACTCAT   8320
8241                                   ................................................................   8320

8321   GAAATGTACTACGTGTCTGGAGCCCGCAGCAATGTCACATTTACTGTGAACCAAACATCCCGCCTCCTGATGAGGAGAAT   8400
8321                                   ................................................................   8400

8401   GAGGCGTCCAACTGGAAAAGTGACCCTGGAGGCTGACGTCATCCTCCCAATTGGGACACGCAGTGTTGAGACAGACAAGG   8480
8401                                   ................................................................   8480

8481   GACCCCTGGACAAAGAGGCCATAGAAGAAAGGGTTGAGAGGATAAAATCTGAGTACATGACCTCTTGGTTTTATGACAAT   8560
8481                                   ................................................................   8560

8561   GACAACCCCTACAGGACCTGGCACTACTGTGGCTCCTATGTCACAAAAACCTCCGGAAGTGCGGCGAGCATGGTAAATGG   8640
8561                                   ................................................................   8640

8641   TGTTATTAAAATTCTGACATATCCATGGGACAGGATAGAGGAGGTCACAAGAATGGCAATGACTGACACAACCCCTTTTG   8720
8641                                   ................................................................   8720

8721   GACAGCAAAGAGTGTTTAAAGAAAAAGTTGACACCAGAGCAAAGGATCCACCAGCGGGAACTAGGAAGATCATGAAAGTT   8800
8721                                   ................................................................   8800

8801   GTCAACAGGTGGCTGTTCCGCCACCTGGCCAGAGAAAAGAACCCCAGACTGTGCACAAAGGAAGAATTTATTGCAAAGGT   8880
8801                                   ................................................................   8880

8881   CCGAAGTCATGCAGCCATTGGAGCTTACCTGGAAGAACAAGAACAGTGGAAGACTGCCAATGAGGCTGTCCAAGACCCAA   8960
8881                                   ................................................................   8960

8961   AGTTCTGGGAACTGGTGGATCAAGAAAGGAAGCTGCACCAACAAGGCAGGTGTCGGACTTGTGTGTACAACATGATGGGG   9040
8961                                   ................................................................   9040

9041   AAAAGAGAGAAGAAGCTGTCAGAGTTTGGGAAAGCAAAGGGAAGCCGTGCCATATGGTATATGTGGCTGGGAGCGCGGTA   9120
9041                                   ................................................................   9120

9121   TCTTGAGTTTGAGGCCCTGGGATTCCTGAATGAGGACCATTGGGCTTCCAGGGAAAACTCAGGAGGAGGAGTGGAAGGCA   9200
9121                                   ................................................................   9200

9201   TTGGCTTACAATACCTAGGATATGTGATCAGAGACCTGGCTGCAATGGATGGTGGTGGATTCTACGCGGATGACACCGCT   9280
9201                                   ................................................................   9280

9281   GGATGGGACACGCGCATCACAGAGGCAGACCTTGATGATGAACAGGAGATCTTGAACTACATGAGCCCACATCACAAAAA   9360
```

```
9281 ............................................................................ 9360
9361 ACTGGCACAAGCAGTGATGGAAATGACATACAAGAACAAAGTGGTGAAAGTGTTGAGACCAGCCCCAGGAGGGAAAGCCT 9440
9361 ............................................................................ 9440

9441 ACATGGATGTCATAAGTCGACGAGACCAGAGAGGATCCGGGCAGGTAGTGACTTATGCTCTGAACACCATCACCAACTTG 9520
9441 ............................................................................ 9520

9521 AAAGTCCAATTGATCAGAATGGCAGAAGCAGAGATGGTGATACATCACCAACATGTTCAAGATTGTGATGAATCAGTTCT 9600
9521 ............................................................................ 9600

9601 GACCAGGCTGGAGGCATGGCTCACTGAGCACGGATGTGACAGACTGAAGAGGATGGCGGTGAGTGGAGACGACTGTGTGG 9680
9601 ............................................................................ 9680

9681 TCCGGCCCATCGATGACAGGTTCGGCCTGGCCCTGTCCCATCTCAACGCCATGTCCAAGGTTAGAAAGGACATATCTGAA 9760
9681 ............................................................................ 9760

9761 TGGCAGCCATCAAAAGGGTGGAATGATTGGGAGAATGTGCCCTTCTGTTCCCACCACTTCCATGAACTACAGCTGAAGGA 9840
9761 ............................................................................ 9840

9841 TGGCAGGAGGATTGTGGTGCCTTGCCGAGAACAGGACGAGCTCATTGGGAGAGGAAGGGTGTCTCCAGGAAACGGCTGGA 9920
9841 ............................................................................ 9920

9921 TGATCAAGGAAACAGCTTGCCTCAGCAAAGCCTATGCCAACATGTGGTCACTGATGTATTTTCACAAAAGGGACATGAGG 10000
9921 ............................................................................ 10000

10001 CTACTGTCATTGGCTGTTTCCTCAGCTGTTCCCACCTCATGGGTTCCACAAGGACGCACAACATGGTCGATTCATGGGAA 10080
10001 ............................................................................ 10080

10081 AGGGGAGTGGATGACCACGGAAGACATGCTTGAGGTGTGGAACAGAGTATGGATAACCAACAACCCACACATGCAGGACA 10160
10081 ............................................................................ 10160

10161 AGACAATGGTGAAAAAATGGAGAGATGTCCCTTATCTAACCAAGAGACAAGACAAGCTGTGCGGATCACTGATTGGAATG 10240
10161 ............................................................................ 10240
```

DNA Strider ™ 13f7 ### Thursday, Oct. 21, 2004 3:10:16 PM

WN02 M Prot. x M66 M Prot. = → Protein Alignment

Protein sequence 75 aa SLTVQTHGESTL . . . VVLLLLVAPAYS

Protein sequence 75 aa SLTVQTHGESTL . . . VVPLLLVAPAYS

Layout:           Standard

Method:           Single Block

Block Length ≤:   6-aa

Mismatch penalty: Smaller (1)

Gap penalty:      Medium (2)

Weighting:        BLOSOM62

```
              .         20         .         40         .         60         .
    1 SLTVQTHGESTLANKKGAWMDSTKATRYLVKTESWILRNPGYALVAAVIGWMLGSNTMQRVVFVVLLLLVAPAYS    75

SLTVQTHGESTLANKKGAWMDSTKATRYLVKTESWILRNPGYALVAAVIGWMLGSNTMQRVVFVV LLLVAPAYS

1 SLTVQTEGESTLANKKGAWMDSTKATRYLVKTESWILRNPGYALVAAVIGWMLGSNTMQRVVFVVPLLLVAPAYS    75
              .         20         .         40         .         60         .
```
% Identity = 98.7 (74/75)

---

The invention claimed is:

1. A method of producing a flavivirus, the method comprising culturing the flavivirus on Vero cells, wherein the flavivirus comprises the membrane and envelope proteins of Japanese encephalitis virus (JEV) strain SA14-14-2, and the membrane protein of said JEV strain SA14-14-2 comprises a substitution of arginine with cysteine at amino acid position 60.

2. The method of claim 1, wherein said flavivirus is a chimeric flavivirus comprising sequences encoding capsid and non-structural proteins of a yellow fever virus and membrane and envelope proteins of said JEV strain SA14-14-2 comprising said substitution.

3. The method of claim 2, wherein said yellow fever virus is strain YF-17D.

4. The method of claim 1, wherein said flavivirus is intact JEV virus strain SA14-14-2 comprising said substitution.

5. The method of claim 1, further comprising harvesting said flavivirus from said Vero cells.

6. The method of claim 5, further comprising formulating said flavivirus for administration.

* * * * *

SEQUENCE LISTING

<160> NUMBER OF SEQ ID NOS: 38

<210> SEQ ID NO 1
<211> LENGTH: 21
<212> TYPE: DNA
<213> ORGANISM: Artificial Sequence
<220> FEATURE:
<223> OTHER INFORMATION: Derived from Yellow Fever virus and West Nile
      virus

<400> SEQUENCE: 1

```
cactgggaga gcttgaaggt c                                              21
```

<210> SEQ ID NO 2
<211> LENGTH: 25
<212> TYPE: DNA
<213> ORGANISM: Artificial Sequence
<220> FEATURE:
<223> OTHER INFORMATION: Derived from Yellow Fever virus and West Nile
      virus

<400> SEQUENCE: 2

```
aaagccagtt gcagccgcgg tttaa                                          25
```

<210> SEQ ID NO 3
<211> LENGTH: 21
<212> TYPE: DNA
<213> ORGANISM: Artificial Sequence
<220> FEATURE:
<223> OTHER INFORMATION: Derived from Yellow Fever virus and Dengue-1
      virus

<400> SEQUENCE: 3

```
aaggtagact ggtgggctcc c                                              21
```

<210> SEQ ID NO 4
<211> LENGTH: 26
<212> TYPE: DNA
<213> ORGANISM: Artificial Sequence
<220> FEATURE:
<223> OTHER INFORMATION: Derived from Yellow Fever virus and Dengue-1
      virus

<400> SEQUENCE: 4

```
gatcctcagt accaaccgcg gtttaa                                         26
```

<210> SEQ ID NO 5
<211> LENGTH: 21
<212> TYPE: DNA
<213> ORGANISM: Artificial Sequence
<220> FEATURE:
<223> OTHER INFORMATION: Derived from Yellow Fever virus and Dengue-2
      virus

<400> SEQUENCE: 5

```
aaggtagatt ggtgtgcatt g                                              21
```

<210> SEQ ID NO 6
<211> LENGTH: 26
<212> TYPE: DNA
<213> ORGANISM: Artificial Sequence
<220> FEATURE:
<223> OTHER INFORMATION: Derived from Yellow Fever virus and Dengue-2
      virus

<400> SEQUENCE: 6

```
aaccctcagt accacccgcg gtttaa                                         26
```

<210> SEQ ID NO 7
<211> LENGTH: 21
<212> TYPE: DNA
<213> ORGANISM: Artificial Sequence
<220> FEATURE:
<223> OTHER INFORMATION: Derived from Yellow Fever virus and Dengue-3
      virus

<400> SEQUENCE: 7

```
aaggtgaatt gaagtgctct a                                              21
```

```
<210> SEQ ID NO 8
<211> LENGTH: 25
<212> TYPE: DNA
<213> ORGANISM: Artificial Sequence
<220> FEATURE:
<223> OTHER INFORMATION: Derived from Yellow Fever virus and Dengue-3
      virus

<400> SEQUENCE: 8 accccccagca ccacccgcgg tttaa                                              25

<210> SEQ ID NO 9
<211> LENGTH: 21
<212> TYPE: DNA
<213> ORGANISM: Artificial Sequence
<220> FEATURE:
<223> OTHER INFORMATION: Derived from Yellow Fever virus and Dengue-4
      virus

<400> SEQUENCE: 9
aaaaggaaca gttgttctct a                                                   21

<210> SEQ ID NO 10
<211> LENGTH: 25
<212> TYPE: DNA
<213> ORGANISM: Artificial Sequence
<220> FEATURE:
<223> OTHER INFORMATION: Derived from Yellow Fever virus and Dengue-4
      virus

<400> SEQUENCE: 10
acccgaagtg tcaaccgcgg tttaa                                               25

<210> SEQ ID NO 11
<211> LENGTH: 21
<212> TYPE: DNA
<213> ORGANISM: Artificial Sequence
<220> FEATURE:
<223> OTHER INFORMATION: Derived from Yellow Fever virus and St. Louis
      Encephalitis virus

<400> SEQUENCE: 11
aacgtgaata gttggatagt c                                                   21

<210> SEQ ID NO 12
<211> LENGTH: 25
<212> TYPE: DNA
<213> ORGANISM: Artificial Sequence
<220> FEATURE:
<223> OTHER INFORMATION: Derived from Yellow Fever virus and St. Louis
      Encephalitis virus

<400> SEQUENCE: 12
accgttggtc gcacccgcgg tttaa                                               25

<210> SEQ ID NO 13
<211> LENGTH: 21
<212> TYPE: DNA
<213> ORGANISM: Artificial Sequence
<220> FEATURE:
<223> OTHER INFORMATION: Derived from Yellow Fever virus and Murray
      Valley Encephalitis virus

<400> SEQUENCE: 13
aatttcgaaa ggtggaaggt c                                                   21
```

```
<210> SEQ ID NO 14
<211> LENGTH: 26
<212> TYPE: DNA
<213> ORGANISM: Artificial Sequence
<220> FEATURE:
<223> OTHER INFORMATION: Derived from Yellow Fever virus and Murray
      Valley Encephalitis virus

<400> SEQUENCE: 14
gaccggtgtt tacagccgcg gtttaa                                          26

<210> SEQ ID NO 15
<211> LENGTH: 21
<212> TYPE: DNA
<213> ORGANISM: Artificial Sequence
<220> FEATURE:
<223> OTHER INFORMATION: Derived from Yellow Fever virus and Tick-Borne
      Encephalitis virus

<400> SEQUENCE: 15
tactgcgaac gacgttgcca c                                               21

<210> SEQ ID NO 16
<211> LENGTH: 25
<212> TYPE: DNA
<213> ORGANISM: Artificial Sequence
<220> FEATURE:
<223> OTHER INFORMATION: Derived from Yellow Fever virus and Tick-Borne
      Encephalitis virus

<400> SEQUENCE: 16
actgggaacc tcacccgcgg tttaa                                           25

<210> SEQ ID NO 17
<211> LENGTH: 16
<212> TYPE: DNA
<213> ORGANISM: Artificial Sequence
<220> FEATURE:
<223> OTHER INFORMATION: Derived from Yellow Fever virus

<400> SEQUENCE: 17
ggttagagga gaccct                                                     16

<210> SEQ ID NO 18
<211> LENGTH: 39
<212> TYPE: PRT
<213> ORGANISM: Artificial Sequence
<220> FEATURE:
<223> OTHER INFORMATION: Derived from West Nile virus

<400> SEQUENCE: 18

Ser Leu Thr Val Gln Thr His Gly Glu Ser Thr Leu Ala Asn Lys Lys
1               5                   10                  15

Gly Ala Trp Met Asp Ser Thr Lys Ala Thr Arg Tyr Leu Val Lys Thr
            20                  25                  30

Glu Ser Trp Ile Leu Arg Asn
        35

<210> SEQ ID NO 19
<211> LENGTH: 36
<212> TYPE: PRT
<213> ORGANISM: Artificial Sequence
<220> FEATURE:
<223> OTHER INFORMATION: Derived from West Nile virus

<400> SEQUENCE: 19

Pro Gly Tyr Ala Leu Val Ala Ala Val Ile Gly Trp Met Leu Gly Ser
```

```
                    1               5                  10                 15
              Asn Thr Met Gln Arg Val Val Phe Val Val Leu Leu Leu Val Ala
                                  20                 25                 30

Pro Ala Tyr Ser
                        35

<210> SEQ ID NO 20
<211> LENGTH: 10896
<212> TYPE: DNA
<213> ORGANISM: Artificial Sequence
<220> FEATURE:
<223> OTHER INFORMATION: Derived from Yellow Fever Virus and West Nile
      virus
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: CDS
<222> LOCATION: (119)..(10384)

<400> SEQUENCE: 20
ngtaaatcct gtgtgctaat tgaggtgcat tggtctgcaa atcgagttgc taggcaataa          60
acacatttgg attaatttta atcgttcgtt gagcgattag cagagaactg accagaac          118 atg tct ggt cgt aaa gct cag gga aaa acc ctg ggc gtc aat atg gta          166
Met Ser Gly Arg Lys Ala Gln Gly Lys Thr Leu Gly Val Asn Met Val
1               5                  10                 15 cga cga gga gtt cgc tcc ttg tca aac aaa ata aaa caa aaa aca aaa          214
Arg Arg Gly Val Arg Ser Leu Ser Asn Lys Ile Lys Gln Lys Thr Lys
                20                  25                 30 caa att gga aac aga cct gga cct tca aga ggt gtt caa gga ttt atc          262
Gln Ile Gly Asn Arg Pro Gly Pro Ser Arg Gly Val Gln Gly Phe Ile
            35                  40                  45 ttt ttc ttt ttg ttc aac att ttg act gga aaa aag atc aca gcc cac          310
Phe Phe Phe Leu Phe Asn Ile Leu Thr Gly Lys Lys Ile Thr Ala His
50                  55                  60 cta aag agg ttg tgg aaa atg ctg gac cca aga caa ggc ttg gct gtt          358
Leu Lys Arg Leu Trp Lys Met Leu Asp Pro Arg Gln Gly Leu Ala Val
65                  70                  75                  80 cta agg aaa gtc aag aga gtg gtg gcc agt ttg atg aga gga ttg tcc          406
Leu Arg Lys Val Lys Arg Val Val Ala Ser Leu Met Arg Gly Leu Ser
                85                  90                  95 tca agg aaa cgc cgt tcc cat gat gtt ctg act gtg caa ttc cta att          454
Ser Arg Lys Arg Arg Ser His Asp Val Leu Thr Val Gln Phe Leu Ile
                100                 105                110 ttg gga atg ctg ttg atg acg ggt gga gtt acc ctc tct aac ttc caa          502
Leu Gly Met Leu Leu Met Thr Gly Gly Val Thr Leu Ser Asn Phe Gln
            115                 120                 125 ggg aag gtg atg atg acg gta aat gct act gac gtc aca gat gtc atc          550
Gly Lys Val Met Met Thr Val Asn Ala Thr Asp Val Thr Asp Val Ile
130                 135                 140 acg att cca aca gct gct gga aag aac cta tgc att gtc aga gca atg          598
Thr Ile Pro Thr Ala Ala Gly Lys Asn Leu Cys Ile Val Arg Ala Met
145                 150                 155                 160 gat gtg gga tac atg tgc gat gat act atc act tat gaa tgc cca gtg          646
Asp Val Gly Tyr Met Cys Asp Asp Thr Ile Thr Tyr Glu Cys Pro Val
                165                 170                 175 ctg tcg gct ggt aat gat cca gaa gac atc gac tgt tgg tgc aca aag          694
Leu Ser Ala Gly Asn Asp Pro Glu Asp Ile Asp Cys Trp Cys Thr Lys
                180                 185                 190 tca gca gtc tac gtc agg tat gga aga tgc acc aag aca cgc cac tca          742
Ser Ala Val Tyr Val Arg Tyr Gly Arg Cys Thr Lys Thr Arg His Ser
```

```
              195                 200                 205
aga cgc agt cgg agg tca ctg aca gtg cag aca cac gga gaa agc act        790
Arg Arg Ser Arg Arg Ser Leu Thr Val Gln Thr His Gly Glu Ser Thr
210                 215                 220 cta gcg aac aag aag ggg gct tgg atg gac agc acc aag gcc aca agg        838
Leu Ala Asn Lys Lys Gly Ala Trp Met Asp Ser Thr Lys Ala Thr Arg
225                 230                 235                 240 tat ttg gta aaa aca gaa tca tgg atc ttg agg aac cct gga tat gcc        886
Tyr Leu Val Lys Thr Glu Ser Trp Ile Leu Arg Asn Pro Gly Tyr Ala
                245                 250                 255 ctg gtg gca gcc gtc att ggt tgg atg ctt ggg agc aac acc atg cag        934
Leu Val Ala Ala Val Ile Gly Trp Met Leu Gly Ser Asn Thr Met Gln
                260                 265                 270 aga gtt gtg ttt gtc gtg cta ttg ctt ttg gtg gcc cca gct tac agc        982
Arg Val Val Phe Val Val Leu Leu Leu Leu Val Ala Pro Ala Tyr Ser
            275                 280                 285 ttc aac tgc ctt gga atg agc aac aga gac ttc ttg gaa gga gtg tct       1030
Phe Asn Cys Leu Gly Met Ser Asn Arg Asp Phe Leu Glu Gly Val Ser
        290                 295                 300 gga gca aca tgg gtg gat ttg gtt ctc gaa ggc gac agc tgc gtg act       1078
Gly Ala Thr Trp Val Asp Leu Val Leu Glu Gly Asp Ser Cys Val Thr
305                 310                 315                 320 atc atg tct aag gac aag cct acc atc gac gtc aag atg atg aat atg       1126
Ile Met Ser Lys Asp Lys Pro Thr Ile Asp Val Lys Met Met Asn Met
                325                 330                 335 gag gcg gcc aac ctg gca gag gtc cgc agt tat tgc tat ttg gct acc       1174
Glu Ala Ala Asn Leu Ala Glu Val Arg Ser Tyr Cys Tyr Leu Ala Thr
                340                 345                 350 gtc agc gat ctc tcc acc aaa gct gca tgc ccg acc atg gga gaa gct       1222
Val Ser Asp Leu Ser Thr Lys Ala Ala Cys Pro Thr Met Gly Glu Ala
            355                 360                 365 cac aat gac aaa cgt gct gac cca gct ttt gtg tgc aga caa gga gtg       1270
His Asn Asp Lys Arg Ala Asp Pro Ala Phe Val Cys Arg Gln Gly Val
        370                 375                 380 gtg gac agg ggc tgg ggc aac ggc tgc gga ttt ttt ggc aaa gga tcc       1318
Val Asp Arg Gly Trp Gly Asn Gly Cys Gly Phe Phe Gly Lys Gly Ser
385                 390                 395                 400 att gac aca tgc gcc aaa ttt gcc tgc tct acc aag gca ata gga aga       1366
Ile Asp Thr Cys Ala Lys Phe Ala Cys Ser Thr Lys Ala Ile Gly Arg
                405                 410                 415 acc atc ttg aaa gag aat atc aag tac gaa gtg gcc att ttt gtc cat       1414
Thr Ile Leu Lys Glu Asn Ile Lys Tyr Glu Val Ala Ile Phe Val His
                420                 425                 430 gga cca act act gtg gag tcg cac gga aat tac tcc aca cag gtt gga       1462
Gly Pro Thr Thr Val Glu Ser His Gly Asn Tyr Ser Thr Gln Val Gly
            435                 440                 445 gcc act cag gcc ggc cga ttc agc atc act cct gct gcg cct tca tac       1510
Ala Thr Gln Ala Gly Arg Phe Ser Ile Thr Pro Ala Ala Pro Ser Tyr
        450                 455                 460 aca cta aag ctt gga gaa tat gga gag gtg aca gtg gac tgt gaa cca       1558
Thr Leu Lys Leu Gly Glu Tyr Gly Glu Val Thr Val Asp Cys Glu Pro
465                 470                 475                 480 cgg tca ggg att gac acc aat gca tac tac gtg atg act gtt gga aca       1606
Arg Ser Gly Ile Asp Thr Asn Ala Tyr Tyr Val Met Thr Val Gly Thr
                485                 490                 495 aag acg ttc ttg gtc cat cgt gag tgg ttc atg gac ctc aac ctc cct       1654
Lys Thr Phe Leu Val His Arg Glu Trp Phe Met Asp Leu Asn Leu Pro
                500                 505                 510 tgg agc agt gct gga agt act gtg tgg agg aac aga gag acg tta atg       1702
Trp Ser Ser Ala Gly Ser Thr Val Trp Arg Asn Arg Glu Thr Leu Met
```

-continued

```
                515                 520                 525
gag ttt gag gaa cca cac gcc acg aag cag tct gtg ata gca ttg ggc    1750
Glu Phe Glu Glu Pro His Ala Thr Lys Gln Ser Val Ile Ala Leu Gly
        530                 535                 540 tca caa gag gga gct ctg cat caa gct ttg gct gga gcc att cct gtg    1798
Ser Gln Glu Gly Ala Leu His Gln Ala Leu Ala Gly Ala Ile Pro Val
545                 550                 555                 560 gaa ttt tca agc aac act gtc aag ttg acg tcg ggt cat ttg aag tgt    1846
Glu Phe Ser Ser Asn Thr Val Lys Leu Thr Ser Gly His Leu Lys Cys
                565                 570                 575 aga gtg aag atg gaa aaa ttg cag ttg aag gga aca acc tat ggc gtc    1894
Arg Val Lys Met Glu Lys Leu Gln Leu Lys Gly Thr Thr Tyr Gly Val
            580                 585                 590 tgt tca aag gct ttc aag ttt ctt agg act ccc gtg gac acc ggt cac    1942
Cys Ser Lys Ala Phe Lys Phe Leu Arg Thr Pro Val Asp Thr Gly His
        595                 600                 605 ggc act gtg gtg ttg gaa ttg cag tac act ggc acg gat gga cct tgc    1990
Gly Thr Val Val Leu Glu Leu Gln Tyr Thr Gly Thr Asp Gly Pro Cys
610                 615                 620 aaa gtt cct atc tcg tca gtg gct tca ttg aac gac cta acg cca gtg    2038
Lys Val Pro Ile Ser Ser Val Ala Ser Leu Asn Asp Leu Thr Pro Val
625                 630                 635                 640 ggc aga ttg gtc act gtc aac cct ttt gtt tca gtg gcc acg gcc aac    2086
Gly Arg Leu Val Thr Val Asn Pro Phe Val Ser Val Ala Thr Ala Asn
                645                 650                 655 gct aag gtc ctg att gaa ttg gaa cca ccc ttt gga gac tca tac ata    2134
Ala Lys Val Leu Ile Glu Leu Glu Pro Pro Phe Gly Asp Ser Tyr Ile
            660                 665                 670 gtg gtg ggc aga gga gaa caa cag atc aat cac cat tgg cac aag tct    2182
Val Val Gly Arg Gly Glu Gln Gln Ile Asn His His Trp His Lys Ser
675                 680                 685 gga agc agc att ggc aaa gcc ttt aca acc acc ctc aaa gga gcg cag    2230
Gly Ser Ser Ile Gly Lys Ala Phe Thr Thr Thr Leu Lys Gly Ala Gln
690                 695                 700 aga cta gcc gct cta gga gac aca gct tgg gac ttt gga tca gtt gga    2278
Arg Leu Ala Ala Leu Gly Asp Thr Ala Trp Asp Phe Gly Ser Val Gly
705                 710                 715                 720 ggg gtg ttc act agt gtt ggg cgg gct gtc cat caa gtg ttc gga gga    2326
Gly Val Phe Thr Ser Val Gly Arg Ala Val His Gln Val Phe Gly Gly
                725                 730                 735 gca ttc cgc tca ctg ttc gga ggc atg tcc tgg ata acg caa gga ttg    2374
Ala Phe Arg Ser Leu Phe Gly Gly Met Ser Trp Ile Thr Gln Gly Leu
            740                 745                 750 ctg ggg gct ctc ctg ttg tgg atg ggc atc aat gct cgt gat agg tcc    2422
Leu Gly Ala Leu Leu Leu Trp Met Gly Ile Asn Ala Arg Asp Arg Ser
755                 760                 765 ata gct ctc acg ttt ctc gca gtt gga gga gtt ctg ctc ttc ctc tcc    2470
Ile Ala Leu Thr Phe Leu Ala Val Gly Gly Val Leu Leu Phe Leu Ser
770                 775                 780 gtg aac gtg ggc gcc gat caa gga tgc gcc atc aac ttt ggc aag aga    2518
Val Asn Val Gly Ala Asp Gln Gly Cys Ala Ile Asn Phe Gly Lys Arg
785                 790                 795                 800 gag ctc aag tgc gga gat ggt atc ttc ata ttt aga gac tct gat gac    2566
Glu Leu Lys Cys Gly Asp Gly Ile Phe Ile Phe Arg Asp Ser Asp Asp
                805                 810                 815 tgg ctg aac aag tac tca tac tat cca gaa gat cct gtg aag ctt gca    2614
Trp Leu Asn Lys Tyr Ser Tyr Tyr Pro Glu Asp Pro Val Lys Leu Ala
            820                 825                 830 tca ata gtg aaa gcc tct ttt gaa gaa ggg aag tgt ggc cta aat tca    2662
Ser Ile Val Lys Ala Ser Phe Glu Glu Gly Lys Cys Gly Leu Asn Ser
```

```
                    835                840                845
gtt gac tcc ctt gag cat gag atg tgg aga agc agg gca gat gag atc    2710
Val Asp Ser Leu Glu His Glu Met Trp Arg Ser Arg Ala Asp Glu Ile
850                     855                     860 aat gcc att ttt gag gaa aac gag gtg gac att tct gtt gtc gtg cag    2758
Asn Ala Ile Phe Glu Glu Asn Glu Val Asp Ile Ser Val Val Val Gln
865                     870                     875            880 gat cca aag aat gtt tac cag aga gga act cat cca ttt tcc aga att    2806
Asp Pro Lys Asn Val Tyr Gln Arg Gly Thr His Pro Phe Ser Arg Ile
                885                     890                     895 cgg gat ggt ctg cag tat ggt tgg aag act tgg ggt aag aac ctt gtg    2854
Arg Asp Gly Leu Gln Tyr Gly Trp Lys Thr Trp Gly Lys Asn Leu Val
            900                     905                     910 ttc tcc cca ggg agg aag aat gga agc ttc atc ata gat gga aag tcc    2902
Phe Ser Pro Gly Arg Lys Asn Gly Ser Phe Ile Ile Asp Gly Lys Ser
        915                     920                     925 agg aaa gaa tgc ccg ttt tca aac cgg gtc tgg aat tct ttc cag ata    2950
Arg Lys Glu Cys Pro Phe Ser Asn Arg Val Trp Asn Ser Phe Gln Ile
    930                     935                     940 gag gag ttt ggg acg gga gtg ttc acc aca cgc gtg tac atg gac gca    2998
Glu Glu Phe Gly Thr Gly Val Phe Thr Thr Arg Val Tyr Met Asp Ala
945                     950                     955                 960 gtc ttt gaa tac acc ata gac tgc gat gga tct atc ttg ggt gca gcg    3046
Val Phe Glu Tyr Thr Ile Asp Cys Asp Gly Ser Ile Leu Gly Ala Ala
                965                     970                     975 gtg aac gga aaa aag agt gcc cat ggc tct cca aca ttt tgg atg gga    3094
Val Asn Gly Lys Lys Ser Ala His Gly Ser Pro Thr Phe Trp Met Gly
            980                     985                     990 agt cat gaa gta aat ggg aca tgg atg atc cac acc ttg gag gca tta    3142
Ser His Glu Val Asn Gly Thr Trp Met Ile His Thr Leu Glu Ala Leu
        995                     1000                    1005 gat tac aag gag tgt gag tgg cca ctg aca cat acg att gga aca        3187
Asp Tyr Lys Glu Cys Glu Trp Pro Leu Thr His Thr Ile Gly Thr
    1010                    1015                    1020 tca gtt gaa gag agt gaa atg ttc atg ccg aga tca atc gga ggc        3232
Ser Val Glu Glu Ser Glu Met Phe Met Pro Arg Ser Ile Gly Gly
1025                    1030                    1035 cca gtt agc tct cac aat cat atc cct gga tac aag gtt cag acg        3277
Pro Val Ser Ser His Asn His Ile Pro Gly Tyr Lys Val Gln Thr
    1040                    1045                    1050 aac gga cct tgg atg cag gta cca cta gaa gtg aag aga gaa gct        3322
Asn Gly Pro Trp Met Gln Val Pro Leu Glu Val Lys Arg Glu Ala
    1055                    1060                    1065 tgc cca ggg act agc gtg atc att gat ggc aac tgt gat gga cgg        3367
Cys Pro Gly Thr Ser Val Ile Ile Asp Gly Asn Cys Asp Gly Arg
    1070                    1075                    1080 gga aaa tca acc aga tcc acc acg gat agc ggg aaa gtt att cct        3412
Gly Lys Ser Thr Arg Ser Thr Thr Asp Ser Gly Lys Val Ile Pro
    1085                    1090                    1095 gaa tgg tgt tgc cgc tcc tgc aca atg ccg cct gtg agc ttc cat        3457
Glu Trp Cys Cys Arg Ser Cys Thr Met Pro Pro Val Ser Phe His
    1100                    1105                    1110 ggt agt gat ggg tgt tgg tat ccc atg gaa att agg cca agg aaa        3502
Gly Ser Asp Gly Cys Trp Tyr Pro Met Glu Ile Arg Pro Arg Lys
    1115                    1120                    1125 acg cat gaa agc cat ctg gtg cgc tcc tgg gtt aca gct gga gaa        3547
Thr His Glu Ser His Leu Val Arg Ser Trp Val Thr Ala Gly Glu
    1130                    1135                    1140 ata cat gct gtc cct ttt ggt ttg gtg agc atg atg ata gca atg        3592
Ile His Ala Val Pro Phe Gly Leu Val Ser Met Met Ile Ala Met
```

-continued

|  |  |  |  |  |
|---|---|---|---|---|
| 1145 | 1150 | 1155 | | |
| gaa gtg gtc cta agg aaa aga cag gga cca aag caa atg ttg gtt<br>Glu Val Val Leu Arg Lys Arg Gln Gly Pro Lys Gln Met Leu Val<br>1160                            1165                            1170 | | | | 3637 |
| gga gga gta gtg ctc ttg gga gca atg ctg gtc ggg caa gta act<br>Gly Gly Val Val Leu Leu Gly Ala Met Leu Val Gly Gln Val Thr<br>1175                            1180                            1185 | | | | 3682 |
| ctc ctt gat ttg ctg aaa ctc aca gtg gct gtg gga ttg cat ttc<br>Leu Leu Asp Leu Leu Lys Leu Thr Val Ala Val Gly Leu His Phe<br>1190                            1195                            1200 | | | | 3727 |
| cat gag atg aac aat gga gga gac gcc atg tat atg gcg ttg att<br>His Glu Met Asn Asn Gly Gly Asp Ala Met Tyr Met Ala Leu Ile<br>1205                            1210                            1215 | | | | 3772 |
| gct gcc ttt tca atc aga cca ggg ctg ctc atc ggc ttt ggg ctc<br>Ala Ala Phe Ser Ile Arg Pro Gly Leu Leu Ile Gly Phe Gly Leu<br>1220                            1225                            1230 | | | | 3817 |
| agg acc cta tgg agc cct cgg gaa cgc ctt gtg ctg acc cta gga<br>Arg Thr Leu Trp Ser Pro Arg Glu Arg Leu Val Leu Thr Leu Gly<br>1235                            1240                            1245 | | | | 3862 |
| gca gcc atg gtg gag att gcc ttg ggt ggc gtg atg ggc ggc ctg<br>Ala Ala Met Val Glu Ile Ala Leu Gly Gly Val Met Gly Gly Leu<br>1250                            1255                            1260 | | | | 3907 |
| tgg aag tat cta aat gca gtt tct ctc tgc atc ctg aca ata aat<br>Trp Lys Tyr Leu Asn Ala Val Ser Leu Cys Ile Leu Thr Ile Asn<br>1265                            1270                            1275 | | | | 3952 |
| gct gtt gct tct agg aaa gca tca aat acc atc ttg ccc ctc atg<br>Ala Val Ala Ser Arg Lys Ala Ser Asn Thr Ile Leu Pro Leu Met<br>1280                            1285                            1290 | | | | 3997 |
| gct ctg ttg aca cct gtc act atg gct gag gtg aga ctt gcc gca<br>Ala Leu Leu Thr Pro Val Thr Met Ala Glu Val Arg Leu Ala Ala<br>1295                            1300                            1305 | | | | 4042 |
| atg ttc ttt tgt gcc atg gtt atc ata ggg gtc ctt cac cag aat<br>Met Phe Phe Cys Ala Met Val Ile Ile Gly Val Leu His Gln Asn<br>1310                            1315                            1320 | | | | 4087 |
| ttc aag gac acc tcc atg cag aag act ata cct ctg gtg gcc ctc<br>Phe Lys Asp Thr Ser Met Gln Lys Thr Ile Pro Leu Val Ala Leu<br>1325                            1330                            1335 | | | | 4132 |
| aca ctc aca tct tac ctg ggc ttg aca caa cct ttt ttg ggc ctg<br>Thr Leu Thr Ser Tyr Leu Gly Leu Thr Gln Pro Phe Leu Gly Leu<br>1340                            1345                            1350 | | | | 4177 |
| tgt gca ttt ctg gca acc cgc ata ttt ggg cga agg agt atc cca<br>Cys Ala Phe Leu Ala Thr Arg Ile Phe Gly Arg Arg Ser Ile Pro<br>1355                            1360                            1365 | | | | 4222 |
| gtg aat gag gca ctc gca gca gct ggt cta gtg gga gtg ctg gca<br>Val Asn Glu Ala Leu Ala Ala Ala Gly Leu Val Gly Val Leu Ala<br>1370                            1375                            1380 | | | | 4267 |
| gga ctg gct ttt cag gag atg gag aac ttc ctt ggt ccg att gca<br>Gly Leu Ala Phe Gln Glu Met Glu Asn Phe Leu Gly Pro Ile Ala<br>1385                            1390                            1395 | | | | 4312 |
| gtt gga gga ctc ctg atg atg ctg gtt agc gtg gct ggg agg gtg<br>Val Gly Gly Leu Leu Met Met Leu Val Ser Val Ala Gly Arg Val<br>1400                            1405                            1410 | | | | 4357 |
| gat ggg cta gag ctc aag aag ctt ggt gaa gtt tca tgg gaa gag<br>Asp Gly Leu Glu Leu Lys Lys Leu Gly Glu Val Ser Trp Glu Glu<br>1415                            1420                            1425 | | | | 4402 |
| gag gcg gag atc agc ggg agt tcc gcc cgc tat gat gtg gca ctc<br>Glu Ala Glu Ile Ser Gly Ser Ser Ala Arg Tyr Asp Val Ala Leu<br>1430                            1435                            1440 | | | | 4447 |
| agt gaa caa ggg gag ttc aag ctg ctt tct gaa gag aaa gtg cca<br>Ser Glu Gln Gly Glu Phe Lys Leu Leu Ser Glu Glu Lys Val Pro | | | | 4492 |

```
                         1445                1450                1455
tgg gac cag gtt gtg atg acc tcg ctg gcc ttg gtt ggg gct gcc       4537
Trp Asp Gln Val Val Met Thr Ser Leu Ala Leu Val Gly Ala Ala
1460                1465                1470 ctc cat cca ttt gct ctt ctg ctg gtc ctt gct ggg tgg ctg ttt       4582
Leu His Pro Phe Ala Leu Leu Leu Val Leu Ala Gly Trp Leu Phe
    1475                1480                1485 cat gtc agg gga gct agg aga agt ggg gat gtc ttg tgg gat att       4627
His Val Arg Gly Ala Arg Arg Ser Gly Asp Val Leu Trp Asp Ile
1490                1495                1500 ccc act cct aag atc atc gag gaa tgt gaa cat ctg gag gat ggg       4672
Pro Thr Pro Lys Ile Ile Glu Glu Cys Glu His Leu Glu Asp Gly
    1505                1510                1515 att tat ggc ata ttc cag tca acc ttc ttg ggg gcc tcc cag cga       4717
Ile Tyr Gly Ile Phe Gln Ser Thr Phe Leu Gly Ala Ser Gln Arg
1520                1525                1530 gga gtg gga gtg gca cag gga ggg gtg ttc cac aca atg tgg cat       4762
Gly Val Gly Val Ala Gln Gly Gly Val Phe His Thr Met Trp His
    1535                1540                1545 gtc aca aga gga gct ttc ctt gtc agg aat ggc aag aag ttg att       4807
Val Thr Arg Gly Ala Phe Leu Val Arg Asn Gly Lys Lys Leu Ile
1550                1555                1560 cca tct tgg gct tca gta aag gaa gac ctt gtc gcc tat ggt ggc       4852
Pro Ser Trp Ala Ser Val Lys Glu Asp Leu Val Ala Tyr Gly Gly
    1565                1570                1575 tca tgg aag ttg gaa ggc aga tgg gat gga gag gag gtc cag           4897
Ser Trp Lys Leu Glu Gly Arg Trp Asp Gly Glu Glu Val Gln
1580                1585                1590 ttg atc gcg gct gtt cca gga aag aac gtg gtc aac gtc cag aca       4942
Leu Ile Ala Ala Val Pro Gly Lys Asn Val Val Asn Val Gln Thr
    1595                1600                1605 aaa ccg agc ttg ttc aaa gtg agg aat ggg gga gaa atc ggg gct       4987
Lys Pro Ser Leu Phe Lys Val Arg Asn Gly Gly Glu Ile Gly Ala
1610                1615                1620 gtc gct ctt gac tat ccg agt ggc act tca gga tct cct att gtt       5032
Val Ala Leu Asp Tyr Pro Ser Gly Thr Ser Gly Ser Pro Ile Val
    1625                1630                1635 aac agg aac gga gag gtg att ggg ctg tac ggc aat ggc atc ctt       5077
Asn Arg Asn Gly Glu Val Ile Gly Leu Tyr Gly Asn Gly Ile Leu
1640                1645                1650 gtc ggt gac aac tcc ttc gtg tcc gcc ata tcc cag act gag gtg       5122
Val Gly Asp Asn Ser Phe Val Ser Ala Ile Ser Gln Thr Glu Val
    1655                1660                1665 aag gaa gaa gga aag gag gag ctc caa gag atc ccg aca atg cta       5167
Lys Glu Glu Gly Lys Glu Glu Leu Gln Glu Ile Pro Thr Met Leu
1670                1675                1680 aag aaa gga atg aca act gtc ctt gat ttt cat cct gga gct ggg       5212
Lys Lys Gly Met Thr Thr Val Leu Asp Phe His Pro Gly Ala Gly
    1685                1690                1695 aag aca aga cgt ttc ctc cca cag atc ttg gcc gag tgc gca cgg       5257
Lys Thr Arg Arg Phe Leu Pro Gln Ile Leu Ala Glu Cys Ala Arg
1700                1705                1710 aga cgc ttg cgc act ctt gtg ttg gcc ccc acc agg gtt gtt ctt       5302
Arg Arg Leu Arg Thr Leu Val Leu Ala Pro Thr Arg Val Val Leu
    1715                1720                1725 tct gaa atg aag gag gct ttt cac ggc ctg gac gtg aaa ttc cac       5347
Ser Glu Met Lys Glu Ala Phe His Gly Leu Asp Val Lys Phe His
1730                1735                1740 aca cag gct ttt tcc gct cac ggc agc ggg aga gaa gtc att gat       5392
Thr Gln Ala Phe Ser Ala His Gly Ser Gly Arg Glu Val Ile Asp
```

-continued

```
          1745                1750                1755
gcc atg tgc cat gcc acc cta act tac agg atg ttg gaa cca act      5437
Ala Met Cys His Ala Thr Leu Thr Tyr Arg Met Leu Glu Pro Thr
1760                1765                1770 agg gtt gtt aac tgg gaa gtg atc att atg gat gaa gcc cat ttt      5482
Arg Val Val Asn Trp Glu Val Ile Ile Met Asp Glu Ala His Phe
1775                1780                1785 ttg gat cca gcc agc ata gcc gct aga ggt tgg gca gcg cac aga      5527
Leu Asp Pro Ala Ser Ile Ala Ala Arg Gly Trp Ala Ala His Arg
1790                1795                1800 gct agg gca aat gaa agt gca aca atc ttg atg aca gcc aca ccg      5572
Ala Arg Ala Asn Glu Ser Ala Thr Ile Leu Met Thr Ala Thr Pro
1805                1810                1815 cct ggg act agt gat gaa ttt cca cat tca aat ggt gaa ata gaa      5617
Pro Gly Thr Ser Asp Glu Phe Pro His Ser Asn Gly Glu Ile Glu
1820                1825                1830 gat gtt caa acg gac ata ccc agt gag ccc tgg aac aca ggg cat      5662
Asp Val Gln Thr Asp Ile Pro Ser Glu Pro Trp Asn Thr Gly His
1835                1840                1845 gac tgg atc ctg gct gac aaa agg ccc acg gca tgg ttc ctt cca      5707
Asp Trp Ile Leu Ala Asp Lys Arg Pro Thr Ala Trp Phe Leu Pro
1850                1855                1860 tcc atc aga gct gca aat gtc atg gct gcc tct ttg cgt aag gct      5752
Ser Ile Arg Ala Ala Asn Val Met Ala Ala Ser Leu Arg Lys Ala
1865                1870                1875 gga aag agt gtg gtg gtc ctg aac agg aaa acc ttt gag aga gaa      5797
Gly Lys Ser Val Val Val Leu Asn Arg Lys Thr Phe Glu Arg Glu
1880                1885                1890 tac ccc acg ata aag cag aag aaa cct gac ttt ata ttg gcc act      5842
Tyr Pro Thr Ile Lys Gln Lys Lys Pro Asp Phe Ile Leu Ala Thr
1895                1900                1905 gac ata gct gaa atg gga gcc aac ctt tgc gtg gag cga gtg ctg      5887
Asp Ile Ala Glu Met Gly Ala Asn Leu Cys Val Glu Arg Val Leu
1910                1915                1920 gat tgc agg acg gct ttt aag cct gtg ctt gtg gat gaa ggg agg      5932
Asp Cys Arg Thr Ala Phe Lys Pro Val Leu Val Asp Glu Gly Arg
1925                1930                1935 aag gtg gca ata aaa ggg cca ctt cgt atc tcc gca tcc tct gct      5977
Lys Val Ala Ile Lys Gly Pro Leu Arg Ile Ser Ala Ser Ser Ala
1940                1945                1950 gct caa agg agg ggg cgc att ggg aga aat ccc aac aga gat gga      6022
Ala Gln Arg Arg Gly Arg Ile Gly Arg Asn Pro Asn Arg Asp Gly
1955                1960                1965 gac tca tac tac tat tct gag cct aca agt gaa aat aat gcc cac      6067
Asp Ser Tyr Tyr Tyr Ser Glu Pro Thr Ser Glu Asn Asn Ala His
1970                1975                1980 cac gtc tgc tgg ttg gag gcc tca atg ctc ttg gac aac atg gag      6112
His Val Cys Trp Leu Glu Ala Ser Met Leu Leu Asp Asn Met Glu
1985                1990                1995 gtg agg ggt gga atg gtc gcc cca ctc tat ggc gtt gaa gga act      6157
Val Arg Gly Gly Met Val Ala Pro Leu Tyr Gly Val Glu Gly Thr
2000                2005                2010 aaa aca cca gtt tcc cct ggt gaa atg aga ctg agg gat gac cag      6202
Lys Thr Pro Val Ser Pro Gly Glu Met Arg Leu Arg Asp Asp Gln
2015                2020                2025 agg aaa gtc ttc aga gaa cta gtg agg aat tgt gac ctg ccc gtt      6247
Arg Lys Val Phe Arg Glu Leu Val Arg Asn Cys Asp Leu Pro Val
2030                2035                2040 tgg ctt tcg tgg caa gtg gcc aag gct ggt ttg aag acg aat gat      6292
Trp Leu Ser Trp Gln Val Ala Lys Ala Gly Leu Lys Thr Asn Asp
```

-continued

|   |   |
|---|---|
| cgt aag tgg tgt ttt gaa ggc cct gag gaa cat gag atc ttg aat<br>Arg Lys Trp Cys Phe Glu Gly Pro Glu Glu His Glu Ile Leu Asn<br>2060                      2065                   2070 | 6337 |
| gac agc ggt gaa aca gtg aag tgc agg gct cct gga gga gca aag<br>Asp Ser Gly Glu Thr Val Lys Cys Arg Ala Pro Gly Gly Ala Lys<br>2075                      2080                   2085 | 6382 |
| aag cct ctg cgc cca agg tgg tgt gat gaa agg gtg tca tct gac<br>Lys Pro Leu Arg Pro Arg Trp Cys Asp Glu Arg Val Ser Ser Asp<br>2090                      2095                   2100 | 6427 |
| cag agt gcg ctg tct gaa ttt att aag ttt gct gaa ggt agg agg<br>Gln Ser Ala Leu Ser Glu Phe Ile Lys Phe Ala Glu Gly Arg Arg<br>2105                      2110                   2115 | 6472 |
| gga gct gct gaa gtg cta gtt gtg ctg agt gaa ctc cct gat ttc<br>Gly Ala Ala Glu Val Leu Val Val Leu Ser Glu Leu Pro Asp Phe<br>2120                      2125                   2130 | 6517 |
| ctg gct aaa aaa ggt gga gag gca atg gat acc atc agt gtg ttc<br>Leu Ala Lys Lys Gly Gly Glu Ala Met Asp Thr Ile Ser Val Phe<br>2135                      2140                   2145 | 6562 |
| ctc cac tct gag gaa ggc tct agg gct tac cgc aat gca cta tca<br>Leu His Ser Glu Glu Gly Ser Arg Ala Tyr Arg Asn Ala Leu Ser<br>2150                      2155                   2160 | 6607 |
| atg atg cct gag gca atg aca ata gtc atg ctg ttt ata ctg gct<br>Met Met Pro Glu Ala Met Thr Ile Val Met Leu Phe Ile Leu Ala<br>2165                      2170                   2175 | 6652 |
| gga cta ctg aca tcg gga atg gtc atc ttt ttc atg tct ccc aaa<br>Gly Leu Leu Thr Ser Gly Met Val Ile Phe Phe Met Ser Pro Lys<br>2180                      2185                   2190 | 6697 |
| ggc atc agt aga atg tct atg gcg atg ggc aca atg gcc ggc tgt<br>Gly Ile Ser Arg Met Ser Met Ala Met Gly Thr Met Ala Gly Cys<br>2195                      2200                   2205 | 6742 |
| gga tat ctc atg ttc ctt gga ggc gtc aaa ccc act cac atc tcc<br>Gly Tyr Leu Met Phe Leu Gly Gly Val Lys Pro Thr His Ile Ser<br>2210                      2215                   2220 | 6787 |
| tat gtc atg ctc ata ttc ttt gtc ctg atg gtg gtt gtg atc ccc<br>Tyr Val Met Leu Ile Phe Phe Val Leu Met Val Val Val Ile Pro<br>2225                      2230                   2235 | 6832 |
| gag cca ggg caa caa agg tcc atc caa gac aac caa gtg gca tac<br>Glu Pro Gly Gln Gln Arg Ser Ile Gln Asp Asn Gln Val Ala Tyr<br>2240                      2245                   2250 | 6877 |
| ctc att att ggc atc ctg acg ctg gtt tca gcg gtg gca gcc aac<br>Leu Ile Ile Gly Ile Leu Thr Leu Val Ser Ala Val Ala Ala Asn<br>2255                      2260                   2265 | 6922 |
| gag cta ggc atg ctg gag aaa acc aaa gag gac ctc ttt ggg aag<br>Glu Leu Gly Met Leu Glu Lys Thr Lys Glu Asp Leu Phe Gly Lys<br>2270                      2275                   2280 | 6967 |
| aag aac tta att cca tct agt gct tca ccc tgg agt tgg ccg gat<br>Lys Asn Leu Ile Pro Ser Ser Ala Ser Pro Trp Ser Trp Pro Asp<br>2285                      2290                   2295 | 7012 |
| ctt gac ctg aag cca gga gct gcc tgg aca gtg tac gtt ggc att<br>Leu Asp Leu Lys Pro Gly Ala Ala Trp Thr Val Tyr Val Gly Ile<br>2300                      2305                   2310 | 7057 |
| gtt aca atg ctc tct cca atg ttg cac cac tgg atc aaa gtc gaa<br>Val Thr Met Leu Ser Pro Met Leu His His Trp Ile Lys Val Glu<br>2315                      2320                   2325 | 7102 |
| tat ggc aac ctg tct ctg tct gga ata gcc cag tca gcc tca gtc<br>Tyr Gly Asn Leu Ser Leu Ser Gly Ile Ala Gln Ser Ala Ser Val<br>2330                      2335                   2340 | 7147 |
| ctt tct ttc atg gac aag ggg ata cca ttc atg aag atg aat atc<br>Leu Ser Phe Met Asp Lys Gly Ile Pro Phe Met Lys Met Asn Ile | 7192 |

```
                    2345                2350                2355
tcg gtc ata atg ctg ctg gtc agt ggc tgg aat tca ata aca gtg    7237
Ser Val Ile Met Leu Leu Val Ser Gly Trp Asn Ser Ile Thr Val
2360                2365                2370 atg cct ctg ctc tgt ggc ata ggg tgc gcc atg ctc cac tgg tct    7282
Met Pro Leu Leu Cys Gly Ile Gly Cys Ala Met Leu His Trp Ser
2375                2380                2385 ctc att tta cct gga atc aaa gcg cag cag tca aag ctt gca cag    7327
Leu Ile Leu Pro Gly Ile Lys Ala Gln Gln Ser Lys Leu Ala Gln
2390                2395                2400 aga agg gtg ttc cat ggc gtt gcc aag aac cct gtg gtt gat ggg    7372
Arg Arg Val Phe His Gly Val Ala Lys Asn Pro Val Val Asp Gly
2405                2410                2415 aat cca aca gtt gac att gag gaa gct cct gaa atg cct gcc ctt    7417
Asn Pro Thr Val Asp Ile Glu Glu Ala Pro Glu Met Pro Ala Leu
2420                2425                2430 tat gag aag aaa ctg gct cta tat ctc ctt ctt gct ctc agc cta    7462
Tyr Glu Lys Lys Leu Ala Leu Tyr Leu Leu Leu Ala Leu Ser Leu
2435                2440                2445 gct tct gtt gcc atg tgc aga acg ccc ttt tca ttg gct gaa ggc    7507
Ala Ser Val Ala Met Cys Arg Thr Pro Phe Ser Leu Ala Glu Gly
2450                2455                2460 att gtc cta gca tca gct gcc tta ggg ccg ctc ata gag gga aac    7552
Ile Val Leu Ala Ser Ala Ala Leu Gly Pro Leu Ile Glu Gly Asn
2465                2470                2475 acc agc ctt ctt tgg aat gga ccc atg gct gtc tcc atg aca gga    7597
Thr Ser Leu Leu Trp Asn Gly Pro Met Ala Val Ser Met Thr Gly
2480                2485                2490 gtc atg agg ggg aat cac tat gct ttt gtg gga gtc atg tac aat    7642
Val Met Arg Gly Asn His Tyr Ala Phe Val Gly Val Met Tyr Asn
2495                2500                2505 cta tgg aag atg aaa act gga cgc cgg ggg agc gcg aat gga aaa    7687
Leu Trp Lys Met Lys Thr Gly Arg Arg Gly Ser Ala Asn Gly Lys
2510                2515                2520 act ttg ggt gaa gtc tgg aag agg gaa ctg aat ctg ttg gac aag    7732
Thr Leu Gly Glu Val Trp Lys Arg Glu Leu Asn Leu Leu Asp Lys
2525                2530                2535 cga cag ttt gag ttg tat aaa agg acc gac att gtg gag gtg gat    7777
Arg Gln Phe Glu Leu Tyr Lys Arg Thr Asp Ile Val Glu Val Asp
2540                2545                2550 cgt gat acg gca cgc agg cat ttg gcc gaa ggg aag gtg gac acc    7822
Arg Asp Thr Ala Arg Arg His Leu Ala Glu Gly Lys Val Asp Thr
2555                2560                2565 ggg gtg gcg gtc tcc agg ggg acc gca aag tta agg tgg ttc cat    7867
Gly Val Ala Val Ser Arg Gly Thr Ala Lys Leu Arg Trp Phe His
2570                2575                2580 gag cgt ggc tat gtc aag ctg gaa ggt agg gtg att gac ctg ggg    7912
Glu Arg Gly Tyr Val Lys Leu Glu Gly Arg Val Ile Asp Leu Gly
2585                2590                2595 tgt ggc cgc gga ggc tgg tgt tac tac gct gct gcg caa aag gaa    7957
Cys Gly Arg Gly Gly Trp Cys Tyr Tyr Ala Ala Ala Gln Lys Glu
2600                2605                2610 gtg agt ggg gtc aaa gga ttt act ctt gga aga gac ggc cat gag    8002
Val Ser Gly Val Lys Gly Phe Thr Leu Gly Arg Asp Gly His Glu
2615                2620                2625 aaa ccc atg aat gtg caa agt ctg gga tgg aac atc atc acc ttc    8047
Lys Pro Met Asn Val Gln Ser Leu Gly Trp Asn Ile Ile Thr Phe
2630                2635                2640 aag gac aaa act gat atc cac cgc cta gaa cca gtg aaa tgt gac    8092
Lys Asp Lys Thr Asp Ile His Arg Leu Glu Pro Val Lys Cys Asp
```

-continued

|  |  |  |
|---|---|---|
| 2645 | 2650 | 2655 |

| acc Thr | ctt Leu | ttg Leu | tgt Cys | gac Asp | att Ile | gga Gly | gag Glu | tca Ser | tca Ser | tcg Ser | tca Ser | tcg Ser | gtc Val | aca Thr | 8137 |
| 2660 | | | | | 2665 | | | | | 2670 | | | | | |
| gag Glu | ggg Gly | gaa Glu | agg Arg | acc Thr | gtg Val | aga Arg | gtt Val | ctt Leu | gat Asp | act Thr | gta Val | gaa Glu | aaa Lys | tgg Trp | 8182 |
| 2675 | | | | | 2680 | | | | | 2685 | | | | | |
| ctg Leu | gct Ala | tgt Cys | ggg Gly | gtt Val | gac Asp | aac Asn | ttc Phe | tgt Cys | gtg Val | aag Lys | gtg Val | tta Leu | gct Ala | cca Pro | 8227 |
| 2690 | | | | | 2695 | | | | | 2700 | | | | | |
| tac Tyr | atg Met | cca Pro | gat Asp | gtt Val | ctt Leu | gag Glu | aaa Lys | ctg Leu | gaa Glu | ttg Leu | ctc Leu | caa Gln | agg Arg | agg Arg | 8272 |
| 2705 | | | | | 2710 | | | | | 2715 | | | | | |
| ttt Phe | ggc Gly | gga Gly | aca Thr | gtg Val | atc Ile | agg Arg | aac Asn | cct Pro | ctc Leu | tcc Ser | agg Arg | aat Asn | tcc Ser | act Thr | 8317 |
| 2720 | | | | | 2725 | | | | | 2730 | | | | | |
| cat His | gaa Glu | atg Met | tac Tyr | tac Tyr | gtg Val | tct Ser | gga Gly | gcc Ala | cgc Arg | agc Ser | aat Asn | gtc Val | aca Thr | ttt Phe | 8362 |
| 2735 | | | | | 2740 | | | | | 2745 | | | | | |
| act Thr | gtg Val | aac Asn | caa Gln | aca Thr | tcc Ser | cgc Arg | ctc Leu | ctg Leu | atg Met | agg Arg | aga Arg | atg Met | agg Arg | cgt Arg | 8407 |
| 2750 | | | | | 2755 | | | | | 2760 | | | | | |
| cca Pro | act Thr | gga Gly | aaa Lys | gtg Val | acc Thr | ctg Leu | gag Glu | gct Ala | gac Asp | gtc Val | atc Ile | ctc Leu | cca Pro | att Ile | 8452 |
| 2765 | | | | | 2770 | | | | | 2775 | | | | | |
| ggg Gly | aca Thr | cgc Arg | agt Ser | gtt Val | gag Glu | aca Thr | gac Asp | aag Lys | gga Gly | ccc Pro | ctg Leu | gac Asp | aaa Lys | gag Glu | 8497 |
| 2780 | | | | | 2785 | | | | | 2790 | | | | | |
| gcc Ala | ata Ile | gaa Glu | gaa Glu | agg Arg | gtt Val | gag Glu | agg Arg | ata Ile | aaa Lys | tct Ser | gag Glu | tac Tyr | atg Met | acc Thr | 8542 |
| 2795 | | | | | 2800 | | | | | 2805 | | | | | |
| tct Ser | tgg Trp | ttt Phe | tat Tyr | gac Asp | aat Asn | gac Asp | aac Asn | ccc Pro | tac Tyr | agg Arg | acc Thr | tgg Trp | cac His | tac Tyr | 8587 |
| 2810 | | | | | 2815 | | | | | 2820 | | | | | |
| tgt Cys | ggc Gly | tcc Ser | tat Tyr | gtc Val | aca Thr | aaa Lys | acc Thr | tcc Ser | gga Gly | agt Ser | gcg Ala | gcg Ala | agc Ser | atg Met | 8632 |
| 2825 | | | | | 2830 | | | | | 2835 | | | | | |
| gta Val | aat Asn | ggt Gly | gtt Val | att Ile | aaa Lys | att Ile | ctg Leu | aca Thr | tat Tyr | cca Pro | tgg Trp | gac Asp | agg Arg | ata Ile | 8677 |
| 2840 | | | | | 2845 | | | | | 2850 | | | | | |
| gag Glu | gag Glu | gtc Val | aca Thr | aga Arg | atg Met | gca Ala | atg Met | act Thr | gac Asp | aca Thr | acc Thr | cct Pro | ttt Phe | gga Gly | 8722 |
| 2855 | | | | | 2860 | | | | | 2865 | | | | | |
| cag Gln | caa Gln | aga Arg | gtg Val | ttt Phe | aaa Lys | gaa Glu | aaa Lys | gtt Val | gac Asp | acc Thr | aga Arg | gca Ala | aag Lys | gat Asp | 8767 |
| 2870 | | | | | 2875 | | | | | 2880 | | | | | |
| cca Pro | cca Pro | gcg Ala | gga Gly | act Thr | agg Arg | aag Lys | atc Ile | atg Met | aaa Lys | gtt Val | gtc Val | aac Asn | agg Arg | tgg Trp | 8812 |
| 2885 | | | | | 2890 | | | | | 2895 | | | | | |
| ctg Leu | ttc Phe | cgc Arg | cac His | ctg Leu | gcc Ala | aga Arg | gaa Glu | aag Lys | aac Asn | ccc Pro | aga Arg | ctg Leu | tgc Cys | aca Thr | 8857 |
| 2900 | | | | | 2905 | | | | | 2910 | | | | | |
| aag Lys | gaa Glu | gaa Glu | ttt Phe | att Ile | gca Ala | aaa Lys | gtc Val | cga Arg | agt Ser | cat His | gca Ala | gcc Ala | att Ile | gga Gly | 8902 |
| 2915 | | | | | 2920 | | | | | 2925 | | | | | |
| gct Ala | tac Tyr | ctg Leu | gaa Glu | gaa Glu | caa Gln | gaa Glu | cag Gln | tgg Trp | aag Lys | act Thr | gcc Ala | aat Asn | gag Glu | gct Ala | 8947 |
| 2930 | | | | | 2935 | | | | | 2940 | | | | | |
| gtc Val | caa Gln | gac Asp | cca Pro | aag Lys | ttc Phe | tgg Trp | gaa Glu | ctg Leu | gtg Val | gat Asp | gaa Glu | gaa Glu | agg Arg | aag Lys | 8992 |

```
              2945                2950                2955
ctg cac caa caa ggc agg tgt cgg act tgt gtg tac aac atg atg     9037
Leu His Gln Gln Gly Arg Cys Arg Thr Cys Val Tyr Asn Met Met
    2960                2965                2970 ggg aaa aga gag aag aag ctg tca gag ttt ggg aaa gca aag gga     9082
Gly Lys Arg Glu Lys Lys Leu Ser Glu Phe Gly Lys Ala Lys Gly
    2975                2980                2985 agc cgt gcc ata tgg tat atg tgg ctg gga gcg cgg tat ctt gag     9127
Ser Arg Ala Ile Trp Tyr Met Trp Leu Gly Ala Arg Tyr Leu Glu
    2990                2995                3000 ttt gag gcc ctg gga ttc ctg aat gag gac cat tgg gct tcc agg     9172
Phe Glu Ala Leu Gly Phe Leu Asn Glu Asp His Trp Ala Ser Arg
    3005                3010                3015 gaa aac tca gga gga gga gtg gaa ggc att ggc tta caa tac cta     9217
Glu Asn Ser Gly Gly Gly Val Glu Gly Ile Gly Leu Gln Tyr Leu
    3020                3025                3030 gga tat gtg atc aga gac ctg gct gca atg gat ggt ggt gga ttc     9262
Gly Tyr Val Ile Arg Asp Leu Ala Ala Met Asp Gly Gly Gly Phe
    3035                3040                3045 tac gcg gat gac acc gct gga tgg gac acg cgc atc aca gag gca     9307
Tyr Ala Asp Asp Thr Ala Gly Trp Asp Thr Arg Ile Thr Glu Ala
    3050                3055                3060 gac ctt gat gat gaa cag gag atc ttg aac tac atg agc cca cat     9352
Asp Leu Asp Asp Glu Gln Glu Ile Leu Asn Tyr Met Ser Pro His
    3065                3070                3075 cac aaa aaa ctg gca caa gca gtg atg gaa atg aca tac aag aac     9397
His Lys Lys Leu Ala Gln Ala Val Met Glu Met Thr Tyr Lys Asn
    3080                3085                3090 aaa gtg gtg aaa gtg ttg aga cca gcc cca gga ggg aaa gcc tac     9442
Lys Val Val Lys Val Leu Arg Pro Ala Pro Gly Gly Lys Ala Tyr
    3095                3100                3105 atg gat gtc ata agt cga cga gac cag aga gga tcc ggg cag gta     9487
Met Asp Val Ile Ser Arg Arg Asp Gln Arg Gly Ser Gly Gln Val
    3110                3115                3120 gtg act tat gct ctg aac acc atc acc aac ttg aaa gtc caa ttg     9532
Val Thr Tyr Ala Leu Asn Thr Ile Thr Asn Leu Lys Val Gln Leu
    3125                3130                3135 atc aga atg gca gaa gca gag atg gtg ata cat cac caa cat gtt     9577
Ile Arg Met Ala Glu Ala Glu Met Val Ile His His Gln His Val
    3140                3145                3150 caa gat tgt gat gaa tca gtt ctg acc agg ctg gag gca tgg ctc     9622
Gln Asp Cys Asp Glu Ser Val Leu Thr Arg Leu Glu Ala Trp Leu
    3155                3160                3165 act gag cac gga tgt gac aga ctg aag agg atg gcg gtg agt gga     9667
Thr Glu His Gly Cys Asp Arg Leu Lys Arg Met Ala Val Ser Gly
    3170                3175                3180 gac gac tgt gtg gtc cgg ccc atc gat gac agg ttc ggc ctg gcc     9712
Asp Asp Cys Val Val Arg Pro Ile Asp Asp Arg Phe Gly Leu Ala
    3185                3190                3195 ctg tcc cat ctc aac gcc atg tcc aag gtt aga aag gac ata tct     9757
Leu Ser His Leu Asn Ala Met Ser Lys Val Arg Lys Asp Ile Ser
    3200                3205                3210 gaa tgg cag cca tca aaa ggg tgg aat gat tgg gag aat gtg ccc     9802
Glu Trp Gln Pro Ser Lys Gly Trp Asn Asp Trp Glu Asn Val Pro
    3215                3220                3225 ttc tgt tcc cac cac ttc cat gaa cta cag ctg aag gat ggc agg     9847
Phe Cys Ser His His Phe His Glu Leu Gln Leu Lys Asp Gly Arg
    3230                3235                3240 agg att gtg gtg cct tgc cga gaa cag gac gag ctc att ggg aga     9892
Arg Ile Val Val Pro Cys Arg Glu Gln Asp Glu Leu Ile Gly Arg
```

```
                3245                3250                3255
gga agg gtg tct cca gga aac ggc tgg atg atc aag gaa aca gct    9937
Gly Arg Val Ser Pro Gly Asn Gly Trp Met Ile Lys Glu Thr Ala
    3260                3265                3270 tgc ctc agc aaa gcc tat gcc aac atg tgg tca ctg atg tat ttt    9982
Cys Leu Ser Lys Ala Tyr Ala Asn Met Trp Ser Leu Met Tyr Phe
    3275                3280                3285 cac aaa agg gac atg agg cta ctg tca ttg gct gtt tcc tca gct    10027
His Lys Arg Asp Met Arg Leu Leu Ser Leu Ala Val Ser Ser Ala
    3290                3295                3300 gtt ccc acc tca tgg gtt cca caa gga cgc aca aca tgg tcg att    10072
Val Pro Thr Ser Trp Val Pro Gln Gly Arg Thr Thr Trp Ser Ile
    3305                3310                3315 cat ggg aaa ggg gag tgg atg acc acg gaa gac atg ctt gag gtg    10117
His Gly Lys Gly Glu Trp Met Thr Thr Glu Asp Met Leu Glu Val
    3320                3325                3330 tgg aac aga gta tgg ata acc aac aac cca cac atg cag gac aag    10162
Trp Asn Arg Val Trp Ile Thr Asn Asn Pro His Met Gln Asp Lys
    3335                3340                3345 aca atg gtg aaa aaa tgg aga gat gtc cct tat cta acc aag aga    10207
Thr Met Val Lys Lys Trp Arg Asp Val Pro Tyr Leu Thr Lys Arg
    3350                3355                3360 caa gac aag ctg tgc gga tca ctg att gga atg acc aat agg gcc    10252
Gln Asp Lys Leu Cys Gly Ser Leu Ile Gly Met Thr Asn Arg Ala
    3365                3370                3375 acc tgg gcc tcc cac atc cat tta gtc atc cat cgt atc cga acg    10297
Thr Trp Ala Ser His Ile His Leu Val Ile His Arg Ile Arg Thr
    3380                3385                3390 ctg att gga cag gag aaa tac act gac tac cta aca gtc atg gac    10342
Leu Ile Gly Gln Glu Lys Tyr Thr Asp Tyr Leu Thr Val Met Asp
    3395                3400                3405 agg tat tct gtg gat gct gac ctg caa ctg ggt gag ctt atc         10384
Arg Tyr Ser Val Asp Ala Asp Leu Gln Leu Gly Glu Leu Ile
    3410                3415                3420 tgaaacacca tctaacagga ataaccggga tacaaaccac gggtggagaa ccggactccc  10444
cacaacctga aaccgggata taaaccacgg ctggagaacc ggactccgca cttaaaatga  10504
aacagaaacc gggataaaaa ctacggatgg agaaccggac tccacacatt gagacagaag  10564
aagttgtcag cccagaaccc cacacgagtt ttgccactgc taagctgtga ggcagtgcag  10624
gctgggacag ccgacctcca ggttgcgaaa aacctggttt ctgggacctc ccaccccaga  10684
gtaaaaagaa cggagcctcc gctaccaccc tcccacgtgg tggtagaaag acggggtcta  10744
gaggttagag gagaccctcc agggaacaaa tagtgggacc atattgacgc cagggaaaga  10804
ccggagtggt tctctgcttt tcctccagag gtctgtgagc acagtttgct caagaataag  10864
cagaccttg gatgacaaac acaaaaccac aa                                10896

<210> SEQ ID NO 21
<211> LENGTH: 3422
<212> TYPE: PRT
<213> ORGANISM: Artificial Sequence
<220> FEATURE:
<223> OTHER INFORMATION: Synthetic Construct

<400> SEQUENCE: 21

Met Ser Gly Arg Lys Ala Gln Gly Lys Thr Leu Gly Val Asn Met Val
1               5                   10                  15

Arg Arg Gly Val Arg Ser Leu Ser Asn Lys Ile Lys Gln Lys Thr Lys
            20                  25                  30
```

-continued

```
Gln Ile Gly Asn Arg Pro Gly Pro Ser Arg Gly Val Gln Gly Phe Ile
         35                  40                  45

Phe Phe Phe Leu Phe Asn Ile Leu Thr Gly Lys Lys Ile Thr Ala His
 50                  55                  60

Leu Lys Arg Leu Trp Lys Met Leu Asp Pro Arg Gln Gly Leu Ala Val
 65                  70                  75                  80

Leu Arg Lys Val Lys Arg Val Ala Ser Leu Met Arg Gly Leu Ser
                 85                  90                  95

Ser Arg Lys Arg Arg Ser His Asp Val Leu Thr Val Gln Phe Leu Ile
                100                 105                 110

Leu Gly Met Leu Leu Met Thr Gly Gly Val Thr Leu Ser Asn Phe Gln
            115                 120                 125

Gly Lys Val Met Met Thr Val Asn Ala Thr Asp Val Thr Asp Val Ile
        130                 135                 140

Thr Ile Pro Thr Ala Ala Gly Lys Asn Leu Cys Ile Val Arg Ala Met
145                 150                 155                 160

Asp Val Gly Tyr Met Cys Asp Asp Thr Ile Thr Tyr Glu Cys Pro Val
                    165                 170                 175

Leu Ser Ala Gly Asn Asp Pro Glu Asp Ile Asp Cys Trp Cys Thr Lys
                180                 185                 190

Ser Ala Val Tyr Val Arg Tyr Gly Arg Cys Thr Lys Thr Arg His Ser
            195                 200                 205

Arg Arg Ser Arg Arg Ser Leu Thr Val Gln Thr His Gly Glu Ser Thr
210                 215                 220

Leu Ala Asn Lys Lys Gly Ala Trp Met Asp Ser Thr Lys Ala Thr Arg
225                 230                 235                 240

Tyr Leu Val Lys Thr Glu Ser Trp Ile Leu Arg Asn Pro Gly Tyr Ala
                    245                 250                 255

Leu Val Ala Ala Val Ile Gly Trp Met Leu Gly Ser Asn Thr Met Gln
                260                 265                 270

Arg Val Val Phe Val Val Leu Leu Leu Val Ala Pro Ala Tyr Ser
            275                 280                 285

Phe Asn Cys Leu Gly Met Ser Asn Arg Asp Phe Leu Glu Gly Val Ser
290                 295                 300

Gly Ala Thr Trp Val Asp Leu Val Leu Glu Gly Asp Ser Cys Val Thr
305                 310                 315                 320

Ile Met Ser Lys Asp Lys Pro Thr Ile Asp Val Lys Met Met Asn Met
                    325                 330                 335

Glu Ala Ala Asn Leu Ala Glu Val Arg Ser Tyr Cys Tyr Leu Ala Thr
                340                 345                 350

Val Ser Asp Leu Ser Thr Lys Ala Ala Cys Pro Thr Met Gly Glu Ala
            355                 360                 365

His Asn Asp Lys Arg Ala Asp Pro Ala Phe Val Cys Arg Gln Gly Val
370                 375                 380

Val Asp Arg Gly Trp Gly Asn Gly Cys Gly Phe Gly Lys Gly Ser
385                 390                 395                 400

Ile Asp Thr Cys Ala Lys Phe Ala Cys Ser Thr Lys Ala Ile Gly Arg
                    405                 410                 415

Thr Ile Leu Lys Glu Asn Ile Lys Tyr Glu Val Ala Ile Phe Val His
                420                 425                 430

Gly Pro Thr Thr Val Glu Ser His Gly Asn Tyr Ser Thr Gln Val Gly
            435                 440                 445

Ala Thr Gln Ala Gly Arg Phe Ser Ile Thr Pro Ala Ala Pro Ser Tyr
450                 455                 460
```

```
Thr Leu Lys Leu Gly Glu Tyr Gly Glu Val Thr Val Asp Cys Glu Pro
465                 470                 475                 480

Arg Ser Gly Ile Asp Thr Asn Ala Tyr Tyr Val Met Thr Val Gly Thr
            485                 490                 495

Lys Thr Phe Leu Val His Arg Glu Trp Phe Met Asp Leu Asn Leu Pro
            500                 505                 510

Trp Ser Ser Ala Gly Ser Thr Val Trp Arg Asn Arg Glu Thr Leu Met
            515                 520                 525

Glu Phe Glu Glu Pro His Ala Thr Lys Gln Ser Val Ile Ala Leu Gly
    530                 535                 540

Ser Gln Glu Gly Ala Leu His Gln Ala Leu Ala Gly Ala Ile Pro Val
545                 550                 555                 560

Glu Phe Ser Ser Asn Thr Val Lys Leu Thr Ser Gly His Leu Lys Cys
                565                 570                 575

Arg Val Lys Met Glu Lys Leu Gln Leu Lys Gly Thr Thr Tyr Gly Val
            580                 585                 590

Cys Ser Lys Ala Phe Lys Phe Leu Arg Thr Pro Val Asp Thr Gly His
            595                 600                 605

Gly Thr Val Val Leu Glu Leu Gln Tyr Thr Gly Thr Asp Gly Pro Cys
    610                 615                 620

Lys Val Pro Ile Ser Ser Val Ala Ser Leu Asn Asp Leu Thr Pro Val
625                 630                 635                 640

Gly Arg Leu Val Thr Val Asn Pro Phe Val Ser Val Ala Thr Ala Asn
                645                 650                 655

Ala Lys Val Leu Ile Glu Leu Glu Pro Pro Phe Gly Asp Ser Tyr Ile
            660                 665                 670

Val Val Gly Arg Gly Glu Gln Gln Ile Asn His His Trp His Lys Ser
            675                 680                 685

Gly Ser Ser Ile Gly Lys Ala Phe Thr Thr Thr Leu Lys Gly Ala Gln
    690                 695                 700

Arg Leu Ala Ala Leu Gly Asp Thr Ala Trp Asp Phe Gly Ser Val Gly
705                 710                 715                 720

Gly Val Phe Thr Ser Val Gly Arg Ala Val His Gln Val Phe Gly Gly
                725                 730                 735

Ala Phe Arg Ser Leu Phe Gly Gly Met Ser Trp Ile Thr Gln Gly Leu
            740                 745                 750

Leu Gly Ala Leu Leu Leu Trp Met Gly Ile Asn Ala Arg Asp Arg Ser
            755                 760                 765

Ile Ala Leu Thr Phe Leu Ala Val Gly Gly Val Leu Leu Phe Leu Ser
    770                 775                 780

Val Asn Val Gly Ala Asp Gln Gly Cys Ala Ile Asn Phe Gly Lys Arg
785                 790                 795                 800

Glu Leu Lys Cys Gly Asp Gly Ile Phe Ile Phe Arg Asp Ser Asp Asp
                805                 810                 815

Trp Leu Asn Lys Tyr Ser Tyr Tyr Pro Glu Asp Pro Val Lys Leu Ala
            820                 825                 830

Ser Ile Val Lys Ala Ser Phe Glu Glu Gly Lys Cys Gly Leu Asn Ser
    835                 840                 845

Val Asp Ser Leu Glu His Glu Met Trp Arg Ser Arg Ala Asp Glu Ile
850                 855                 860

Asn Ala Ile Phe Glu Glu Asn Glu Val Asp Ile Ser Val Val Val Gln
865                 870                 875                 880

Asp Pro Lys Asn Val Tyr Gln Arg Gly Thr His Pro Phe Ser Arg Ile
```

```
                885               890              895
Arg Asp Gly Leu Gln Tyr Gly Trp Lys Thr Trp Gly Lys Asn Leu Val
                    900               905              910

Phe Ser Pro Gly Arg Lys Asn Gly Ser Phe Ile Ile Asp Gly Lys Ser
        915               920              925

Arg Lys Glu Cys Pro Phe Ser Asn Arg Val Trp Asn Ser Phe Gln Ile
930              935               940

Glu Glu Phe Gly Thr Gly Val Phe Thr Thr Arg Val Tyr Met Asp Ala
945                  950              955               960

Val Phe Glu Tyr Thr Ile Asp Cys Asp Gly Ser Ile Leu Gly Ala Ala
                965               970              975

Val Asn Gly Lys Lys Ser Ala His Gly Ser Pro Thr Phe Trp Met Gly
            980              985              990

Ser His Glu Val Asn Gly Thr Trp Met Ile His Thr Leu Glu Ala Leu
                995              1000              1005

Asp Tyr Lys Glu Cys Glu Trp Pro Leu Thr His Thr Ile Gly Thr
    1010              1015              1020

Ser Val Glu Glu Ser Glu Met Phe Met Pro Arg Ser Ile Gly Gly
    1025              1030              1035

Pro Val Ser Ser His Asn His Ile Pro Gly Tyr Lys Val Gln Thr
    1040              1045              1050

Asn Gly Pro Trp Met Gln Val Pro Leu Glu Val Lys Arg Glu Ala
    1055              1060              1065

Cys Pro Gly Thr Ser Val Ile Ile Asp Gly Asn Cys Asp Gly Arg
    1070              1075              1080

Gly Lys Ser Thr Arg Ser Thr Thr Asp Ser Gly Lys Val Ile Pro
    1085              1090              1095

Glu Trp Cys Cys Arg Ser Cys Thr Met Pro Pro Val Ser Phe His
    1100              1105              1110

Gly Ser Asp Gly Cys Trp Tyr Pro Met Glu Ile Arg Pro Arg Lys
    1115              1120              1125

Thr His Glu Ser His Leu Val Arg Ser Trp Val Thr Ala Gly Glu
    1130              1135              1140

Ile His Ala Val Pro Phe Gly Leu Val Ser Met Met Ile Ala Met
    1145              1150              1155

Glu Val Val Leu Arg Lys Arg Gln Gly Pro Lys Gln Met Leu Val
    1160              1165              1170

Gly Gly Val Val Leu Leu Gly Ala Met Leu Val Gly Gln Val Thr
    1175              1180              1185

Leu Leu Asp Leu Leu Lys Leu Thr Val Ala Val Gly Leu His Phe
    1190              1195              1200

His Glu Met Asn Asn Gly Gly Asp Ala Met Tyr Met Ala Leu Ile
    1205              1210              1215

Ala Ala Phe Ser Ile Arg Pro Gly Leu Leu Ile Gly Phe Gly Leu
    1220              1225              1230

Arg Thr Leu Trp Ser Pro Arg Glu Arg Leu Val Leu Thr Leu Gly
    1235              1240              1245

Ala Ala Met Val Glu Ile Ala Leu Gly Gly Val Met Gly Gly Leu
    1250              1255              1260

Trp Lys Tyr Leu Asn Ala Val Ser Leu Cys Ile Leu Thr Ile Asn
    1265              1270              1275

Ala Val Ala Ser Arg Lys Ala Ser Asn Thr Ile Leu Pro Leu Met
    1280              1285              1290
```

```
Ala Leu Leu Thr Pro Val Thr Met Ala Glu Val Arg Leu Ala Ala
1295                1300                1305

Met Phe Phe Cys Ala Met Val Ile Ile Gly Val Leu His Gln Asn
1310                1315                1320

Phe Lys Asp Thr Ser Met Gln Lys Thr Ile Pro Leu Val Ala Leu
1325                1330                1335

Thr Leu Thr Ser Tyr Leu Gly Leu Thr Gln Pro Phe Leu Gly Leu
1340                1345                1350

Cys Ala Phe Leu Ala Thr Arg Ile Phe Gly Arg Arg Ser Ile Pro
1355                1360                1365

Val Asn Glu Ala Leu Ala Ala Gly Leu Val Gly Val Leu Ala
1370                1375                1380

Gly Leu Ala Phe Gln Glu Met Glu Asn Phe Leu Gly Pro Ile Ala
1385                1390                1395

Val Gly Gly Leu Leu Met Met Leu Val Ser Val Ala Gly Arg Val
1400                1405                1410

Asp Gly Leu Glu Leu Lys Lys Leu Gly Glu Val Ser Trp Glu Glu
1415                1420                1425

Glu Ala Glu Ile Ser Gly Ser Ser Ala Arg Tyr Asp Val Ala Leu
1430                1435                1440

Ser Glu Gln Gly Glu Phe Lys Leu Leu Ser Glu Lys Val Pro
1445                1450                1455

Trp Asp Gln Val Val Met Thr Ser Leu Ala Leu Val Gly Ala Ala
1460                1465                1470

Leu His Pro Phe Ala Leu Leu Leu Val Leu Ala Gly Trp Leu Phe
1475                1480                1485

His Val Arg Gly Ala Arg Arg Ser Gly Asp Val Leu Trp Asp Ile
1490                1495                1500

Pro Thr Pro Lys Ile Ile Glu Glu Cys Glu His Leu Glu Asp Gly
1505                1510                1515

Ile Tyr Gly Ile Phe Gln Ser Thr Phe Leu Gly Ala Ser Gln Arg
1520                1525                1530

Gly Val Gly Val Ala Gln Gly Gly Val Phe His Thr Met Trp His
1535                1540                1545

Val Thr Arg Gly Ala Phe Leu Val Arg Asn Gly Lys Lys Leu Ile
1550                1555                1560

Pro Ser Trp Ala Ser Val Lys Glu Asp Leu Val Ala Tyr Gly Gly
1565                1570                1575

Ser Trp Lys Leu Glu Gly Arg Trp Asp Gly Glu Glu Val Gln
1580                1585                1590

Leu Ile Ala Ala Val Pro Gly Lys Asn Val Val Asn Val Gln Thr
1595                1600                1605

Lys Pro Ser Leu Phe Lys Val Arg Asn Gly Gly Glu Ile Gly Ala
1610                1615                1620

Val Ala Leu Asp Tyr Pro Ser Gly Thr Ser Gly Ser Pro Ile Val
1625                1630                1635

Asn Arg Asn Gly Glu Val Ile Gly Leu Tyr Gly Asn Gly Ile Leu
1640                1645                1650

Val Gly Asp Asn Ser Phe Val Ser Ala Ile Ser Gln Thr Glu Val
1655                1660                1665

Lys Glu Glu Gly Lys Glu Glu Leu Gln Glu Ile Pro Thr Met Leu
1670                1675                1680

Lys Lys Gly Met Thr Thr Val Leu Asp Phe His Pro Gly Ala Gly
1685                1690                1695
```

```
Lys Thr Arg Arg Phe Leu Pro Gln Ile Leu Ala Glu Cys Ala Arg
    1700            1705                1710

Arg Arg Leu Arg Thr Leu Val Leu Ala Pro Thr Arg Val Val Leu
    1715            1720                1725

Ser Glu Met Lys Glu Ala Phe His Gly Leu Asp Val Lys Phe His
    1730            1735                1740

Thr Gln Ala Phe Ser Ala His Gly Ser Gly Arg Glu Val Ile Asp
    1745            1750                1755

Ala Met Cys His Ala Thr Leu Thr Tyr Arg Met Leu Glu Pro Thr
    1760            1765                1770

Arg Val Val Asn Trp Glu Val Ile Ile Met Asp Glu Ala His Phe
    1775            1780                1785

Leu Asp Pro Ala Ser Ile Ala Ala Arg Gly Trp Ala Ala His Arg
    1790            1795                1800

Ala Arg Ala Asn Glu Ser Ala Thr Ile Leu Met Thr Ala Thr Pro
    1805            1810                1815

Pro Gly Thr Ser Asp Glu Phe Pro His Ser Asn Gly Glu Ile Glu
    1820            1825                1830

Asp Val Gln Thr Asp Ile Pro Ser Glu Pro Trp Asn Thr Gly His
    1835            1840                1845

Asp Trp Ile Leu Ala Asp Lys Arg Pro Thr Ala Trp Phe Leu Pro
    1850            1855                1860

Ser Ile Arg Ala Ala Asn Val Met Ala Ala Ser Leu Arg Lys Ala
    1865            1870                1875

Gly Lys Ser Val Val Val Leu Asn Arg Lys Thr Phe Glu Arg Glu
    1880            1885                1890

Tyr Pro Thr Ile Lys Gln Lys Lys Pro Asp Phe Ile Leu Ala Thr
    1895            1900                1905

Asp Ile Ala Glu Met Gly Ala Asn Leu Cys Val Glu Arg Val Leu
    1910            1915                1920

Asp Cys Arg Thr Ala Phe Lys Pro Val Leu Val Asp Glu Gly Arg
    1925            1930                1935

Lys Val Ala Ile Lys Gly Pro Leu Arg Ile Ser Ala Ser Ser Ala
    1940            1945                1950

Ala Gln Arg Arg Gly Arg Ile Gly Arg Asn Pro Asn Arg Asp Gly
    1955            1960                1965

Asp Ser Tyr Tyr Tyr Ser Glu Pro Thr Ser Glu Asn Asn Ala His
    1970            1975                1980

His Val Cys Trp Leu Glu Ala Ser Met Leu Leu Asp Asn Met Glu
    1985            1990                1995

Val Arg Gly Gly Met Val Ala Pro Leu Tyr Gly Val Glu Gly Thr
    2000            2005                2010

Lys Thr Pro Val Ser Pro Gly Glu Met Arg Leu Arg Asp Asp Gln
    2015            2020                2025

Arg Lys Val Phe Arg Glu Leu Val Arg Asn Cys Asp Leu Pro Val
    2030            2035                2040

Trp Leu Ser Trp Gln Val Ala Lys Ala Gly Leu Lys Thr Asn Asp
    2045            2050                2055

Arg Lys Trp Cys Phe Glu Gly Pro Glu Glu His Glu Ile Leu Asn
    2060            2065                2070

Asp Ser Gly Glu Thr Val Lys Cys Arg Ala Pro Gly Gly Ala Lys
    2075            2080                2085

Lys Pro Leu Arg Pro Arg Trp Cys Asp Glu Arg Val Ser Ser Asp
```

-continued

```
            2090                2095                2100
Gln Ser Ala Leu Ser Glu Phe Ile Lys Phe Ala Glu Gly Arg Arg
        2105                2110                2115
Gly Ala Ala Glu Val Leu Val Val Leu Ser Glu Leu Pro Asp Phe
        2120                2125                2130
Leu Ala Lys Lys Gly Gly Glu Ala Met Asp Thr Ile Ser Val Phe
        2135                2140                2145
Leu His Ser Glu Glu Gly Ser Arg Ala Tyr Arg Asn Ala Leu Ser
        2150                2155                2160
Met Met Pro Glu Ala Met Thr Ile Val Met Leu Phe Ile Leu Ala
        2165                2170                2175
Gly Leu Leu Thr Ser Gly Met Val Ile Phe Phe Met Ser Pro Lys
        2180                2185                2190
Gly Ile Ser Arg Met Ser Met Ala Met Gly Thr Met Ala Gly Cys
        2195                2200                2205
Gly Tyr Leu Met Phe Leu Gly Gly Val Lys Pro Thr His Ile Ser
        2210                2215                2220
Tyr Val Met Leu Ile Phe Phe Val Leu Met Val Val Ile Pro
        2225                2230                2235
Glu Pro Gly Gln Gln Arg Ser Ile Gln Asp Asn Gln Val Ala Tyr
        2240                2245                2250
Leu Ile Ile Gly Ile Leu Thr Leu Val Ser Ala Val Ala Ala Asn
        2255                2260                2265
Glu Leu Gly Met Leu Glu Lys Thr Lys Glu Asp Leu Phe Gly Lys
        2270                2275                2280
Lys Asn Leu Ile Pro Ser Ser Ala Ser Pro Trp Ser Trp Pro Asp
        2285                2290                2295
Leu Asp Leu Lys Pro Gly Ala Ala Trp Thr Val Tyr Val Gly Ile
        2300                2305                2310
Val Thr Met Leu Ser Pro Met Leu His His Trp Ile Lys Val Glu
        2315                2320                2325
Tyr Gly Asn Leu Ser Leu Ser Gly Ile Ala Gln Ser Ala Ser Val
        2330                2335                2340
Leu Ser Phe Met Asp Lys Gly Ile Pro Phe Met Lys Met Asn Ile
        2345                2350                2355
Ser Val Ile Met Leu Leu Val Ser Gly Trp Asn Ser Ile Thr Val
        2360                2365                2370
Met Pro Leu Leu Cys Gly Ile Gly Cys Ala Met Leu His Trp Ser
        2375                2380                2385
Leu Ile Leu Pro Gly Ile Lys Ala Gln Gln Ser Lys Leu Ala Gln
        2390                2395                2400
Arg Arg Val Phe His Gly Val Ala Lys Asn Pro Val Val Asp Gly
        2405                2410                2415
Asn Pro Thr Val Asp Ile Glu Glu Ala Pro Glu Met Pro Ala Leu
        2420                2425                2430
Tyr Glu Lys Lys Leu Ala Leu Tyr Leu Leu Leu Ala Leu Ser Leu
        2435                2440                2445
Ala Ser Val Ala Met Cys Arg Thr Pro Phe Ser Leu Ala Glu Gly
        2450                2455                2460
Ile Val Leu Ala Ser Ala Ala Leu Gly Pro Leu Ile Glu Gly Asn
        2465                2470                2475
Thr Ser Leu Leu Trp Asn Gly Pro Met Ala Val Ser Met Thr Gly
        2480                2485                2490
```

-continued

| | | | | | | | | | | | |
|---|---|---|---|---|---|---|---|---|---|---|---|
|Val|Met|Arg|Gly|Asn|His|Tyr|Ala|Phe|Val|Gly|Val|Met|Tyr|Asn|
|2495| | | | |2500| | | | |2505| | | | |

Val Met Arg Gly Asn His Tyr Ala Phe Val Gly Val Met Tyr Asn
2495                 2500                2505

Leu Trp Lys Met Lys Thr Gly Arg Arg Gly Ser Ala Asn Gly Lys
2510                 2515                2520

Thr Leu Gly Glu Val Trp Lys Arg Glu Leu Asn Leu Leu Asp Lys
2525                 2530                2535

Arg Gln Phe Glu Leu Tyr Lys Arg Thr Asp Ile Val Glu Val Asp
2540                 2545                2550

Arg Asp Thr Ala Arg Arg His Leu Ala Glu Gly Lys Val Asp Thr
2555                 2560                2565

Gly Val Ala Val Ser Arg Gly Thr Ala Lys Leu Arg Trp Phe His
2570                 2575                2580

Glu Arg Gly Tyr Val Lys Leu Glu Gly Arg Val Ile Asp Leu Gly
2585                 2590                2595

Cys Gly Arg Gly Gly Trp Cys Tyr Tyr Ala Ala Ala Gln Lys Glu
2600                 2605                2610

Val Ser Gly Val Lys Gly Phe Thr Leu Gly Arg Asp Gly His Glu
2615                 2620                2625

Lys Pro Met Asn Val Gln Ser Leu Gly Trp Asn Ile Ile Thr Phe
2630                 2635                2640

Lys Asp Lys Thr Asp Ile His Arg Leu Glu Pro Val Lys Cys Asp
2645                 2650                2655

Thr Leu Leu Cys Asp Ile Gly Glu Ser Ser Ser Ser Val Thr
2660                 2665                2670

Glu Gly Glu Arg Thr Val Arg Val Leu Asp Thr Val Glu Lys Trp
2675                 2680                2685

Leu Ala Cys Gly Val Asp Asn Phe Cys Val Lys Val Leu Ala Pro
2690                 2695                2700

Tyr Met Pro Asp Val Leu Glu Lys Leu Glu Leu Leu Gln Arg Arg
2705                 2710                2715

Phe Gly Gly Thr Val Ile Arg Asn Pro Leu Ser Arg Asn Ser Thr
2720                 2725                2730

His Glu Met Tyr Tyr Val Ser Gly Ala Arg Ser Asn Val Thr Phe
2735                 2740                2745

Thr Val Asn Gln Thr Ser Arg Leu Leu Met Arg Arg Met Arg Arg
2750                 2755                2760

Pro Thr Gly Lys Val Thr Leu Glu Ala Asp Val Ile Leu Pro Ile
2765                 2770                2775

Gly Thr Arg Ser Val Glu Thr Asp Lys Gly Pro Leu Asp Lys Glu
2780                 2785                2790

Ala Ile Glu Glu Arg Val Glu Arg Ile Lys Ser Glu Tyr Met Thr
2795                 2800                2805

Ser Trp Phe Tyr Asp Asn Asp Asn Pro Tyr Arg Thr Trp His Tyr
2810                 2815                2820

Cys Gly Ser Tyr Val Thr Lys Thr Ser Gly Ser Ala Ala Ser Met
2825                 2830                2835

Val Asn Gly Val Ile Lys Ile Leu Thr Tyr Pro Trp Asp Arg Ile
2840                 2845                2850

Glu Glu Val Thr Arg Met Ala Met Thr Asp Thr Pro Phe Gly
2855                 2860                2865

Gln Gln Arg Val Phe Lys Glu Lys Val Asp Thr Arg Ala Lys Asp
2870                 2875                2880

Pro Pro Ala Gly Thr Arg Lys Ile Met Lys Val Val Asn Arg Trp
2885                 2890                2895

-continued

```
Leu Phe Arg His Leu Ala Arg Glu Lys Asn Pro Arg Leu Cys Thr
    2900                2905                2910

Lys Glu Glu Phe Ile Ala Lys Val Arg Ser His Ala Ala Ile Gly
    2915                2920                2925

Ala Tyr Leu Glu Glu Gln Gln Trp Lys Thr Ala Asn Glu Ala
    2930                2935                2940

Val Gln Asp Pro Lys Phe Trp Glu Leu Val Asp Glu Glu Arg Lys
    2945                2950                2955

Leu His Gln Gln Gly Arg Cys Arg Thr Cys Val Tyr Asn Met Met
    2960                2965                2970

Gly Lys Arg Glu Lys Lys Leu Ser Glu Phe Gly Lys Ala Lys Gly
    2975                2980                2985

Ser Arg Ala Ile Trp Tyr Met Trp Leu Gly Ala Arg Tyr Leu Glu
    2990                2995                3000

Phe Glu Ala Leu Gly Phe Leu Asn Glu Asp His Trp Ala Ser Arg
    3005                3010                3015

Glu Asn Ser Gly Gly Gly Val Glu Gly Ile Gly Leu Gln Tyr Leu
    3020                3025                3030

Gly Tyr Val Ile Arg Asp Leu Ala Ala Met Asp Gly Gly Gly Phe
    3035                3040                3045

Tyr Ala Asp Asp Thr Ala Gly Trp Asp Thr Arg Ile Thr Glu Ala
    3050                3055                3060

Asp Leu Asp Asp Glu Gln Glu Ile Leu Asn Tyr Met Ser Pro His
    3065                3070                3075

His Lys Lys Leu Ala Gln Ala Val Met Glu Met Thr Tyr Lys Asn
    3080                3085                3090

Lys Val Val Lys Val Leu Arg Pro Ala Pro Gly Gly Lys Ala Tyr
    3095                3100                3105

Met Asp Val Ile Ser Arg Arg Asp Gln Arg Gly Ser Gly Gln Val
    3110                3115                3120

Val Thr Tyr Ala Leu Asn Thr Ile Thr Asn Leu Lys Val Gln Leu
    3125                3130                3135

Ile Arg Met Ala Glu Ala Glu Met Val Ile His His Gln His Val
    3140                3145                3150

Gln Asp Cys Asp Glu Ser Val Leu Thr Arg Leu Glu Ala Trp Leu
    3155                3160                3165

Thr Glu His Gly Cys Asp Arg Leu Lys Arg Met Ala Val Ser Gly
    3170                3175                3180

Asp Asp Cys Val Val Arg Pro Ile Asp Asp Arg Phe Gly Leu Ala
    3185                3190                3195

Leu Ser His Leu Asn Ala Met Ser Lys Val Arg Lys Asp Ile Ser
    3200                3205                3210

Glu Trp Gln Pro Ser Lys Gly Trp Asn Asp Trp Glu Asn Val Pro
    3215                3220                3225

Phe Cys Ser His His Phe His Glu Leu Gln Leu Lys Asp Gly Arg
    3230                3235                3240

Arg Ile Val Val Pro Cys Arg Glu Gln Asp Glu Leu Ile Gly Arg
    3245                3250                3255

Gly Arg Val Ser Pro Gly Asn Gly Trp Met Ile Lys Glu Thr Ala
    3260                3265                3270

Cys Leu Ser Lys Ala Tyr Ala Asn Met Trp Ser Leu Met Tyr Phe
    3275                3280                3285

His Lys Arg Asp Met Arg Leu Leu Ser Leu Ala Val Ser Ser Ala
```

```
                    3290                3295                3300
Val Pro Thr Ser Trp Val Pro Gln Gly Arg Thr Thr Trp Ser Ile
    3305                3310                3315

His Gly Lys Gly Glu Trp Met Thr Thr Glu Asp Met Leu Glu Val
    3320                3325                3330

Trp Asn Arg Val Trp Ile Thr Asn Asn Pro His Met Gln Asp Lys
    3335                3340                3345

Thr Met Val Lys Lys Trp Arg Asp Val Pro Tyr Leu Thr Lys Arg
    3350                3355                3360

Gln Asp Lys Leu Cys Gly Ser Leu Ile Gly Met Thr Asn Arg Ala
    3365                3370                3375

Thr Trp Ala Ser His Ile His Leu Val Ile His Arg Ile Arg Thr
    3380                3385                3390

Leu Ile Gly Gln Glu Lys Tyr Thr Asp Tyr Leu Thr Val Met Asp
    3395                3400                3405

Arg Tyr Ser Val Asp Ala Asp Leu Gln Leu Gly Glu Leu Ile
    3410                3415                3420

<210> SEQ ID NO 22
<211> LENGTH: 10896
<212> TYPE: DNA
<213> ORGANISM: Artificial Sequence
<220> FEATURE:
<223> OTHER INFORMATION: Derived from Yellow Fever Virus and West Nile
      virus
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: CDS
<222> LOCATION: (119)..(10384)

<400> SEQUENCE: 22
ngtaaatcct gtgtgctaat tgaggtgcat tggtctgcaa atcgagttgc taggcaataa      60
acacatttgg attaatttta atcgttcgtt gagcgattag cagagaactg accagaac      118 atg tct ggt cgt aaa gct cag gga aaa acc ctg ggc gtc aat atg gta      166
Met Ser Gly Arg Lys Ala Gln Gly Lys Thr Leu Gly Val Asn Met Val
1               5                   10                  15 cga cga gga gtt cgc tcc ttg tca aac aaa ata aaa caa aaa aca aaa      214
Arg Arg Gly Val Arg Ser Leu Ser Asn Lys Ile Lys Gln Lys Thr Lys
                20                  25                  30 caa att gga aac aga cct gga cct tca aga ggt gtt caa gga ttt atc      262
Gln Ile Gly Asn Arg Pro Gly Pro Ser Arg Gly Val Gln Gly Phe Ile
            35                  40                  45 ttt ttc ttt ttg ttc aac att ttg act gga aaa aag atc aca gcc cac      310
Phe Phe Phe Leu Phe Asn Ile Leu Thr Gly Lys Lys Ile Thr Ala His
        50                  55                  60 cta aag agg ttg tgg aaa atg ctg gac cca aga caa ggc ttg gct gtt      358
Leu Lys Arg Leu Trp Lys Met Leu Asp Pro Arg Gln Gly Leu Ala Val
65                  70                  75                  80 cta agg aaa gtc aag aga gtg gtg gcc agt ttg atg aga gga ttg tcc      406
Leu Arg Lys Val Lys Arg Val Val Ala Ser Leu Met Arg Gly Leu Ser
                85                  90                  95 tca agg aaa cgc cgt tcc cat gat gtt ctg act gtg caa ttc cta att      454
Ser Arg Lys Arg Arg Ser His Asp Val Leu Thr Val Gln Phe Leu Ile
                100                 105                 110 ttg gga atg ctg ttg atg acg ggt gga gtt acc ctc tct aac ttc caa      502
Leu Gly Met Leu Leu Met Thr Gly Gly Val Thr Leu Ser Asn Phe Gln
        115                 120                 125
```

-continued

```
ggg aag gtg atg atg acg gta aat gct act gac gtc aca gat gtc atc      550
Gly Lys Val Met Met Thr Val Asn Ala Thr Asp Val Thr Asp Val Ile
    130                 135                 140 acg att cca aca gct gct gga aag aac cta tgc att gtc aga gca atg      598
Thr Ile Pro Thr Ala Ala Gly Lys Asn Leu Cys Ile Val Arg Ala Met
145                 150                 155                 160 gat gtg gga tac atg tgc gat gat act atc act tat gaa tgc cca gtg      646
Asp Val Gly Tyr Met Cys Asp Asp Thr Ile Thr Tyr Glu Cys Pro Val
                165                 170                 175 ctg tcg gct ggt aat gat cca gaa gac atc gac tgt tgg tgc aca aag      694
Leu Ser Ala Gly Asn Asp Pro Glu Asp Ile Asp Cys Trp Cys Thr Lys
            180                 185                 190 tca gca gtc tac gtc agg tat gga aga tgc acc aag aca cgc cac tca      742
Ser Ala Val Tyr Val Arg Tyr Gly Arg Cys Thr Lys Thr Arg His Ser
        195                 200                 205 aga cgc agt cgg agg tca ctg aca gtg cag aca cac gga gaa agc act      790
Arg Arg Ser Arg Arg Ser Leu Thr Val Gln Thr His Gly Glu Ser Thr
    210                 215                 220 cta gcg aac aag aag ggg gct tgg atg gac agc acc aag gcc aca agg      838
Leu Ala Asn Lys Lys Gly Ala Trp Met Asp Ser Thr Lys Ala Thr Arg
225                 230                 235                 240 tat ttg gta aaa aca gaa tca tgg atc ttg agg aac cct gga tat gcc      886
Tyr Leu Val Lys Thr Glu Ser Trp Ile Leu Arg Asn Pro Gly Tyr Ala
                245                 250                 255 ctg gtg gca gcc gtc att ggt tgg atg ctt ggg agc aac acc atg cag      934
Leu Val Ala Ala Val Ile Gly Trp Met Leu Gly Ser Asn Thr Met Gln
            260                 265                 270 aga gtt gtg ttt gtc gtg cca ttg ctt ttg gtg gcc cca gct tac agc      982
Arg Val Val Phe Val Val Pro Leu Leu Leu Val Ala Pro Ala Tyr Ser
        275                 280                 285 ttc aac tgc ctt gga atg agc aac aga gac ttc ttg gaa gga gtg tct     1030
Phe Asn Cys Leu Gly Met Ser Asn Arg Asp Phe Leu Glu Gly Val Ser
    290                 295                 300 gga gca aca tgg gtg gat ttg gtt ctc gaa ggc gac agc tgc gtg act     1078
Gly Ala Thr Trp Val Asp Leu Val Leu Glu Gly Asp Ser Cys Val Thr
305                 310                 315                 320 atc atg tct aag gac aag cct acc atc gac gtc aag atg atg aat atg     1126
Ile Met Ser Lys Asp Lys Pro Thr Ile Asp Val Lys Met Met Asn Met
                325                 330                 335 gag gcg gcc aac ctg gca gag gtc cgc agt tat tgc tat ttg gct acc     1174
Glu Ala Ala Asn Leu Ala Glu Val Arg Ser Tyr Cys Tyr Leu Ala Thr
            340                 345                 350 gtc agc gat ctc tcc acc aaa gct gca tgc ccg acc atg gga gaa gct     1222
Val Ser Asp Leu Ser Thr Lys Ala Ala Cys Pro Thr Met Gly Glu Ala
        355                 360                 365 cac aat gac aaa cgt gct gac cca gct ttt gtg tgc aga caa gga gtg     1270
His Asn Asp Lys Arg Ala Asp Pro Ala Phe Val Cys Arg Gln Gly Val
    370                 375                 380 gtg gac agg ggc tgg ggc aac ggc tgc gga ttt ttt ggc aaa gga tcc     1318
Val Asp Arg Gly Trp Gly Asn Gly Cys Gly Phe Phe Gly Lys Gly Ser
385                 390                 395                 400 att gac aca tgc gcc aaa ttt gcc tgc tct acc aag gca ata gga aga     1366
Ile Asp Thr Cys Ala Lys Phe Ala Cys Ser Thr Lys Ala Ile Gly Arg
                405                 410                 415 acc atc ttg aaa gag aat atc aag tac gaa gtg gcc att ttt gtc cat     1414
Thr Ile Leu Lys Glu Asn Ile Lys Tyr Glu Val Ala Ile Phe Val His
            420                 425                 430 gga cca act act gtg gag tcg cac gga aat tac tcc aca cag gtt gga     1462
Gly Pro Thr Thr Val Glu Ser His Gly Asn Tyr Ser Thr Gln Val Gly
        435                 440                 445
```

```
gcc act cag gcc ggc cga ttc agc atc act cct gct gcg cct tca tac      1510
Ala Thr Gln Ala Gly Arg Phe Ser Ile Thr Pro Ala Ala Pro Ser Tyr
    450                 455                 460 aca cta aag ctt gga gaa tat gga gag gtg aca gtg gac tgt gaa cca      1558
Thr Leu Lys Leu Gly Glu Tyr Gly Glu Val Thr Val Asp Cys Glu Pro
465                 470                 475                 480 cgg tca ggg att gac acc aat gca tac tac gtg atg act gtt gga aca      1606
Arg Ser Gly Ile Asp Thr Asn Ala Tyr Tyr Val Met Thr Val Gly Thr
                485                 490                 495 aag acg ttc ttg gtc cat cgt gag tgg ttc atg gac ctc aac ctc cct      1654
Lys Thr Phe Leu Val His Arg Glu Trp Phe Met Asp Leu Asn Leu Pro
            500                 505                 510 tgg agc agt gct gga agt act gtg tgg agg aac aga gag acg tta atg      1702
Trp Ser Ser Ala Gly Ser Thr Val Trp Arg Asn Arg Glu Thr Leu Met
        515                 520                 525 gag ttt gag gaa cca cac gcc acg aag cag tct gtg ata gca ttg ggc      1750
Glu Phe Glu Glu Pro His Ala Thr Lys Gln Ser Val Ile Ala Leu Gly
530                 535                 540 tca caa gag gga gct ctg cat caa gct ttg gct gga gcc att cct gtg      1798
Ser Gln Glu Gly Ala Leu His Gln Ala Leu Ala Gly Ala Ile Pro Val
545                 550                 555                 560 gaa ttt tca agc aac act gtc aag ttg acg tcg ggt cat ttg aag tgt      1846
Glu Phe Ser Ser Asn Thr Val Lys Leu Thr Ser Gly His Leu Lys Cys
                565                 570                 575 aga gtg aag atg gaa aaa ttg cag ttg aag gga aca acc tat ggc gtc      1894
Arg Val Lys Met Glu Lys Leu Gln Leu Lys Gly Thr Thr Tyr Gly Val
            580                 585                 590 tgt tca aag gct ttc aag ttt ctt agg act ccc gtg gac acc ggt cac      1942
Cys Ser Lys Ala Phe Lys Phe Leu Arg Thr Pro Val Asp Thr Gly His
        595                 600                 605 ggc act gtg gtg ttg gaa ttg cag tac act ggc acg gat gga cct tgc      1990
Gly Thr Val Val Leu Glu Leu Gln Tyr Thr Gly Thr Asp Gly Pro Cys
610                 615                 620 aaa gtt cct atc tcg tca gtg gct tca ttg aac gac cta acg cca gtg      2038
Lys Val Pro Ile Ser Ser Val Ala Ser Leu Asn Asp Leu Thr Pro Val
625                 630                 635                 640 ggc aga ttg gtc act gtc aac cct ttt gtt tca gtg gcc acg gcc aac      2086
Gly Arg Leu Val Thr Val Asn Pro Phe Val Ser Val Ala Thr Ala Asn
                645                 650                 655 gct aag gtc ctg att gaa ttg gaa cca ccc ttt gga gac tca tac ata      2134
Ala Lys Val Leu Ile Glu Leu Glu Pro Pro Phe Gly Asp Ser Tyr Ile
            660                 665                 670 gtg gtg ggc aga gga gaa caa cag atc aat cac cat tgg cac aag tct      2182
Val Val Gly Arg Gly Glu Gln Gln Ile Asn His His Trp His Lys Ser
        675                 680                 685 gga agc agc att ggc aaa gcc ttt aca acc acc ctc aaa gga gcg cag      2230
Gly Ser Ser Ile Gly Lys Ala Phe Thr Thr Thr Leu Lys Gly Ala Gln
690                 695                 700 aga cta gcc gct cta gga gac aca gct tgg gac ttt gga tca gtt gga      2278
Arg Leu Ala Ala Leu Gly Asp Thr Ala Trp Asp Phe Gly Ser Val Gly
705                 710                 715                 720 ggg gtg ttc act agt gtt ggg cgg gct gtc cat caa gtg ttc gga gga      2326
Gly Val Phe Thr Ser Val Gly Arg Ala Val His Gln Val Phe Gly Gly
                725                 730                 735 gca ttc cgc tca ctg ttc gga ggc atg tcc tgg ata acg caa gga ttg      2374
Ala Phe Arg Ser Leu Phe Gly Gly Met Ser Trp Ile Thr Gln Gly Leu
            740                 745                 750 ctg ggg gct ctc ctg ttg tgg atg ggc atc aat gct cgt gat agg tcc      2422
Leu Gly Ala Leu Leu Leu Trp Met Gly Ile Asn Ala Arg Asp Arg Ser
        755                 760                 765
```

```
ata gct ctc acg ttt ctc gca gtt gga gga gtt ctg ctc ttc ctc tcc    2470
Ile Ala Leu Thr Phe Leu Ala Val Gly Gly Val Leu Leu Phe Leu Ser
770             775                 780 gtg aac gtg ggc gcc gat caa gga tgc gcc atc aac ttt ggc aag aga    2518
Val Asn Val Gly Ala Asp Gln Gly Cys Ala Ile Asn Phe Gly Lys Arg
785             790                 795                 800 gag ctc aag tgc gga gat ggt atc ttc ata ttt aga gac tct gat gac    2566
Glu Leu Lys Cys Gly Asp Gly Ile Phe Ile Phe Arg Asp Ser Asp Asp
            805                 810                 815 tgg ctg aac aag tac tca tac tat cca gaa gat cct gtg aag ctt gca    2614
Trp Leu Asn Lys Tyr Ser Tyr Tyr Pro Glu Asp Pro Val Lys Leu Ala
        820                 825                 830 tca ata gtg aaa gcc tct ttt gaa gaa ggg aag tgt ggc cta aat tca    2662
Ser Ile Val Lys Ala Ser Phe Glu Glu Gly Lys Cys Gly Leu Asn Ser
    835                 840                 845 gtt gac tcc ctt gag cat gag atg tgg aga agc agg gca gat gag atc    2710
Val Asp Ser Leu Glu His Glu Met Trp Arg Ser Arg Ala Asp Glu Ile
850             855                 860 aat gcc att ttt gag gaa aac gag gtg gac att tct gtt gtc gtg cag    2758
Asn Ala Ile Phe Glu Glu Asn Glu Val Asp Ile Ser Val Val Val Gln
865             870                 875                 880 gat cca aag aat gtt tac cag aga gga act cat cca ttt tcc aga att    2806
Asp Pro Lys Asn Val Tyr Gln Arg Gly Thr His Pro Phe Ser Arg Ile
            885                 890                 895 cgg gat ggt ctg cag tat ggt tgg aag act tgg ggt aag aac ctt gtg    2854
Arg Asp Gly Leu Gln Tyr Gly Trp Lys Thr Trp Gly Lys Asn Leu Val
        900                 905                 910 ttc tcc cca ggg agg aag aat gga agc ttc atc ata gat gga aag tcc    2902
Phe Ser Pro Gly Arg Lys Asn Gly Ser Phe Ile Ile Asp Gly Lys Ser
    915                 920                 925 agg aaa gaa tgc ccg ttt tca aac cgg gtc tgg aat tct ttc cag ata    2950
Arg Lys Glu Cys Pro Phe Ser Asn Arg Val Trp Asn Ser Phe Gln Ile
930             935                 940 gag gag ttt ggg acg gga gtg ttc acc aca cgc gtg tac atg gac gca    2998
Glu Glu Phe Gly Thr Gly Val Phe Thr Thr Arg Val Tyr Met Asp Ala
945             950                 955                 960 gtc ttt gaa tac acc ata gac tgc gat gga tct atc ttg ggt gca gcg    3046
Val Phe Glu Tyr Thr Ile Asp Cys Asp Gly Ser Ile Leu Gly Ala Ala
            965                 970                 975 gtg aac gga aaa aag agt gcc cat ggc tct cca aca ttt tgg atg gga    3094
Val Asn Gly Lys Lys Ser Ala His Gly Ser Pro Thr Phe Trp Met Gly
        980                 985                 990 agt cat gaa gta aat ggg aca tgg atg atc cac acc ttg gag gca tta    3142
Ser His Glu Val Asn Gly Thr Trp Met Ile His Thr Leu Glu Ala Leu
    995                 1000                1005 gat tac aag gag tgt gag tgg cca ctg aca cat acg att gga aca         3187
Asp Tyr Lys Glu Cys Glu Trp Pro Leu Thr His Thr Ile Gly Thr
1010                1015                1020 tca gtt gaa gag agt gaa atg ttc atg ccg aga tca atc gga ggc         3232
Ser Val Glu Glu Ser Glu Met Phe Met Pro Arg Ser Ile Gly Gly
1025                1030                1035 cca gtt agc tct cac aat cat atc cct gga tac aag gtt cag acg         3277
Pro Val Ser Ser His Asn His Ile Pro Gly Tyr Lys Val Gln Thr
1040                1045                1050 aac gga cct tgg atg cag gta cca cta gaa gtg aag aga gaa gct         3322
Asn Gly Pro Trp Met Gln Val Pro Leu Glu Val Lys Arg Glu Ala
1055                1060                1065 tgc cca ggg act agc gtg atc att gat ggc aac tgt gat gga cgg         3367
Cys Pro Gly Thr Ser Val Ile Ile Asp Gly Asn Cys Asp Gly Arg
1070                1075                1080
```

| | | | | | | | | | | | | | |
|---|---|---|---|---|---|---|---|---|---|---|---|---|---|
| gga | aaa | tca | acc | aga | tcc | acc | acg | gat | agc | ggg | aaa | gtt | att | cct | 3412 |
| Gly | Lys | Ser | Thr | Arg | Ser | Thr | Thr | Asp | Ser | Gly | Lys | Val | Ile | Pro | |
| | 1085 | | | | 1090 | | | | | 1095 | | | | | |
| gaa | tgg | tgt | tgc | cgc | tcc | tgc | aca | atg | ccg | cct | gtg | agc | ttc | cat | 3457 |
| Glu | Trp | Cys | Cys | Arg | Ser | Cys | Thr | Met | Pro | Pro | Val | Ser | Phe | His | |
| | 1100 | | | | 1105 | | | | | 1110 | | | | | |
| ggt | agt | gat | ggg | tgt | tgg | tat | ccc | atg | gaa | att | agg | cca | agg | aaa | 3502 |
| Gly | Ser | Asp | Gly | Cys | Trp | Tyr | Pro | Met | Glu | Ile | Arg | Pro | Arg | Lys | |
| | 1115 | | | | 1120 | | | | | 1125 | | | | | |
| acg | cat | gaa | agc | cat | ctg | gtg | cgc | tcc | tgg | gtt | aca | gct | gga | gaa | 3547 |
| Thr | His | Glu | Ser | His | Leu | Val | Arg | Ser | Trp | Val | Thr | Ala | Gly | Glu | |
| | 1130 | | | | 1135 | | | | | 1140 | | | | | |
| ata | cat | gct | gtc | cct | ttt | ggt | ttg | gtg | agc | atg | atg | ata | gca | atg | 3592 |
| Ile | His | Ala | Val | Pro | Phe | Gly | Leu | Val | Ser | Met | Met | Ile | Ala | Met | |
| | 1145 | | | | 1150 | | | | | 1155 | | | | | |
| gaa | gtg | gtc | cta | agg | aaa | aga | cag | gga | cca | aag | caa | atg | ttg | gtt | 3637 |
| Glu | Val | Val | Leu | Arg | Lys | Arg | Gln | Gly | Pro | Lys | Gln | Met | Leu | Val | |
| | 1160 | | | | 1165 | | | | | 1170 | | | | | |
| gga | gga | gta | gtg | ctc | ttg | gga | gca | atg | ctg | gtc | ggg | caa | gta | act | 3682 |
| Gly | Gly | Val | Val | Leu | Leu | Gly | Ala | Met | Leu | Val | Gly | Gln | Val | Thr | |
| | 1175 | | | | 1180 | | | | | 1185 | | | | | |
| ctc | ctt | gat | ttg | ctg | aaa | ctc | aca | gtg | gct | gtg | gga | ttg | cat | ttc | 3727 |
| Leu | Leu | Asp | Leu | Leu | Lys | Leu | Thr | Val | Ala | Val | Gly | Leu | His | Phe | |
| | 1190 | | | | 1195 | | | | | 1200 | | | | | |
| cat | gag | atg | aac | aat | gga | gga | gac | gcc | atg | tat | atg | gcg | ttg | att | 3772 |
| His | Glu | Met | Asn | Asn | Gly | Gly | Asp | Ala | Met | Tyr | Met | Ala | Leu | Ile | |
| | 1205 | | | | 1210 | | | | | 1215 | | | | | |
| gct | gcc | ttt | tca | atc | aga | cca | ggg | ctg | ctc | atc | ggc | ttt | ggg | ctc | 3817 |
| Ala | Ala | Phe | Ser | Ile | Arg | Pro | Gly | Leu | Leu | Ile | Gly | Phe | Gly | Leu | |
| | 1220 | | | | 1225 | | | | | 1230 | | | | | |
| agg | acc | cta | tgg | agc | cct | cgg | gaa | cgc | ctt | gtg | ctg | acc | cta | gga | 3862 |
| Arg | Thr | Leu | Trp | Ser | Pro | Arg | Glu | Arg | Leu | Val | Leu | Thr | Leu | Gly | |
| | 1235 | | | | 1240 | | | | | 1245 | | | | | |
| gca | gcc | atg | gtg | gag | att | gcc | ttg | ggt | ggc | gtg | atg | ggc | ggc | ctg | 3907 |
| Ala | Ala | Met | Val | Glu | Ile | Ala | Leu | Gly | Gly | Val | Met | Gly | Gly | Leu | |
| | 1250 | | | | 1255 | | | | | 1260 | | | | | |
| tgg | aag | tat | cta | aat | gca | gtt | tct | ctc | tgc | atc | ctg | aca | ata | aat | 3952 |
| Trp | Lys | Tyr | Leu | Asn | Ala | Val | Ser | Leu | Cys | Ile | Leu | Thr | Ile | Asn | |
| | 1265 | | | | 1270 | | | | | 1275 | | | | | |
| gct | gtt | gct | tct | agg | aaa | gca | tca | aat | acc | atc | ttg | ccc | ctc | atg | 3997 |
| Ala | Val | Ala | Ser | Arg | Lys | Ala | Ser | Asn | Thr | Ile | Leu | Pro | Leu | Met | |
| | 1280 | | | | 1285 | | | | | 1290 | | | | | |
| gct | ctg | ttg | aca | cct | gtc | act | atg | gct | gag | gtg | aga | ctt | gcc | gca | 4042 |
| Ala | Leu | Leu | Thr | Pro | Val | Thr | Met | Ala | Glu | Val | Arg | Leu | Ala | Ala | |
| | 1295 | | | | 1300 | | | | | 1305 | | | | | |
| atg | ttc | ttt | tgt | gcc | atg | gtt | atc | ata | ggg | gtc | ctt | cac | cag | aat | 4087 |
| Met | Phe | Phe | Cys | Ala | Met | Val | Ile | Ile | Gly | Val | Leu | His | Gln | Asn | |
| | 1310 | | | | 1315 | | | | | 1320 | | | | | |
| ttc | aag | gac | acc | tcc | atg | cag | aag | act | ata | cct | ctg | gtg | gcc | ctc | 4132 |
| Phe | Lys | Asp | Thr | Ser | Met | Gln | Lys | Thr | Ile | Pro | Leu | Val | Ala | Leu | |
| | 1325 | | | | 1330 | | | | | 1335 | | | | | |
| aca | ctc | aca | tct | tac | ctg | ggc | ttg | aca | caa | cct | ttt | ttg | ggc | ctg | 4177 |
| Thr | Leu | Thr | Ser | Tyr | Leu | Gly | Leu | Thr | Gln | Pro | Phe | Leu | Gly | Leu | |
| | 1340 | | | | 1345 | | | | | 1350 | | | | | |
| tgt | gca | ttt | ctg | gca | acc | cgc | ata | ttt | ggg | cga | agg | agt | atc | cca | 4222 |
| Cys | Ala | Phe | Leu | Ala | Thr | Arg | Ile | Phe | Gly | Arg | Arg | Ser | Ile | Pro | |
| | 1355 | | | | 1360 | | | | | 1365 | | | | | |
| gtg | aat | gag | gca | ctc | gca | gca | gct | ggt | cta | gtg | gga | gtg | ctg | gca | 4267 |
| Val | Asn | Glu | Ala | Leu | Ala | Ala | Ala | Gly | Leu | Val | Gly | Val | Leu | Ala | |
| | 1370 | | | | 1375 | | | | | 1380 | | | | | |

```
gga ctg gct ttt cag gag atg gag aac ttc ctt ggt ccg att gca    4312
Gly Leu Ala Phe Gln Glu Met Glu Asn Phe Leu Gly Pro Ile Ala
    1385                1390                1395 gtt gga gga ctc ctg atg atg ctg gtt agc gtg gct ggg agg gtg    4357
Val Gly Gly Leu Leu Met Met Leu Val Ser Val Ala Gly Arg Val
1400                1405                1410 gat ggg cta gag ctc aag aag ctt ggt gaa gtt tca tgg gaa gag    4402
Asp Gly Leu Glu Leu Lys Lys Leu Gly Glu Val Ser Trp Glu Glu
    1415                1420                1425 gag gcg gag atc agc ggg agt tcc gcc cgc tat gat gtg gca ctc    4447
Glu Ala Glu Ile Ser Gly Ser Ser Ala Arg Tyr Asp Val Ala Leu
1430                1435                1440 agt gaa caa ggg gag ttc aag ctg ctt tct gaa gag aaa gtg cca    4492
Ser Glu Gln Gly Glu Phe Lys Leu Leu Ser Glu Glu Lys Val Pro
    1445                1450                1455 tgg gac cag gtt gtg atg acc tcg ctg gcc ttg gtt ggg gct gcc    4537
Trp Asp Gln Val Val Met Thr Ser Leu Ala Leu Val Gly Ala Ala
1460                1465                1470 ctc cat cca ttt gct ctt ctg ctg gtc ctt gct ggg tgg ctg ttt    4582
Leu His Pro Phe Ala Leu Leu Leu Val Leu Ala Gly Trp Leu Phe
    1475                1480                1485 cat gtc agg gga gct agg aga agt ggg gat gtc ttg tgg gat att    4627
His Val Arg Gly Ala Arg Arg Ser Gly Asp Val Leu Trp Asp Ile
1490                1495                1500 ccc act cct aag atc atc gag gaa tgt gaa cat ctg gag gat ggg    4672
Pro Thr Pro Lys Ile Ile Glu Glu Cys Glu His Leu Glu Asp Gly
    1505                1510                1515 att tat ggc ata ttc cag tca acc ttc ttg ggg gcc tcc cag cga    4717
Ile Tyr Gly Ile Phe Gln Ser Thr Phe Leu Gly Ala Ser Gln Arg
1520                1525                1530 gga gtg gga gtg gca cag gga ggg gtg ttc cac aca atg tgg cat    4762
Gly Val Gly Val Ala Gln Gly Gly Val Phe His Thr Met Trp His
    1535                1540                1545 gtc aca aga gga gct ttc ctt gtc agg aat ggc aag aag ttg att    4807
Val Thr Arg Gly Ala Phe Leu Val Arg Asn Gly Lys Lys Leu Ile
1550                1555                1560 cca tct tgg gct tca gta aag gaa gac ctt gtc gcc tat ggt ggc    4852
Pro Ser Trp Ala Ser Val Lys Glu Asp Leu Val Ala Tyr Gly Gly
    1565                1570                1575 tca tgg aag ttg gaa ggc aga tgg gat gga gag gag gtc cag        4897
Ser Trp Lys Leu Glu Gly Arg Trp Asp Gly Glu Glu Glu Val Gln
1580                1585                1590 ttg atc gcg gct gtt cca gga aag aac gtg gtc aac gtc cag aca    4942
Leu Ile Ala Ala Val Pro Gly Lys Asn Val Val Asn Val Gln Thr
    1595                1600                1605 aaa ccg agc ttg ttc aaa gtg agg aat ggg gga gaa atc ggg gct    4987
Lys Pro Ser Leu Phe Lys Val Arg Asn Gly Gly Glu Ile Gly Ala
1610                1615                1620 gtc gct ctt gac tat ccg agt ggc act tca gga tct cct att gtt    5032
Val Ala Leu Asp Tyr Pro Ser Gly Thr Ser Gly Ser Pro Ile Val
    1625                1630                1635 aac agg aac gga gag gtg att ggg ctg tac ggc aat ggc atc ctt    5077
Asn Arg Asn Gly Glu Val Ile Gly Leu Tyr Gly Asn Gly Ile Leu
1640                1645                1650 gtc ggt gac aac tcc ttc gtg tcc gcc ata tcc cag act gag gtg    5122
Val Gly Asp Asn Ser Phe Val Ser Ala Ile Ser Gln Thr Glu Val
    1655                1660                1665 aag gaa gaa gga aag gag gag ctc caa gag atc ccg aca atg cta    5167
Lys Glu Glu Gly Lys Glu Glu Leu Gln Glu Ile Pro Thr Met Leu
1670                1675                1680
```

```
aag aaa gga atg aca act gtc ctt gat ttt cat cct gga gct ggg        5212
Lys Lys Gly Met Thr Thr Val Leu Asp Phe His Pro Gly Ala Gly
1685                1690                1695 aag aca aga cgt ttc ctc cca cag atc ttg gcc gag tgc gca cgg        5257
Lys Thr Arg Arg Phe Leu Pro Gln Ile Leu Ala Glu Cys Ala Arg
     1700                1705                1710 aga cgc ttg cgc act ctt gtg ttg gcc ccc acc agg gtt gtt ctt        5302
Arg Arg Leu Arg Thr Leu Val Leu Ala Pro Thr Arg Val Val Leu
1715                1720                1725 tct gaa atg aag gag gct ttt cac ggc ctg gac gtg aaa ttc cac        5347
Ser Glu Met Lys Glu Ala Phe His Gly Leu Asp Val Lys Phe His
     1730                1735                1740 aca cag gct ttt tcc gct cac ggc agc ggg aga gaa gtc att gat        5392
Thr Gln Ala Phe Ser Ala His Gly Ser Gly Arg Glu Val Ile Asp
1745                1750                1755 gcc atg tgc cat gcc acc cta act tac agg atg ttg gaa cca act        5437
Ala Met Cys His Ala Thr Leu Thr Tyr Arg Met Leu Glu Pro Thr
     1760                1765                1770 agg gtt gtt aac tgg gaa gtg atc att atg gat gaa gcc cat ttt        5482
Arg Val Val Asn Trp Glu Val Ile Ile Met Asp Glu Ala His Phe
1775                1780                1785 ttg gat cca gcc agc ata gcc gct aga ggt tgg gca gcg cac aga        5527
Leu Asp Pro Ala Ser Ile Ala Ala Arg Gly Trp Ala Ala His Arg
     1790                1795                1800 gct agg gca aat gaa agt gca aca atc ttg atg aca gcc aca ccg        5572
Ala Arg Ala Asn Glu Ser Ala Thr Ile Leu Met Thr Ala Thr Pro
1805                1810                1815 cct ggg act agt gat gaa ttt cca cat tca aat ggt gaa ata gaa        5617
Pro Gly Thr Ser Asp Glu Phe Pro His Ser Asn Gly Glu Ile Glu
     1820                1825                1830 gat gtt caa acg gac ata ccc agt gag ccc tgg aac aca ggg cat        5662
Asp Val Gln Thr Asp Ile Pro Ser Glu Pro Trp Asn Thr Gly His
1835                1840                1845 gac tgg atc ctg gct gac aaa agg ccc acg gca tgg ttc ctt cca        5707
Asp Trp Ile Leu Ala Asp Lys Arg Pro Thr Ala Trp Phe Leu Pro
     1850                1855                1860 tcc atc aga gct gca aat gtc atg gct gcc tct ttg cgt aag gct        5752
Ser Ile Arg Ala Ala Asn Val Met Ala Ala Ser Leu Arg Lys Ala
1865                1870                1875 gga aag agt gtg gtg gtc ctg aac agg aaa acc ttt gag aga gaa        5797
Gly Lys Ser Val Val Val Leu Asn Arg Lys Thr Phe Glu Arg Glu
     1880                1885                1890 tac ccc acg ata aag cag aag aaa cct gac ttt ata ttg gcc act        5842
Tyr Pro Thr Ile Lys Gln Lys Lys Pro Asp Phe Ile Leu Ala Thr
1895                1900                1905 gac ata gct gaa atg gga gcc aac ctt tgc gtg gag cga gtg ctg        5887
Asp Ile Ala Glu Met Gly Ala Asn Leu Cys Val Glu Arg Val Leu
     1910                1915                1920 gat tgc agg acg gct ttt aag cct gtg ctt gtg gat gaa ggg agg        5932
Asp Cys Arg Thr Ala Phe Lys Pro Val Leu Val Asp Glu Gly Arg
1925                1930                1935 aag gtg gca ata aaa ggg cca ctt cgt atc tcc gca tcc tct gct        5977
Lys Val Ala Ile Lys Gly Pro Leu Arg Ile Ser Ala Ser Ser Ala
     1940                1945                1950 gct caa agg agg ggg cgc att ggg aga aat ccc aac aga gat gga        6022
Ala Gln Arg Arg Gly Arg Ile Gly Arg Asn Pro Asn Arg Asp Gly
1955                1960                1965 gac tca tac tac tat tct gag cct aca agt gaa aat aat gcc cac        6067
Asp Ser Tyr Tyr Tyr Ser Glu Pro Thr Ser Glu Asn Asn Ala His
     1970                1975                1980
```

```
cac gtc tgc tgg ttg gag gcc tca atg ctc ttg gac aac atg gag      6112
His Val Cys Trp Leu Glu Ala Ser Met Leu Leu Asp Asn Met Glu
    1985                1990                1995 gtg agg ggt gga atg gtc gcc cca ctc tat ggc gtt gaa gga act      6157
Val Arg Gly Gly Met Val Ala Pro Leu Tyr Gly Val Glu Gly Thr
2000                2005                2010 aaa aca cca gtt tcc cct ggt gaa atg aga ctg agg gat gac cag      6202
Lys Thr Pro Val Ser Pro Gly Glu Met Arg Leu Arg Asp Asp Gln
    2015                2020                2025 agg aaa gtc ttc aga gaa cta gtg agg aat tgt gac ctg ccc gtt      6247
Arg Lys Val Phe Arg Glu Leu Val Arg Asn Cys Asp Leu Pro Val
2030                2035                2040 tgg ctt tcg tgg caa gtg gcc aag gct ggt ttg aag acg aat gat      6292
Trp Leu Ser Trp Gln Val Ala Lys Ala Gly Leu Lys Thr Asn Asp
    2045                2050                2055 cgt aag tgg tgt ttt gaa ggc cct gag gaa cat gag atc ttg aat      6337
Arg Lys Trp Cys Phe Glu Gly Pro Glu Glu His Glu Ile Leu Asn
2060                2065                2070 gac agc ggt gaa aca gtg aag tgc agg gct cct gga gga gca aag      6382
Asp Ser Gly Glu Thr Val Lys Cys Arg Ala Pro Gly Gly Ala Lys
    2075                2080                2085 aag cct ctg cgc cca agg tgg tgt gat gaa agg gtg tca tct gac      6427
Lys Pro Leu Arg Pro Arg Trp Cys Asp Glu Arg Val Ser Ser Asp
2090                2095                2100 cag agt gcg ctg tct gaa ttt att aag ttt gct gaa ggt agg agg      6472
Gln Ser Ala Leu Ser Glu Phe Ile Lys Phe Ala Glu Gly Arg Arg
    2105                2110                2115 gga gct gct gaa gtg cta gtt gtg ctg agt gaa ctc cct gat ttc      6517
Gly Ala Ala Glu Val Leu Val Val Leu Ser Glu Leu Pro Asp Phe
2120                2125                2130 ctg gct aaa aaa ggt gga gag gca atg gat acc atc agt gtg ttc      6562
Leu Ala Lys Lys Gly Gly Glu Ala Met Asp Thr Ile Ser Val Phe
    2135                2140                2145 ctc cac tct gag gaa ggc tct agg gct tac cgc aat gca cta tca      6607
Leu His Ser Glu Glu Gly Ser Arg Ala Tyr Arg Asn Ala Leu Ser
2150                2155                2160 atg atg cct gag gca atg aca ata gtc atg ctg ttt ata ctg gct      6652
Met Met Pro Glu Ala Met Thr Ile Val Met Leu Phe Ile Leu Ala
    2165                2170                2175 gga cta ctg aca tcg gga atg gtc atc ttt ttc atg tct ccc aaa      6697
Gly Leu Leu Thr Ser Gly Met Val Ile Phe Phe Met Ser Pro Lys
2180                2185                2190 ggc atc agt aga atg tct atg gcg atg ggc aca atg gcc ggc tgt      6742
Gly Ile Ser Arg Met Ser Met Ala Met Gly Thr Met Ala Gly Cys
    2195                2200                2205 gga tat ctc atg ttc ctt gga ggc gtc aaa ccc act cac atc tcc      6787
Gly Tyr Leu Met Phe Leu Gly Gly Val Lys Pro Thr His Ile Ser
2210                2215                2220 tat gtc atg ctc ata ttc ttt gtc ctg atg gtg gtt gtg atc ccc      6832
Tyr Val Met Leu Ile Phe Phe Val Leu Met Val Val Val Ile Pro
    2225                2230                2235 gag cca ggg caa caa agg tcc atc caa gac aac caa gtg gca tac      6877
Glu Pro Gly Gln Gln Arg Ser Ile Gln Asp Asn Gln Val Ala Tyr
2240                2245                2250 ctc att att ggc atc ctg acg ctg gtt tca gcg gtg gca gcc aac      6922
Leu Ile Ile Gly Ile Leu Thr Leu Val Ser Ala Val Ala Ala Asn
    2255                2260                2265 gag cta ggc atg ctg gag aaa acc aaa gag gac ctc ttt ggg aag      6967
Glu Leu Gly Met Leu Glu Lys Thr Lys Glu Asp Leu Phe Gly Lys
2270                2275                2280
```

```
aag aac tta att cca tct agt gct tca ccc tgg agt tgg ccg gat      7012
Lys Asn Leu Ile Pro Ser Ser Ala Ser Pro Trp Ser Trp Pro Asp
2285            2290                2295 ctt gac ctg aag cca gga gct gcc tgg aca gtg tac gtt ggc att      7057
Leu Asp Leu Lys Pro Gly Ala Ala Trp Thr Val Tyr Val Gly Ile
    2300            2305                2310 gtt aca atg ctc tct cca atg ttg cac cac tgg atc aaa gtc gaa      7102
Val Thr Met Leu Ser Pro Met Leu His His Trp Ile Lys Val Glu
2315            2320                2325 tat ggc aac ctg tct ctg tct gga ata gcc cag tca gcc tca gtc      7147
Tyr Gly Asn Leu Ser Leu Ser Gly Ile Ala Gln Ser Ala Ser Val
    2330            2335                2340 ctt tct ttc atg gac aag ggg ata cca ttc atg aag atg aat atc      7192
Leu Ser Phe Met Asp Lys Gly Ile Pro Phe Met Lys Met Asn Ile
2345            2350                2355 tcg gtc ata atg ctg ctg gtc agt ggc tgg aat tca ata aca gtg      7237
Ser Val Ile Met Leu Leu Val Ser Gly Trp Asn Ser Ile Thr Val
    2360            2365                2370 atg cct ctg ctc tgt ggc ata ggg tgc gcc atg ctc cac tgg tct      7282
Met Pro Leu Leu Cys Gly Ile Gly Cys Ala Met Leu His Trp Ser
2375            2380                2385 ctc att tta cct gga atc aaa gcg cag cag tca aag ctt gca cag      7327
Leu Ile Leu Pro Gly Ile Lys Ala Gln Gln Ser Lys Leu Ala Gln
    2390            2395                2400 aga agg gtg ttc cat ggc gtt gcc aag aac cct gtg gtt gat ggg      7372
Arg Arg Val Phe His Gly Val Ala Lys Asn Pro Val Val Asp Gly
2405            2410                2415 aat cca aca gtt gac att gag gaa gct cct gaa atg cct gcc ctt      7417
Asn Pro Thr Val Asp Ile Glu Glu Ala Pro Glu Met Pro Ala Leu
    2420            2425                2430 tat gag aag aaa ctg gct cta tat ctc ctt ctt gct ctc agc cta      7462
Tyr Glu Lys Lys Leu Ala Leu Tyr Leu Leu Leu Ala Leu Ser Leu
2435            2440                2445 gct tct gtt gcc atg tgc aga acg ccc ttt tca ttg gct gaa ggc      7507
Ala Ser Val Ala Met Cys Arg Thr Pro Phe Ser Leu Ala Glu Gly
    2450            2455                2460 att gtc cta gca tca gct gcc tta ggg ccg ctc ata gag gga aac      7552
Ile Val Leu Ala Ser Ala Ala Leu Gly Pro Leu Ile Glu Gly Asn
2465            2470                2475 acc agc ctt ctt tgg aat gga ccc atg gct gtc tcc atg aca gga      7597
Thr Ser Leu Leu Trp Asn Gly Pro Met Ala Val Ser Met Thr Gly
    2480            2485                2490 gtc atg agg ggg aat cac tat gct ttt gtg gga gtc atg tac aat      7642
Val Met Arg Gly Asn His Tyr Ala Phe Val Gly Val Met Tyr Asn
2495            2500                2505 cta tgg aag atg aaa act gga cgc cgg ggg agc gcg aat gga aaa      7687
Leu Trp Lys Met Lys Thr Gly Arg Arg Gly Ser Ala Asn Gly Lys
    2510            2515                2520 act ttg ggt gaa gtc tgg aag agg gaa ctg aat ctg ttg gac aag      7732
Thr Leu Gly Glu Val Trp Lys Arg Glu Leu Asn Leu Leu Asp Lys
2525            2530                2535 cga cag ttt gag ttg tat aaa agg acc gac att gtg gag gtg gat      7777
Arg Gln Phe Glu Leu Tyr Lys Arg Thr Asp Ile Val Glu Val Asp
    2540            2545                2550 cgt gat acg gca cgc agg cat ttg gcc gaa ggg aag gtg gac acc      7822
Arg Asp Thr Ala Arg Arg His Leu Ala Glu Gly Lys Val Asp Thr
2555            2560                2565 ggg gtg gcg gtc tcc agg ggg acc gca aag tta agg tgg ttc cat      7867
Gly Val Ala Val Ser Arg Gly Thr Ala Lys Leu Arg Trp Phe His
    2570            2575                2580
```

```
                                                         -continued
gag cgt ggc tat gtc aag ctg gaa ggt agg gtg att gac ctg ggg       7912
Glu Arg Gly Tyr Val Lys Leu Glu Gly Arg Val Ile Asp Leu Gly
2585                2590                2595 tgt ggc cgc gga ggc tgg tgt tac tac gct gct gcg caa aag gaa       7957
Cys Gly Arg Gly Gly Trp Cys Tyr Tyr Ala Ala Ala Gln Lys Glu
        2600                2605                2610 gtg agt ggg gtc aaa gga ttt act ctt gga aga gac ggc cat gag       8002
Val Ser Gly Val Lys Gly Phe Thr Leu Gly Arg Asp Gly His Glu
2615                2620                2625 aaa ccc atg aat gtg caa agt ctg gga tgg aac atc atc acc ttc       8047
Lys Pro Met Asn Val Gln Ser Leu Gly Trp Asn Ile Ile Thr Phe
        2630                2635                2640 aag gac aaa act gat atc cac cgc cta gaa cca gtg aaa tgt gac       8092
Lys Asp Lys Thr Asp Ile His Arg Leu Glu Pro Val Lys Cys Asp
2645                2650                2655 acc ctt ttg tgt gac att gga gag tca tca tcg tca tcg gtc aca       8137
Thr Leu Leu Cys Asp Ile Gly Glu Ser Ser Ser Ser Ser Val Thr
        2660                2665                2670 gag ggg gaa agg acc gtg aga gtt ctt gat act gta gaa aaa tgg       8182
Glu Gly Glu Arg Thr Val Arg Val Leu Asp Thr Val Glu Lys Trp
2675                2680                2685 ctg gct tgt ggg gtt gac aac ttc tgt gtg aag gtg tta gct cca       8227
Leu Ala Cys Gly Val Asp Asn Phe Cys Val Lys Val Leu Ala Pro
        2690                2695                2700 tac atg cca gat gtt ctt gag aaa ctg gaa ttg ctc caa agg agg       8272
Tyr Met Pro Asp Val Leu Glu Lys Leu Glu Leu Leu Gln Arg Arg
2705                2710                2715 ttt ggc gga aca gtg atc agg aac cct ctc tcc agg aat tcc act       8317
Phe Gly Gly Thr Val Ile Arg Asn Pro Leu Ser Arg Asn Ser Thr
        2720                2725                2730 cat gaa atg tac tac gtg tct gga gcc cgc agc aat gtc aca ttt       8362
His Glu Met Tyr Tyr Val Ser Gly Ala Arg Ser Asn Val Thr Phe
2735                2740                2745 act gtg aac caa aca tcc cgc ctc ctg atg agg aga atg agg cgt       8407
Thr Val Asn Gln Thr Ser Arg Leu Leu Met Arg Arg Met Arg Arg
        2750                2755                2760 cca act gga aaa gtg acc ctg gag gct gac gtc atc ctc cca att       8452
Pro Thr Gly Lys Val Thr Leu Glu Ala Asp Val Ile Leu Pro Ile
2765                2770                2775 ggg aca cgc agt gtt gag aca gac aag gga ccc ctg gac aaa gag       8497
Gly Thr Arg Ser Val Glu Thr Asp Lys Gly Pro Leu Asp Lys Glu
        2780                2785                2790 gcc ata gaa gaa agg gtt gag agg ata aaa tct gag tac atg acc       8542
Ala Ile Glu Glu Arg Val Glu Arg Ile Lys Ser Glu Tyr Met Thr
2795                2800                2805 tct tgg ttt tat gac aat gac aac ccc tac agg acc tgg cac tac       8587
Ser Trp Phe Tyr Asp Asn Asp Asn Pro Tyr Arg Thr Trp His Tyr
        2810                2815                2820 tgt ggc tcc tat gtc aca aaa acc tcc gga agt gcg gcg agc atg       8632
Cys Gly Ser Tyr Val Thr Lys Thr Ser Gly Ser Ala Ala Ser Met
2825                2830                2835 gta aat ggt gtt att aaa att ctg aca tat cca tgg gac agg ata       8677
Val Asn Gly Val Ile Lys Ile Leu Thr Tyr Pro Trp Asp Arg Ile
        2840                2845                2850 gag gag gtc aca aga atg gca atg act gac aca acc cct ttt gga       8722
Glu Glu Val Thr Arg Met Ala Met Thr Asp Thr Thr Pro Phe Gly
2855                2860                2865 cag caa aga gtg ttt aaa gaa aaa gtt gac acc aga gca aag gat       8767
Gln Gln Arg Val Phe Lys Glu Lys Val Asp Thr Arg Ala Lys Asp
        2870                2875                2880
```

|  |  |
|---|---|
| cca cca gcg gga act agg aag atc atg aaa gtt gtc aac agg tgg<br>Pro Pro Ala Gly Thr Arg Lys Ile Met Lys Val Val Asn Arg Trp<br>2885                       2890                       2895 | 8812 |
| ctg ttc cgc cac ctg gcc aga gaa aag aac ccc aga ctg tgc aca<br>Leu Phe Arg His Leu Ala Arg Glu Lys Asn Pro Arg Leu Cys Thr<br>2900                       2905                       2910 | 8857 |
| aag gaa gaa ttt att gca aaa gtc cga agt cat gca gcc att gga<br>Lys Glu Glu Phe Ile Ala Lys Val Arg Ser His Ala Ala Ile Gly<br>2915                       2920                       2925 | 8902 |
| gct tac ctg gaa gaa caa gaa cag tgg aag act gcc aat gag gct<br>Ala Tyr Leu Glu Glu Gln Glu Gln Trp Lys Thr Ala Asn Glu Ala<br>2930                       2935                       2940 | 8947 |
| gtc caa gac cca aag ttc tgg gaa ctg gtg gat gaa gaa agg aag<br>Val Gln Asp Pro Lys Phe Trp Glu Leu Val Asp Glu Glu Arg Lys<br>2945                       2950                       2955 | 8992 |
| ctg cac caa caa ggc agg tgt cgg act tgt gtg tac aac atg atg<br>Leu His Gln Gln Gly Arg Cys Arg Thr Cys Val Tyr Asn Met Met<br>2960                       2965                       2970 | 9037 |
| ggg aaa aga gag aag aag ctg tca gag ttt ggg aaa gca aag gga<br>Gly Lys Arg Glu Lys Lys Leu Ser Glu Phe Gly Lys Ala Lys Gly<br>2975                       2980                       2985 | 9082 |
| agc cgt gcc ata tgg tat atg tgg ctg gga gcg cgg tat ctt gag<br>Ser Arg Ala Ile Trp Tyr Met Trp Leu Gly Ala Arg Tyr Leu Glu<br>2990                       2995                       3000 | 9127 |
| ttt gag gcc ctg gga ttc ctg aat gag gac cat tgg gct tcc agg<br>Phe Glu Ala Leu Gly Phe Leu Asn Glu Asp His Trp Ala Ser Arg<br>3005                       3010                       3015 | 9172 |
| gaa aac tca gga gga gga gtg gaa ggc att ggc tta caa tac cta<br>Glu Asn Ser Gly Gly Gly Val Glu Gly Ile Gly Leu Gln Tyr Leu<br>3020                       3025                       3030 | 9217 |
| gga tat gtg atc aga gac ctg gct gca atg gat ggt ggt gga ttc<br>Gly Tyr Val Ile Arg Asp Leu Ala Ala Met Asp Gly Gly Gly Phe<br>3035                       3040                       3045 | 9262 |
| tac gcg gat gac acc gct gga tgg gac acg cgc atc aca gag gca<br>Tyr Ala Asp Asp Thr Ala Gly Trp Asp Thr Arg Ile Thr Glu Ala<br>3050                       3055                       3060 | 9307 |
| gac ctt gat gat gaa cag gag atc ttg aac tac atg agc cca cat<br>Asp Leu Asp Asp Glu Gln Glu Ile Leu Asn Tyr Met Ser Pro His<br>3065                       3070                       3075 | 9352 |
| cac aaa aaa ctg gca caa gca gtg atg gaa atg aca tac aag aac<br>His Lys Lys Leu Ala Gln Ala Val Met Glu Met Thr Tyr Lys Asn<br>3080                       3085                       3090 | 9397 |
| aaa gtg gtg aaa gtg ttg aga cca gcc cca gga ggg aaa gcc tac<br>Lys Val Val Lys Val Leu Arg Pro Ala Pro Gly Gly Lys Ala Tyr<br>3095                       3100                       3105 | 9442 |
| atg gat gtc ata agt cga cga gac cag aga gga tcc ggg cag gta<br>Met Asp Val Ile Ser Arg Arg Asp Gln Arg Gly Ser Gly Gln Val<br>3110                       3115                       3120 | 9487 |
| gtg act tat gct ctg aac acc atc acc aac ttg aaa gtc caa ttg<br>Val Thr Tyr Ala Leu Asn Thr Ile Thr Asn Leu Lys Val Gln Leu<br>3125                       3130                       3135 | 9532 |
| atc aga atg gca gaa gca gag atg gtg ata cat cac caa cat gtt<br>Ile Arg Met Ala Glu Ala Glu Met Val Ile His His Gln His Val<br>3140                       3145                       3150 | 9577 |
| caa gat tgt gat gaa tca gtt ctg acc agg ctg gag gca tgg ctc<br>Gln Asp Cys Asp Glu Ser Val Leu Thr Arg Leu Glu Ala Trp Leu<br>3155                       3160                       3165 | 9622 |
| act gag cac gga tgt gac aga ctg aag agg atg gcg gtg agt gga<br>Thr Glu His Gly Cys Asp Arg Leu Lys Arg Met Ala Val Ser Gly<br>3170                       3175                       3180 | 9667 |

```
gac gac tgt gtg gtc cgg ccc atc gat gac agg ttc ggc ctg gcc         9712
Asp Asp Cys Val Val Arg Pro Ile Asp Asp Arg Phe Gly Leu Ala
    3185            3190            3195 ctg tcc cat ctc aac gcc atg tcc aag gtt aga aag gac ata tct         9757
Leu Ser His Leu Asn Ala Met Ser Lys Val Arg Lys Asp Ile Ser
3200            3205            3210 gaa tgg cag cca tca aaa ggg tgg aat gat tgg gag aat gtg ccc         9802
Glu Trp Gln Pro Ser Lys Gly Trp Asn Asp Trp Glu Asn Val Pro
    3215            3220            3225 ttc tgt tcc cac cac ttc cat gaa cta cag ctg aag gat ggc agg         9847
Phe Cys Ser His His Phe His Glu Leu Gln Leu Lys Asp Gly Arg
    3230            3235            3240 agg att gtg gtg cct tgc cga gaa cag gac gag ctc att ggg aga         9892
Arg Ile Val Val Pro Cys Arg Glu Gln Asp Glu Leu Ile Gly Arg
    3245            3250            3255 gga agg gtg tct cca gga aac ggc tgg atg atc aag gaa aca gct         9937
Gly Arg Val Ser Pro Gly Asn Gly Trp Met Ile Lys Glu Thr Ala
3260            3265            3270 tgc ctc agc aaa gcc tat gcc aac atg tgg tca ctg atg tat ttt         9982
Cys Leu Ser Lys Ala Tyr Ala Asn Met Trp Ser Leu Met Tyr Phe
    3275            3280            3285 cac aaa agg gac atg agg cta ctg tca ttg gct gtt tcc tca gct        10027
His Lys Arg Asp Met Arg Leu Leu Ser Leu Ala Val Ser Ser Ala
    3290            3295            3300 gtt ccc acc tca tgg gtt cca caa gga cgc aca aca tgg tcg att        10072
Val Pro Thr Ser Trp Val Pro Gln Gly Arg Thr Thr Trp Ser Ile
3305            3310            3315 cat ggg aaa ggg gag tgg atg acc acg gaa gac atg ctt gag gtg        10117
His Gly Lys Gly Glu Trp Met Thr Thr Glu Asp Met Leu Glu Val
    3320            3325            3330 tgg aac aga gta tgg ata acc aac aac cca cac atg cag gac aag        10162
Trp Asn Arg Val Trp Ile Thr Asn Asn Pro His Met Gln Asp Lys
    3335            3340            3345 aca atg gtg aaa aaa tgg aga gat gtc cct tat cta acc aag aga        10207
Thr Met Val Lys Lys Trp Arg Asp Val Pro Tyr Leu Thr Lys Arg
3350            3355            3360 caa gac aag ctg tgc gga tca ctg att gga atg acc aat agg gcc        10252
Gln Asp Lys Leu Cys Gly Ser Leu Ile Gly Met Thr Asn Arg Ala
    3365            3370            3375 acc tgg gcc tcc cac atc cat tta gtc atc cat cgt atc cga acg        10297
Thr Trp Ala Ser His Ile His Leu Val Ile His Arg Ile Arg Thr
    3380            3385            3390 ctg att gga cag gag aaa tac act gac tac cta aca gtc atg gac        10342
Leu Ile Gly Gln Glu Lys Tyr Thr Asp Tyr Leu Thr Val Met Asp
3395            3400            3405 agg tat tct gtg gat gct gac ctg caa ctg ggt gag ctt atc             10384
Arg Tyr Ser Val Asp Ala Asp Leu Gln Leu Gly Glu Leu Ile
    3410            3415            3420 tgaaacacca tctaacagga ataaccggga tacaaaccac gggtggagaa ccggactccc  10444
cacaacctga aaccgggata taaaccacgg ctggagaacc ggactccgca cttaaaatga  10504
aacagaaacc gggataaaaa ctacggatgg agaaccggac tccacacatt gagacagaag  10564
aagttgtcag cccagaaccc cacacgagtt ttgccactgc taagctgtga ggcagtgcag  10624
gctgggacag ccgacctcca ggttgcgaaa aacctggttt ctgggacctc caccccaga  10684 gtaaaaagaa cggagcctcc gctaccaccc tcccacgtgg tggtagaaag acgggtctta  10744
gaggttagag gagaccctcc agggaacaaa tagtgggacc atattgacgc cagggaaaga  10804
ccggagtggt tctctgcttt tcctccagag gtctgtgagc acagtttgct caagaataag  10864
```

-continued cagacctttg gatgacaaac acaaaaccac aa 10896

<210> SEQ ID NO 23
<211> LENGTH: 3422
<212> TYPE: PRT
<213> ORGANISM: Artificial Sequence
<220> FEATURE:
<223> OTHER INFORMATION: Synthetic Construct

<400> SEQUENCE: 23

```
Met Ser Gly Arg Lys Ala Gln Gly Lys Thr Leu Gly Val Asn Met Val
1               5                   10                  15

Arg Arg Gly Val Arg Ser Leu Ser Asn Lys Ile Lys Gln Lys Thr Lys
            20                  25                  30

Gln Ile Gly Asn Arg Pro Gly Pro Ser Arg Gly Val Gln Gly Phe Ile
        35                  40                  45

Phe Phe Phe Leu Phe Asn Ile Leu Thr Gly Lys Lys Ile Thr Ala His
    50                  55                  60

Leu Lys Arg Leu Trp Lys Met Leu Asp Pro Arg Gln Gly Leu Ala Val
65                  70                  75                  80

Leu Arg Lys Val Lys Arg Val Ala Ser Leu Met Arg Gly Leu Ser
                85                  90                  95

Ser Arg Lys Arg Arg Ser His Asp Val Leu Thr Val Gln Phe Leu Ile
            100                 105                 110

Leu Gly Met Leu Leu Met Thr Gly Gly Val Thr Leu Ser Asn Phe Gln
        115                 120                 125

Gly Lys Val Met Met Thr Val Asn Ala Thr Asp Val Thr Asp Val Ile
    130                 135                 140

Thr Ile Pro Thr Ala Ala Gly Lys Asn Leu Cys Ile Val Arg Ala Met
145                 150                 155                 160

Asp Val Gly Tyr Met Cys Asp Asp Thr Ile Thr Tyr Glu Cys Pro Val
                165                 170                 175

Leu Ser Ala Gly Asn Asp Pro Glu Asp Ile Asp Cys Trp Cys Thr Lys
            180                 185                 190

Ser Ala Val Tyr Val Arg Tyr Gly Arg Cys Thr Lys Thr Arg His Ser
        195                 200                 205

Arg Arg Ser Arg Arg Ser Leu Thr Val Gln Thr His Gly Glu Ser Thr
    210                 215                 220

Leu Ala Asn Lys Lys Gly Ala Trp Met Asp Ser Thr Lys Ala Thr Arg
225                 230                 235                 240

Tyr Leu Val Lys Thr Glu Ser Trp Ile Leu Arg Asn Pro Gly Tyr Ala
                245                 250                 255

Leu Val Ala Ala Val Ile Gly Trp Met Leu Gly Ser Asn Thr Met Gln
            260                 265                 270

Arg Val Val Phe Val Val Pro Leu Leu Leu Val Ala Pro Ala Tyr Ser
        275                 280                 285

Phe Asn Cys Leu Gly Met Ser Asn Arg Asp Phe Leu Glu Gly Val Ser
    290                 295                 300

Gly Ala Thr Trp Val Asp Leu Val Leu Glu Gly Asp Ser Cys Val Thr
305                 310                 315                 320

Ile Met Ser Lys Asp Lys Pro Thr Ile Asp Val Lys Met Met Asn Met
                325                 330                 335

Glu Ala Ala Asn Leu Ala Glu Val Arg Ser Tyr Cys Tyr Leu Ala Thr
            340                 345                 350

Val Ser Asp Leu Ser Thr Lys Ala Ala Cys Pro Thr Met Gly Glu Ala
        355                 360                 365
```

His Asn Asp Lys Arg Ala Asp Pro Ala Phe Val Cys Arg Gln Gly Val
    370                 375                 380

Val Asp Arg Gly Trp Gly Asn Gly Cys Gly Phe Gly Lys Gly Ser
385                 390                 395                 400

Ile Asp Thr Cys Ala Lys Phe Ala Cys Ser Thr Lys Ala Ile Gly Arg
                405                 410                 415

Thr Ile Leu Lys Glu Asn Ile Lys Tyr Glu Val Ala Ile Phe Val His
            420                 425                 430

Gly Pro Thr Thr Val Glu Ser His Gly Asn Tyr Ser Thr Gln Val Gly
        435                 440                 445

Ala Thr Gln Ala Gly Arg Phe Ser Ile Thr Pro Ala Ala Pro Ser Tyr
    450                 455                 460

Thr Leu Lys Leu Gly Glu Tyr Gly Glu Val Thr Val Asp Cys Glu Pro
465                 470                 475                 480

Arg Ser Gly Ile Asp Thr Asn Ala Tyr Tyr Val Met Thr Val Gly Thr
                485                 490                 495

Lys Thr Phe Leu Val His Arg Glu Trp Phe Met Asp Leu Asn Leu Pro
            500                 505                 510

Trp Ser Ala Gly Ser Thr Val Trp Arg Asn Arg Glu Thr Leu Met
        515                 520                 525

Glu Phe Glu Glu Pro His Ala Thr Lys Gln Ser Val Ile Ala Leu Gly
    530                 535                 540

Ser Gln Glu Gly Ala Leu His Gln Ala Leu Ala Gly Ala Ile Pro Val
545                 550                 555                 560

Glu Phe Ser Ser Asn Thr Val Lys Leu Thr Ser Gly His Leu Lys Cys
                565                 570                 575

Arg Val Lys Met Glu Lys Leu Gln Leu Lys Gly Thr Thr Tyr Gly Val
            580                 585                 590

Cys Ser Lys Ala Phe Lys Phe Leu Arg Thr Pro Val Asp Thr Gly His
        595                 600                 605

Gly Thr Val Val Leu Glu Leu Gln Tyr Thr Gly Thr Asp Gly Pro Cys
    610                 615                 620

Lys Val Pro Ile Ser Ser Val Ala Ser Leu Asn Asp Leu Thr Pro Val
625                 630                 635                 640

Gly Arg Leu Val Thr Val Asn Pro Phe Val Ser Val Ala Thr Ala Asn
                645                 650                 655

Ala Lys Val Leu Ile Glu Leu Glu Pro Pro Phe Gly Asp Ser Tyr Ile
            660                 665                 670

Val Val Gly Arg Gly Glu Gln Gln Ile Asn His His Trp His Lys Ser
        675                 680                 685

Gly Ser Ser Ile Gly Lys Ala Phe Thr Thr Thr Leu Lys Gly Ala Gln
    690                 695                 700

Arg Leu Ala Ala Leu Gly Asp Thr Ala Trp Asp Phe Gly Ser Val Gly
705                 710                 715                 720

Gly Val Phe Thr Ser Val Gly Arg Ala Val His Gln Val Phe Gly Gly
                725                 730                 735

Ala Phe Arg Ser Leu Phe Gly Gly Met Ser Trp Ile Thr Gln Gly Leu
            740                 745                 750

Leu Gly Ala Leu Leu Leu Trp Met Gly Ile Asn Ala Arg Asp Arg Ser
        755                 760                 765

Ile Ala Leu Thr Phe Leu Ala Val Gly Gly Val Leu Leu Phe Leu Ser
    770                 775                 780

Val Asn Val Gly Ala Asp Gln Gly Cys Ala Ile Asn Phe Gly Lys Arg

```
            785                 790                 795                 800
Glu Leu Lys Cys Gly Asp Gly Ile Phe Ile Phe Arg Asp Ser Asp Asp
                    805                 810                 815
Trp Leu Asn Lys Tyr Ser Tyr Tyr Pro Glu Asp Pro Val Lys Leu Ala
                    820                 825                 830
Ser Ile Val Lys Ala Ser Phe Glu Glu Gly Lys Cys Gly Leu Asn Ser
                    835                 840                 845
Val Asp Ser Leu Glu His Glu Met Trp Arg Ser Arg Ala Asp Glu Ile
850                 855                 860
Asn Ala Ile Phe Glu Glu Asn Glu Val Asp Ile Ser Val Val Val Gln
865                 870                 875                 880
Asp Pro Lys Asn Val Tyr Gln Arg Gly Thr His Pro Phe Ser Arg Ile
                    885                 890                 895
Arg Asp Gly Leu Gln Tyr Gly Trp Lys Thr Trp Gly Lys Asn Leu Val
                    900                 905                 910
Phe Ser Pro Gly Arg Lys Asn Gly Ser Phe Ile Ile Asp Gly Lys Ser
                    915                 920                 925
Arg Lys Glu Cys Pro Phe Ser Asn Arg Val Trp Asn Ser Phe Gln Ile
                    930                 935                 940
Glu Glu Phe Gly Thr Gly Val Phe Thr Thr Arg Val Tyr Met Asp Ala
945                 950                 955                 960
Val Phe Glu Tyr Thr Ile Asp Cys Asp Gly Ser Ile Leu Gly Ala Ala
                    965                 970                 975
Val Asn Gly Lys Lys Ser Ala His Gly Ser Pro Thr Phe Trp Met Gly
                    980                 985                 990
Ser His Glu Val Asn Gly Thr Trp Met Ile His Thr Leu Glu Ala Leu
                    995                 1000                1005
Asp Tyr Lys Glu Cys Glu Trp Pro Leu Thr His Thr Ile Gly Thr
      1010                1015                1020
Ser Val Glu Glu Ser Glu Met Phe Met Pro Arg Ser Ile Gly Gly
      1025                1030                1035
Pro Val Ser Ser His Asn His Ile Pro Gly Tyr Lys Val Gln Thr
      1040                1045                1050
Asn Gly Pro Trp Met Gln Val Pro Leu Glu Val Lys Arg Glu Ala
      1055                1060                1065
Cys Pro Gly Thr Ser Val Ile Ile Asp Gly Asn Cys Asp Gly Arg
      1070                1075                1080
Gly Lys Ser Thr Arg Ser Thr Asp Ser Gly Lys Val Ile Pro
      1085                1090                1095
Glu Trp Cys Cys Arg Ser Cys Thr Met Pro Pro Val Ser Phe His
      1100                1105                1110
Gly Ser Asp Gly Cys Trp Tyr Pro Met Glu Ile Arg Pro Arg Lys
      1115                1120                1125
Thr His Glu Ser His Leu Val Arg Ser Trp Val Thr Ala Gly Glu
      1130                1135                1140
Ile His Ala Val Pro Phe Gly Leu Val Ser Met Met Ile Ala Met
      1145                1150                1155
Glu Val Val Leu Arg Lys Arg Gln Gly Pro Lys Gln Met Leu Val
      1160                1165                1170
Gly Gly Val Val Leu Leu Gly Ala Met Leu Val Gly Gln Val Thr
      1175                1180                1185
Leu Leu Asp Leu Leu Lys Leu Thr Val Ala Val Gly Leu His Phe
      1190                1195                1200
```

-continued

```
His Glu Met Asn Asn Gly Gly Asp Ala Met Tyr Met Ala Leu Ile
1205                1210                1215

Ala Ala Phe Ser Ile Arg Pro Gly Leu Leu Ile Gly Phe Gly Leu
1220                1225                1230

Arg Thr Leu Trp Ser Pro Arg Glu Arg Leu Val Leu Thr Leu Gly
1235                1240                1245

Ala Ala Met Val Glu Ile Ala Leu Gly Gly Val Met Gly Gly Leu
1250                1255                1260

Trp Lys Tyr Leu Asn Ala Val Ser Leu Cys Ile Leu Thr Ile Asn
1265                1270                1275

Ala Val Ala Ser Arg Lys Ala Ser Asn Thr Ile Leu Pro Leu Met
1280                1285                1290

Ala Leu Leu Thr Pro Val Thr Met Ala Glu Val Arg Leu Ala Ala
1295                1300                1305

Met Phe Phe Cys Ala Met Val Ile Ile Gly Val Leu His Gln Asn
1310                1315                1320

Phe Lys Asp Thr Ser Met Gln Lys Thr Ile Pro Leu Val Ala Leu
1325                1330                1335

Thr Leu Thr Ser Tyr Leu Gly Leu Thr Gln Pro Phe Leu Gly Leu
1340                1345                1350

Cys Ala Phe Leu Ala Thr Arg Ile Phe Gly Arg Arg Ser Ile Pro
1355                1360                1365

Val Asn Glu Ala Leu Ala Ala Ala Gly Leu Val Gly Val Leu Ala
1370                1375                1380

Gly Leu Ala Phe Gln Glu Met Glu Asn Phe Leu Gly Pro Ile Ala
1385                1390                1395

Val Gly Gly Leu Leu Met Met Leu Val Ser Val Ala Gly Arg Val
1400                1405                1410

Asp Gly Leu Glu Leu Lys Lys Leu Gly Glu Val Ser Trp Glu Glu
1415                1420                1425

Glu Ala Glu Ile Ser Gly Ser Ser Ala Arg Tyr Asp Val Ala Leu
1430                1435                1440

Ser Glu Gln Gly Glu Phe Lys Leu Leu Ser Glu Glu Lys Val Pro
1445                1450                1455

Trp Asp Gln Val Val Met Thr Ser Leu Ala Leu Val Gly Ala Ala
1460                1465                1470

Leu His Pro Phe Ala Leu Leu Leu Val Leu Ala Gly Trp Leu Phe
1475                1480                1485

His Val Arg Gly Ala Arg Arg Ser Gly Asp Val Leu Trp Asp Ile
1490                1495                1500

Pro Thr Pro Lys Ile Ile Glu Glu Cys Glu His Leu Glu Asp Gly
1505                1510                1515

Ile Tyr Gly Ile Phe Gln Ser Thr Phe Leu Gly Ala Ser Gln Arg
1520                1525                1530

Gly Val Gly Val Ala Gln Gly Gly Val Phe His Thr Met Trp His
1535                1540                1545

Val Thr Arg Gly Ala Phe Leu Val Arg Asn Gly Lys Lys Leu Ile
1550                1555                1560

Pro Ser Trp Ala Ser Val Lys Glu Asp Leu Val Ala Tyr Gly Gly
1565                1570                1575

Ser Trp Lys Leu Glu Gly Arg Trp Asp Gly Glu Glu Glu Val Gln
1580                1585                1590

Leu Ile Ala Ala Val Pro Gly Lys Asn Val Val Asn Val Gln Thr
1595                1600                1605
```

```
Lys Pro Ser Leu Phe Lys Val Arg Asn Gly Gly Glu Ile Gly Ala
    1610            1615                1620

Val Ala Leu Asp Tyr Pro Ser Gly Thr Ser Gly Ser Pro Ile Val
    1625            1630                1635

Asn Arg Asn Gly Glu Val Ile Gly Leu Tyr Gly Asn Gly Ile Leu
    1640            1645                1650

Val Gly Asp Asn Ser Phe Val Ser Ala Ile Ser Gln Thr Glu Val
    1655            1660                1665

Lys Glu Glu Gly Lys Glu Glu Leu Gln Glu Ile Pro Thr Met Leu
    1670            1675                1680

Lys Lys Gly Met Thr Thr Val Leu Asp Phe His Pro Gly Ala Gly
    1685            1690                1695

Lys Thr Arg Arg Phe Leu Pro Gln Ile Leu Ala Glu Cys Ala Arg
    1700            1705                1710

Arg Arg Leu Arg Thr Leu Val Leu Ala Pro Thr Arg Val Val Leu
    1715            1720                1725

Ser Glu Met Lys Glu Ala Phe His Gly Leu Asp Val Lys Phe His
    1730            1735                1740

Thr Gln Ala Phe Ser Ala His Gly Ser Gly Arg Glu Val Ile Asp
    1745            1750                1755

Ala Met Cys His Ala Thr Leu Thr Tyr Arg Met Leu Glu Pro Thr
    1760            1765                1770

Arg Val Val Asn Trp Glu Val Ile Ile Met Asp Glu Ala His Phe
    1775            1780                1785

Leu Asp Pro Ala Ser Ile Ala Ala Arg Gly Trp Ala Ala His Arg
    1790            1795                1800

Ala Arg Ala Asn Glu Ser Ala Thr Ile Leu Met Thr Ala Thr Pro
    1805            1810                1815

Pro Gly Thr Ser Asp Glu Phe Pro His Ser Asn Gly Glu Ile Glu
    1820            1825                1830

Asp Val Gln Thr Asp Ile Pro Ser Glu Pro Trp Asn Thr Gly His
    1835            1840                1845

Asp Trp Ile Leu Ala Asp Lys Arg Pro Thr Ala Trp Phe Leu Pro
    1850            1855                1860

Ser Ile Arg Ala Ala Asn Val Met Ala Ala Ser Leu Arg Lys Ala
    1865            1870                1875

Gly Lys Ser Val Val Leu Asn Arg Lys Thr Phe Glu Arg Glu
    1880            1885                1890

Tyr Pro Thr Ile Lys Gln Lys Lys Pro Asp Phe Ile Leu Ala Thr
    1895            1900                1905

Asp Ile Ala Glu Met Gly Ala Asn Leu Cys Val Glu Arg Val Leu
    1910            1915                1920

Asp Cys Arg Thr Ala Phe Lys Pro Val Leu Val Asp Glu Gly Arg
    1925            1930                1935

Lys Val Ala Ile Lys Gly Pro Leu Arg Ile Ser Ala Ser Ser Ala
    1940            1945                1950

Ala Gln Arg Arg Gly Arg Ile Gly Arg Asn Pro Asn Arg Asp Gly
    1955            1960                1965

Asp Ser Tyr Tyr Tyr Ser Glu Pro Thr Ser Glu Asn Asn Ala His
    1970            1975                1980

His Val Cys Trp Leu Glu Ala Ser Met Leu Leu Asp Asn Met Glu
    1985            1990                1995

Val Arg Gly Gly Met Val Ala Pro Leu Tyr Gly Val Glu Gly Thr
```

-continued

```
              2000                2005                2010

Lys Thr Pro Val Ser Pro Gly Glu Met Arg Leu Arg Asp Asp Gln
    2015                2020                2025

Arg Lys Val Phe Arg Glu Leu Val Arg Asn Cys Asp Leu Pro Val
    2030                2035                2040

Trp Leu Ser Trp Gln Val Ala Lys Ala Gly Leu Lys Thr Asn Asp
    2045                2050                2055

Arg Lys Trp Cys Phe Glu Gly Pro Glu Glu His Glu Ile Leu Asn
    2060                2065                2070

Asp Ser Gly Glu Thr Val Lys Cys Arg Ala Pro Gly Gly Ala Lys
    2075                2080                2085

Lys Pro Leu Arg Pro Arg Trp Cys Asp Glu Arg Val Ser Ser Asp
    2090                2095                2100

Gln Ser Ala Leu Ser Glu Phe Ile Lys Phe Ala Glu Gly Arg Arg
    2105                2110                2115

Gly Ala Ala Glu Val Leu Val Val Leu Ser Glu Leu Pro Asp Phe
    2120                2125                2130

Leu Ala Lys Lys Gly Gly Glu Ala Met Asp Thr Ile Ser Val Phe
    2135                2140                2145

Leu His Ser Glu Glu Gly Ser Arg Ala Tyr Arg Asn Ala Leu Ser
    2150                2155                2160

Met Met Pro Glu Ala Met Thr Ile Val Met Leu Phe Ile Leu Ala
    2165                2170                2175

Gly Leu Leu Thr Ser Gly Met Val Ile Phe Phe Met Ser Pro Lys
    2180                2185                2190

Gly Ile Ser Arg Met Ser Met Ala Met Gly Thr Met Ala Gly Cys
    2195                2200                2205

Gly Tyr Leu Met Phe Leu Gly Gly Val Lys Pro Thr His Ile Ser
    2210                2215                2220

Tyr Val Met Leu Ile Phe Phe Val Leu Met Val Val Val Ile Pro
    2225                2230                2235

Glu Pro Gly Gln Gln Arg Ser Ile Gln Asp Asn Gln Val Ala Tyr
    2240                2245                2250

Leu Ile Ile Gly Ile Leu Thr Leu Val Ser Ala Val Ala Ala Asn
    2255                2260                2265

Glu Leu Gly Met Leu Glu Lys Thr Lys Glu Asp Leu Phe Gly Lys
    2270                2275                2280

Lys Asn Leu Ile Pro Ser Ser Ala Ser Pro Trp Ser Trp Pro Asp
    2285                2290                2295

Leu Asp Leu Lys Pro Gly Ala Ala Trp Thr Val Tyr Val Gly Ile
    2300                2305                2310

Val Thr Met Leu Ser Pro Met Leu His His Trp Ile Lys Val Glu
    2315                2320                2325

Tyr Gly Asn Leu Ser Leu Ser Gly Ile Ala Gln Ser Ala Ser Val
    2330                2335                2340

Leu Ser Phe Met Asp Lys Gly Ile Pro Phe Met Lys Met Asn Ile
    2345                2350                2355

Ser Val Ile Met Leu Leu Val Ser Gly Trp Asn Ser Ile Thr Val
    2360                2365                2370

Met Pro Leu Leu Cys Gly Ile Gly Cys Ala Met Leu His Trp Ser
    2375                2380                2385

Leu Ile Leu Pro Gly Ile Lys Ala Gln Gln Ser Lys Leu Ala Gln
    2390                2395                2400
```

-continued

Arg Arg Val Phe His Gly Val Ala Lys Asn Pro Val Val Asp Gly
2405                 2410                2415

Asn Pro Thr Val Asp Ile Glu Glu Ala Pro Glu Met Pro Ala Leu
2420                 2425                2430

Tyr Glu Lys Lys Leu Ala Leu Tyr Leu Leu Leu Ala Leu Ser Leu
2435                 2440                2445

Ala Ser Val Ala Met Cys Arg Thr Pro Phe Ser Leu Ala Glu Gly
2450                 2455                2460

Ile Val Leu Ala Ser Ala Ala Leu Gly Pro Leu Ile Glu Gly Asn
2465                 2470                2475

Thr Ser Leu Leu Trp Asn Gly Pro Met Ala Val Ser Met Thr Gly
2480                 2485                2490

Val Met Arg Gly Asn His Tyr Ala Phe Val Gly Val Met Tyr Asn
2495                 2500                2505

Leu Trp Lys Met Lys Thr Gly Arg Arg Gly Ser Ala Asn Gly Lys
2510                 2515                2520

Thr Leu Gly Glu Val Trp Lys Arg Glu Leu Asn Leu Leu Asp Lys
2525                 2530                2535

Arg Gln Phe Glu Leu Tyr Lys Arg Thr Asp Ile Val Glu Val Asp
2540                 2545                2550

Arg Asp Thr Ala Arg Arg His Leu Ala Glu Gly Lys Val Asp Thr
2555                 2560                2565

Gly Val Ala Val Ser Arg Gly Thr Ala Lys Leu Arg Trp Phe His
2570                 2575                2580

Glu Arg Gly Tyr Val Lys Leu Glu Gly Arg Val Ile Asp Leu Gly
2585                 2590                2595

Cys Gly Arg Gly Gly Trp Cys Tyr Tyr Ala Ala Ala Gln Lys Glu
2600                 2605                2610

Val Ser Gly Val Lys Gly Phe Thr Leu Gly Arg Asp Gly His Glu
2615                 2620                2625

Lys Pro Met Asn Val Gln Ser Leu Gly Trp Asn Ile Ile Thr Phe
2630                 2635                2640

Lys Asp Lys Thr Asp Ile His Arg Leu Glu Pro Val Lys Cys Asp
2645                 2650                2655

Thr Leu Leu Cys Asp Ile Gly Glu Ser Ser Ser Ser Ser Val Thr
2660                 2665                2670

Glu Gly Glu Arg Thr Val Arg Val Leu Asp Thr Val Glu Lys Trp
2675                 2680                2685

Leu Ala Cys Gly Val Asp Asn Phe Cys Val Lys Val Leu Ala Pro
2690                 2695                2700

Tyr Met Pro Asp Val Leu Glu Lys Leu Glu Leu Leu Gln Arg Arg
2705                 2710                2715

Phe Gly Gly Thr Val Ile Arg Asn Pro Leu Ser Arg Asn Ser Thr
2720                 2725                2730

His Glu Met Tyr Tyr Val Ser Gly Ala Arg Ser Asn Val Thr Phe
2735                 2740                2745

Thr Val Asn Gln Thr Ser Arg Leu Leu Met Arg Arg Met Arg Arg
2750                 2755                2760

Pro Thr Gly Lys Val Thr Leu Glu Ala Asp Val Ile Leu Pro Ile
2765                 2770                2775

Gly Thr Arg Ser Val Glu Thr Asp Lys Gly Pro Leu Asp Lys Glu
2780                 2785                2790

Ala Ile Glu Glu Arg Val Glu Arg Ile Lys Ser Glu Tyr Met Thr
2795                 2800                2805

```
Ser Trp Phe Tyr Asp Asn Asp Asn Pro Tyr Arg Thr Trp His Tyr
    2810            2815            2820

Cys Gly Ser Tyr Val Thr Lys Thr Ser Gly Ser Ala Ala Ser Met
    2825            2830            2835

Val Asn Gly Val Ile Lys Ile Leu Thr Tyr Pro Trp Asp Arg Ile
    2840            2845            2850

Glu Glu Val Thr Arg Met Ala Met Thr Asp Thr Thr Pro Phe Gly
    2855            2860            2865

Gln Gln Arg Val Phe Lys Glu Lys Val Asp Thr Arg Ala Lys Asp
    2870            2875            2880

Pro Pro Ala Gly Thr Arg Lys Ile Met Lys Val Val Asn Arg Trp
    2885            2890            2895

Leu Phe Arg His Leu Ala Arg Glu Lys Asn Pro Arg Leu Cys Thr
    2900            2905            2910

Lys Glu Glu Phe Ile Ala Lys Val Arg Ser His Ala Ala Ile Gly
    2915            2920            2925

Ala Tyr Leu Glu Glu Gln Glu Gln Trp Lys Thr Ala Asn Glu Ala
    2930            2935            2940

Val Gln Asp Pro Lys Phe Trp Glu Leu Val Asp Glu Glu Arg Lys
    2945            2950            2955

Leu His Gln Gln Gly Arg Cys Arg Thr Cys Val Tyr Asn Met Met
    2960            2965            2970

Gly Lys Arg Glu Lys Lys Leu Ser Glu Phe Gly Lys Ala Lys Gly
    2975            2980            2985

Ser Arg Ala Ile Trp Tyr Met Trp Leu Gly Ala Arg Tyr Leu Glu
    2990            2995            3000

Phe Glu Ala Leu Gly Phe Leu Asn Glu Asp His Trp Ala Ser Arg
    3005            3010            3015

Glu Asn Ser Gly Gly Val Glu Gly Ile Gly Leu Gln Tyr Leu
    3020            3025            3030

Gly Tyr Val Ile Arg Asp Leu Ala Ala Met Asp Gly Gly Gly Phe
    3035            3040            3045

Tyr Ala Asp Asp Thr Ala Gly Trp Asp Thr Arg Ile Thr Glu Ala
    3050            3055            3060

Asp Leu Asp Asp Glu Gln Glu Ile Leu Asn Tyr Met Ser Pro His
    3065            3070            3075

His Lys Lys Leu Ala Gln Ala Val Met Glu Met Thr Tyr Lys Asn
    3080            3085            3090

Lys Val Val Lys Val Leu Arg Pro Ala Pro Gly Gly Lys Ala Tyr
    3095            3100            3105

Met Asp Val Ile Ser Arg Arg Asp Gln Arg Gly Ser Gly Gln Val
    3110            3115            3120

Val Thr Tyr Ala Leu Asn Thr Ile Thr Asn Leu Lys Val Gln Leu
    3125            3130            3135

Ile Arg Met Ala Glu Ala Glu Met Val Ile His His Gln His Val
    3140            3145            3150

Gln Asp Cys Asp Glu Ser Val Leu Thr Arg Leu Glu Ala Trp Leu
    3155            3160            3165

Thr Glu His Gly Cys Asp Arg Leu Lys Arg Met Ala Val Ser Gly
    3170            3175            3180

Asp Asp Cys Val Val Arg Pro Ile Asp Asp Arg Phe Gly Leu Ala
    3185            3190            3195

Leu Ser His Leu Asn Ala Met Ser Lys Val Arg Lys Asp Ile Ser
```

| | | | | | | | | | | | |
|---|---|---|---|---|---|---|---|---|---|---|---|
| | | 3200 | | | 3205 | | | 3210 | | | |
| Glu | Trp | Gln | Pro | Ser | Lys | Gly | Trp | Asn | Asp | Trp | Glu | Asn | Val | Pro |
| | 3215 | | | | 3220 | | | | 3225 | | |

| Phe | Cys | Ser | His | His | Phe | His | Glu | Leu | Gln | Leu | Lys | Asp | Gly | Arg |
| | 3230 | | | | 3235 | | | | 3240 | | |

| Arg | Ile | Val | Val | Pro | Cys | Arg | Glu | Gln | Asp | Glu | Leu | Ile | Gly | Arg |
| | 3245 | | | | 3250 | | | | 3255 | | |

| Gly | Arg | Val | Ser | Pro | Gly | Asn | Gly | Trp | Met | Ile | Lys | Glu | Thr | Ala |
| | 3260 | | | | 3265 | | | | 3270 | | |

| Cys | Leu | Ser | Lys | Ala | Tyr | Ala | Asn | Met | Trp | Ser | Leu | Met | Tyr | Phe |
| | 3275 | | | | 3280 | | | | 3285 | | |

| His | Lys | Arg | Asp | Met | Arg | Leu | Leu | Ser | Leu | Ala | Val | Ser | Ser | Ala |
| | 3290 | | | | 3295 | | | | 3300 | | |

| Val | Pro | Thr | Ser | Trp | Val | Pro | Gln | Gly | Arg | Thr | Thr | Trp | Ser | Ile |
| | 3305 | | | | 3310 | | | | 3315 | | |

| His | Gly | Lys | Gly | Glu | Trp | Met | Thr | Thr | Glu | Asp | Met | Leu | Glu | Val |
| | 3320 | | | | 3325 | | | | 3330 | | |

| Trp | Asn | Arg | Val | Trp | Ile | Thr | Asn | Asn | Pro | His | Met | Gln | Asp | Lys |
| | 3335 | | | | 3340 | | | | 3345 | | |

| Thr | Met | Val | Lys | Lys | Trp | Arg | Asp | Val | Pro | Tyr | Leu | Thr | Lys | Arg |
| | 3350 | | | | 3355 | | | | 3360 | | |

| Gln | Asp | Lys | Leu | Cys | Gly | Ser | Leu | Ile | Gly | Met | Thr | Asn | Arg | Ala |
| | 3365 | | | | 3370 | | | | 3375 | | |

| Thr | Trp | Ala | Ser | His | Ile | His | Leu | Val | Ile | His | Arg | Ile | Arg | Thr |
| | 3380 | | | | 3385 | | | | 3390 | | |

| Leu | Ile | Gly | Gln | Glu | Lys | Tyr | Thr | Asp | Tyr | Leu | Thr | Val | Met | Asp |
| | 3395 | | | | 3400 | | | | 3405 | | |

| Arg | Tyr | Ser | Val | Asp | Ala | Asp | Leu | Gln | Leu | Gly | Glu | Leu | Ile | |
| | 3410 | | | | 3415 | | | | 3420 | | |

```
<210> SEQ ID NO 24
<211> LENGTH: 10239
<212> TYPE: DNA
<213> ORGANISM: Artificial sequence
<220> FEATURE:
<223> OTHER INFORMATION: Derived from Yellow Fever virus and West Nile
      virus

<400> SEQUENCE: 24
gtaaatcctg tgtgctaatt gaggtgcatt ggtctgcaaa tcgagttgct aggcaataaa      60
cacatttgga ttaattttaa tcgttcgttg agcgattagc agagaactga ccagaacatg     120
tctggtcgta aagctcaggg aaaaaccctg ggcgtcaata tggtacgacg aggagttcgc     180
tccttgtcaa acaaaataaa acaaaaaaca aaacaaattg gaaacagacc tggaccttca     240
agaggtgttc aaggatttat cttttttcttt ttgttcaaca ttttgactgg aaaaaagatc     300
acagcccacc taagaggtt gtggaaaatg ctggacccaa gacaaggctt ggctgttcta     360
aggaaagtca agagagtggt ggccagtttg atgagaggat tgtcctcaag gaaacgccgt     420
tcccatgatg ttctgactgt gcaattccta attttgggaa tgctgttgat gacgggtgga     480
gttaccctct ctaacttcca agggaaggtg atgatgacgg taaatgctac tgacgtcaca     540
gatgtcatca cgattccaac agctgctgga agaacctat gcattgtcag agcaatggat     600
gtgggataca tgtgcgatga tactatcact tatgaatgcc cagtgctgtc ggctggtaat     660
gatccagaag acatcgactg ttggtgcaca aagtcagcag tctacgtcag gtatggaaga     720
tgcaccaaga cacgccactc aagacgcagt cggaggtcac tgacagtgca gacacacgga     780
```

```
gaaagcactc tagcgaacaa gaagggggct tggatggaca gcaccaaggc cacaaggtat      840
ttggtaaaaa cagaatcatg gatcttgagg aaccctggat atgccctggt ggcagccgtc      900
attggttgga tgcttgggag caacaccatg cagagagttg tgtttgtcgt gctattgctt      960
ttggtggccc cagcttacag cttcaactgc cttggaatga gcaacagaga cttcttggaa     1020
ggagtgtctg gagcaacatg ggtggatttg gttctcgaag cgacagctg cgtgactatc      1080
atgtctaagg acaagcctac catcgacgtc aagatgatga atatggaggc ggccaacctg     1140
gcagaggtcc gcagttattg ctatttggct accgtcagcg atctctccac caaagctgca     1200
tgcccgacca tgggagaagc tcacaatgac aaacgtgctg acccagcttt tgtgtgcaga     1260
caaggagtgg tggacagggg ctggggcaac ggctgcggat tttttggcaa aggatccatt     1320
gacacatgcg ccaaatttgc ctgctctacc aaggcaatag aagaaccat cttgaaagag      1380
aatatcaagt acgaagtggc cattttttgtc catggaccaa ctactgtgga gtcgcacgga     1440
aattactcca cacaggttgg agccactcag gccggccgat tcagcatcac tcctgctgcg     1500
ccttcataca cactaaagct tggagaatat ggagaggtga cagtggactg tgaaccacgg     1560
tcagggattg acaccaatgc atactacgtg atgactgttg aacaaagac gttcttggtc      1620
catcgtgagt ggttcatgga cctcaacctc ccttggagca gtgctggaag tactgtgtgg     1680
aggaacagag agacgttaat ggagtttgag gaaccacacg ccacgaagca gtctgtgata     1740
gcattgggct cacaagaggg agctctgcat caagctttgg ctggagccat tcctgtggaa     1800
ttttcaagca cactgtcaa gttgacgtcg ggtcatttga agtgtagagt gaagatggaa      1860
aaattgcagt tgaagggaac aacctatggc gtctgttcaa aggctttcaa gtttcttagg     1920
actcccgtgg acaccggtca cggcactgtg tgtgttggaat tgcagtacac tggcacggat     1980
ggaccttgca aagttcctat ctcgtcagtg gcttcattga acgacctaac gccagtgggc     2040
agattggtca ctgtcaaccc tttttgttttca gtggccacgg ccaacgctaa ggtcctgatt     2100
gaattggaac caccctttgg agactcatac atagtggtgg gcagaggaga acaacagatc     2160
aatcaccatt ggcacaagtc tggaagcagc attggcaaag cctttacaac caccctcaaa     2220
ggagcgcaga gactagccgc tctaggagac acagcttggg actttggatc agttggaggg     2280
gtgttcacta tgtgttggcg ggctgtccat caagtgttcg gaggagcatt ccgctcactg     2340
ttcggaggca tgtcctggat aacgcaagga ttgctggggg ctctcctgtt gtggatgggc     2400
atcaatgctc gtgataggtc catagctctc acgtttctcg cagttggagg agttctgctc     2460
ttcctctccg tgaacgtggg cgccgatcaa ggatgcgcca tcaactttgg caagagagag     2520
ctcaagtgcg gagatggtat cttcatattt agagactctg atgactggct gaacaagtac     2580
tcatactatc cagaagatcc tgtgaagctt gcatcaatag tgaaagcctc ttttgaagaa     2640
gggaagtgtg gcctaaattc agttgactcc cttgagcatg agatgtggag aagcagggca     2700
gatgagatca atgccatttt tgaggaaaac gaggtggaca tttctgttgt cgtgcaggat     2760
ccaaagaatg tttaccagag aggaactcat ccatttttcca gaattcggga tggtctgcag     2820
tatggttgga gacttggggg taagaacctt gtgttctccc cagggaggaa gatggaagc      2880
ttcatcatag atggaaagtc cagggaagaa tgcccgtttt caaaccgggt ctggaattct     2940
ttccagatag aggagtttgg gacggagtg ttcaccacac gcgtgtacat ggacgcagtc      3000
tttgaataca ccatagactg cgatggatct atcttgggtg cagcggtgaa cggaaaaaag     3060
agtgcccatg gctctccaac attttggatg ggaagtcatg aagtaaatgg gacatggatg     3120
atccacacct tggaggcatt agattacaag gagtgtgagt ggccactgac acatacgatt     3180
```

```
ggaacatcag ttgaagagag tgaaatgttc atgccgagat caatcggagg cccagttagc    3240
tctcacaatc atatccctgg atacaaggtt cagacgaacg gaccttggat gcaggtacca    3300
ctagaagtga agagagaagc ttgcccaggg actagcgtga tcattgatgg caactgtgat    3360
ggacggggaa aatcaaccag atccaccacg gatagcggga aagttattcc tgaatggtgt    3420
tgccgctcct gcacaatgcc gcctgtgagc ttccatggta gtgatgggtg ttggtatccc    3480
atggaaatta ggccaaggaa aacgcatgaa agccatctgg tgcgctcctg ggttacagct    3540
ggagaaatac atgctgtccc ttttggtttg gtgagcatga tgatagcaat ggaagtggtc    3600
ctaaggaaaa gacagggacc aaagcaaatg ttggttggag gagtagtgct cttgggagca    3660
atgctggtcg ggcaagtaac tctccttgat ttgctgaaac tcacagtggc tgtgggattg    3720
catttccatg agatgaacaa tggaggagac gccatgtata tggcgttgat tgctgccttt    3780
tcaatcagac cagggctgct catcggcttt gggctcagga ccctatggag ccctcgggaa    3840
cgccttgtgc tgaccctagg agcagccatg gtggagattg ccttgggtgg cgtgatgggc    3900
ggcctgtgga agtatctaaa tgcagtttct ctctgcatcc tgacaataaa tgctgttgct    3960
tctaggaaag catcaaatac catcttgccc ctcatggctc tgttgacacc tgtcactatg    4020
gctgaggtga gacttgccgc aatgttcttt tgtgccatgg ttatcatagg ggtccttcac    4080
cagaatttca aggacacctc catgcagaag actataccct ggtgggccct cacactcaca    4140
tcttacctgg gcttgacaca acctttttg ggcctgtgtg catttctggc aacccgcata    4200
tttgggcgaa ggagtatccc agtgaatgag gcactcgcag cagctggtct agtgggagtg    4260
ctggcaggac tggcttttca ggagatggag aacttccttg gtccgattgc agttggagga    4320
ctcctgatga tgctggttag cgtggctggg agggtggatg ggctagagct caagaagctt    4380
ggtgaagttt catgggaaga ggaggcggag atcagcggga gttccgcccg ctatgatgtg    4440
gcactcagtg aacaagggga gttcaagctg ctttctgaag agaaagtgcc atgggaccag    4500
gttgtgatga cctcgctggc cttggttggg gctgccctcc atccatttgc tcttctgctg    4560
gtccttgctg ggtggctgtt tcatgtcagg ggagctagga gaagtgggga tgtcttgtgg    4620
gatattccca ctcctaagat catcgaggaa tgtgaacatc tggaggatgg gatttatggc    4680
atattccagt caaccttctt gggggcctcc cagcgaggag tgggagtggc acagggaggg    4740
gtgttccaca caatgtggca tgtcacaaga ggagctttcc ttgtcaggaa tggcaagaag    4800
ttgattccat cttgggcttc agtaaaggaa gaccttgtcg cctatggtgg ctcatggaag    4860
ttggaaggca gatgggatgg agaggaagag gtccagttga tcgcggctgt tccaggaaag    4920
aacgtggtca acgtccagac aaaaccgagc ttgttcaaag tgaggaatgg gggagaaatc    4980
ggggctgtcg ctcttgacta tccgagtggc acttcaggat ctcctattgt taacaggaac    5040
ggagaggtga ttgggctgta cggcaatggc atccttgtcg gtgacaactc cttcgtgtcc    5100
gccatatccc agactgaggt gaaggaagaa ggaaaggagg agctccaaga gatcccgaca    5160
atgctaaaga aaggaatgac aactgtcctt gattttcatc ctggagctgg aagacaagaa    5220
cgtttcctcc cacagatctt ggccgagtgc gcacggagac gcttgcgcac tcttgtgttg    5280
gcccccacca gggttgttct ttctgaaatg aaggaggctt tcacggcct ggacgtgaaa    5340 ttccacacac aggcttttc cgctcacggc agcgggagag aagtcattga tgccatgtgc    5400
catgccaccc taacttacag gatgttggaa ccaactaggg ttgttaactg ggaagtgatc    5460
attatggatg aagcccattt tttgatccca gccagcatag ccgctagagg ttgggcagcg    5520
cacagagcta gggcaaatga aagtgcaaca atcttgatga cagccacacc gcctgggact    5580
```

```
agtgatgaat tccacattc  aaatggtgaa atagaagatg ttcaaacgga catacccagt   5640
gagccctgga acacagggca tgactggatc ctggctgaca aaaggcccac ggcatggttc   5700
cttccatcca tcagagctgc aaatgtcatg gctgcctctt tgcgtaaggc tggaaagagt   5760
gtggtggtcc tgaacaggaa aacctttgag agagaatacc ccacgataaa gcagaagaaa   5820
cctgacttta tattggccac tgacatagct gaaatgggag ccaacctttg cgtggagcga   5880
gtgctggatt gcaggacggc ttttaagcct gtgcttgtgg atgaagggag gaaggtggca   5940 ataaagggc cacttcgtat ctccgcatcc tctgctgctc aaggaggggg gcgcattggg    6000
agaaatccca acagagatgg agactcatac tactattctg agcctacaag tgaaaataat   6060
gcccaccacg tctgctggtt ggaggcctca atgctcttgg acaacatgga ggtgaggggt   6120
ggaatggtcg ccccactcta tggcgttgaa ggaactaaaa caccagtttc ccctggtgaa   6180
atgagactga gggatgacca gaggaaagtc ttcagagaac tagtgaggaa ttgtgacctg   6240
cccgtttggc tttcgtggca agtggccaag gctggtttga agacgaatga tcgtaagtgg   6300
tgttttgaag gccctgagga acatgagatc ttgaatgaca gcggtgaaac agtgaagtgc   6360
agggctcctg gaggagcaaa gaagcctctg cgcccaaggt ggtgtgatga agggtgtca   6420 tctgaccaga gtgcgctgtc tgaatttatt aagtttgctg aaggtaggag gggagctgct   6480
gaagtgctag ttgtgctgag tgaactccct gatttcctgg ctaaaaaagg tggagaggca   6540
atggatacca tcagtgtgtt cctccactct gaggaaggct ctagggctta ccgcaatgca   6600
ctatcaatga tgcctgaggc aatgacaata gtcatgctgt ttatactggc tggactactg   6660
acatcgggaa tggtcatctt tttcatgtct cccaaaggca tcagtagaat gtctatggcg   6720
atgggcacaa tggccggctg tggatatctc atgttccttg gaggcgtcaa acccactcac   6780
atctcctatg tcatgctcat attctttgtc ctgatggtgg ttgtgatccc cgagccaggg   6840
caacaaaggt ccatccaaga caaccaagtg catacctca ttattggcat cctgacgctg    6900
gtttcagcgg tggcagccaa cgagctaggc atgctggaga aaaccaaaga ggacctcttt   6960
gggaagaaga acttaattcc atctagtgct tcaccctgga gttggccgga tcttgacctg   7020
aagccaggag ctgcctggac agtgtacgtt ggcattgtta caatgctctc tccaatgttg   7080
caccactgga tcaaagtcga atatggcaac ctgtctctgt ctggaatagc ccagtcagcc   7140
tcagtccttt ctttcatgga caaggggata ccattcatga agatgaatat ctcggtcata   7200
atgctgctgg tcagtggctg gaattcaata acagtgatgc ctctgctctg tggcataggg   7260
tgcgccatgc tccactggtc tctcattta cctggaatca aagcgcagca gtcaaagctt   7320
gcacagagaa gggtgttcca tggcgttgcc aagaaccctg tggttgatgg gaatccaaca   7380
gttgacattg aggaagctcc tgaaatgcct gcccttatg agaagaaact ggctctatat   7440
ctccttcttg ctctcagcct agcttctgtt gccatgtgca gaacgccctt tcattggct    7500 gaaggcattg tcctagcatc agctgcctta gggccgctca tagagggaaa caccagcctt   7560
ctttggaatg gacccatggc tgtctccatg acaggagtca tgagggggaa tcactatgct   7620
tttgtgggag tcatgtacaa tctatggaag atgaaaactg gacgccgggg gagcgcgaat   7680
ggaaaaactt tgggtgaagt ctggaagagg gaactgaatc tgttggacaa gcgacagttt   7740
gagttgtata aaaggaccga cattgtggag gtggatcgtg atacgcacg caggcatttg    7800 gccgaaggga aggtggacac cggggtggcg gtctccaggg ggaccgcaaa gttaaggtgg   7860
ttccatgagc gtggctatgt caagctggaa ggtagggtga ttgacctggg gtgtggccgc   7920
ggaggctggt gttactacgc tgctgcgcaa aaggaagtga gtgggtcaa aggatttact   7980
```

```
cttggaagag acggccatga gaaacccatg aatgtgcaaa gtctgggatg aacatcatc    8040
accttcaagg acaaaactga tatccaccgc ctagaaccag tgaaatgtga cacccttttg   8100
tgtgacattg gagagtcatc atcgtcatcg gtcacagagg gggaaaggac cgtgagagtt   8160
cttgatactg tagaaaaatg gctggcttgt ggggttgaca acttctgtgt gaaggtgtta   8220
gctccataca tgccagatgt tcttgagaaa ctggaattgc tccaaaggag gtttggcgga   8280
acagtgatca ggaaccctct ctccaggaat tccactcatg aaatgtacta cgtgtctgga   8340
gcccgcagca atgtcacatt tactgtgaac caaacatccc gcctcctgat gaggagaatg   8400
aggcgtccaa ctggaaaagt gaccctggag gctgacgtca tcctcccaat tgggacacgc   8460
agtgttgaga cagacaaggg accccctgga caaagaggcca tagaagaaag ggttgagagg   8520
ataaaatctg agtacatgac ctcttggttt tatgacaatg acaaccccta caggacctgg   8580
cactactgtg gctcctatgt cacaaaaaac ctccggaagtg cggcgagcat ggtaaatggt   8640
gttattaaaa ttctgacata tccatgggac aggatagagg aggtcacaag aatggcaatg   8700
actgacacaa ccccttttgg acagcaaaga gtgtttaaag aaaaagttga caccagagca   8760
aaggatccac cagcgggaac taggaagatc atgaaagttg tcaacaggtg gctgttccgc   8820
cacctggcca gagaaaagaa ccccagactg tgcacaaagg aagaatttat tgcaaaagtc   8880
cgaagtcatg cagccattgg agcttacctg gaagaacaag aacagtggaa gactgccaat   8940
gaggctgtcc aagacccaaa gttctgggaa ctggtggatg aagaaaggaa gctgcaccaa   9000
caaggcaggt gtcggacttg tgtgtacaac atgatgggga aaagagagaa gaagctgtca   9060
gagtttggga agcaaagggg aagccgtgcc atatggtata tgtggctggg agcgcggtat   9120
cttgagtttg aggccctggg attcctgaat gaggaccatt gggcttccag ggaaaactca   9180
ggaggaggag tggaaggcat tggcttacaa tacctaggat atgtgatcag agacctggct   9240
gcaatggatg gtggtggatt ctacgcggat gacaccgctg gatgggacac gcgcatcaca   9300
gaggcagacc ttgatgatga acaggagatc ttgaactaca tgagcccaca tcacaaaaaa   9360
ctggcacaag cagtgatgga aatgacatac aagaacaaag tggtgaaagt gttgagacca   9420
gccccaggag ggaaagccta catggatgtc ataagtcgac gagaccagag aggatccggg   9480
caggtagtga cttatgctct gaacaccatc accaacttga aagtccaatt gatcagaatg   9540
gcagaagcag agatggtgat acatcaccaa catgttcaag attgtgatga atcagttctg   9600
accaggctgg aggcatggct cactgagcac ggatgtgaca gactgaagag gatggcggtg   9660
agtggagacg actgtgtggt ccggcccatc gatgacaggt tcggcctggc cctgtcccat   9720
ctcaacgcca tgtccaaggt tagaaaggac atatctgaat ggcagccatc aaaagggtgg   9780
aatgattggg agaatgtgcc cttctgttcc caccacttcc atgaactaca gctgaaggat   9840
ggcaggagga ttgtggtgcc ttgccgagaa caggacgagc tcattgggag aggaagggtg   9900
tctccaggaa acggctggat gatcaaggaa acagcttgcc tcagcaaagc ctatgccaac   9960
atgtggtcac tgatgtattt tcacaaaagg gacatgaggc tactgtcatt ggctgtttcc  10020
tcagctgttc ccacctcatg ggttccacaa ggacgcacaa catggtcgat tcatgggaaa  10080
ggggagtgga tgaccacgga agacatgctt gaggtgtgga acagagtatg gataaccaac  10140
aacccacaca tgcaggacaa gacaatggtg aaaaaatgga gagatgtccc ttatctaacc  10200
aagagacaag acaagctgtg cggatcactg attggaatg                        10239
```

<210> SEQ ID NO 25
<211> LENGTH: 12

```
<212> TYPE: PRT
<213> ORGANISM: Artificial Sequence
<220> FEATURE:
<223> OTHER INFORMATION: Derived from West Nile virus

<400> SEQUENCE: 25

Ser Leu Thr Val Gln Thr His Gly Glu Ser Thr Leu
1               5                   10

<210> SEQ ID NO 26
<211> LENGTH: 12
<212> TYPE: PRT
<213> ORGANISM: Artificial Sequence
<220> FEATURE:
<223> OTHER INFORMATION: Derived from West Nile virus

<400> SEQUENCE: 26

Val Val Leu Leu Leu Leu Val Ala Pro Ala Tyr Ser
1               5                   10

<210> SEQ ID NO 27
<211> LENGTH: 12
<212> TYPE: PRT
<213> ORGANISM: Artificial Sequence
<220> FEATURE:
<223> OTHER INFORMATION: Derived from West Nile virus

<400> SEQUENCE: 27

Val Val Pro Leu Leu Leu Val Ala Pro Ala Tyr Ser
1               5                   10

<210> SEQ ID NO 28
<211> LENGTH: 75
<212> TYPE: PRT
<213> ORGANISM: Artificial Sequence
<220> FEATURE:
<223> OTHER INFORMATION: Derived from West Nile virus

<400> SEQUENCE: 28

Ser Leu Thr Val Gln Thr His Gly Glu Ser Thr Leu Ala Asn Lys Lys
1               5                   10                  15

Gly Ala Trp Met Asp Ser Thr Lys Ala Thr Arg Tyr Leu Val Lys Thr
                20                  25                  30

Glu Ser Trp Ile Leu Arg Asn Pro Gly Tyr Ala Leu Val Ala Ala Val
            35                  40                  45

Ile Gly Trp Met Leu Gly Ser Asn Thr Met Gln Arg Val Val Phe Val
        50                  55                  60

Val Leu Leu Leu Leu Val Ala Pro Ala Tyr Ser
65                  70                  75

<210> SEQ ID NO 29
<211> LENGTH: 74
<212> TYPE: PRT
<213> ORGANISM: Artificial Sequence
<220> FEATURE:
<223> OTHER INFORMATION: Derived from West Nile virus

<400> SEQUENCE: 29

Ser Leu Thr Val Gln Thr His Gly Glu Ser Thr Leu Ala Asn Lys Lys
1               5                   10                  15

Gly Ala Trp Met Asp Ser Thr Lys Ala Thr Arg Tyr Leu Val Lys Thr
                20                  25                  30

Glu Ser Trp Ile Leu Arg Asn Pro Gly Tyr Ala Leu Val Ala Ala Val
            35                  40                  45
```

Ile Gly Trp Met Leu Gly Ser Asn Thr Met Gln Arg Val Val Phe Val
 50                  55                  60

Val Leu Leu Leu Val Ala Pro Ala Tyr Ser
 65                  70

<210> SEQ ID NO 30
<211> LENGTH: 75
<212> TYPE: PRT
<213> ORGANISM: Artificial Sequence
<220> FEATURE:
<223> OTHER INFORMATION: Derived from West Nile virus

<400> SEQUENCE: 30

Ser Leu Thr Val Gln Thr His Gly Glu Ser Thr Leu Ala Asn Lys Lys
 1               5                  10                  15

Gly Ala Trp Met Asp Ser Thr Lys Ala Thr Arg Tyr Leu Val Lys Thr
             20                  25                  30

Glu Ser Trp Ile Leu Arg Asn Pro Gly Tyr Ala Leu Val Ala Ala Val
         35                  40                  45

Ile Gly Trp Met Leu Gly Ser Asn Thr Met Gln Arg Val Val Phe Val
 50                  55                  60

Val Pro Leu Leu Leu Val Ala Pro Ala Tyr Ser
 65                  70                  75

<210> SEQ ID NO 31
<211> LENGTH: 377
<212> TYPE: DNA
<213> ORGANISM: Artificial Sequence
<220> FEATURE:
<223> OTHER INFORMATION: Derived from Yellow Fever virus

<400> SEQUENCE: 31
taaaaactac ggatggagaa ccggactcca cacattgaga cagaagaagt tgtcagccca      60 gaacccaca cgagttttgc cactgctaag ctgtgaggca gtgcaggctg ggacagccga     120
cctccaggtt gcgataaacc tggtttctgg gacctcccac cccagagtaa aagaacgga     180 gcctccgcta ccaccttccc acgtggtggt agaaagacgg ggtctagagg ttagaggaga    240
ccctccaggg aacaaatagt gggaccatat tgacgccagg gaaagaccgg agtggttctc    300
tgcttttcct ccagaggtct gtgagcacag tttgctcaag aataagcaga cctttggatg    360
acaaacacaa aaccact                                                  377

<210> SEQ ID NO 32
<211> LENGTH: 343
<212> TYPE: RNA
<213> ORGANISM: Artificial Sequence
<220> FEATURE:
<223> OTHER INFORMATION: Derived from Yellow Fever virus

<400> SEQUENCE: 32
uugagacaga agaaguuguc agcccagaac cccacacgag uuuugccacu gcuaagcugu      60
gaggcagugc aggcugggac agccgaccuc agguugcga aaaaccuggu uucugggacc     120
ucccacccca gaguaaaaag aacggagccu ccgcuaccac ccucccacgu gguggugaaa    180 agacggguc uagagguuag aggaccccu ccagggaaca auaguggga ccauauugac       240 gccagggaaa gaccggagug guucucugcu uuuccuccag aggucuguga gcacaguuug    300
cucaagaaua agcagaccuu uggaugacaa acacaaaaacc acu                     343

<210> SEQ ID NO 33
<211> LENGTH: 338

```
<212> TYPE: RNA
<213> ORGANISM: Artificial Sequence
<220> FEATURE:
<223> OTHER INFORMATION: Derived from Yellow Fever virus

<400> SEQUENCE: 33
uugagacaga agaaguuguc agcccagaac cccacacgag uuuugccacu gcuaagcugu      60
gaggcagugc aggcugggac agccgaccuc cagguugcga aaaccugguu uucugggacc    120
ucccaccgua aaagaaggg agccucggcu accacccucc cacguggugg uagaaagacg    180
gggucuagag guuagaggag acccuccagg gaacaaauag ugggaccaua uugaggccag    240
ggaaagaccg gagugguucu cugcuuuucc uccagagguc ugugagcaca guuugcucaa    300
gaauaagcag accuuuggau gacaaacaga aaaccacu                            338

<210> SEQ ID NO 34
<211> LENGTH: 116
<212> TYPE: PRT
<213> ORGANISM: Artificial Sequence
<220> FEATURE:
<223> OTHER INFORMATION: Derived from Tick-borne Encephalitis virus

<400> SEQUENCE: 34

Met Val Lys Lys Ala Ile Leu Lys Gly Lys Gly Gly Pro Pro Arg
1               5                   10                  15

Arg Val Ser Lys Glu Thr Ala Thr Lys Thr Arg Gln Pro Arg Val Gln
                20                  25                  30

Met Pro Asn Gly Leu Val Leu Met Arg Met Met Gly Ile Leu Trp His
            35                  40                  45

Ala Val Ala Gly Thr Ala Arg Asn Pro Val Leu Lys Ala Phe Trp Asn
        50                  55                  60

Ser Val Pro Leu Lys Gln Ala Thr Ala Ala Leu Arg Lys Ile Lys Arg
65                  70                  75                  80

Thr Val Ser Ala Leu Met Val Gly Leu Gln Lys Arg Gly Lys Arg Arg
                85                  90                  95

Ser Ala Thr Asp Trp Met Ser Trp Leu Leu Val Ile Thr Leu Leu Gly
            100                 105                 110

Met Thr Leu Ala
        115

<210> SEQ ID NO 35
<211> LENGTH: 121
<212> TYPE: PRT
<213> ORGANISM: Artificial Sequence
<220> FEATURE:
<223> OTHER INFORMATION: Derived from Yellow Fever virus

<400> SEQUENCE: 35

Met Ser Gly Arg Lys Ala Gln Gly Lys Thr Leu Gly Val Asn Met Val
1               5                   10                  15

Arg Arg Gly Val Arg Ser Leu Ser Asn Lys Ile Lys Gln Lys Thr Lys
                20                  25                  30

Gln Ile Gly Asn Arg Pro Gly Pro Ser Arg Gly Val Gln Gly Phe Ile
            35                  40                  45

Phe Phe Phe Leu Phe Asn Ile Leu Thr Gly Lys Lys Ile Thr Ala His
        50                  55                  60

Leu Lys Arg Leu Trp Lys Met Leu Asp Pro Arg Gln Gly Leu Ala Val
65                  70                  75                  80

Leu Arg Lys Val Lys Arg Val Val Ala Ser Leu Met Arg Gly Leu Ser
                85                  90                  95
```

Ser Arg Lys Arg Arg Ser His Asp Val Leu Thr Val Gln Phe Leu Ile
                 100                 105                 110
Leu Gly Met Leu Leu Met Thr Gly Gly
            115                 120

<210> SEQ ID NO 36
<211> LENGTH: 11
<212> TYPE: DNA
<213> ORGANISM: Artificial sequence
<220> FEATURE:
<223> OTHER INFORMATION: Synthetic construct

<400> SEQUENCE: 36
gtaaatcctg t                                                              11

<210> SEQ ID NO 37
<211> LENGTH: 12
<212> TYPE: DNA
<213> ORGANISM: Artificial sequence
<220> FEATURE:
<223> OTHER INFORMATION: Synthetic construct

<400> SEQUENCE: 37
acaaaaccac aa                                                             12

<210> SEQ ID NO 38
<211> LENGTH: 10239
<212> TYPE: DNA
<213> ORGANISM: Artificial sequence
<220> FEATURE:
<223> OTHER INFORMATION: Derived from Yellow Fever virus and West Nile
      virus

<400> SEQUENCE: 38
gtaaatcctg tgtgctaatt gaggtgcatt ggtctgcaaa tcgagttgct aggcaataaa        60
cacatttgga ttaattttaa tcgttcgttg agcgattagc agagaactga ccagaacatg       120
tctggtcgta aagctcaggg aaaaaccctg ggcgtcaata tggtacgacg aggagttcgc       180
tccttgtcaa acaaaataaa acaaaaaaca aacaaattg gaaacagacc tggaccttca        240
agaggtgttc aaggatttat cttttttcttt ttgttcaaca ttttgactgg aaaaaagatc     300
acagcccacc taaagaggtt gtggaaaatg ctggacccaa gacaaggctt ggctgttcta       360
aggaaagtca agagagtggt ggccagtttg atgagaggat tgtcctcaag gaaacgccgt       420
tcccatgatg ttctgactgt gcaattccta atttttgggaa tgctgttgat gacgggtgga     480
gttaccctct ctaacttcca agggaaggtg atgatgacgg taaatgctac tgacgtcaca       540
gatgtcatca cgattccaac agctgctgga aagaacctat gcattgtcag agcaatggat      600
gtgggataca tgtgcgatga tactatcact tatgaatgcc cagtgctgtc ggctggtaat       660
gatccagaag acatcgactg ttggtgcaca aagtcagcag tctacgtcag gtatggaaga       720
tgcaccaaga cacgccactc aagacgcagt cggaggtcac tgacagtgca gacacacgga       780
gaaagcactc tagcgaacaa gaagggggct tggatggaca gcaccaaggc cacaaggtat      840
ttggtaaaaa cagaatcatg gatcttgagg aaccctggat atgccctggt ggcagccgtc       900
attggttgga tgcttgggag caacaccatg cagagagttg tgtttgtcgt gccattgctt       960
ttggtggccc cagcttacag cttcaactgc cttggaatga gcaacagaga cttcttggaa      1020
ggagtgtctg agcaacatg gtggattttg ttctcgaag cgacagctg cgtgactatc        1080 atgtctaagg acaagcctac catcgacgtc aagatgatga tatggaggc ggccaacctg       1140

```
gcagaggtcc gcagttattg ctatttggct accgtcagcg atctctccac caaagctgca    1200
tgcccgacca tgggagaagc tcacaatgac aaacgtgctg acccagcttt tgtgtgcaga    1260
caaggagtgg tggacagggg ctggggcaac ggctgcggat tttttggcaa aggatccatt    1320
gacacatgcg ccaaatttgc ctgctctacc aaggcaatag aagaaccat cttgaaagag     1380 aatatcaagt acgaagtggc cattttttgtc catggaccaa ctactgtgga gtcgcacgga    1440
aattactcca cacaggttgg agccactcag gccggccgat tcagcatcac tcctgctgcg    1500
ccttcataca cactaaagct tggagaatat ggagaggtga cagtggactg tgaaccacgg    1560
tcagggattg acaccaatgc atactacgtg atgactgttg aacaaagac gttcttggtc     1620 catcgtgagt ggttcatgga cctcaacctc ccttggagca gtgctggaag tactgtgtgg    1680
aggaacagag agacgttaat ggagtttgag gaaccacacg ccacgaagca gtctgtgata    1740
gcattgggct cacaagaggg agctctgcat caagctttgg ctggagccat tcctgtggaa    1800
ttttcaagca acactgtcaa gttgacgtcg ggtcatttga agtgtagagt gaagatggaa    1860
aaattgcagt tgaagggaac aacctatggc gtctgttcaa aggctttcaa gtttcttagg    1920
actcccgtgg acaccggtca cggcactgtg gtgttggaat tgcagtacac tggcacggat    1980
ggaccttgca aagttcctat ctcgtcagtg gcttcattga acgacctaac gccagtgggc    2040
agattggtca ctgtcaaccc ttttgtttca gtggccacgg ccaacgctaa ggtcctgatt    2100
gaattggaac caccctttgg agactcatac atagtggtgg gcagaggaga caacagatc    2160 aatcaccatt ggcacaagtc tggaagcagc attggcaaag cctttacaac caccctcaaa    2220
ggagcgcaga gactagccgc tctaggagac acagcttggg actttggatc agttggaggg    2280
gtgttcacta gtgttgggcg ggctgtccat caagtgttcg gaggagcatt ccgctcactg    2340
ttcggaggca tgtcctggat aacgcaagga ttgctggggg ctctcctgtt gtggatgggc    2400
atcaatgctc gtgataggtc catagctctc acgtttctcg cagttggagg agttctgctc    2460
ttcctctccg tgaacgtggg cgccgatcaa ggatgcgcca tcaactttgg caagagagag    2520
ctcaagtgcg gagatggtat cttcatattt agagactctg atgactggct gaacaagtac    2580
tcatactatc cagaagatcc tgtgaagctt gcatcaatag tgaaagcctc ttttgaagaa    2640
gggaagtgtg gcctaaattc agttgactcc cttgagcatg agatgtggag aagcagggca    2700
gatgagatca atgccatttt tgaggaaaac gaggtggaca tttctgttgt cgtgcaggat    2760
ccaaagaatg tttaccagag aggaactcat ccattttcca gaattcggga tggtctgcag    2820
tatggttgga gacttggggt aagaaccttg tgttctccc cagggaggaa gaatggaagc    2880
ttcatcatag atggaaagtc caggaaagaa tgcccgtttt caaaccgggt ctggaattct    2940
ttccagatag aggagtttgg gacgggagtg ttcaccacac gcgtgtacat ggacgcagtc    3000
tttgaataca ccatagactg cgatggatct atcttgggtg cagcggtgaa cggaaaaaag    3060
agtgcccatg ctctccaac attttggatg ggaagtcatg aagtaaatgg acatggatg     3120 atccacacct tggaggcatt agattacaag gagtgtgagt ggccactgac acatacgatt    3180
ggaacatcag ttgaagagag tgaaatgttc atgccgagat caatcggagg cccagttagc    3240
tctcacaatc atatccctgg atacaaggtt cagacgaacg gaccttggat gcaggtacca    3300
ctagaagtga gagagaagc ttgcccaggg actagcgtga tcattgatgg caactgtgat    3360
ggacggggaa aatcaaccag atccaccacg gatagcggga aagttattcc tgaatggtgt    3420
tgccgctcct gcacaatgcc gcctgtgagc ttcatggta gtgatgggtg ttggtatccc    3480
atggaaatta ggccaaggaa aacgcatgaa agccatctgg tgcgctcctg ggttacagct    3540
```

```
ggagaaatac atgctgtccc ttttggtttg gtgagcatga tgatagcaat ggaagtggtc    3600
ctaaggaaaa gacagggacc aaagcaaatg ttggttggag gagtagtgct cttgggagca    3660
atgctggtcg ggcaagtaac tctccttgat ttgctgaaac tcacagtggc tgtgggattg    3720
catttccatg agatgaacaa tggaggagac gccatgtata tggcgttgat tgctgccttt    3780
tcaatcagac cagggctgct catcggcttt gggctcagga ccctatggag ccctcgggaa    3840
cgccttgtgc tgaccctagg agcagccatg gtggagattg ccttgggtgg cgtgatgggc    3900
ggcctgtgga agtatctaaa tgcagtttct ctctgcatcc tgacaataaa tgctgttgct    3960
tctaggaaag catcaaatac catcttgccc ctcatggctc tgttgacacc tgtcactatg    4020
gctgaggtga gacttgccgc aatgttcttt tgtgccatgg ttatcatagg ggtccttcac    4080
cagaatttca aggacacctc catgcagaag actatacctc tggtggccct cacactcaca    4140
tcttacctgg gcttgacaca accttttttg ggcctgtgtg catttctggc aacccgcata    4200
tttgggcgaa ggagtatccc agtgaatgag gcactcgcag cagctggtct agtgggagtg    4260
ctggcaggac tggcttttca ggagatggag aacttccttg gtccgattgc agttggagga    4320
ctcctgatga tgctggttag cgtggctggg agggtggatg ggctagagct caagaagctt    4380
ggtgaagttt catgggaaga ggaggcggag atcagcggga gttccgcccg ctatgatgtg    4440
gcactcagtg aacaagggga gttcaagctg ctttctgaag agaaagtgcc atgggaccag    4500
gttgtgatga cctcgctggc cttggttggg gctgccctcc atccatttgc tcttctgctg    4560
gtccttgctg ggtggctgtt tcatgtcagg ggagctagga gaagtgggga tgtcttgtgg    4620
gatattccca ctcctaagat catcgaggaa tgtgaacatc tggaggatgg gatttatggc    4680
atattccagt caaccttctt ggggcctcc cagcgaggag tgggagtggc acagggaggg    4740
gtgttccaca caatgtggca tgtcacaaga ggagctttcc ttgtcaggaa tggcaagaag    4800
ttgattccat cttgggcttc agtaaaggaa gaccttgtcg cctatggtgg ctcatggaag    4860
ttggaaggca gatgggatgg agaggaagag gtccagttga tcgcggctgt tccaggaaag    4920
aacgtggtca acgtccagac aaaaccgagc ttgttcaaag tgaggaatgg gggagaaatc    4980
ggggctgtcg ctcttgacta tccgagtggc acttcaggat ctcctattgt taacaggaac    5040
ggagaggtga ttgggctgta cggcaatggc atccttgtcg gtgacaactc cttcgtgtcc    5100
gccatatccc agactgaggt gaaggaagaa ggaaaggagg agctccaaga gatcccgaca    5160
atgctaaaga aaggaatgac aactgtcctt gattttcatc ctggagctgg gaagacaaga    5220
cgtttcctcc cacagatctt ggccgagtgc gcacggagac gcttgcgcac tcttgtgttg    5280
gcccccacca gggttgttct ttctgaaatg aaggaggctt ttcacggcct ggacgtgaaa    5340
ttccacacac aggcttttc cgctcacggc agcgggagag aagtcattga tgccatgtgc    5400
catgccaccc taacttacag gatgttggaa ccaactaggg ttgttaactg ggaagtgatc    5460
attatggatg aagcccattt tttggatcca gccagcatag ccgctagagg ttgggcagcg    5520
cacagagcta gggcaaatga aagtgcaaca atcttgatga cagccacacc gcctgggact    5580
agtgatgaat tccacattc aaatggtgaa atagaagatg ttcaaacgga tacccagt    5640 gagccctgga acacagggca tgactggatc ctggctgaca aaaggcccac ggcatggttc    5700
cttccatcca tcagagctgc aaatgtcatg gctgcctctt tgcgtaaggc tggaaagagt    5760
gtggtggtcc tgaacaggaa aaccctttgag agagaatacc ccacgataaa gcagaagaaa    5820
cctgacttta tattggccac tgacatagct gaaatgggag ccaaccttg cgtggagcga    5880 gtgctggatt gcaggacggc ttttaagcct gtgcttgtgg atgaagggag gaaggtggca    5940
```

```
ataaaagggc cacttcgtat ctccgcatcc tctgctgctc aaaggagggg gcgcattggg   6000
agaaatccca acagagatgg agactcatac tactattctg agcctacaag tgaaaataat   6060
gcccaccacg tctgctggtt ggaggcctca atgctcttgg acaacatgga ggtgaggggt   6120
ggaatggtcg ccccactcta tggcgttgaa ggaactaaaa caccagtttc ccctggtgaa   6180
atgagactga gggatgacca gaggaaagtc ttcagagaac tagtgaggaa ttgtgacctg   6240
cccgtttggc tttcgtggca agtggccaag gctggtttga agacaatga tcgtaagtgg   6300 tgttttgaag gccctgagga acatgagatc ttgaatgaca gcggtgaaac agtgaagtgc   6360
agggctcctg gaggagcaaa gaagcctctg cgcccaaggt ggtgtgatga aagggtgtca   6420
tctgaccaga gtgcgctgtc tgaatttatt aagtttgctg aaggtaggag gggagctgct   6480
gaagtgctag ttgtgctgag tgaactccct gatttcctgg ctaaaaaagg tggagaggca   6540
atggatacca tcagtgtgtt cctccactct gaggaaggct ctagggctta ccgcaatgca   6600
ctatcaatga tgcctgaggc aatgacaata gtcatgctgt ttatactggc tggactactg   6660
acatcgggaa tggtcatctt tttcatgtct cccaaaggca tcagtagaat gtctatggcg   6720
atgggcacaa tggccggctg tggatatctc atgttccttg gaggcgtcaa acccactcac   6780
atctcctatg tcatgctcat attctttgtc ctgatggtgg ttgtgatccc cgagccaggg   6840
caacaaaggt ccatccaaga caaccaagtg gcatacctca ttattggcat cctgacgctg   6900
gtttcagcgg tggcagccaa cgagctaggc atgctggaga aaaccaaaga ggacctcttt   6960
gggaagaaga acttaattcc atctagtgct tcaccctgga gttggccgga tcttgacctg   7020
aagccaggag ctgcctggac agtgtacgtt ggcattgtta caatgctctc tccaatgttg   7080
caccactgga tcaaagtcga atatggcaac ctgtctctgt ctggaatagc ccagtcagcc   7140
tcagtccttt ctttcatgga caaggggata ccattcatga agatgaatat ctcggtcata   7200
atgctgctgg tcagtggctg gaattcaata acagtgatgc ctctgctctg tggcataggg   7260
tgcgccatgc tccactggtc tctcatttta cctggaatca aagcgcagca gtcaaagctt   7320
gcacagagaa gggtgttcca tggcgttgcc aagaaccctg tggttgatgg gaatccaaca   7380
gttgacattg aggaagctcc tgaaatgcct gcccttttatg agaagaaact ggctctatat   7440
ctccttcttg ctctcagcct agcttctgtt gccatgtgca gaacgcccctt ttcattggct   7500 gaaggcattg tcctagcatc agctgcctta gggccgctca tagagggaaa caccagcctt   7560 cttggaatg gacccatggc tgtctccatg acaggagtca tgaggggggaa tcactatgct   7620 tttgtgggag tcatgtacaa tctatggaag atgaaaactg gacgccgggg gagcgcgaat   7680
ggaaaaactt tgggtgaagt ctggaagagg gaactgaatc tgttggacaa gcgacagttt   7740
gagttgtata aaaggaccga cattgtggag gtggatcgtg atacggcacg caggcatttg   7800
gccgaaggga aggtggacac cggggtggcg tctccagggg gaccgcaaa gttaaggtgg   7860 ttccatgagc gtggctatgt caagctgaa ggtaggggta ttgacctggg gtgtggccgc   7920
ggaggctggt gttactacgc tgctgcgcaa aaggaagtga gtgggggtcaa aggatttact   7980 cttggaagag acgccatga gaaacccatg aatgtgcaaa gtctgggatg gaacatcatc   8040
accttcaagg acaaaactga tatccaccgc ctagaaccag tgaaatgtga cacccttttg   8100
tgtgacattg gaggagtcatc atcgtcatcg gtcacagagg gggaaaggac cgtgagagtt   8160
cttgatactg tagaaaatg gctggcttgt ggggttgaca acttctgtgt gaaggtgtta   8220
gctccataca tgccagatgt tcttgagaaa ctggaattgc tccaaaggag gtttggcgga   8280
acagtgatca ggaaccctct ctccaggaat tccactcatg aaatgtacta cgtgtctgga   8340
```

-continued

```
gcccgcagca atgtcacatt tactgtgaac caaacatccc gcctcctgat gaggagaatg    8400
aggcgtccaa ctggaaaagt gaccctggag gctgacgtca tcctcccaat tgggacacgc    8460
agtgttgaga cagacaaggg acccctggac aaagaggcca tagaagaaag ggttgagagg    8520
ataaaatctg agtacatgac ctcttggttt tatgacaatg acaaccccta caggacctgg    8580
cactactgtg gctcctatgt cacaaaaacc tccggaagtg cggcgagcat ggtaaatggt    8640
gttattaaaa ttctgacata tccatgggac aggatagagg aggtcacaag aatggcaatg    8700
actgacacaa ccccttttgg acagcaaaga gtgtttaaag aaaaagttga caccagagca    8760
aaggatccac cagcgggaac taggaagatc atgaaagttg tcaacaggtg gctgttccgc    8820
cacctggcca gagaaaagaa ccccagactg tgcacaaagg aagaatttat tgcaaaagtc    8880
cgaagtcatg cagccattgg agcttacctg gaagaacaag aacagtggaa gactgccaat    8940
gaggctgtcc aagacccaaa gttctgggaa ctggtggatg aagaaaggaa gctgcaccaa    9000
caaggcaggt gtcggacttg tgtgtacaac atgatgggga aaagagagaa gaagctgtca    9060
gagtttggga agcaaaggg aagccgtgcc atatggtata tgtggctggg agcgcggtat    9120
cttgagtttg aggccctggg attcctgaat gaggaccatt gggcttccag ggaaaactca    9180
ggaggaggag tggaaggcat tggcttacaa tacctaggat atgtgatcag agacctggct    9240
gcaatggatg gtggtggatt ctacgcggat gacaccgctg gatgggacac gcgcatcaca    9300
gaggcagacc ttgatgatga acaggagatc ttgaactaca tgagcccaca tcacaaaaaa    9360
ctggcacaag cagtgatgga aatgacatac aagaacaaag tggtgaaagt gttgagacca    9420
gccccaggag ggaaagccta catggatgtc ataagtcgac gagaccagag aggatccggg    9480
caggtagtga cttatgctct gaacaccatc accaacttga aagtccaatt gatcagaatg    9540
gcagaagcag agatggtgat acatcaccaa catgttcaag attgtgatga atcagttctg    9600
accaggctgg aggcatggct cactgagcac ggatgtgaca gactgaagag gatggcggtg    9660
agtggagacg actgtgtggt ccggcccatc gatgacaggt tcggcctggc cctgtcccat    9720
ctcaacgcca tgtccaaggt tagaaaggac atatctgaat ggcagccatc aaaagggtgg    9780
aatgattggg agaatgtgcc cttctgttcc caccacttcc atgaactaca gctgaaggat    9840
ggcaggagga ttgtggtgcc ttgccgagaa caggacgagc tcattgggag aggaagggtg    9900
tctccaggaa acggctggat gatcaaggaa acagcttgcc tcagcaaagc ctatgccaac    9960
atgtggtcac tgatgtattt tcacaaaagg gacatgaggc tactgtcatt ggctgtttcc    10020
tcagctgttc ccacctcatg ggttccacaa ggacgcacaa catggtcgat tcatgggaaa    10080
ggggagtgga tgaccacgga agacatgctt gaggtgtgga acagagtatg gataaccaac    10140
aacccacaca tgcaggacaa gacaatggtg aaaaaatgga gagatgtccc ttatctaacc    10200
aagagacaag acaagctgtg cggatcactg attggaatg                           10239
```